(12) United States Patent
Gibson et al.

(10) Patent No.: US 12,090,168 B2
(45) Date of Patent: Sep. 17, 2024

(54) GLUCOSE GLYCANS FOR TREATING UREA CYCLE DISORDERS

(71) Applicant: DSM Nutritional Products, LLC, Parsippany, NJ (US)

(72) Inventors: Molly Krisann Gibson, Medford, MA (US); Nathan Wilson Stebbins, Cambridge, MA (US); Ruth Thieroff-Ekerdt, Concord, MA (US); Geoffrey A. von Maltzahn, Boston, MA (US)

(73) Assignee: DSM Nutritional Products, LLC, Parsippany, NJ (US)

( * ) Notice: Subject to any disclaimer, the term of this patent is extended or adjusted under 35 U.S.C. 154(b) by 577 days.

(21) Appl. No.: 16/761,107

(22) PCT Filed: Nov. 3, 2018

(86) PCT No.: PCT/US2018/059102
§ 371 (c)(1),
(2) Date: May 1, 2020

(87) PCT Pub. No.: WO2019/090182
PCT Pub. Date: May 9, 2019

(65) Prior Publication Data
US 2022/0233577 A1 Jul. 28, 2022

Related U.S. Application Data

(60) Provisional application No. 62/720,924, filed on Aug. 21, 2018, provisional application No. 62/673,754, filed on May 18, 2018, provisional application No. 62/581,583, filed on Nov. 3, 2017.

(51) Int. Cl.
| | |
|---|---|
| *A61K 31/716* | (2006.01) |
| *A61K 35/741* | (2015.01) |
| *A61K 47/10* | (2017.01) |
| *A61P 3/12* | (2006.01) |

(52) U.S. Cl.
CPC .......... *A61K 31/716* (2013.01); *A61K 35/741* (2013.01); *A61K 47/10* (2013.01); *A61P 3/12* (2018.01)

(58) Field of Classification Search
CPC ......... A61P 3/12; A61K 31/716; A61K 45/06; A61K 31/715; A61K 35/741; A61K 47/10
See application file for complete search history.

(56) References Cited

U.S. PATENT DOCUMENTS

| | | | |
|---|---|---|---|
| 2,027,904 A | 1/1936 | Farber | |
| 2,436,967 A | 3/1948 | Leuck | |
| 3,766,165 A | 10/1973 | Rennhard | |
| 3,876,794 A | 4/1975 | Rennhard | |
| 3,973,049 A | 8/1976 | Furda et al. | |
| 4,965,354 A | 10/1990 | Yanaki et al. | |
| 5,085,883 A | 2/1992 | Garleb et al. | |
| 5,424,418 A | 6/1995 | Duflot | |
| 5,580,762 A | 12/1996 | Karube et al. | |
| 5,645,647 A | 7/1997 | Guzek et al. | |
| 6,475,552 B1 | 11/2002 | Shah et al. | |
| 6,559,302 B1 | 5/2003 | Shah et al. | |
| 6,677,142 B1 | 1/2004 | Weissmuller et al. | |
| 7,608,291 B2 | 10/2009 | Baillon et al. | |
| 7,615,365 B2 | 11/2009 | Caimi et al. | |
| 8,057,840 B2 | 11/2011 | Harrison et al. | |
| 8,227,448 B2 | 7/2012 | Van Laere et al. | |
| 8,466,242 B2 | 6/2013 | Geremia et al. | |
| 8,476,388 B2 | 7/2013 | Geremia et al. | |
| 8,741,376 B2 | 6/2014 | Broekaert et al. | |
| 8,993,039 B2 | 3/2015 | Harrison et al. | |
| 9,079,171 B2 | 7/2015 | Geremia et al. | |
| 9,205,418 B2 | 12/2015 | Geremia et al. | |
| 9,238,845 B2 | 1/2016 | Baynes et al. | |
| 9,487,764 B2 | 11/2016 | Falb et al. | |
| 9,492,473 B2 * | 11/2016 | von Maltzahn | .... A61K 31/7048 |
| 9,512,239 B2 | 12/2016 | Naeye et al. | |
| 9,757,403 B2 | 9/2017 | von Maltzahn et al. | |
| 9,783,619 B2 | 10/2017 | Bureau et al. | |
| 9,901,595 B2 * | 2/2018 | von Maltzahn | ...... A61K 31/706 |
| 10,314,853 B2 * | 6/2019 | von Maltzahn | ...... A61K 31/715 |
| 10,702,542 B2 | 7/2020 | von Maltzahn et al. | |
| 10,881,676 B2 | 1/2021 | von Maltzahn et al. | |

(Continued)

FOREIGN PATENT DOCUMENTS

| | | |
|---|---|---|
| EP | 0549748 A1 | 7/1993 |
| EP | 1634599 A1 | 3/2006 |

(Continued)

OTHER PUBLICATIONS

International Search Report and Written Opinion for Application No. PCT/US2018/059102, mailed Apr. 24, 2019.
International Preliminary Report on Patentabiliity for Application No. PCT/US2018/059102, mailed May 14, 2020.
Arn et al., Hyperammonemia in women with a mutation at the ornithine carbamoyltransferase locus. A cause of postpartum coma. N Engl J Med. Jun. 7, 1990;322(23):1652-5. doi: 10.1056/NEJM199006073222307.
Boltje et al., Opportunities and challenges in synthetic oligosaccharide and glycoconjugate research. Nat Chem. Nov. 2009;1(8):611-22. doi: 10.1038/nchem.399. Author Manuscript.

(Continued)

*Primary Examiner* — Aaron J Kosar
(74) *Attorney, Agent, or Firm* — Clark & Elbing LLP

(57) ABSTRACT

Compositions, e.g., pharmaceutical compositions, nutritional compositions, medical foods, and food ingredients, as well as their methods of use, are provided, for treating diseases associated with hyperammonemia, e.g., urea cycle disorders (UCD) and hepatic encephalopathy (HE), e.g., minimal HE (MHE) and overt HE (OHE), and modulating enzyme activities and levels of microbes and taxa, and metabolites (e.g., ammonia) in the microbiome of a subject.

21 Claims, 19 Drawing Sheets

(56) References Cited

U.S. PATENT DOCUMENTS

| | | | |
|---|---|---|---|
| 11,169,101 | B2 | 11/2021 | Liu et al. |
| 11,229,660 | B2 | 1/2022 | von Maltzahn et al. |
| 2004/0220389 | A1 | 11/2004 | Buchwald et al. |
| 2004/0235789 | A1 | 11/2004 | Day et al. |
| 2005/0004070 | A1 | 1/2005 | Stahl et al. |
| 2006/0008574 | A1 | 1/2006 | Begli et al. |
| 2006/0014717 | A1 | 1/2006 | Angstrom et al. |
| 2006/0051812 | A1 | 3/2006 | Helin et al. |
| 2006/0127448 | A1 | 6/2006 | Carlson et al. |
| 2006/0257977 | A1 | 11/2006 | Hamaker et al. |
| 2007/0148728 | A1 | 6/2007 | Johnson et al. |
| 2007/0249524 | A1 | 10/2007 | Dieckgraefe |
| 2008/0051573 | A1 | 2/2008 | Hirth et al. |
| 2012/0220740 | A1 | 8/2012 | Geremia et al. |
| 2013/0216693 | A1 | 8/2013 | Harrison et al. |
| 2014/0060522 | A1 | 3/2014 | Baynes et al. |
| 2014/0187474 | A1 | 7/2014 | Sonnenburg |
| 2015/0087616 | A1 | 3/2015 | Ritter et al. |
| 2015/0202607 | A1 | 7/2015 | Geremia et al. |
| 2015/0238948 | A1 | 8/2015 | Geremia |
| 2015/0352133 | A1 | 12/2015 | Jennewein |
| 2016/0007642 | A1 | 1/2016 | Geremia et al. |
| 2016/0015065 | A1 | 1/2016 | Sumner et al. |
| 2016/0032038 | A1 | 2/2016 | Baynes et al. |
| 2016/0122447 | A1 | 5/2016 | Geremia et al. |
| 2016/0213702 | A1* | 7/2016 | von Maltzahn ...... A61K 31/716 |
| 2016/0366909 | A1 | 12/2016 | Geremia et al. |
| 2017/0151268 | A1 | 6/2017 | von Maltzahn et al. |
| 2017/0151269 | A1 | 6/2017 | von Maltzahn et al. |
| 2018/0037599 | A1 | 2/2018 | Duflot et al. |
| 2018/0147222 | A1* | 5/2018 | von Maltzahn ...... A61K 35/741 |
| 2018/0235987 | A1* | 8/2018 | von Maltzahn ...... A61K 31/702 |

FOREIGN PATENT DOCUMENTS

| | | | |
|---|---|---|---|
| EP | 1887017 | A1 | 2/2008 |
| EP | 2138048 | A1 | 12/2009 |
| EP | 2248907 | A1 | 11/2010 |
| EP | 2401925 | A1 | 1/2012 |
| EP | 2666788 | A1 | 11/2013 |
| JP | H01-031487 | B2 | 6/1989 |
| JP | 2009-102324 | A | 5/2009 |
| WO | WO 1998/041544 | A1 | 9/1998 |
| WO | WO 2004/052121 | A1 | 6/2004 |
| WO | WO 2005/003329 | A1 | 1/2005 |
| WO | WO-2006/041930 | A2 | 4/2006 |
| WO | WO-2007/010084 | A2 | 1/2007 |
| WO | WO-2007/050656 | A2 | 5/2007 |
| WO | WO-2007/117175 | A1 | 10/2007 |
| WO | WO-2008/037839 | A1 | 4/2008 |
| WO | WO-2008/156354 | A1 | 12/2008 |
| WO | WO 2009/082214 | A1 | 7/2009 |
| WO | WO-2010/105207 | A1 | 9/2010 |
| WO | WO-2010/136742 | A1 | 12/2010 |
| WO | WO-2011/008086 | A1 | 1/2011 |
| WO | WO-2011/016866 | A1 | 2/2011 |
| WO | WO 2012/118767 | A1 | 9/2012 |
| WO | WO 2014/031956 | A1 | 2/2014 |
| WO | WO-2014/145276 | A1 | 9/2014 |
| WO | WO-2015/153841 | A1 | 10/2015 |
| WO | WO 2016/007778 | A1 | 1/2016 |
| WO | WO 2016/122884 | A1 | 8/2016 |
| WO | WO 2016/122885 | A1 | 8/2016 |
| WO | WO-2016/122887 | A1 | 8/2016 |
| WO | WO 2016/122889 | A1 | 8/2016 |
| WO | WO 2016/172657 | A2 | 10/2016 |
| WO | WO 2016/172658 | A2 | 10/2016 |
| WO | WO 2017/035412 | A1 | 3/2017 |
| WO | WO-2017/083520 | A1 | 5/2017 |
| WO | WO 2018/013871 | A1 | 1/2018 |
| WO | WO 2018/106845 | * | 6/2018 |
| WO | WO 2018/106845 | A1 | 6/2018 |

OTHER PUBLICATIONS

Braissant et al., Current concepts in the pathogenesis of urea cycle disorders. Mol Genet Metab. 2010;100 Suppl 1:S3-S12. doi: 10.1016/j.ymgme.2010.02.010. Epub Feb. 14, 2010.

Burton, Inborn errors of metabolism in infancy: a guide to diagnosis. Pediatrics. Dec. 1998;102(6):E69. doi: 10.1542/peds.102.6.e69.

Caporaso et al., Ultra-high-throughput microbial community analysis on the Illumina HiSeq and MiSeq platforms. ISME J. Aug. 2012;6(8):1621-4. doi: 10.1038/ismej.2012.8. Epub Mar. 8, 2012.

Cavicchi et al., Hypocitrullinemia in expanded newborn screening by LC-MS/MS is not a reliable marker for ornithine transcarbamylase deficiency. J Pharm Biomed Anal. Jul. 12, 2009;49(5):1292-5. doi: 10.1016/j.jpba.2009.03.001. Epub Mar. 20, 2009.

Cordwell et al., Exploring and exploiting bacterial proteomes. Methods Mol Biol. 2004;266:115-35. doi: 10.1385/1-59259-763-7:115.

Darmaun et al., Phenylbutyrate-induced glutamine depletion in humans: effect on leucine metabolism. Am J Physiol. May 1998;274(5):E801-7. doi: 10.1152/ajpendo.1998.274.5.E801.

De Preter et al., Effect of lactulose and Saccharomyces boulardii administration on the colonic urea-nitrogen metabolism and the bifidobacteria concentration in healthy human subjects. Aliment Pharmacol Ther. Apr. 1, 2006;23(7):963-74. doi: 10.1111/j.1365-2036.2006.02834.x.

Díez-Municio et al., Synthesis of novel bioactive lactose-derived oligosaccharides by microbial glycoside hydrolases. Microb Biotechnol. Jul. 2014;7(4):315-31. doi: 10.1111/1751-7915.12124. Epub Apr. 1, 2014.

Gibson et al., Dietary modulation of the human colonic microbiota: introducing the concept of prebiotics. J Nutr. Jun. 1995;125(6):1401-12. doi: 10.1093/jn/125.6.1401.

Heiss et al., The structure of Cryptococcus neoformans galactoxylomannan contains beta-D-glucuronic acid. Carbohydr Res. May 12, 2009;344(7):915-20. doi: 10.1016/j.carres.2009.03.003. Epub Mar. 10, 2009.

Huang et al., Tandem mass neonatal screening in Taiwan—report from one center. J Formos Med Assoc. Nov. 2006; 105(11):882-6. doi: 10.1016/S0929-6646(09)60173-X.

Kuechel et al., Short communication: Development of a rapid laboratory method to polymerize lactose to nondigestible carbohydrates. J Dairy Sci. Apr. 2018;101(4):2862-2866. doi: 10.3168/jds.2017-13813. Epub Feb. 7, 2018.

Lee et al., In vivo urea cycle flux distinguishes and correlates with phenotypic severity in disorders of the urea cycle. Proc Natl Acad Sci U S A. Jul. 5, 2000;97(14):8021-6. doi: 10.1073/pnas.140082197.

Maestri et al., The phenotype of ostensibly healthy women who are carriers for ornithine transcarbamylase deficiency. Medicine (Baltimore). Nov. 1998;77(6):389-97.

McCleary et al., Determination of insoluble, soluble, and total dietary fiber (CODEX definition) by enzymatic-gravimetric method and liquid chromatography: collaborative study. J Aoac Int. May-Jun. 2012;95(3):824-44. doi: 10.5740/jaoacint.cs2011_25.

McCleary et al., Determination of total dietary fiber (CODEX definition) by enzymatic-gravimetric method and liquid chromatography: collaborative study. J Aoac Int. Jan.-Feb. 2010;93(1):221-33.

Miles et al., Hepatocyte glycogen accumulation in patients undergoing dietary management of urea cycle defects mimics storage disease. J Pediatr Gastroenterol Nutr. Apr. 2005;40(4):471-6. doi: 10.1097/01.mpg.0000157200.33486.ce.

Paik et al., Comparison of rifaximin and lactulose for the treatment of hepatic encephalopathy: a prospective randomized study. Yonsei Med J. Jun. 30, 2005;46(3):399-407. doi: 10.3349/ymj.2005.46.3.399.

Palframan et al., Development of a quantitative tool for the comparison of the prebiotic effect of dietary oligosaccharides. Lett Appl Microbiol. 2003;37(4):281-4. doi: 10.1046/j.1472-765x.2003.01398.x.

Quinonez et al., Citrullinemia Type I. GeneReviews. Adam MP, Ardinger HH, Pagon RA, et al., editors. Seattle (WA): University of Washington, Seattle; 1993-2021. Retrieved from www.ncbi.nlm.nih.gov/books/NBK1458. Accessed on Jun. 14, 2011. 19 pages.

(56) References Cited

OTHER PUBLICATIONS

Sajilata et al., Resistant Starch—A Review. Compr Rev Food Sci Food Saf. Jan. 2006;5(1):1-17. doi: 10.1111/j.1541-4337.2006.tb00076.x.

Scaglia et al., Clinical consequences of urea cycle enzyme deficiencies and potential links to arginine and nitric oxide metabolism. J Nutr. Oct. 2004;134(10 Suppl):2775S-2782S; discussion 2796S-2797S. doi: 10.1093/jn/134.10.2775S.

Schaefer et al., Dialysis in neonates with inborn errors of metabolism. Nephrol Dial Transplant. Apr. 1999;14(4):910-8. doi: 10.1093/ndt/14.4.910.

Seeberger et al., Solid-phase oligosaccharide synthesis and combinatorial carbohydrate libraries. Chem Rev. Dec. 13, 2000;100(12):4349-94. doi: 10.1021/cr9903104.

Sharma et al., Randomized controlled trial comparing lactulose plus albumin versus lactulose alone for treatment of hepatic encephalopathy. J Gastroenterol Hepatol. Jun. 2017;32(6):1234-1239. doi: 10.1111/jgh.13666.

Shchelochkov et al., High-frequency detection of deletions and variable rearrangements at the ornithine transcarbamylase (OTC) locus by oligonucleotide array CGH. Mol Genet Metab. Mar. 2009;96(3):97-105. doi: 10.1016/j.ymgme.2008.11.167. Epub Jan. 12, 2009.

Sreenath Nagamani et al., Argininosuccinate Lyase Deficiency. GeneReviews. Adam MP, Ardinger HH, Pagon RA, et al., editors. Seattle (WA): University of Washington, Seattle; 1993-2021. Retrieved from www.ncbi.nlm.nih.gov/books/NBK51784. Accessed on Jun. 14, 2011. 24 pages.

Summar et al., Current strategies for the management of neonatal urea cycle disorders. J Pediatr. Jan. 2001;138(1 Suppl):S30-9. doi: 10.1067/mpd.2001.111834.

Summar et al., Diagnosis, symptoms, frequency and mortality of 260 patients with urea cycle disorders from a 21-year, multicentre study of acute hyperammonaemic episodes. Acta Paediatr. Oct. 2008;97(10):1420-5. doi: 10.1111/j.1651-2227.2008.00952.x. Epub Jul. 17, 2008. Author Manuscript.

Summar et al., Proceedings of a consensus conference for the management of patients with urea cycle disorders. J Pediatr. Jan. 2001; 138(1 Suppl):S6-10. doi: 10.1067/mpd.2001.111831.

Sun et al., Arginase Deficiency. GeneReviews. Adam MP, Ardinger HH, Pagon RA, et al., editors. Seattle (WA): University of Washington, Seattle; 1993-2021. Retrieved from ncbi.nlm.nih.gov/books/NBK1159. Accessed on Jun. 14, 2011. 23 pages.

Theriot et al., Antibiotic-induced shifts in the mouse gut microbiome and metabolome increase susceptibility to Clostridium difficile infection. Nat Commun. 2014;5:3114. doi: 10.1038/ncomms4114. Author Manuscript.

Titgemeyer et al., Fermentability of various fiber sources by human fecal bacteria in vitro. Am J Clin Nutr. Jun. 1991;53(6):1418-24. doi: 10.1093/ajcn/53.6.1418.

Tuchman et al., Blood levels of ammonia and nitrogen scavenging amino acids in patients with inherited hyperammonemia. Mol Genet Metab. Jan. 1999;66(1):10-5. doi: 10.1006/mgme.1998.2783.

Vera et al., Synthesis and purification of galacto-oligosaccharides: state of the art. World J Microbiol Biotechnol. Dec. 2016;32(12):197. doi: 10.1007/s11274-016-2159-4. Epub Oct. 18, 2016. 20 pages.

Wang et al., Naive Bayesian classifier for rapid assignment of rRNA sequences into the new bacterial taxonomy. Appl Environ Microbiol. Aug. 2007;73(16):5261-7. doi: 10.1128/AEM.00062-07. Epub Jun. 22, 2007.

Xiao et al., Chemical synthesis of polysaccharides and polysaccharide mimetics. Prog Poly Science. Nov. 2017;74:78-116. doi: 10.1016/j.progpolymsci.2017.07.009.

Zeuner et al., Methods for improving enzymatic trans-glycosylation for synthesis of human milk oligosaccharide biomimetics. J Agric Food Chem. Oct. 8, 2014;62(40):9615-31. doi: 10.1021/jf502619p. Epub Sep. 23, 2014.

U.S. Appl. No. 17/157,292, filed Jan. 25, 2021, Liu et al.

U.S. Appl. No. 16/883,107, filed May 26, 2020, von Maltzahn et al.

PCT/US2018/059102, Apr. 24, 2019, International Search Report and Written Opinion.

PCT/US2018/059102, May 14, 2020, International Preliminary Report on Patentability.

"Hyperornithinemia-hyperammonemia homocitrullinuria syndrome," Orphanet, search results, retrieved from <https://www.orpha.net/consor/www/cgi-bin/OC_Exp.php?lng=EN&Expert=415> Jun. 23, 2023 (5 pages).

Adamberg et al., "Degradation of fructans and production of propionic acid by Bacteroides thetaiotaomicron are enhanced by the shortage of amino acids," Front Nutr (Dec. 2014) vol. 1, Article 21, 10 pages.

Aida et al., "Mushroom as a potential source of prebiotics: a review", Trends in Food Science & Technology, 20, pp. 567-575, (Dec. 2009).

Alam et al., "Efficacy of Partially Hydrolyzed Guar Gum-Added Oral Rehydration Solution in the Treatment of Severe Cholera in Adults" Digestion (Sep. 2008) vol. 78, pp. 24-29.

Beards et al., "Bacterial, SCFA and gas profiles a range of food ingredients following in vitro fermentation by human colonic microbiota," Anaerobe (May 2010) vol. 16, pp. 420-425.

Belknap et al., "The effects of psyllium hydrophilic mucilloid on diarrhea in enterally fed patients" Heart & Lung (May 1997) vol. 26, No. 3, pp. 229-237.

Bergstrom K. et al. Defective Intestinal Mucin-type O-Glycosylation Causes Spontaneous Colitis Associated Cancer in Mice. Gastroenterology (accepted manuscript). Mar. 27, 2016 (49 pages).

Bier et al., "Generally Recognized As Safe (GRAS) Determination for the Addition of Polydextrose to Infant Formula as a Prebiotic Ingredient in Combination with Galactooligosaccharides", U.S. Food and Drug Administration, GRAS Notice, dated Aug. 2007 (116 pages).

Casellas et al., "Oral oligofructose-enriched inulin supplementation in acute ulcerative colitis is well tolerated and associated with lowered faecal calprotectin," Aliment Pharmacol Ther. (May 2007) vol. 25, pp. 1061-1067.

Chen et al., "Comparative Effects of Cellulose and Soluble Fibers (Pectin, Konjac Glucomannan, Inulin) on Fecal Water Toxicity toward Caco-2 Cells, Fecal Bacteria Enzymes, Bile Acid, and Short-Chain Fatty Acids," J Agric Food Chem (2010) vol. 58, pp. 10277-10281.

Clemente et al., "The Impact of the Gut Microbiota on Human Health: an Integrative View," available in PMC Oct. 4, 2016, published in final edited form as: Cell (Mar. 2012) vol. 148, No. 6 (24 pages).

Deng et al., "Effect of dietary fiber on intestinal barrier function of 5-Fu stressed rats" Res Exp Med. (Oct. 1999) vol. 199, pp. 111-119.

Duggan et al., "Protective nutrients and functional foods for the gastrointestinal tract," Am J Clin Nutr (May 2002) vol. 75, p. 789-808.

Dutton et al., "The Constitution of a Synthetic Xylan" Canadian Journal of Chemistry (Aug. 1962) vol. 40, No. 8, pp. 1479-1482 (4 pages).

Extended European Search Report for EP Application No. 15819734.3 dated Feb. 7, 2018 (12 pages).

Extended European Search Report for EP Application No. 167 43841.5 dated Jul. 13, 2018 (11 pages).

Extended European Search Report for EP Application No. 16743842.3 dated Jul. 9, 2018 (12 pages).

Extended European Search Report for EP Application No. 16743843.1 dated Jun. 6, 2018 (9 pages).

Extended European Search Report for EP Application No. 17206409.9 dated Jun. 21, 2018 (8 pages).

Fasina et al. "Comparative efficacy of a yeast product and bacitracin methylene disalicylate in enhancing early growth and intestinal maturation in broiler chicks from breeder hens of different ages," Poult Sci. (May 2011) vol. 90, pp. 1067-1073.

Fischer et al., "The gel-forming polysaccharide of psyllium husk {Plantago ovata Forsk)" Carbohydrate Research (Jul. 2004) vol. 339, pp. 2009-2017.

Fuhrer et al., "Milk sialyllactose influences colitis in mice through selective intestinal bacterial colonization," J Exp Med (Dec. 2010) vol. 207, No. 13, pp. 2843-2854.

(56) References Cited

OTHER PUBLICATIONS

Hopkins et al., "Nondigestible Oligosaccharides Enhance Bacterial Colonization Resistance against Clostridium difficile In Vitro," App Env Micro (Apr. 2003) vol. 69, No. 4, pp. 1920-1927.
International Search Report and Written Opinion for International Application No. PCT/US2016/029082 dated Oct. 14, 2016 (17 pages).
International Search Report and Written Opinion for International Application No. PCT/US2016/029083 dated Oct. 14, 2016 (16 pages).
International Search Report and Written Opinion issued in PCT/US2015/039795, mailed Oct. 7, 2015 (9 pages).
International Search Report and Written Opinion issued in PCT/US2016/013265, mailed Mar. 11, 2016 (9 pages).
International Search Report and Written Opinion issued in PCT/US2016/013271, mailed Mar. 11, 2016 (8 pages).
International Search Report and Written Opinion issued in PCT/US2016/013280 mailed Mar. 21, 2016 (12 pages).
Islek et al., "The role of Bifidobacterium lactis B94 plus inulin in the treatment of acute infectious diarrhea in children" Turk J Gastroenterol (Dec. 2014) vol. 25, pp. 628-633.
Kau et al., "Human nutrition, the gut microbiome, and immune system: envisioning the future," available in PMC Mar. 9, 2012, published in final edited form as: Nature. 474(7351):327-336 (2011).
Kellow et al., "Metabolic benefits of dietary prebiotics in human subjects: a systematic review of randomised controlled trials," Br J Nutr (Nov. 2013) vol. 111, pp. 1147-1161.
Lewis et al. "Effect of the Prebiotic Oligofructose on Relapse of Clostridium difficile-Associated Diarrhea: A Randomized, Controlled Study" Clinical Gastroenterology and Hepatology (May 2005) vol. 3, pp. 442-448.
Lin et al., "Irinotecan {CPT-11} Chemotherapy Alters Intestinal Microbiota in Tumour Bearing Rats" PLoS One. (Jul. 2012) vol. 7, No. 7, e39764 (8 pages).
Louis et al., "How to Manipulate the Microbiota: Prebiotics" Microbiota of the Human Body, Advances in Experimental Medicine and Biology. (2016) 902, pp. 119-142.
Marlett et al., "A Poorly Fermented Gel from Psyllium Seed Husk Increases Excreta Moisture and Bile Acid Excretion in Rats" The Journal of Nutrition (Sep. 2002) vol. 132, pp. 2638-2643.
Mora et al., "Synthetic Polysaccharides. V. Polymerization of Various Aldoses" Journal of the American Chemical Society (Jul. 1960) vol. 83, pp. 3418-3421.
Nakamura et al., "Suppressive effect of partially hydrolyzed guar gum on transitory diarrhea induced by ingestion of maltitol and lactitol in healthy humans" European Journal of Clinical Nutrition (Jan. 2007) vol. 61, pp. 1086-1093.
Neyrinck et al., "Prebiotic Effects of Wheat Arabinoxylan Related to the Increase in Bifidobacteria, Roseburia and Bacteroides/ Prevotella in Diet-Induced Obese Mice" PLoS One (Jun. 2011) vol. 6, No. 6, e20944, (12 pages).
Prisciandaro et al., "Probiotic factors partially improve parameters of 5-fluorouracil-induced intestinal mucositis in rats" Cancer Biology & Therapy. (Apr. 2011) vol. 11, No. 7, pp. 671-677.
Roytio et al. "The fermentation of polydextrose in the large intestine and its beneficial effects," Benef Microb (Sep. 2014) vol. 5, No. 3, pp. 305-314 (9 pages).
Saku et al., "Effects of polydextrose on serum lipids, lipoproteins, and apolipoproteins in healthy subjects" Clin Ther (Mar. 1991) vol. 13, No. 2, pp. 254-258. (Abstract) (1 page).
Sanz et al., "Influence of Glycosidic Linkages and Molecular Weight on the Fermentation of Maltose-Based Oligosaccharides by Human Gut Bacteria" J Agric Food Chem. (Dec. 2006) vol. 54, pp. 9779-9784.
Schley et al., "The immune-enhancing effects of dietary fibres and prebiotics," Br J Nutr (May 2002) vol. 87, Suppl 2, pp. S221-S230.
Scott et al. "Prebiotic stimulation of human colonic butyrate-producing bacteria and bifidobacteria, in vitro" FEMS Microbiology Ecology (Aug. 2013) vol. 87, pp. 30-40.
Sharon N. Carbohydrates as Future Anti-Adhesion Drugs for Infectious Diseases. Biochimica et Biophysica Acta 1760(4)527-537, Apr. 2006.
Simpson et al., "Review article: dietary fibre-microbiota interactions" Alimentary Pharmacology and Therapeutics. (May 2015) vol. 42, 158-179.
Synytsya et al., "Glucans from fruit bodies of cultivated mushrooms Pleurotus ostreatus and Pleurotus eryngii: Structure and potential prebiotic activity" Carbohydrate Polymers, (Nov. 2008) vol. 76, pp. 548-556.
Tomlin et al., "A comparative study of the effects on colon function caused by feeding ispaghula husk and polydextrose" Aliment Pharmacol Ther. (Dec. 1988) vol. 2, No. 6, pp. 513-519.
Wang et al., "Preparation and structural characterization of polymannose synthesized by phosphoric acid catalyzation under microwave irradation" Carbohydrate Polymers (Jan. 2015) vol. 121, pp. 355-361.
Wang et al., "Rapid microwave-assisted synthesis of polydextrose and identification of structure and function" Carbohydrate Polymers (Jul. 2014) vol. 113, pp. 225-230.
Winfree et al., "Effects of Dietary Protein and Energy on Growth, Feed Conversion Efficiency and Body Composition of Tilapia aurea," J Nutr (Jun. 1981) vol. 111, pp. 1001-1012.
Wu et al., "Diminution of the gut resistome after a gut microbiota-targeted dietary intervention in obese children," Nature Scientific Reports (Apr. 2016) vol. 6, Article 24030, 9 pages.

\* cited by examiner

GLUCOSE GLYCANS FOR TREATING UREA CYCLE DISORDERS

RELATED APPLICATIONS

This application is a U.S. national phase application and claims the benefit of priority under 35 U.S.C. § 371 of International Application No. PCT/US2018/059102, filed Nov. 3, 2018, which claims the benefit under 35 U.S.C. § 119(e) of U.S. Provisional Application No. 62/581,583, entitled "GLYCAN PREPARATIONS AND METHODS OF USE IN UREA CYCLE DISORDERS", filed Nov. 3, 2017, U.S. Provisional Application No. 62/673,754, entitled "GLYCAN PREPARATIONS AND METHODS OF USE IN UREA CYCLE DISORDERS", filed May 18, 2018, and U.S. Provisional Application No. 62/720,924, entitled "OLIGOSACCHARIDE COMPOSITIONS AND METHODS OF USE THEREOF FOR REDUCING AMMONIA LEVELS", filed Aug. 21, 2018, the entire contents of each of which are incorporated herein by reference.

BACKGROUND OF THE INVENTION

Maintaining or restoring human health faces a large number of challenges many of which result from the lack of effective treatment options. There is a continued need for novel therapies and treatment regimens.

SUMMARY OF THE INVENTION

The present invention is, in part, based on the discovery that glycan preparations are useful for: treating diseases associated with hyperammonemia, e.g., urea cycle disorders (UCDs), and hepatic encephalopathy (HE) in a subject; for increasing or decreasing enzymatic activities in a subject; increasing or decreasing the level of a metabolite in a subject; modulating the processing of a metabolite, e.g., ammonia, citrulline, argininosuccinic acid, glutamine, glutamate, orotic acid, or arginine, or modulating, e.g., increasing or decreasing, an enzymatic activity, in a subject; and identifying or selecting a treatment regimen for a subject having a UCD. In some embodiments, a glycan preparation described herein is useful in treating a UCD. In other embodiments, a glycan preparation described herein is useful in treating HE.

Accordingly, in one aspect the invention is directed to a method for treating a urea cycle disorder (UCD) (e.g., carbamyl phosphate synthetase I (CPSI) deficiency, ornithine transcarbamylase (OTC) deficiency, argininosuccinate synthetase (ASS), deficiency, argininosuccinate lyase (ASL) deficiency, N-acetyl glutamate synthetase (NAGS) deficiency, hyperornithinemia-hyperammonemia-homocitrullinuria (HHH) syndrome, citrullinemia type II (CIT II) disorder or arginase deficiency) in a subject, e.g., a human subject, comprising:
administering a glycan preparation in an amount effective and for a time sufficient to treat the UCD,
wherein:
i) the glycan preparation comprises glycan polymers that comprise glucose, galactose, arabinose, mannose, fructose, xylose, fucose, or rhamnose glycan units;
ii) the average degree of branching (DB) of the glycan polymers in the glycan preparation is 0, between 0.01 and 0.6, between 0.05 and 0.5, between 0.1 and 0.4, or between 0.15 and 0.4;
iii) at least 50% (at least 60%, 65%, 70%, 75%, 80%, or 85%, or less than 50%) of the glycan polymers in the glycan preparation have a degree of polymerization (DP) of at least 3 and less than 30 glycan units, at least 3 and less than 10 glycan units, at least 5 and less than 25 glycan units, or at least 10 and less than 35 glycan units;
iv) the average DP (mean DP) of the glycan preparation is between about 5 and 8, between about 8 and 13, between about 13 and 25, between about 5 and 15, between about 5 and 20, or between about 5-15;
v) the ratio of alpha- to beta-glycosidic bonds present in the glycan polymers of the glycan preparation is 0, or between about 0.8:1 to about 5:1, between about 1:1 to about 5:1, between about 1:1 to about 3:1, between about 3:2 to about 2:1, or between about 3:2 to about 3:1;
vi) the glycan preparation comprises between 15 mol % and 75 mol % (between 20 mol % and 60 mol %, between 25 mol % and 50 mol %, or between 30 mol % and 45 mol %) 1,6 glycosidic bonds;
vii) the glycan preparation comprises between 1 mol % and 40 mol % (between 1 mol % and 30 mol %, between 5 mol % and 25 mol %, between 10 mol % and 20 mol %) of each at least one, two, or three of 1,2; 1,3; and 1,4 glycosidic bonds;
viii) the glycan preparation has a final solubility limit in water of at least about 50 (at least about 60, 70, at least about 75, or less than 50) Brix at 23° C.;
ix) the glycan preparation has a dietary fiber content of at least 50% (at least 60%, 70%, 80%, or at least 90%, or less than 50%); or
x) any combination of two, three, four, five, six, seven, eight, or nine of i), ii), iii), iv), v), vi), vii), viii), and ix).

In another aspect, the invention is directed to a method for increasing or decreasing an enzymatic activity (e.g., carbamyl phosphate synthetase I (CPSI), ornithine transcarbamylase (OTC), argininosuccinate synthetase (ASS), argininosuccinate lyase (ASL), N-acetyl glutamate synthetase (NAGS), ornithine translocase, citrin, or arginase activity) in a subject, e.g., a human subject, comprising:
administering a glycan preparation in an amount effective and for a time sufficient to increase or decrease the enzymatic activity (e.g., carbamyl phosphate synthetase I (CPSI), ornithine transcarbamylase (OTC), argininosuccinate synthetase (ASS), argininosuccinate lyase (ASL), N-acetyl glutamate synthetase (NAGS), ornithine translocase, citrin, or arginase activity),
wherein:
i) the glycan preparation comprises glycan polymers that comprise glucose, galactose, arabinose, mannose, fructose, xylose, fucose, or rhamnose glycan units;
ii) the average degree of branching (DB) of the glycan polymers in the glycan preparation is 0, between 0.01 and 0.6, between 0.05 and 0.5, between 0.1 and 0.4, or between 0.15 and 0.4;
iii) at least 50% (at least 60%, 65%, 70%, 75%, 80%, or 85%, or less than 50%) of the glycan polymers in the glycan preparation have a degree of polymerization (DP) of at least 3 and less than 30 glycan units, at least 3 and less than 10 glycan units, at least 5 and less than 25 glycan units, or at least 10 and less than 35 glycan units;
iv) the average DP (mean DP) of the glycan preparation is between about 5 and 8, between about 8 and 13, between about 13 and 25, between about 5 and 15, between about 5 and 20, or between about 5-15;
v) the ratio of alpha- to beta-glycosidic bonds present in the glycan polymers of the glycan preparation is 0, or between about 0.8:1 to about 5:1, between about 1:1 to about 5:1, between about 1:1 to about 3:1, between about 3:2 to about 2:1, or between about 3:2 to about 3:1;

vi) the glycan preparation comprises between 15 mol % and 75 mol % (between 20 mol % and 60 mol %, between 25 mol % and 50 mol %, or between 30 mol % and 45 mol %) 1,6 glycosidic bonds;

vii) the glycan preparation comprises between 1 mol % and 40 mol % (between 1 mol % and 30 mol %, between 5 mol % and 25 mol %, between 10 mol % and 20 mol %) of each at least one, two, or three of 1,2; 1,3; and 1,4 glycosidic bonds;

viii) the glycan preparation has a final solubility limit in water of at least about 50 (at least about 60, 70, at least about 75, or less than 50) Brix at 23° C.;

ix) the glycan preparation has a dietary fiber content of at least 50% (at least 60%, 70%, 80%, or at least 90%, or less than 50%); or x) any combination of two, three, four, five, six, seven, eight, or nine of i), ii), iii), iv), v), vi), vii), viii), and ix).

In another aspect, the invention is directed to a method for decreasing the level of a metabolite, e.g., ammonia, citrulline, argininosuccinic acid, glutamine, glutamate, orotic acid, or arginine, in a subject, e.g., a human subject, comprising:

administering a glycan preparation in an amount effective and for a time sufficient to decrease the level of the metabolite, e.g., ammonia, citrulline, argininosuccinic acid, glutamine, glutamate, orotic acid, or arginine, wherein:

i) the glycan preparation comprises glycan polymers that comprise glucose, galactose, arabinose, mannose, fructose, xylose, fucose, or rhamnose glycan units;

ii) the average degree of branching (DB) of the glycan polymers in the glycan preparation is 0, between 0.01 and 0.6, between 0.05 and 0.5, between 0.1 and 0.4, or between 0.15 and 0.4;

iii) at least 50% (at least 60%, 65%, 70%, 75%, 80%, or 85%, or less than 50%) of the glycan polymers in the glycan preparation have a degree of polymerization (DP) of at least 3 and less than 30 glycan units, at least 3 and less than 10 glycan units, at least 5 and less than 25 glycan units, or at least 10 and less than 35 glycan units;

iv) the average DP (mean DP) of the glycan preparation is between about 5 and 8, between about 8 and 13, between about 13 and 25, between about 5 and 15, between about 5 and 20, or between about 5-15;

v) the ratio of alpha- to beta-glycosidic bonds present in the glycan polymers of the glycan preparation is 0, or between about 0.8:1 to about 5:1, between about 1:1 to about 5:1, between about 1:1 to about 3:1, between about 3:2 to about 2:1, or between about 3:2 to about 3:1;

vi) the glycan preparation comprises between 15 mol % and 75 mol % (between 20 mol % and 60 mol %, between 25 mol % and 50 mol %, or between 30 mol % and 45 mol %) 1,6 glycosidic bonds;

vii) the glycan preparation comprises between 1 mol % and 40 mol % (between 1 mol % and 30 mol %, between 5 mol % and 25 mol %, between 10 mol % and 20 mol %) of each at least one, two, or three of 1,2; 1,3; and 1,4 glycosidic bonds;

viii) the glycan preparation has a final solubility limit in water of at least about 50 (at least about 60, 70, at least about 75, or less than 50) Brix at 23° C.;

ix) the glycan preparation has a dietary fiber content of at least 50% (at least 60%, 70%, 80%, or at least 90%, or less than 50%); or x) any combination of two, three, four, five, six, seven, eight, or nine of i), ii), iii), iv), v), vi), vii), viii), and ix).

In another aspect, the invention is directed to a method of:

(a) modulating the processing of a metabolite, e.g., ammonia, citrulline, argininosuccinic acid, glutamine, glutamate, orotic acid, or arginine, or (b) modulating, e.g., increasing or decreasing, an enzymatic activity (e.g., carbamyl phosphate synthetase I (CPSI), ornithine transcarbamylase (OTC), argininosuccinate synthetase (ASS), argininosuccinate lyase (ASL), N-acetyl glutamate synthetase (NAGS), ornithine translocase, citrin, or arginase activity) in the gastrointestinal tract of, in a subject comprising:

administering a glycan composition in an amount effective and for a time sufficient to modulate the processing of the metabolite, e.g., ammonia, citrulline, argininosuccinic acid, glutamine, glutamate, orotic acid, or arginine, or modulate, e.g., increase or decrease, the enzymatic activity (e.g., carbamyl phosphate synthetase I (CPSI), ornithine transcarbamylase (OTC), argininosuccinate synthetase (ASS), argininosuccinate lyase (ASL), N-acetyl glutamate synthetase (NAGS), ornithine translocase, citrin, or arginase activity), wherein:

i) the glycan preparation comprises glycan polymers that comprise glucose, galactose, arabinose, mannose, fructose, xylose, fucose, or rhamnose glycan units;

ii) the average degree of branching (DB) of the glycan polymers in the glycan preparation is 0, between 0.01 and 0.6, between 0.05 and 0.5, between 0.1 and 0.4, or between 0.15 and 0.4;

iii) at least 50% (at least 60%, 65%, 70%, 75%, 80%, or 85%, or less than 50%) of the glycan polymers in the glycan preparation have a degree of polymerization (DP) of at least 3 and less than 30 glycan units, at least 3 and less than 10 glycan units, at least 5 and less than 25 glycan units, or at least 10 and less than 35 glycan units;

iv) the average DP (mean DP) of the glycan preparation is between about 5 and 8, between about 8 and 13, between about 13 and 25, between about 5 and 15, between about 5 and 20, or between about 5-15;

v) the ratio of alpha- to beta-glycosidic bonds present in the glycan polymers of the glycan preparation is 0, or between about 0.8:1 to about 5:1, between about 1:1 to about 5:1, between about 1:1 to about 3:1, between about 3:2 to about 2:1, or between about 3:2 to about 3:1;

vi) the glycan preparation comprises between 15 mol % and 75 mol % (between 20 mol % and 60 mol %, between 25 mol % and 50 mol %, or between 30 mol % and 45 mol %) 1,6 glycosidic bonds;

vii) the glycan preparation comprises between 1 mol % and 40 mol % (between 1 mol % and 30 mol %, between 5 mol % and 25 mol %, between 10 mol % and 20 mol %) of each at least one, two, or three of 1,2; 1,3; and 1,4 glycosidic bonds;

viii) the glycan preparation has a final solubility limit in water of at least about 50 (at least about 60, 70, at least about 75, or less than 50) Brix at 23° C.;

ix) the glycan preparation has a dietary fiber content of at least 50% (at least 60%, 70%, 80%, or at least 90%, or less than 50%); or x) any combination of two, three, four, five, six, seven, eight, or nine of i), ii), iii), iv), v), vi), vii), viii), and ix).

In another aspect, the invention is directed to a method of identifying or selecting a treatment regimen for a subject having a urea cycle disorder (UCD) (e.g., carbamyl phosphate synthetase I (CPSI) deficiency, ornithine transcarbamylase (OTC) deficiency, argininosuccinate synthetase (ASS), deficiency, argininosuccinate lyase (ASL) deficiency, N-acetyl glutamate synthetase (NAGS) deficiency, hyperornithinemia-hyperammonemia-homocitrullinuria (HHH) syndrome, citrullinemia type II (CIT II) disorder or arginase deficiency) comprising a) acquiring a value for the presence or level of a bacterial taxa or a microbial metabolite or an enzymatic activity in the subject;

b) responsive to the value, selecting a treatment comprising a glycan preparation to treat the subject, and c) administering the glycan preparation in an effective amount and for a time sufficient to treat the subject, wherein:

i) the glycan preparation comprises glycan polymers that comprise glucose, galactose, arabinose, mannose, fructose, xylose, fucose, or rhamnose glycan units;

ii) the average degree of branching (DB) of the glycan polymers in the glycan preparation is 0, between 0.01 and 0.6, between 0.05 and 0.5, between 0.1 and 0.4, or between 0.15 and 0.4;

iii) at least 50% (at least 60%, 65%, 70%, 75%, 80%, or 85%, or less than 50%) of the glycan polymers in the glycan preparation have a degree of polymerization (DP) of at least 3 and less than 30 glycan units, at least 3 and less than 10 glycan units, at least 5 and less than 25 glycan units, or at least 10 and less than 35 glycan units;

iv) the average DP (mean DP) of the glycan preparation is between about 5 and 8, between about 8 and 13, between about 13 and 25, between about 5 and 15, between about 5 and 20, or between about 5-15;

v) the ratio of alpha- to beta-glycosidic bonds present in the glycan polymers of the glycan preparation is 0, or between about 0.8:1 to about 5:1, between about 1:1 to about 5:1, between about 1:1 to about 3:1, between about 3:2 to about 2:1, or between about 3:2 to about 3:1;

vi) the glycan preparation comprises between 15 mol % and 75 mol % (between 20 mol % and 60 mol %, between 25 mol % and 50 mol %, or between 30 mol % and 45 mol %) 1,6 glycosidic bonds;

vii) the glycan preparation comprises between 1 mol % and 40 mol % (between 1 mol % and 30 mol %, between 5 mol % and 25 mol %, between 10 mol % and 20 mol %) of each at least one, two, or three of 1,2; 1,3; and 1,4 glycosidic bonds;

viii) the glycan preparation has a final solubility limit in water of at least about 50 (at least about 60, 70, at least about 75, or less than 50) Brix at 23° C.;

ix) the glycan preparation has a dietary fiber content of at least 50% (at least 60%, 70%, 80%, or at least 90%, or less than 50%); or x) any combination of two, three, four, five, six, seven, eight, or nine of i), ii), iii), iv), v), vi), vii), viii), and ix).

In another aspect, the invention is directed to a method of reducing gut-derived ammonia in a subject, e.g., a human subject, comprising:

administering a glycan preparation in an amount effective and for a time sufficient to reduce gut-derived ammonia in the subject, wherein:

i) the glycan preparation comprises glycan polymers that comprise glucose, galactose, arabinose, mannose, fructose, xylose, fucose, or rhamnose glycan units;

ii) the average degree of branching (DB) of the glycan polymers in the glycan preparation is 0, between 0.01 and 0.6, between 0.05 and 0.5, between 0.1 and 0.4, or between 0.15 and 0.4;

iii) at least 50% (at least 60%, 65%, 70%, 75%, 80%, or 85%, or less than 50%) of the glycan polymers in the glycan preparation have a degree of polymerization (DP) of at least 3 and less than 30 glycan units, at least 3 and less than 10 glycan units, at least 5 and less than 25 glycan units, or at least 10 and less than 35 glycan units;

iv) the average DP (mean DP) of the glycan preparation is between about 5 and 8, between about 8 and 13, between about 13 and 25, between about 5 and 15, between about 5 and 20, or between about 5-15;

v) the ratio of alpha- to beta-glycosidic bonds present in the glycan polymers of the glycan preparation is 0, or between about 0.8:1 to about 5:1, between about 1:1 to about 5:1, between about 1:1 to about 3:1, between about 3:2 to about 2:1, or between about 3:2 to about 3:1;

vi) the glycan preparation comprises between 15 mol % and 75 mol % (between 20 mol % and 60 mol %, between 25 mol % and 50 mol %, or between 30 mol % and 45 mol %) 1,6 glycosidic bonds;

vii) the glycan preparation comprises between 1 mol % and 40 mol % (between 1 mol % and 30 mol %, between 5 mol % and 25 mol %, between 10 mol % and 20 mol %) of each at least one, two, or three of 1,2; 1,3; and 1,4 glycosidic bonds;

viii) the glycan preparation has a final solubility limit in water of at least about 50 (at least about 60, 70, at least about 75, or less than 50) Brix at 23° C.;

ix) the glycan preparation has a dietary fiber content of at least 50% (at least 60%, 70%, 80%, or at least 90%, or less than 50%); or x) any combination of two, three, four, five, six, seven, eight, or nine of i), ii), iii), iv), v), vi), vii), viii), and ix).

In some embodiments, the glycan preparation is a glycan preparation described or used in Example 10.

In another aspect, the invention is directed to a method of treating hyperammonemia in a subject, e.g., a human subject, comprising:

administering a glycan preparation in an amount effective and for a time sufficient to treat hyperammonemia in the subject, wherein:

i) the glycan preparation comprises glycan polymers that comprise glucose, galactose, arabinose, mannose, fructose, xylose, fucose, or rhamnose glycan units;

ii) the average degree of branching (DB) of the glycan polymers in the glycan preparation is 0, between 0.01 and 0.6, between 0.05 and 0.5, between 0.1 and 0.4, or between 0.15 and 0.4;

iii) at least 50% (at least 60%, 65%, 70%, 75%, 80%, or 85%, or less than 50%) of the glycan polymers in the glycan preparation have a degree of polymerization (DP) of at least 3 and less than 30 glycan units, at least 3 and less than 10 glycan units, at least 5 and less than 25 glycan units, or at least 10 and less than 35 glycan units;

iv) the average DP (mean DP) of the glycan preparation is between about 5 and 8, between about 8 and 13, between about 13 and 25, between about 5 and 15, between about 5 and 20, or between about 5-15;

v) the ratio of alpha- to beta-glycosidic bonds present in the glycan polymers of the glycan preparation is 0, or between about 0.8:1 to about 5:1, between about 1:1 to about 5:1, between about 1:1 to about 3:1, between about 3:2 to about 2:1, or between about 3:2 to about 3:1;

vi) the glycan preparation comprises between 15 mol % and 75 mol % (between 20 mol % and 60 mol %, between 25 mol % and 50 mol %, or between 30 mol % and 45 mol %) 1,6 glycosidic bonds;

vii) the glycan preparation comprises between 1 mol % and 40 mol % (between 1 mol % and 30 mol %, between 5 mol % and 25 mol %, between 10 mol % and 20 mol %) of each at least one, two, or three of 1,2; 1,3; and 1,4 glycosidic bonds;

viii) the glycan preparation has a final solubility limit in water of at least about 50 (at least about 60, 70, at least about 75, or less than 50) Brix at 23° C.;

ix) the glycan preparation has a dietary fiber content of at least 50% (at least 60%, 70%, 80%, or at least 90%, or less than 50%); or x) any combination of two, three, four, five, six, seven, eight, or nine of i), ii), iii), iv), v), vi), vii), viii), and ix). In some embodiments, the glycan preparation is a glycan preparation described or used in Example 10.

In another aspect, the invention is directed to glycan preparations that comprises glycan polymers that comprise:
i) glucose glycan units;
ii) the average degree of branching (DB) of the glycan polymers in the glycan preparation is between 0.05 and 0.25, or between 0.1 and 0.2;
iii) the $MW_w$ (g/mol) of the glycan preparation is between about 700 and 1200, between about 800 and 1100, or between about 850 and 1050;
iv) the $MW_n$ (g/mol) of the glycan preparation is between about 500 and 800, between about 550 and 750, or between about 600 and 700;
v) the ratio of alpha- to beta-glycosidic bonds present in the glycan polymers of the glycan preparation between about 1:1 to about 1.5:1;
vi) the glycan preparation comprises between 30 mol % and 60 mol %, between 35 mol % and 55 mol %, or between 40 mol % and 50 mol % 1,6 glycosidic bonds;
vii) the glycan preparation comprises between 5 mol % and 30 mol %, between 10 mol % and 25 mol %, or between 15 mol % and 25 mol % of each of 1,2; 1,3; and 1,4 glycosidic bonds; viii) the glycan preparation has a final solubility limit in water of at least about 50, 60, or at least about 70 Brix at 23° C.;
ix) the glycan preparation has a dietary fiber content of at least about 60%, 70%, or at least 80%;
x) the glycan preparation has a glucose monomer content of less than 15%, 10%, or less than 5%;
xi) the glycan preparation has a DP2+ content of at least about 80%, 85%, 90%, or at least about 95%;
xii) the glycan preparation has a dextrose equivalent (DE) of between 10 and 30, 15 and 25 or 16 and 24,
xiii) the glycan preparation has a total furanose content of between 1% and 10% or 2% and 6%; or
x) any combination of two, three, four, five, six, seven, eight, or nine, ten, eleven, twelve, or thirteen of i), ii), iii), iv), v), vi), vii), viii), ix), x), xi), xii) and xiii). In some embodiments, the glycan preparation is a glycan preparation (glu100) described or used in Example 10.

In another aspect, the invention is directed to glycan preparations that comprises glycan polymers that comprise:
i) glucose and galactose glycan units;
ii) the average degree of branching (DB) of the glycan polymers in the glycan preparation is between 0.05 and 0.25, or between 0.1 and 0.2;
iii) the $MW_w$ (g/mol) of the glycan preparation is between about 800 and 1300, between about 900 and 1200, or between about 950 and 1150;
iv) the $MW_n$ (g/mol) of the glycan preparation is between about 600 and 900, between about 650 and 850, or between about 700 and 850;
v) the ratio of alpha- to beta-glycosidic bonds present in the glycan polymers of the glycan preparation between about 1:1 to about 2:1;
vi) the glycan preparation comprises between 30 mol % and 60 mol %, between 35 mol % and 55 mol %, or between 40 mol % and 50 mol % 1,6 glycosidic bonds;
vii) the glycan preparation comprises between 5 mol % and 35 mol %, between 10 mol % and 30 mol %, or between 15 mol % and 25 mol % of each of 1,2; 1,3; and 1,4 glycosidic bonds;
viii) the glycan preparation has a final solubility limit in water of at least about 50, 60, or at least about 70 Brix at 23° C.;
ix) the glycan preparation has a dietary fiber content of at least about 60%, 70%, or at least 80%;
x) the glycan preparation has a glucose monomer content of less than 15%, 10%, or less than 5%;
xi) the glycan preparation has a DP2+ content of at least about 80%, 85%, 90%, or at least about 95%;
xii) the glycan preparation has a dextrose equivalent (DE) of between 5 and 40, 10 and 30 or 15 and 25,
xiii) the glycan preparation has a total furanose content of between 1% and 25%, 5% and 25%, or 15% and 20%; or
x) any combination of two, three, four, five, six, seven, eight, or nine, ten, eleven, twelve, or thirteen of i), ii), iii), iv), v), vi), vii), viii), ix), x), xi), xii) and xiii). In one embodiment, the glycan preparation is glu50gal50. In some embodiments, the glycan preparation can be used as described in Example 10.

In another aspect, the invention is directed to a method for treating hepatic encephalopathy (HE) in a subject, e.g., a human subject, comprising:
administering a glycan preparation in an amount effective and for a time sufficient to treat the HE, wherein:
i) the glycan preparation comprises glycan polymers that comprise glucose, galactose, arabinose, mannose, fructose, xylose, fucose, or rhamnose glycan units;
ii) the average degree of branching (DB) of the glycan polymers in the glycan preparation is 0, between 0.01 and 0.6, between 0.05 and 0.5, between 0.1 and 0.4, or between 0.15 and 0.4;
iii) at least 50% (at least 60%, 65%, 70%, 75%, 80%, or 85%, or less than 50%) of the glycan polymers in the glycan preparation have a degree of polymerization (DP) of at least 3 and less than 30 glycan units, at least 3 and less than 10 glycan units, at least 5 and less than 25 glycan units, or at least 10 and less than 35 glycan units;

iv) the average DP (mean DP) of the glycan preparation is between about 5 and 8, between about 8 and 13, between about 13 and 25, between about 5 and 15, between about 5 and 20, or between about 5-15;
v) the ratio of alpha- to beta-glycosidic bonds present in the glycan polymers of the glycan preparation is 0, or between about 0.8:1 to about 5:1, between about 1:1 to about 5:1, between about 1:1 to about 3:1, between about 3:2 to about 2:1, or between about 3:2 to about 3:1;
vi) the glycan preparation comprises between 15 mol % and 75 mol % (between 20 mol % and 60 mol %, between 25 mol % and 50 mol %, or between 30 mol % and 45 mol %) 1,6 glycosidic bonds;
vii) the glycan preparation comprises between 1 mol % and 40 mol % (between 1 mol % and 30 mol %, between 5 mol % and 25 mol %, between 10 mol % and 20 mol %) of each at least one, two, or three of 1,2; 1,3; and 1,4 glycosidic bonds;
viii) the glycan preparation has a final solubility limit in water of at least about 50 (at least about 60, 70, at least about 75, or less than 50) Brix at 23° C.; and/or
ix) the glycan preparation has a dietary fiber content of at least 50% (at least 60%, 70%, 80%, or at least 90%, or less than 50%);
optionally wherein, the glycan preparation comprises two, three, four, five, six, seven, eight, or nine of the selected properties of i), ii), iii), iv), v), vi), vii), viii), and ix).

In another aspect, the invention is directed to a method for treating a urea cycle disorder (UCD) in a subject, e.g., a human subject, comprising:
  administering a glycan preparation in an amount effective and for a time sufficient to treat the UCD, wherein:
  i) glycan polymers that comprise glucose, galactose, arabinose, mannose, fructose, xylose, fucose, or rhamnose glycan units;
  ii) the average degree of branching (DB) of the glycan polymers in the glycan preparation is between 0.05 and 0.5;
  iii) at least 50% of the glycan polymers in the glycan preparation have a degree of polymerization (DP) of at least 3 and less than 30 glycan units;
  iv) the average DP (mean DP) of the glycan preparation is between about 5 and 20;
  v) the ratio of alpha- to beta-glycosidic bonds present in the glycan polymers of the glycan preparation is between about 0.8:1 to about 5:1;
  vi) the glycan preparation comprises between 15 mol % and 75 mol % 1,6 glycosidic bonds;
  vii) the glycan preparation comprises between 1 mol % and 30 mol % of at least one, two, or three of 1,2; 1,3; and 1,4 glycosidic bonds;
  viii) the glycan preparation has a final solubility limit in water of at least about 70 Brix at 23° C.; and/or
  ix) the glycan preparation has a dietary fiber content of at least 70%;
  optionally wherein, the glycan preparation comprises two, three, four, five, six, seven, eight, or nine of the selected properties of i), ii), iii), iv), v), vi), vii), viii), and ix).

In some embodiments, administering a glycan preparation to a subject having UCD reduces the risk, severity and/or frequency of a hyperammonemic crisis (e.g., when compared to a subject (including the same subject) who is not administered the glycan preparation). In some embodiments, the subject is on a low protein or other supplemented diet. In some embodiments, the subject is concurrently treated with glycerol phenylbutyrate (e.g., Ravicti) (or a similar nitrogen scavenger therapy). In some embodiments, the subject is on a low protein or other supplemented diet and is being concurrently treated with glycerol phenylbutyrate (e.g., Ravicti) (or a similar nitrogen scavenger therapy). In some embodiments, the subject does not respond to treatment with a nitrogen scavenger (e.g., glycerol phenylbutyrate). In some embodiments, the subject is an infant, child, or young adult. In some embodiments, the subject has not (yet) received a liver transplant. In some embodiments, the subject has a urea cycle disorder (UCD) (e.g., carbamyl phosphate synthetase I (CPSI) deficiency, ornithine transcarbamylase (OTC) deficiency, argininosuccinate synthetase (ASS) deficiency, argininosuccinate lyase (ASL) deficiency, N-acetyl glutamate synthetase (NAGS) deficiency, or arginase deficiency, ornithine translocase deficiency (HHH), or citrin (CIT II) deficiency. In some embodiments, the treatment for UCD, comprising administering a glycan preparation, is chronic (e.g., for a duration of 1 year, 5 years, 10 years, 20 years, 50 years, or for life).

In another aspect, the invention is directed to a method for treating a urea cycle disorder (UCD) in a subject, e.g., a human subject, comprising:
  administering a glycan preparation in an amount effective and for a time sufficient to treat the UCD, wherein:
  i) glycan polymers that comprise glucose, galactose, arabinose, mannose, fructose, xylose, fucose, or rhamnose glycan units;
  ii) the average degree of branching (DB) of the glycan polymers in the glycan preparation is between 0.05 and 0.5;
  iii) at least 50% of the glycan polymers in the glycan preparation have a degree of polymerization (DP) at least 3 and less than 30 glycan units;
  iv) the average DP (mean DP) of the glycan preparation is between about 5 and 15;
  v) the ratio of alpha- to beta-glycosidic bonds present in the glycan polymers of the glycan preparation is between about 0.8:1 to about 5:1;
  vi) the glycan preparation comprises between 15 mol % and 75 mol % 1,6 glycosidic bonds;
  vii) the glycan preparation comprises between 1 mol % and 30 mol % of at least one, two, or three of 1,2; 1,3; and 1,4 glycosidic bonds;
  viii) the glycan preparation has a final solubility limit in water of at least about 70 Brix at 23° C.; and/or
  ix) the glycan preparation has a dietary fiber content of at least 70%;
  optionally wherein, the glycan preparation comprises two, three, four, five, six, seven, eight, or nine of the selected properties of i), ii), iii), iv), v), vi), vii), viii), and ix).

In some embodiments, administering a glycan preparation to a subject having UCD reduces the risk, severity and/or frequency of a hyperammonemic crisis (e.g., when compared to a subject (including the same subject) who is not administered the glycan preparation). In some embodiments, the subject is on a low protein or other supplemented diet. In some embodiments, the subject is concurrently treated with glycerol phenylbutyrate (e.g., Ravicti) (or a similar nitrogen scavenger therapy). In some embodiments, the subject is on a low protein or other supplemented diet and is being concurrently treated with glycerol phenylbutyrate (e.g., Ravicti) (or a similar nitrogen scavenger therapy). In some embodiments, the subject does not respond to treatment with a nitrogen scavenger (e.g., glycerol phenylbutyrate). In some embodiments, the subject is an infant, child, or young adult. In some embodiments, the subject has not (yet) received a liver transplant. In some embodiments, the subject has a urea cycle disorder (UCD) (e.g., carbamyl phosphate synthetase I (CPSI) deficiency, ornithine transcarbamylase (OTC) deficiency, argininosuccinate synthetase (ASS) deficiency, argininosuccinate lyase (ASL) deficiency, N-acetyl glutamate synthetase (NAGS) deficiency, or arginase deficiency, ornithine translocase deficiency (HHH), or citrin (CIT II) deficiency. In some embodiments, the treatment for UCD, comprising administering a glycan preparation, is chronic (e.g., for a duration of 1 year, 5 years, 10 years, 20 years, 50 years, or for life).

In another aspect, the invention is directed to a method for treating a urea cycle disorder (UCD) in a subject, e.g., a human subject, comprising:

administering a glycan preparation in an amount effective and for a time sufficient to treat the UCD, wherein:
i) glycan polymers that comprise glucose or galactose glycan units;
ii) the average degree of branching (DB) of the glycan polymers in the glycan preparation is between 0.1 and 0.4;
iii) at least 50% of the glycan polymers in the glycan preparation have a degree of polymerization (DP) at least 3 and less than 10 glycan units;
iv) the average DP (mean DP) of the glycan preparation is between about 5 and 8;
v) the ratio of alpha- to beta-glycosidic bonds present in the glycan polymers of the glycan preparation is between about 1:1 to about 3:1;
vi) the glycan preparation comprises between 20 mol % and 60 mol % 1,6 glycosidic bonds;
vii) the glycan preparation comprises between 5 mol % and 25 mol % of at least one, two, or three of 1,2; 1,3; and 1,4 glycosidic bonds;
viii) the glycan preparation has a final solubility limit in water of at least about 70 Brix at 23° C.; and/or
ix) the glycan preparation has a dietary fiber content of at least 70%;
optionally wherein, the glycan preparation comprises two, three, four, five, six, seven, eight, or nine of the selected properties of i), ii), iii), iv), v), vi), vii), viii), and ix).

In some embodiments, administering a glycan preparation to a subject having UCD reduces the risk, severity and/or frequency of a hyperammonemic crisis (e.g., when compared to a subject (including the same subject) who is not administered the glycan preparation). In some embodiments, the subject is on a low protein or other supplemented diet. In some embodiments, the subject is concurrently treated with glycerol phenylbutyrate (e.g., Ravicti) (or a similar nitrogen scavenger therapy). In some embodiments, the subject is on a low protein or other supplemented diet and is being concurrently treated with glycerol phenylbutyrate (e.g., Ravicti) (or a similar nitrogen scavenger therapy). In some embodiments, the subject does not respond to treatment with a nitrogen scavenger (e.g., glycerol phenylbutyrate). In some embodiments, the subject is an infant, child, or young adult. In some embodiments, the subject has not (yet) received a liver transplant. In some embodiments, the subject has a urea cycle disorder (UCD) (e.g., carbamyl phosphate synthetase I (CPSI) deficiency, ornithine transcarbamylase (OTC) deficiency, argininosuccinate synthetase (ASS) deficiency, argininosuccinate lyase (ASL) deficiency, N-acetyl glutamate synthetase (NAGS) deficiency, or arginase deficiency, ornithine translocase deficiency (HHH), or citrin (CIT II) deficiency. In some embodiments, the treatment for UCD, comprising administering a glycan preparation, is chronic (e.g., for a duration of 1 year, 5 years, 10 years, 20 years, 50 years, or for life).

In another aspect, the invention is directed to a method for treating a urea cycle disorder (UCD) in a subject, e.g., a human subject, comprising:

administering a glycan preparation in an amount effective and for a time sufficient to treat UCD, wherein the glycan preparation comprises:
i) glycan polymers that comprise glucose or galactose glycan units;
ii) the average degree of branching (DB) of the glycan polymers in the glycan preparation is between 0.1 to 0.8 (e.g., 0.1-0.5 or 0.1-0.6);
iii) at least 50% of the glycan polymers in the glycan preparation have a degree of polymerization (DP) of at least 3 and less than 30 glycan units;
iv) the average DP (mean DP) of the glycan preparation is between about DP3 to about DP15 (e.g., mean DP of about DP5 to about DP10, about DP5 to about DP15, about DP4 to about DP12 or about DP6 to about DP12);
v) the ratio of alpha- to beta-glycosidic bonds present in the glycan polymers of the glycan preparation is between about 1:1 to about 4:1 (e.g., about 1:1 to about 2:1 or about 1:1 to about 3:1);
vi) the preparation comprising about 50% to about 90% alpha glycosidic bonds (e.g., about 55% to about 75%, or about 50% to about 70% alpha glycosidic bonds),
vii) the preparation comprising about 10% to about 50% beta glycosidic bonds (e.g., about 25% to about 45%, or about 30% to about 50% beta glycosidic bonds),
vii) the glycan preparation comprises between 10-70 mol % (e.g., 30-60 mol %) 1,6-glycosidic bonds (e.g., for xylose, fucose and arabinose containing glycan polymer preparation: 0-60 mol % of 1,6-glycosidic bonds, e.g. 0 mol %),
ix) the glycan preparation comprises between 1-30 mol % (e.g., 3-30 mol %) 1,2-glycosidic bonds; 1-30 mol % (e.g., 3-30 mol %) 1,3-glycosidic bonds, and 1-30 mol % (e.g., 3-30 mol %) 1,4-glycosidic bonds;
x) the glycan preparation has a final solubility limit in water of at least about 70 Brix at 23° C.;
xi) the glycan preparation has a dietary fiber content of at least 70% (as measured by the method AOAC 2009.01);
xii) the glycan preparation has a polydispersity (PD) of between about 1 and 2.8 (e.g., between about 1.1 and about 2.2);
xiii) the glycan preparation has a total furanose content of between about 1% and about 50% (e.g., between about 5% and 30%, or between about 1% and 15%); or
xiv) any combination of two, three, four, five, six, seven, eight, nine, ten, eleven, twelve, or thirteen of i), ii), iii), iv), v), vi), vii), viii), ix), x), xi), xii), and xiii),
optionally, wherein the glycan preparation is pharmaceutical grade (e.g., manufactured under pharmaceutical GMP); or wherein the glycan polymer preparation is food grade (e.g., manufactured under food GMP); further optionally, wherein the glycan preparation is a powder (e.g., dry powder) or a syrup. In some embodiments, the glycan polymers comprise glucose glycan units. In some embodiments, the glycan preparation is a glu100. In some embodiments, the glu100 glycan preparation has the properties of a glu100 described in Table 5a and 5b.

In some embodiments, the glycan polymers comprise glucose and galactose glycan units. In some embodiments, the glycan preparation is a glu50gal50. In some embodiments, the glu50gal50 glycan preparation has the properties of a glu50gal50 described in Table 5a and 5b. In some embodiments, administering a glycan preparation to a subject having UCD reduces the risk, severity and/or frequency of a hyperammonemic crisis (e.g., when compared to a subject (including the same subject) who is not administered the glycan preparation). In some embodiments, the subject is on a low protein or other supplemented diet. In some embodiments, the subject is concurrently treated with glycerol phenylbutyrate (e.g., Ravicti) (or a similar nitrogen scavenger therapy). In some embodiments, the subject is on a low protein or other supplemented diet and is being concurrently treated with glycerol phenylbutyrate (e.g., Ravicti) (or a similar nitrogen scavenger therapy). In some embodiments, the subject does not respond to treatment with a nitrogen scavenger (e.g., glycerol phenylbutyrate). In some embodiments, the subject is an infant, child, or young adult. In some embodiments, the subject has not (yet) received a liver transplant. In some embodiments, the subject has a urea cycle disorder (UCD) (e.g., carbamyl phosphate synthetase I (CPSI) deficiency, ornithine transcarbamylase (OTC) deficiency, argininosuccinate synthetase (ASS) deficiency, argininosuccinate lyase (ASL) deficiency, N-acetyl glutamate synthetase (NAGS) deficiency, or arginase deficiency, ornithine translocase deficiency (HHH), or citrin (CIT II) deficiency. In some embodiments, the treatment for UCD, comprising administering a glycan preparation, is chronic (e.g., for a duration of 1 year, 5 years, 10 years, 20 years, 50 years, or for life). In some embodiments, the treatment for UCD, comprising administering a glycan preparation, is chronic (e.g., for a duration of 1 year, 5 years, 10 years, 20 years, 50 years, or for life).

In another aspect, the invention is directed to a method for treating a urea cycle disorder (UCD) in a subject, e.g., a human subject, comprising:
  administering a glycan preparation in an amount effective and for a time sufficient to treat UCD, wherein the glycan preparation comprises:
    i) glycan polymers that comprise glucose glycan units;
    ii) the average degree of branching (DB) of the glycan polymers in the glycan preparation is between 0.1-0.5;
    iii) at least 50% of the glycan polymers in the glycan preparation have a degree of polymerization (DP) of at least 3 and less than 30 glycan units;
    iv) the average DP (mean DP) of the glycan preparation is between about DP4 to about DP12 (e.g., about DP5 to about DP10);
    v) the ratio of alpha- to beta-glycosidic bonds present in the glycan polymers of the glycan preparation is between about 1:1 to about 2:1;
    vi) the preparation comprising about 50% to about 75% alpha glycosidic bonds,
    vii) the preparation comprising about 25% to about 50% beta glycosidic bonds,
    vii) the glycan preparation comprises between 30-70 mol % 1,6-glycosidic bonds,
    ix) the glycan preparation comprises between 1-30 mol % 1,2-glycosidic bonds; 3-30 mol % 1,3-glycosidic bonds, and 3-30 mol % 1,4-glycosidic bonds;
    x) the glycan preparation has a final solubility limit in water of at least about 70 Brix at 23° C.;
    xi) the glycan preparation has a dietary fiber content of at least 70% (as measured by the method AOAC 2009.01);
    xii) the glycan preparation has a polydispersity (PD) of between about 1.1 and 2.2;
    xiii) the glycan preparation has a total furanose content of between about 1% and about 30%; or
    xiv) any combination of two, three, four, five, six, seven, eight, nine, ten, eleven, twelve, or thirteen of i), ii), iii), iv), v), vi), vii), viii), ix), x), xi), xii), and xiii),
  optionally, wherein the glycan preparation is pharmaceutical grade (e.g., manufactured under pharmaceutical GMP); or wherein the glycan polymer preparation is food grade (e.g., manufactured under food GMP); further optionally, wherein the glycan preparation is a powder (e.g., dry powder) or a syrup.

In some embodiments, administering a glycan preparation to a subject having UCD reduces the risk, severity and/or frequency of a hyperammonemic crisis (e.g., when compared to a subject (including the same subject) who is not administered the glycan preparation). In some embodiments, the subject is on a low protein or other supplemented diet. In some embodiments, the subject is concurrently treated with glycerol phenylbutyrate (e.g., Ravicti) (or a similar nitrogen scavenger therapy). In some embodiments, the subject is on a low protein or other supplemented diet and is being concurrently treated with glycerol phenylbutyrate (e.g., Ravicti) (or a similar nitrogen scavenger therapy). In some embodiments, the subject does not respond to treatment with a nitrogen scavenger (e.g., glycerol phenylbutyrate). In some embodiments, the subject is an infant, child, or young adult. In some embodiments, the subject has not (yet) received a liver transplant. In some embodiments, the subject has a urea cycle disorder (UCD) (e.g., carbamyl phosphate synthetase I (CPSI) deficiency, ornithine transcarbamylase (OTC) deficiency, argininosuccinate synthetase (ASS) deficiency, argininosuccinate lyase (ASL) deficiency, N-acetyl glutamate synthetase (NAGS) deficiency, or arginase deficiency, ornithine translocase deficiency (HHH), or citrin (CIT II) deficiency. In some embodiments, the treatment for UCD, comprising administering a glycan preparation, is chronic (e.g., for a duration of 1 year, 5 years, 10 years, 20 years, 50 years, or for life).

In another aspect, the invention is directed to a method for treating a urea cycle disorder (UCD) in a subject, e.g., a human subject, comprising:
  administering a glycan preparation in an amount effective and for a time sufficient to treat UCD, wherein the glycan preparation comprises:
    i) glycan polymers that comprise glucose and galactose glycan units;
    ii) the average degree of branching (DB) of the glycan polymers in the glycan preparation is between 0.1-0.6;
    iii) at least 50% of the glycan polymers in the glycan preparation have a degree of polymerization (DP) of at least 3 and less than 30 glycan units;
    iv) the average DP (mean DP) of the glycan preparation is between about DP5 to about DP15 (DP6 to about DP12);
    v) the ratio of alpha- to beta-glycosidic bonds present in the glycan polymers of the glycan preparation is between about 1:1 to about 3:1;
    vi) the preparation comprising about 55% to about 75%, vii) the preparation comprising about 25% to about 45% beta glycosidic bonds,
vii) the glycan preparation comprises between 10-70 mol % 1,6-glycosidic bonds,
ix) the glycan preparation comprises between 1-30 mol % 1,2-glycosidic bonds; 1-30 mol % 1,3-glycosidic bonds, and 1-30 mol % 1,4-glycosidic bonds;
x) the glycan preparation has a final solubility limit in water of at least about 70 Brix at 23° C.;
xi) the glycan preparation has a dietary fiber content of at least 70% (as measured by the method AOAC 2009.01);
xii) the glycan preparation has a polydispersity (PD) of between about 1.1 and 2.5;
xiii) the glycan preparation has a total furanose content of between about 1% and about 50% (e.g., between about 5% and 30%);
or
xiv) any combination of two, three, four, five, six, seven, eight, nine, ten, eleven, twelve, or thirteen of i), ii), iii), iv), v), vi), vii), viii), ix), x), xi), xii), and xiii),
optionally, wherein the glycan preparation is pharmaceutical grade (e.g., manufactured under pharmaceutical GMP); or wherein the glycan polymer preparation is food grade (e.g., manufactured under food GMP); further optionally, wherein the glycan preparation is a powder (e.g., dry powder) or a syrup.

In some embodiments, administering a glycan preparation to a subject having UCD reduces the risk, severity and/or frequency of a hyperammonemic crisis (e.g., when compared to a subject (including the same subject) who is not administered the glycan preparation). In some embodiments, the subject is on a low protein or other supplemented diet. In some embodiments, the subject is concurrently treated with glycerol phenylbutyrate (e.g., Ravicti) (or a similar nitrogen scavenger therapy). In some embodiments, the subject is on a low protein or other supplemented diet and is being concurrently treated with glycerol phenylbutyrate (e.g., Ravicti) (or a similar nitrogen scavenger therapy). In some embodiments, the subject does not respond to treatment with a nitrogen scavenger (e.g., glycerol phenylbutyrate). In some embodiments, the subject is an infant, child, or young adult. In some embodiments, the subject has not (yet) received a liver transplant. In some embodiments, the subject has a urea cycle disorder (UCD) (e.g., carbamyl phosphate synthetase I (CPSI) deficiency, ornithine transcarbamylase (OTC) deficiency, argininosuccinate synthetase (ASS) deficiency, argininosuccinate lyase (ASL) deficiency, N-acetyl glutamate synthetase (NAGS) deficiency, or arginase deficiency, ornithine translocase deficiency (HHH), or citrin (CIT II) deficiency. In some embodiments, the treatment for UCD, comprising administering a glycan preparation, is chronic (e.g., for a duration of 1 year, 5 years, 10 years, 20 years, 50 years, or for life).

In another aspect, the invention is directed to a method for treating a urea cycle disorder (UCD) in a subject, e.g., a human subject, comprising:
administering a glycan preparation in an amount effective and for a time sufficient to treat UCD, wherein the glycan preparation comprises:
i) glycan polymers that comprise glucose glycan units;
ii) the average degree of branching (DB) of the glycan polymers in the glycan preparation is between 0.1 and 0.4;
iii) 45% to 55% of the glycan polymers in the glycan preparation have a degree of polymerization (DP) of at least 3 and less than or equal to 10 glycan units;
iv) the average DP (mean DP) of the glycan preparation is between about 5 and 8;
v) the ratio of alpha- to beta-glycosidic bonds present in the glycan polymers of the glycan preparation is between about 1:1 to about 1.5:1;
vi) the glycan preparation comprises between 20 mol % and 60 mol % 1,6 glycosidic bonds;
vii) the glycan preparation comprises between 5 mol % and 25 mol % of at least one, two, or three of 1,2; 1,3; and 1,4 glycosidic bonds;
viii) the glycan preparation has a final solubility limit in water of at least about 70 Brix at 23° C.; and/or
ix) the glycan preparation has a dietary fiber content of at least 70%;
optionally wherein, the glycan preparation comprises two, three, four, five, six, seven, eight, or nine of the selected properties of i), ii), iii), iv), v), vi), vii), viii), and ix);
optionally, wherein the glycan preparation is pharmaceutical grade (e.g., manufactured under pharmaceutical GMP); or wherein the glycan polymer preparation is food grade (e.g., manufactured under food GMP); further optionally, wherein the glycan preparation is a powder (e.g., dry powder) or a syrup.

In some embodiments, administering a glycan preparation to a subject having UCD reduces the risk, severity and/or frequency of a hyperammonemic crisis (e.g., when compared to a subject (including the same subject) who is not administered the glycan preparation). In some embodiments, the subject is on a low protein or other supplemented diet. In some embodiments, the subject is concurrently treated with glycerol phenylbutyrate (e.g., Ravicti) (or a similar nitrogen scavenger therapy). In some embodiments, the subject is on a low protein or other supplemented diet and is being concurrently treated with glycerol phenylbutyrate (e.g., Ravicti) (or a similar nitrogen scavenger therapy). In some embodiments, the subject does not respond to treatment with a nitrogen scavenger (e.g., glycerol phenylbutyrate). In some embodiments, the subject is an infant, child, or young adult. In some embodiments, the subject has not (yet) received a liver transplant. In some embodiments, the subject has a urea cycle disorder (UCD) (e.g., carbamyl phosphate synthetase I (CPSI) deficiency, ornithine transcarbamylase (OTC) deficiency, argininosuccinate synthetase (ASS) deficiency, argininosuccinate lyase (ASL) deficiency, N-acetyl glutamate synthetase (NAGS) deficiency, or arginase deficiency, ornithine translocase deficiency (HHH), or citrin (CIT II) deficiency. In some embodiments, the treatment for UCD, comprising administering a glycan preparation, is chronic (e.g., for a duration of 1 year, 5 years, 10 years, 20 years, 50 years, or for life).

In another aspect, the invention is directed to a method for treating a urea cycle disorder (UCD) in a subject, e.g., a human subject, comprising:
administering a glycan preparation in an amount effective and for a time sufficient to treat UCD, wherein the glycan preparation comprises:
i) glycan polymers that comprise glucose and galactose glycan units;
ii) the average degree of branching (DB) of the glycan polymers in the glycan preparation is between 0.1 and 0.4;
iii) 45% to 55% of the glycan polymers in the glycan preparation have a degree of polymerization (DP) of at least 3 and less than or equal to 10 glycan units;

iv) the average DP (mean DP) of the glycan preparation is between about 5 and 8;
v) the ratio of alpha- to beta-glycosidic bonds present in the glycan polymers of the glycan preparation is between about 2:1 to about 3:1;
vi) the glycan preparation comprises between 20 mol % and 60 mol % 1,6 glycosidic bonds;
vii) the glycan preparation comprises between 5 mol % and 25 mol % of at least one, two, or three of 1,2; 1,3; and 1,4 glycosidic bonds;
viii) the glycan preparation has a final solubility limit in water of at least about 70 Brix at 23° C.; and/or
ix) the glycan preparation has a dietary fiber content of at least 70%;
optionally wherein, the glycan preparation comprises two, three, four, five, six, seven, eight, or nine of the selected properties of i), ii), iii), iv), v), vi), vii), viii), and ix).; optionally, wherein the glycan preparation is pharmaceutical grade (e.g., manufactured under pharmaceutical GMP); or wherein the glycan polymer preparation is food grade (e.g., manufactured under food GMP); further optionally, wherein the glycan preparation is a powder (e.g., dry powder) or a syrup.

In some embodiments, administering a glycan preparation to a subject having UCD reduces the risk, severity and/or frequency of a hyperammonemic crisis (e.g., when compared to a subject (including the same subject) who is not administered the glycan preparation). In some embodiments, the subject is on a low protein or other supplemented diet. In some embodiments, the subject is concurrently treated with glycerol phenylbutyrate (e.g., Ravicti) (or a similar nitrogen scavenger therapy). In some embodiments, the subject is on a low protein or other supplemented diet and is being concurrently treated with glycerol phenylbutyrate (e.g., Ravicti) (or a similar nitrogen scavenger therapy). In some embodiments, the subject does not respond to treatment with a nitrogen scavenger (e.g., glycerol phenylbutyrate). In some embodiments, the subject is an infant, child, or young adult. In some embodiments, the subject has not (yet) received a liver transplant. In some embodiments, the subject has a urea cycle disorder (UCD) (e.g., carbamyl phosphate synthetase I (CPSI) deficiency, ornithine transcarbamylase (OTC) deficiency, argininosuccinate synthetase (ASS) deficiency, argininosuccinate lyase (ASL) deficiency, N-acetyl glutamate synthetase (NAGS) deficiency, or arginase deficiency, ornithine translocase deficiency (HHH), or citrin (CIT II) deficiency. In some embodiments, the treatment for UCD, comprising administering a glycan preparation, is chronic (e.g., for a duration of 1 year, 5 years, 10 years, 20 years, 50 years, or for life).

In another aspect, the invention is directed to a method for treating a hepatic encephalopathy (HE) in a subject, e.g., a human subject, comprising:
administering a glycan preparation in an amount effective and for a time sufficient to treat the HE, wherein:
i) glycan polymers that comprise glucose, galactose, arabinose, mannose, fructose, xylose, fucose, or rhamnose glycan units;
ii) the average degree of branching (DB) of the glycan polymers in the glycan preparation is between 0.05 and 0.5;
iii) at least 50% of the glycan polymers in the glycan preparation have a degree of polymerization (DP) of at least 3 and less than 30 glycan units;
iv) the average DP (mean DP) of the glycan preparation is between about 5 and 20;
v) the ratio of alpha- to beta-glycosidic bonds present in the glycan polymers of the glycan preparation is between about 0.8:1 to about 5:1;
vi) the glycan preparation comprises between 15 mol % and 75 mol % 1,6 glycosidic bonds;
vii) the glycan preparation comprises between 1 mol % and 30 mol % of at least one, two, or three of 1,2; 1,3; and 1,4 glycosidic bonds;
viii) the glycan preparation has a final solubility limit in water of at least about 70 Brix at 23° C.; and/or
ix) the glycan preparation has a dietary fiber content of at least 70%; or
optionally wherein, the glycan preparation comprises two, three, four, five, six, seven, eight, or nine of the selected properties of i), ii), iii), iv), v), vi), vii), viii), and ix).

In some embodiments, administering a glycan preparation to a subject having HE reduces the risk for and/or recurrence of HE (e.g., severity and/or frequency of HE), e.g., when compared to a subject (including the same subject) who is not administered the glycan preparation. In some embodiments, the subject is concurrently treated with lactulose. In some embodiments, the subject is concurrently treated with rifaximin. In some embodiments, the subject has been treated with lactulose prior to administering a glycan preparation. In some embodiments, the subject has been treated with rifaximin prior to administering a glycan preparation. In some embodiments, the subject has been treated with lactulose and rifaximin prior to administering a glycan preparation. In some embodiments, the subject has or has been diagnosed with overt hepatic encephalopathy (OHE). In some embodiments, the subject has not (yet) been treated for HE (e.g., prior to administering a glycan preparation). In some embodiments, the subject has minimal hepatic encephalopathy (MHE) and, in some embodiments, the subject is largely non-symptomatic (e.g., for OHE symptoms). In some embodiments, a subject having hyperammonemia is suffering from hepatic encephalopathy (HE). In some embodiments, hyperammonemia is caused by or associated with, at least in part, alcohol and/or alcoholic cirrhosis, autoimmune hepatitis, chronic hepatitis B, or chronic hepatitis C, fatty liver, hepatitis C., hepatitis C and alcohol, iron overload and steatosis, nonalcoholic steatohepatitis, nonalcoholic steatohepatitis and hepatitis B, or primary biliary cirrhosis. In some embodiments, a subject having hyperammonemia has been previously treated or administered with lactulose or rifaximin. In some embodiments, a subject the subject is an adult (e.g., 20-64 years), or an elderly adult (e.g., 65 years and older). In some embodiments, the treatment for HE, comprising administering a glycan preparation, is chronic (e.g., for a duration of 1 year, 5 years, 10 years, 20 years, 50 years, or for life). In some embodiments, the HE is overt hepatic encephalopathy (OHE). In some embodiments, the HE is minimal hepatic encephalopathy (MHE). In some embodiments, the glycan preparation can be used as described in Example 10.

In another aspect, the invention is directed to a method for treating a hepatic encephalopathy (HE) in a subject, e.g., a human subject, comprising:
administering a glycan preparation in an amount effective and for a time sufficient to treat the HE, wherein:
i) glycan polymers that comprise glucose, galactose, arabinose, mannose, fructose, xylose, fucose, or rhamnose glycan units;
ii) the average degree of branching (DB) of the glycan polymers in the glycan preparation is between 0.05 and 0.5;

iii) at least 50% of the glycan polymers in the glycan preparation have a degree of polymerization (DP) at least 3 and less than 30 glycan units;

iv) the average DP (mean DP) of the glycan preparation is between about 5 and 15;

v) the ratio of alpha- to beta-glycosidic bonds present in the glycan polymers of the glycan preparation is between about 0.8:1 to about 5:1;

vi) the glycan preparation comprises between 15 mol % and 75 mol % 1,6 glycosidic bonds;

vii) the glycan preparation comprises between 1 mol % and 30 mol % of at least one, two, or three of 1,2; 1,3; and 1,4 glycosidic bonds;

viii) the glycan preparation has a final solubility limit in water of at least about 70 Brix at 23° C.; and/or ix) the glycan preparation has a dietary fiber content of at least 70%;

optionally wherein, the glycan preparation comprises two, three, four, five, six, seven, eight, or nine of the selected properties of i), ii), iii), iv), v), vi), vii), viii), and ix).

In some embodiments, administering a glycan preparation to a subject having HE reduces the risk for and/or recurrence of HE (e.g., severity and/or frequency of HE), e.g., when compared to a subject (including the same subject) who is not administered the glycan preparation. In some embodiments, the subject is concurrently treated with lactulose. In some embodiments, the subject is concurrently treated with rifaximin. In some embodiments, the subject has been treated with lactulose prior to administering a glycan preparation. In some embodiments, the subject has been treated with rifaximin prior to administering a glycan preparation. In some embodiments, the subject has been treated with lactulose and rifaximin prior to administering a glycan preparation. In some embodiments, the subject has or has been diagnosed with overt hepatic encephalopathy (OHE). In some embodiments, the subject has not (yet) been treated for HE (e.g., prior to administering a glycan preparation). In some embodiments, the subject has minimal hepatic encephalopathy (MHE) and, in some embodiments, the subject is largely non-symptomatic (e.g., for OHE symptoms). In some embodiments, a subject having hyperammonemia is suffering from hepatic encephalopathy (HE). In some embodiments, hyperammonemia is caused by or associated with, at least in part, alcohol and/or alcoholic cirrhosis, autoimmune hepatitis, chronic hepatitis B, or chronic hepatitis C, fatty liver, hepatitis C., hepatitis C and alcohol, iron overload and steatosis, nonalcoholic steatohepatitis, nonalcoholic steatohepatitis and hepatitis B, or primary biliary cirrhosis. In some embodiments, a subject having hyperammonemia has been previously treated or administered with lactulose or rifaximin. In some embodiments, a subject the subject is an adult (e.g., 20-64 years), or an elderly adult (e.g., 65 years and older). In some embodiments, the treatment for HE, comprising administering a glycan preparation, is chronic (e.g., for a duration of 1 year, 5 years, 10 years, 20 years, 50 years, or for life). In some embodiments, the HE is overt hepatic encephalopathy (OHE). In some embodiments, the HE is minimal hepatic encephalopathy (MHE). In some embodiments, the glycan preparation can be used as described in Example 10.

In another aspect, the invention is directed to a method for treating a hepatic encephalopathy (HE) in a subject, e.g., a human subject, comprising:

administering a glycan preparation in an amount effective and for a time sufficient to treat the HE, wherein:

i) glycan polymers that comprise glucose or galactose glycan units;

ii) the average degree of branching (DB) of the glycan polymers in the glycan preparation is between 0.1 and 0.4;

iii) at least 50% of the glycan polymers in the glycan preparation have a degree of polymerization (DP) at least 3 and less than 10 glycan units;

iv) the average DP (mean DP) of the glycan preparation is between about 5 and 8;

v) the ratio of alpha- to beta-glycosidic bonds present in the glycan polymers of the glycan preparation is between about 1:1 to about 3:1;

vi) the glycan preparation comprises between 20 mol % and 60 mol % 1,6 glycosidic bonds;

vii) the glycan preparation comprises between 5 mol % and 25 mol % of at least one, two, or three of 1,2; 1,3; and 1,4 glycosidic bonds;

viii) the glycan preparation has a final solubility limit in water of at least about 70 Brix at 23° C.; and/or ix) the glycan preparation has a dietary fiber content of at least 70%; or optionally wherein, the glycan preparation comprises two, three, four, five, six, seven, eight, or nine of the selected properties of i), ii), iii), iv), v), vi), vii), viii), and ix).

In some embodiments, administering a glycan preparation to a subject having HE reduces the risk for and/or recurrence of HE (e.g., severity and/or frequency of HE), e.g., when compared to a subject (including the same subject) who is not administered the glycan preparation. In some embodiments, the subject is concurrently treated with lactulose. In some embodiments, the subject is concurrently treated with rifaximin. In some embodiments, the subject has been treated with lactulose prior to administering a glycan preparation. In some embodiments, the subject has been treated with rifaximin prior to administering a glycan preparation. In some embodiments, the subject has been treated with lactulose and rifaximin prior to administering a glycan preparation. In some embodiments, the subject has or has been diagnosed with overt hepatic encephalopathy (OHE). In some embodiments, the subject has not (yet) been treated for HE (e.g., prior to administering a glycan preparation). In some embodiments, the subject has minimal hepatic encephalopathy (MHE) and, in some embodiments, the subject is largely non-symptomatic (e.g., for OHE symptoms). In some embodiments, a subject having hyperammonemia is suffering from hepatic encephalopathy (HE). In some embodiments, hyperammonemia is caused by or associated with, at least in part, alcohol and/or alcoholic cirrhosis, autoimmune hepatitis, chronic hepatitis B, or chronic hepatitis C, fatty liver, hepatitis C., hepatitis C and alcohol, iron overload and steatosis, nonalcoholic steatohepatitis, nonalcoholic steatohepatitis and hepatitis B, or primary biliary cirrhosis. In some embodiments, a subject having hyperammonemia has been previously treated or administered with lactulose or rifaximin. In some embodiments, a subject the subject is an adult (e.g., 20-64 years), or an elderly adult (e.g., 65 years and older). In some embodiments, the treatment for HE, comprising administering a glycan preparation, is chronic (e.g., for a duration of 1 year, 5 years, 10 years, 20 years, 50 years, or for life). In some embodiments, the HE is overt hepatic encephalopathy (OHE). In some embodiments, the HE is minimal hepatic encephalopathy (MHE). In some embodiments, the glycan preparation can be used as described in Example 10.

In another aspect, the invention is directed to a method for treating hepatic encephalopathy (HE) in a subject, e.g., a human subject, comprising:

administering a glycan preparation in an amount effective and for a time sufficient to treat HE, wherein the glycan preparation comprises:
  i) glycan polymers that comprise glucose, galactose, mannose, rhamnose, fucose, xylose or arabinose glycan units;
  ii) the average degree of branching (DB) of the glycan polymers in the glycan preparation is between 0.1 to 0.8 (e.g., 0.1-0.5 or 0.1-0.6);
  iii) at least 50% of the glycan polymers in the glycan preparation have a degree of polymerization (DP) of at least 3 and less than 30 glycan units;
  iv) the average DP (mean DP) of the glycan preparation is between about DP3 to about DP15 (e.g., mean DP of about DP5 to about DP10, about DP5 to about DP15, about DP4 to about DP12 or about DP6 to about DP12);
  v) the ratio of alpha- to beta-glycosidic bonds present in the glycan polymers of the glycan preparation is between about 1:1 to about 4:1 (e.g., about 1:1 to about 2:1 or about 1:1 to about 3:1);
  vi) the preparation comprising about 50% to about 90% alpha glycosidic bonds (e.g., about 55% to about 75%, or about 50% to about 70% alpha glycosidic bonds),
  vii) the preparation comprising about 10% to about 50% beta glycosidic bonds (e.g., about 25% to about 45%, or about 30% to about 50% beta glycosidic bonds),
  vii) the glycan preparation comprises between 10-70 mol % (e.g., 30-60 mol %) 1,6-glycosidic bonds (e.g., for xylose, fucose and arabinose containing glycan polymer preparation: 0-60 mol % of 1,6-glycosidic bonds, e.g. 0 mol %),
  ix) the glycan preparation comprises between 1-30 mol % (e.g., 3-30 mol %) 1,2-glycosidic bonds; 1-30 mol % (e.g., 3-30 mol %) 1,3-glycosidic bonds, and 1-30 mol % (e.g., 3-30 mol %) 1,4-glycosidic bonds;
  x) the glycan preparation has a final solubility limit in water of at least about 70 Brix at 23° C.;
  xi) the glycan preparation has a dietary fiber content of at least 70% (as measured by the method AOAC 2009.01);
  xii) the glycan preparation has a polydispersity (PD) of between about 1 and 2.8 (e.g., between about 1.1 and about 2.2);
  xiii) the glycan preparation has a total furanose content of between about 1% and about 50% (e.g., between about 5% and 30%, or between about 1% and 15%); or
  xiv) any combination of two, three, four, five, six, seven, eight, nine, ten, eleven, twelve, or thirteen of i), ii), iii), iv), v), vi), vii), viii), ix), x), xi), xii), and xiii),
optionally, wherein the glycan preparation is pharmaceutical grade (e.g., manufactured under pharmaceutical GMP); or wherein the glycan polymer preparation is food grade (e.g., manufactured under food GMP); further optionally, wherein the glycan preparation is a powder (e.g., dry powder) or a syrup. In some embodiments, the glycan polymers comprise glucose glycan units. In some embodiments, the glycan preparation is a glu100. In some embodiments, the glu100 glycan preparation has the properties of a glu100 described in Table 5a and 5b.

In some embodiments, the glycan polymers comprise glucose and galactose glycan units. In some embodiments, the glycan preparation is a glu50gal50. In some embodiments, the glu50gal50 glycan preparation has the properties of a glu50gal50 described in Table 5a and 5b.

In some embodiments, administering a glycan preparation to a subject having HE reduces the risk for and/or recurrence of HE (e.g., severity and/or frequency of HE), e.g., when compared to a subject (including the same subject) who is not administered the glycan preparation. In some embodiments, the subject is concurrently treated with lactulose. In some embodiments, the subject is concurrently treated with rifaximin. In some embodiments, the subject has been treated with lactulose prior to administering a glycan preparation. In some embodiments, the subject has been treated with rifaximin prior to administering a glycan preparation. In some embodiments, the subject has been treated with lactulose and rifaximin prior to administering a glycan preparation. In some embodiments, the subject has or has been diagnosed with overt hepatic encephalopathy (OHE). In some embodiments, the subject has not (yet) been treated for HE (e.g., prior to administering a glycan preparation). In some embodiments, the subject has minimal hepatic encephalopathy (MHE) and, in some embodiments, the subject is largely non-symptomatic (e.g., for OHE symptoms). In some embodiments, a subject having hyperammonemia is suffering from hepatic encephalopathy (HE). In some embodiments, hyperammonemia is caused by or associated with, at least in part, alcohol and/or alcoholic cirrhosis, autoimmune hepatitis, chronic hepatitis B, or chronic hepatitis C, fatty liver, hepatitis C., hepatitis C and alcohol, iron overload and steatosis, nonalcoholic steatohepatitis, nonalcoholic steatohepatitis and hepatitis B, or primary biliary cirrhosis. In some embodiments, a subject having hyperammonemia has been previously treated or administered with lactulose or rifaximin. In some embodiments, a subject the subject is an adult (e.g., 20-64 years), or an elderly adult (e.g., 65 years and older). In some embodiments, the treatment for HE, comprising administering a glycan preparation, is chronic (e.g., for a duration of 1 year, 5 years, 10 years, 20 years, 50 years, or for life). In some embodiments, the HE is overt hepatic encephalopathy (OHE). In some embodiments, the HE is minimal hepatic encephalopathy (MHE). In some embodiments, the glycan preparation can be used as described in Example 10.

In another aspect, the invention is directed to a method for treating hepatic encephalopathy (HE) in a subject, e.g., a human subject, comprising:
  administering a glycan preparation in an amount effective and for a time sufficient to treat HE, wherein the glycan preparation comprises:
    i) glycan polymers that comprise glucose glycan units;
    ii) the average degree of branching (DB) of the glycan polymers in the glycan preparation is between 0.1-0.5;
    iii) at least 50% of the glycan polymers in the glycan preparation have a degree of polymerization (DP) of at least 3 and less than 30 glycan units;
    iv) the average DP (mean DP) of the glycan preparation is between about DP4 to about DP12 (e.g., about DP5 to about DP10);
    v) the ratio of alpha- to beta-glycosidic bonds present in the glycan polymers of the glycan preparation is between about 1:1 to about 2:1;
    vi) the preparation comprising about 50% to about 75% alpha glycosidic bonds,
    vii) the preparation comprising about 25% to about 50% beta glycosidic bonds, vii) the glycan preparation comprises between 30-70 mol % 1,6-glycosidic bonds, ix) the glycan preparation comprises between 1-30 mol % 1,2-glycosidic bonds; 3-30 mol % 1,3-glycosidic bonds, and 3-30 mol % 1,4-glycosidic bonds;

x) the glycan preparation has a final solubility limit in water of at least about 70 Brix at 23° C.;

xi) the glycan preparation has a dietary fiber content of at least 70% (as measured by the method AOAC 2009.01);

xii) the glycan preparation has a polydispersity (PD) of between about 1.1 and 2.2;

xiii) the glycan preparation has a total furanose content of between about 1% and about 30%;

or xiv) any combination of two, three, four, five, six, seven, eight, nine, ten, eleven, twelve, or thirteen of i), ii), iii), iv), v), vi), vii), viii), ix), x), xi), xii), and xiii), optionally, wherein the glycan preparation is pharmaceutical grade (e.g., manufactured under pharmaceutical GMP); or wherein the glycan polymer preparation is food grade (e.g., manufactured under food GMP); further optionally, wherein the glycan preparation is a powder (e.g., dry powder) or a syrup.

In some embodiments, administering a glycan preparation to a subject having HE reduces the risk for and/or recurrence of HE (e.g., severity and/or frequency of HE), e.g., when compared to a subject (including the same subject) who is not administered the glycan preparation. In some embodiments, the subject is concurrently treated with lactulose. In some embodiments, the subject is concurrently treated with rifaximin. In some embodiments, the subject has been treated with lactulose prior to administering a glycan preparation. In some embodiments, the subject has been treated with rifaximin prior to administering a glycan preparation. In some embodiments, the subject has been treated with lactulose and rifaximin prior to administering a glycan preparation. In some embodiments, the subject has or has been diagnosed with overt hepatic encephalopathy (OHE). In some embodiments, the subject has not (yet) been treated for HE (e.g., prior to administering a glycan preparation). In some embodiments, the subject has minimal hepatic encephalopathy (MHE) and, in some embodiments, the subject is largely non-symptomatic (e.g., for OHE symptoms). In some embodiments, a subject having hyperammonemia is suffering from hepatic encephalopathy (HE). In some embodiments, hyperammonemia is caused by or associated with, at least in part, alcohol and/or alcoholic cirrhosis, autoimmune hepatitis, chronic hepatitis B, or chronic hepatitis C, fatty liver, hepatitis C., hepatitis C and alcohol, iron overload and steatosis, nonalcoholic steatohepatitis, nonalcoholic steatohepatitis and hepatitis B, or primary biliary cirrhosis. In some embodiments, a subject having hyperammonemia has been previously treated or administered with lactulose or rifaximin. In some embodiments, a subject the subject is an adult (e.g., 20-64 years), or an elderly adult (e.g., 65 years and older). In some embodiments, the treatment for HE, comprising administering a glycan preparation, is chronic (e.g., for a duration of 1 year, 5 years, 10 years, 20 years, 50 years, or for life). In some embodiments, the HE is overt hepatic encephalopathy (OHE). In some embodiments, the HE is minimal hepatic encephalopathy (MHE). In one embodiment, the glycan preparation is glu100. In some embodiments, the glycan preparation can be used as described in Example 10.

In another aspect, the invention is directed to a method for treating hepatic encephalopathy (HE) in a subject, e.g., a human subject, comprising:

administering a glycan preparation in an amount effective and for a time sufficient to treat HE, wherein the glycan preparation comprises:

i) glycan polymers that comprise glucose and galactose glycan units;

ii) the average degree of branching (DB) of the glycan polymers in the glycan preparation is between 0.1-0.6;

iii) at least 50% of the glycan polymers in the glycan preparation have a degree of polymerization (DP) of at least 3 and less than 30 glycan units;

iv) the average DP (mean DP) of the glycan preparation is between about DP5 to about DP15 (DP6 to about DP12);

v) the ratio of alpha- to beta-glycosidic bonds present in the glycan polymers of the glycan preparation is between about 1:1 to about 3:1;

vi) the preparation comprising about 55% to about 75%, vii) the preparation comprising about 25% to about 45% beta glycosidic bonds, vii) the glycan preparation comprises between 10-70 mol % 1,6-glycosidic bonds, ix) the glycan preparation comprises between 1-30 mol % 1,2-glycosidic bonds; 1-30 mol % 1,3-glycosidic bonds, and 1-30 mol % 1,4-glycosidic bonds;

x) the glycan preparation has a final solubility limit in water of at least about 70 Brix at 23° C.;

xi) the glycan preparation has a dietary fiber content of at least 70% (as measured by the method AOAC 2009.01);

xii) the glycan preparation has a polydispersity (PD) of between about 1.1 and 2.5;

xiii) the glycan preparation has a total furanose content of between about 1% and about 50% (e.g., between about 5% and 30%);

or xiv) any combination of two, three, four, five, six, seven, eight, nine, ten, eleven, twelve, or thirteen of i), ii), iii), iv), v), vi), vii), viii), ix), x), xi), xii), and xiii), optionally, wherein the glycan preparation is pharmaceutical grade (e.g., manufactured under pharmaceutical GMP); or wherein the glycan polymer preparation is food grade (e.g., manufactured under food GMP); further optionally, wherein the glycan preparation is a powder (e.g., dry powder) or a syrup.

In some embodiments, administering a glycan preparation to a subject having HE reduces the risk for and/or recurrence of HE (e.g., severity and/or frequency of HE), e.g., when compared to a subject (including the same subject) who is not administered the glycan preparation. In some embodiments, the subject is concurrently treated with lactulose. In some embodiments, the subject is concurrently treated with rifaximin. In some embodiments, the subject has been treated with lactulose prior to administering a glycan preparation. In some embodiments, the subject has been treated with rifaximin prior to administering a glycan preparation. In some embodiments, the subject has been treated with lactulose and rifaximin prior to administering a glycan preparation. In some embodiments, the subject has or has been diagnosed with overt hepatic encephalopathy (OHE). In some embodiments, the subject has not (yet) been treated for HE (e.g., prior to administering a glycan preparation). In some embodiments, the subject has minimal hepatic encephalopathy (MHE) and, in some embodiments, the subject is largely non-symptomatic (e.g., for OHE symptoms). In some embodiments, a subject having hyperammonemia is suffering from hepatic encephalopathy (HE). In some embodiments, hyperammonemia is caused by or associated with, at least in part, alcohol and/or alcoholic cirrhosis, autoimmune hepatitis, chronic hepatitis B, or chronic hepatitis C, fatty liver, hepatitis C., hepatitis C and alcohol, iron overload and steatosis, nonalcoholic steatohepatitis, nonalcoholic steatohepatitis and hepatitis B, or primary biliary cirrhosis. In some embodiments, a subject having hyperammonemia has been previously treated or administered with lactulose or rifaximin. In some embodiments, a subject the subject is an adult (e.g., 20-64 years), or an elderly adult (e.g., 65 years and older). In some embodiments, the treatment for HE, comprising administering a glycan preparation, is chronic (e.g., for a duration of 1 year, 5 years, 10 years, 20 years, 50 years, or for life). In some embodiments, the HE is overt hepatic encephalopathy (OHE). In some embodiments, the HE is minimal hepatic encephalopathy (MHE). In one embodiment, the glycan preparation is glu50gal50. In some embodiments, the glycan preparation can be used as described in Example 10.

In another aspect, the invention is directed to a method for treating hepatic encephalopathy (HE) in a subject, e.g., a human subject, comprising:
  administering a glycan preparation in an amount effective and for a time sufficient to treat HE, wherein the glycan preparation comprises:
    i) glycan polymers that comprise glucose glycan units;
    ii) the average degree of branching (DB) of the glycan polymers in the glycan preparation is between 0.1 and 0.4;
    iii) 45% to 55% of the glycan polymers in the glycan preparation have a degree of polymerization (DP) of at least 3 and less than or equal to 10 glycan units;
    iv) the average DP (mean DP) of the glycan preparation is between about 5 and 8;
    v) the ratio of alpha- to beta-glycosidic bonds present in the glycan polymers of the glycan preparation is between about 1:1 to about 1.5:1;
    vi) the glycan preparation comprises between 20 mol % and 60 mol % 1,6 glycosidic bonds;
    vii) the glycan preparation comprises between 5 mol % and 25 mol % of at least one, two, or three of 1,2; 1,3; and 1,4 glycosidic bonds;
    viii) the glycan preparation has a final solubility limit in water of at least about 70 Brix at 23° C.; and/or
    ix) the glycan preparation has a dietary fiber content of at least 70%;
  optionally wherein, the glycan preparation comprises two, three, four, five, six, seven, eight, or nine of the selected properties of i), ii), iii), iv), v), vi), vii), viii), and ix).;
  optionally, wherein the glycan preparation is pharmaceutical grade (e.g., manufactured under pharmaceutical GMP); or wherein the glycan polymer preparation is food grade (e.g., manufactured under food GMP); further optionally, wherein the glycan preparation is a powder (e.g., dry powder) or a syrup.

In some embodiments, administering a glycan preparation to a subject having HE reduces the risk for and/or recurrence of HE (e.g., severity and/or frequency of HE), e.g., when compared to a subject (including the same subject) who is not administered the glycan preparation. In some embodiments, the subject is concurrently treated with lactulose. In some embodiments, the subject is concurrently treated with rifaximin. In some embodiments, the subject has been treated with lactulose prior to administering a glycan preparation. In some embodiments, the subject has been treated with rifaximin prior to administering a glycan preparation. In some embodiments, the subject has been treated with lactulose and rifaximin prior to administering a glycan preparation. In some embodiments, the subject has or has been diagnosed with overt hepatic encephalopathy (OHE). In some embodiments, the subject has not (yet) been treated for HE (e.g., prior to administering a glycan preparation). In some embodiments, the subject has minimal hepatic encephalopathy (MHE) and, in some embodiments, the subject is largely non-symptomatic (e.g., for OHE symptoms). In some embodiments, a subject having hyperammonemia is suffering from hepatic encephalopathy (HE). In some embodiments, hyperammonemia is caused by or associated with, at least in part, alcohol and/or alcoholic cirrhosis, autoimmune hepatitis, chronic hepatitis B, or chronic hepatitis C, fatty liver, hepatitis C., hepatitis C and alcohol, iron overload and steatosis, nonalcoholic steatohepatitis, nonalcoholic steatohepatitis and hepatitis B, or primary biliary cirrhosis. In some embodiments, a subject having hyperammonemia has been previously treated or administered with lactulose or rifaximin. In some embodiments, a subject the subject is an adult (e.g., 20-64 years), or an elderly adult (e.g., 65 years and older). In some embodiments, the treatment for HE, comprising administering a glycan preparation, is chronic (e.g., for a duration of 1 year, 5 years, 10 years, 20 years, 50 years, or for life). In some embodiments, the HE is overt hepatic encephalopathy (OHE). In some embodiments, the HE is minimal hepatic encephalopathy (MHE). In one embodiment, the glycan preparation is glu100. In some embodiments, the glycan preparation can be used as described in Example 10.

In another aspect, the invention is directed to a method for treating hepatic encephalopathy (HE) in a subject, e.g., a human subject, comprising:
  administering a glycan preparation in an amount effective and for a time sufficient to treat HE, wherein the glycan preparation comprises:
    i) glycan polymers that comprise glucose and galactose glycan units;
    ii) the average degree of branching (DB) of the glycan polymers in the glycan preparation is between 0.1 and 0.4;
    iii) 45% to 55% of the glycan polymers in the glycan preparation have a degree of polymerization (DP) of at least 3 and less than or equal to 10 glycan units;
    iv) the average DP (mean DP) of the glycan preparation is between about 5 and 8;
    v) the ratio of alpha- to beta-glycosidic bonds present in the glycan polymers of the glycan preparation is between about 2:1 to about 3:1;
    vi) the glycan preparation comprises between 20 mol % and 60 mol % 1,6 glycosidic bonds;
    vii) the glycan preparation comprises between 5 mol % and 25 mol % of at least one, two, or three of 1,2; 1,3; and 1,4 glycosidic bonds;
    viii) the glycan preparation has a final solubility limit in water of at least about 70 Brix at 23° C.; and/or
    ix) the glycan preparation has a dietary fiber content of at least 70%;
  optionally wherein, the glycan preparation comprises two, three, four, five, six, seven, eight, or nine of the selected properties of i), ii), iii), iv), v), vi), vii), viii), and ix).;
  optionally, wherein the glycan preparation is pharmaceutical grade (e.g., manufactured under pharmaceutical GMP); or wherein the glycan polymer preparation is food grade (e.g., manufactured under food GMP); further optionally, wherein the glycan preparation is a powder (e.g., dry powder) or a syrup.

In some embodiments, administering a glycan preparation to a subject having HE reduces the risk for and/or recurrence of HE (e.g., severity and/or frequency of HE), e.g., when compared to a subject (including the same subject) who is not administered the glycan preparation. In some embodiments, the subject is concurrently treated with lactulose. In some embodiments, the subject is concurrently treated with rifaximin. In some embodiments, the subject has been treated with lactulose prior to administering a glycan preparation. In some embodiments, the subject has been treated with rifaximin prior to administering a glycan preparation. In some embodiments, the subject has been treated with lactulose and rifaximin prior to administering a glycan preparation. In some embodiments, the subject has or has been diagnosed with overt hepatic encephalopathy (OHE). In some embodiments, the subject has not (yet) been treated for HE (e.g., prior to administering a glycan preparation). In some embodiments, the subject has minimal hepatic encephalopathy (MHE) and, in some embodiments, the subject is largely non-symptomatic (e.g., for OHE symptoms). In some embodiments, a subject having hyperammonemia is suffering from hepatic encephalopathy (HE). In some embodiments, hyperammonemia is caused by or associated with, at least in part, alcohol and/or alcoholic cirrhosis, autoimmune hepatitis, chronic hepatitis B, or chronic hepatitis C, fatty liver, hepatitis C., hepatitis C and alcohol, iron overload and steatosis, nonalcoholic steatohepatitis, nonalcoholic steatohepatitis and hepatitis B, or primary biliary cirrhosis. In some embodiments, a subject having hyperammonemia has been previously treated or administered with lactulose or rifaximin. In some embodiments, a subject the subject is an adult (e.g., 20-64 years), or an elderly adult (e.g., 65 years and older). In some embodiments, the treatment for HE, comprising administering a glycan preparation, is chronic (e.g., for a duration of 1 year, 5 years, 10 years, 20 years, 50 years, or for life). In some embodiments, the HE is overt hepatic encephalopathy (OHE). In some embodiments, the HE is minimal hepatic encephalopathy (MHE). In one embodiment, the glycan preparation is glu50gal50. In some embodiments, the glycan preparation can be used as described in Example 10.

In some embodiments, a glycan preparation comprising any of the aforementioned properties is provided. In some embodiments, a glycan preparation obtainable by (or producible from) any of the aforementioned method (or process) is provided.

BRIEF DESCRIPTION OF THE FIGURES

FIG. 9A is a graph that demonstrates a rank-order of glycan preparation based on their effectiveness in modulating ammonia levels, normalized to a negative control (water). Arrows indicate the negative control (water) and a selected glycan preparation "selected oligosaccharide composition" (glu100, composition properties can be found, e.g., in Table 5A and 5B, e.g., Glu100-94 and Glu100-5)). FIG. 9B shows a bar graph of ammonia levels normalized to the negative control (water) for a selected oligosaccharide composition (glu100).

FIG. 10 shows the number of patients reporting diarrhea (out of 12 patients per arm: maltodextrin (placebo), selected glycan preparation "selected oligosaccharide composition" (glu100, composition properties can be found, e.g., in Table 5A and 5B, e.g., Glu100-94 and Glu100-5) and positive control fiber) at different intake dose levels.

FIG. 11A is a graph showing reduction of ammonia by the selected glycan preparation "selected oligosaccharide composition" (glu100) in samples from urea cycle disorder (UCD) patients. FIG. 11B is a graph showing reduction of ammonia by a selected glycan preparation "selected oligosaccharide composition" (glu100) in samples from hepatically impaired patients.

DETAILED DESCRIPTION OF THE INVENTION

Figure 1:
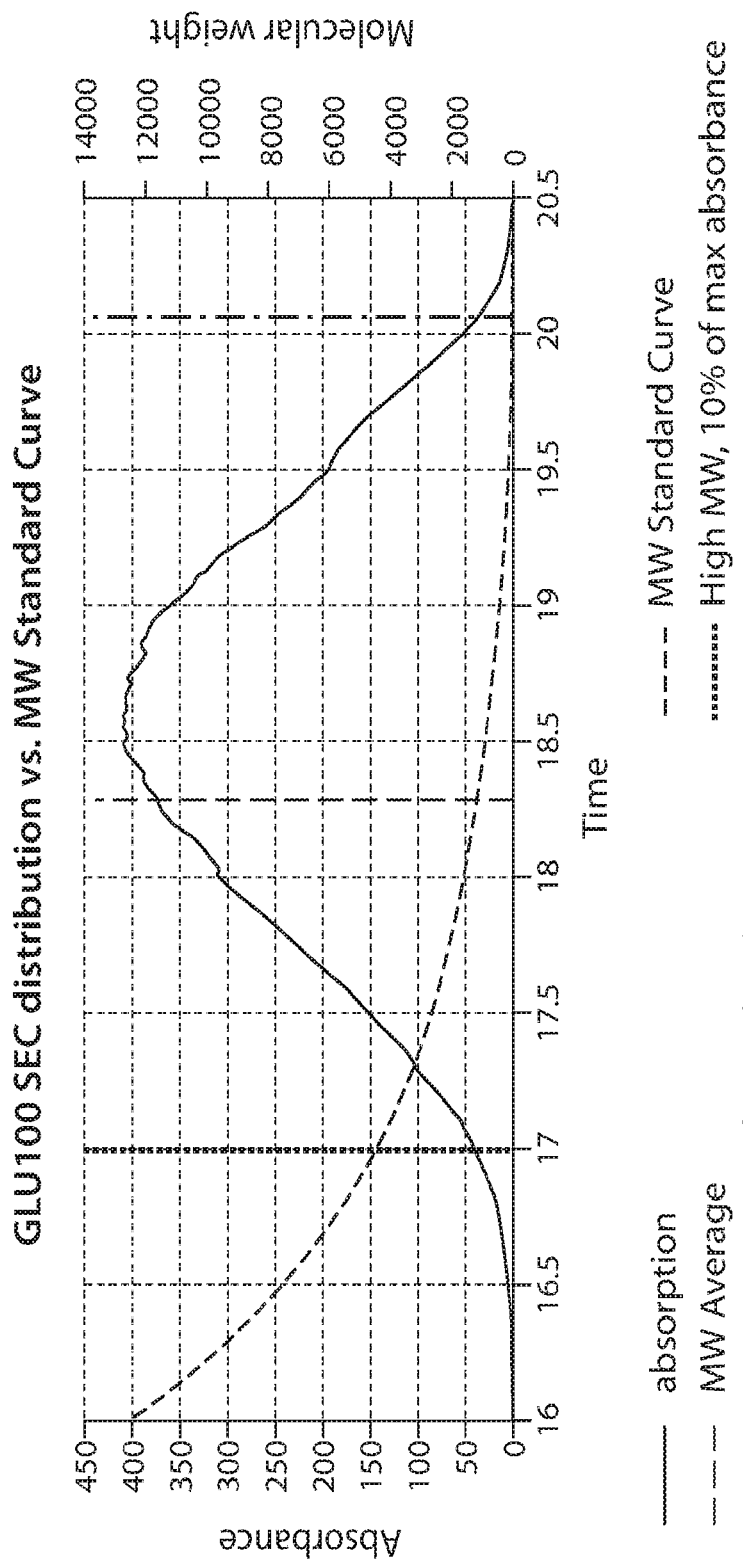
FIG. 1 is a representative SEC curve between 16 and 20.5 minutes of a glu100 sample showing the average MW and the MW at 10% of maximum absorption on both the leading and trailing edges of the curve.

The present invention is, in part, based on the discovery that glycan preparations are useful for: treating conditions associated with hyperammonemia, e.g., urea cycle disorders (UCDs) and hepatic encephalopathy (HE, e.g., MHE or OHE), in a subject; for increasing or decreasing enzymatic activities (e.g., carbamyl phosphate synthetase I (CPSI), ornithine transcarbamylase (OTC), argininosuccinate synthetase (ASS), argininosuccinate lyase (ASL), N-acetyl glutamate synthetase (NAGS), ornithine translocase, citrin, or arginase activity) in a subject; increasing or decreasing the level of a metabolite (e.g., ammonia, citrulline, argininosuccinic acid, glutamine, glutamate, orotic acid, or arginine) in a subject; modulating the processing of a metabolite or modulating, e.g., increasing or decreasing, an enzymatic activity, in a subject; and identifying or selecting a treatment regimen for a subject having a UCD or having HE (e.g., MHE or OHE).

In some embodiments, UCDs are diseases and/or conditions ensuing from the excess or deficiency of one or more enzymatic activities in a subject. Due to the excess or deficiency of enzymatic activity, one or more metabolites (e.g., ammonia) accumulate in the subject, causing disease symptoms. Microbial cells within a subject, e.g., within the gastrointestinal tract of a subject, may also provide the same enzymatic activities that are in excess or deficiency in the subject. Without wishing to be bound by theory, administering a glycan preparation to a subject (e.g., to a subject having UCD or HE (e.g., MHE or OHE)) may modulate (e.g., increase or decrease) an enzymatic activity and/or modulate (e.g., increase or decrease) a metabolite (e.g., the metabolite accumulating and associated with disease symptoms, e.g., ammonia), e.g., the level of a metabolite. In some embodiments, administering a glycan preparation modulates microbes (e.g., a microbial community, e.g., the microbiome) in a subject (e.g., the gastrointestinal tract of a subject), e.g., a subject having UCD or HE (e.g., MHE or OHE) by modulating (e.g., increase or decrease) a microbial enzymatic activity and/or modulating (e.g., increase or decrease) a metabolite (e.g., the metabolite accumulating and associated with disease symptoms, e.g., ammonia), e.g., the level of a metabolite. In some embodiments, administering a glycan preparation modulates (e.g., increases or decreases) the level of one or more taxa of microbes within a subject (e.g., the gastrointestinal tract of a subject), e.g., a subject having UCD or HE (e.g., MHE or OHE), effectively modulating (e.g., increase or decrease) a microbial enzymatic activity and/or modulating (e.g., increase or decrease) a metabolite (e.g., the metabolite accumulating and associated with disease symptoms, e.g., ammonia), e.g., the level of a metabolite.

In some embodiments, administering a glycan preparation to a subject having UCD reduces the risk, severity and/or frequency of a hyperammonemic crisis (e.g., when compared to a subject (including the same subject) who is not administered the glycan preparation). In some embodiments, the subject is on a low protein or other supplemented diet. In some embodiments, the subject is concurrently treated with glycerol phenylbutyrate (e.g., Ravicti) (or a similar nitrogen scavenger therapy). In some embodiments, the subject is on a low protein or other supplemented diet and is being concurrently treated with glycerol phenylbutyrate (e.g., Ravicti) (or a similar nitrogen scavenger therapy). In some embodiments, the subject does not respond to treatment with a nitrogen scavenger (e.g., glycerol phenylbutyrate). In some embodiments, the subject is an infant, child, or young adult. In some embodiments, the subject has not (yet) received a liver transplant.

In some embodiments, administering a glycan preparation to a subject having HE reduces the risk for and/or recurrence of HE (e.g., severity and/or frequency of HE), e.g., when compared to a subject (including the same subject) who is not administered the glycan preparation. In some embodiments, the subject is concurrently treated with lactulose. In some embodiments, the subject is concurrently treated with rifaximin. In some embodiments, the subject has been treated with lactulose prior to administering a glycan preparation. In some embodiments, the subject has been treated with rifaximin prior to administering a glycan preparation. In some embodiments, the subject has been treated with lactulose and rifaximin prior to administering a glycan preparation. In some embodiments, the subject has or has been diagnosed with overt hepatic encephalopathy (OHE). In some embodiments, the subject has not (yet) been treated for HE (e.g., prior to administering a glycan preparation). In some embodiments, the subject has minimal hepatic encephalopathy (MHE) and, in some embodiments, the subject is largely non-symptomatic (e.g., for OHE symptoms).

In some embodiments, the treatment for UCD or HE, comprising administering a glycan preparation, is chronic (e.g., for a duration of 1 year, 5 years, 10 years, 20 years, 50 years, or for life).

Definitions

As used herein, the term "abundance" or "prevalence" as it relates to a microbial taxa refers to the presence of one microbial taxa as compared to another microbial taxa in a defined microbial niche, such as the GI tract, or in the entire host organism (e.g., a human or an animal model).

"Acquire" or "acquiring" as the terms are used herein, refer to obtaining possession of a value, e.g., a numerical value, or image, or a physical entity (e.g., a sample), by "directly acquiring" or "indirectly acquiring" the value or physical entity. "Directly acquiring" means performing a process (e.g., performing a synthetic or analytical method or protocol) to obtain the value or physical entity. "Indirectly acquiring" refers to receiving the value or physical entity from another party or source (e.g., a third-party laboratory that directly acquired the physical entity or value). Directly acquiring a value or physical entity includes performing a process that includes a physical change in a physical substance or the use of a machine or device. Examples of directly acquiring a value include obtaining a sample from a human subject. Directly acquiring a value includes performing a process that uses a machine or device, e.g., an NMR spectrometer to obtain an NMR spectrum.

As used herein, "antibody" is used in the broadest sense and includes monoclonal antibodies (including full length or intact monoclonal antibodies), polyclonal antibodies, multivalent antibodies, multi-specific antibodies (e.g., bispecific antibodies), and antibody fragments so long as they exhibit the desired activity, typically antigen binding.

As used herein, a "combination therapy", "combination treatment", or "administered in combination" means that two (or more) different agents or treatments are administered to a subject as part of a defined treatment regimen for a particular disease or condition. The treatment regimen defines the doses and periodicity of administration of each agent such that the effects of the separate agents on the subject overlap. In some embodiments, the delivery of the two or more agents is simultaneous or concurrent and the agents may be co-formulated. In other embodiments, the two or more agents are not co-formulated and are administered in a sequential manner as part of a prescribed regimen. In some embodiments, administration of two or more agents or treatments in combination is such that the reduction in a symptom, or other parameter related to the disorder is greater than what would be observed with one agent or treatment delivered alone or in the absence of the other. The effect of the two treatments can be partially additive, wholly additive, or greater than additive (e.g., synergistic). Sequential or substantially simultaneous administration of each therapeutic agent can be effected by any appropriate route including oral routes, intravenous routes, intramuscular routes, and direct absorption through mucous membrane tissues. The therapeutic agents can be administered by the same route or by different routes. For example, a first therapeutic agent of the combination may be administered by intravenous injection while a second therapeutic agent of the combination may be administered orally. In some embodiments, a combination therapy means that two (or more) different agents or treatments are administered to a subject as part of a defined treatment regimen in response to a condition related to previous administration of one (or more) of the two (or more) different agents. For example, administration of a first agent may produce an undesirable condition in a subject, prompting administration of a combination therapy comprising the first agent and a second (or further) agent (taken/formulated together or separately) which addresses the undesirable condition, e.g., treats, ameliorates, or mitigates the undesirable condition.

"Distinct" as used herein, e.g. with reference to a species in a glycan polymer, is meant to denote that it is chemically and/or structurally different from another. For example, two sugars are "distinct" if they are chemically different, e.g. a fucose and a xylose, or structurally different, e.g. cyclic vs. acyclic, L- vs. D-form. Two dimers are distinct if they consist of the same two monomers but one pair contains alpha-1,4 bond and the other contains a beta-1,6 bond. Distinct entities may have any other suitable distinguishing characteristic or property that can be detected by methods known in the art and/or described herein.

As used herein, a "dosage regimen", "dosing regimen", or "treatment regimen" is a modality of drug administration that achieves a therapeutic objective. A dosage regimen includes definition of one, two, three, or four of: a route of administration, a unit dose, a frequency of dosage, or a length of treatment.

An "effective amount" of, e.g., a non-pharmaceutical composition (e.g., a food or food ingredient, or a supplement, or medical food), and "therapeutically effective amount" of, e.g., a pharmaceutical composition or a drug agent, is meant a sufficient amount of the composition or agent to provide the desired effect (e.g., modulation (increase/decrease), treatment, improvement, etc.). In some embodiments, a physician or other health professional decides the appropriate amount and dosage regimen. An effective amount also refers to an amount of a pharmaceutical composition or a drug agent that prevents the development or relapse of a medical condition.

As used herein, "about" when referring to a measurable value such as an amount, a temporal duration, and the like, is meant to encompass variations of ±20% or in some instances ±10%, or in some instances ±5%, or in some instances ±1%, or in some instances ±0.1% from the specified value, as such variations are appropriate to perform the disclosed methods.

A "glycan unit" as used herein refers to the individual unit of a glycan disclosed herein, e.g., the building blocks from which the glycan is made.

As used herein, an "isolated" or "purified" glycan composition (or component thereof) is substantially pure and free of contaminants, e.g. pathogens or otherwise unwanted biological material, or toxic or otherwise unwanted organic or inorganic compounds. In some embodiments, pure or isolated compounds, compositions or preparations may contain traces of solvents and/or salts (such as less than 10%, 9%, 8%, 7%, 6%, 5%, 4%, 3%, 2%, 1%, less than 0.5% or 0.1% by w/w, w/v, v/v or molar %). Purified compounds are or preparations contain at least about 60% (by w/w, w/v, v/v or molar %), at least about 75%, at least about 90%, at least about 95%, at least about 97%, at least about 98%, or at least about 99% by w/w, w/v, v/v or molar % the compound(s) of interest. For example, a purified (substantially pure) or isolated glycan composition is one that is at least 80%, 85%, 90%, 91%, 92%, 93%, 94%, 95%, 98%, 99%, 99.5%, 99.8%, 99.9% or 100% of the glycan therapeutic by w/w, w/v, v/v or molar % (i.e. not including any solvent, such as e.g. water, in which the glycan composition may be dissolved) and separated from the components that accompany it, e.g. during manufacture, extraction/purification and/or processing (e.g. such that the glycan composition is substantially free from undesired compounds). Purity may be measured by any appropriate standard method, for example, by column chromatography (e.g., size-exclusion chromatography (SEC)), thin layer chromatography (TLC), gas chromatography (GC), high-performance liquid chromatography (HPLC) or nuclear magnetic resonance (NMR) spectroscopy. Purified or purity may also define a degree of sterility that is safe for administration to a human subject, e.g., lacking viable infectious or toxic agents.

As used herein, "microbiome" refers to the genetic content of the communities of microbes that live in and on a subject (e.g. a human subject), both sustainably and transiently, including eukaryotes, archaea, bacteria, and viruses (including bacterial viruses (e.g., phage)), wherein "genetic content" includes genomic DNA, RNA such as ribosomal RNA and messenger RNA, the epigenome, plasmids, and all other types of genetic information. In some embodiments, microbiome specifically refers to genetic content of the communities of microorganisms in a niche.

"Microbiota" as used herein refers to the community of microorganisms that occur (sustainably or transiently) in and on a subject (e.g. a human subject), including eukaryotes, archaea, bacteria, and viruses (including bacterial viruses, e.g. phage). In some embodiments, microbiota specifically refers to the microbial community in a niche.

"Modulate the microbiota" or "modulating the microbiota" as used herein refers to changing the state of the microbiota. Changing the state of the microbiota may include changing the structure and/or function of the microbiota. A change in the structure of the microbiota is, e.g., a change in the relative composition of a taxa, e.g., in one or more region of the GI tract such as the cecum, ascending colon, transverse colon, descending colon, sigmoid colon, and/or rectum. In an embodiment, a change in the structure of the microbiota comprises a change in the abundance of a taxa, e.g., relative to another taxa or relative to what would be observed in the absence of the modulation. Modulation of the microbiota may also, or in addition, include a change in a function of the microbiota, such as a change in microbiota gene expression, level of a gene product (e.g., RNA or protein), or metabolic output of the microbiota. Modulation of the structure or function of the microbiota may additionally induce a change in one or more functional pathway of the host (e.g., a change in gene expression, level of a gene product, and/or metabolic output of a host cell or host process) as a result of a change in the microbiota or its function.

As used herein, the term "oligosaccharide" refers to a molecule consisting of multiple (i.e., two or more) individual glycan units linked covalently. Each glycan unit may be linked through a glycosidic bond (e.g., a 1->2 glycosidic bond, a 1->3 glycosidic bond, a 1->4 glycosidic bond, a 1->5 glycosidic bond or a 1->6 glycosidic bond) present in either the alpha or beta configuration.

As used herein, a "pharmaceutical composition" or "pharmaceutical preparation" is a composition or preparation having pharmacological activity or other direct effect in the mitigation, treatment, or prevention of disease, and/or a finished dosage form or formulation thereof and is for human use. A pharmaceutical composition or pharmaceutical preparation is typically produced under good manufacturing practices (GMP) conditions. Pharmaceutical compositions or preparations may be sterile or non-sterile. If non-sterile, such pharmaceutical compositions meet the microbiological specifications and criteria for non-sterile pharmaceutical products as described in the U.S. Pharmacopeia (USP) or European Pharmacopoeia (EP). Pharmaceutical compositions may further comprise or may be co-administered with additional active agents, such as, e.g. additional therapeutic agents. Pharmaceutical compositions may also comprise pharmaceutically acceptable excipients, solvents, carriers, fillers, or any combination thereof.

As used herein, the term "polysaccharide" refers to a polymeric molecule consisting of multiple individual glycan units linked covalently. In some embodiments, a polysaccharide comprises at least 10 or more glycan units (e.g., at least 10, at least 15, at least 20, at least 25, or at least 50, at least 100, at least 250, at least 500, or at least 1000 glycan units). Each glycan unit may be linked through a glycosidic bond (e.g., a 1->2 glycosidic bond, a 1->3 glycosidic bond, a 1->4 glycosidic bond, a 1->5 glycosidic bond and a 1->6 glycosidic bond) present in either the alpha or beta configuration. In some embodiments, a polysaccharide is a homogenous polymer comprising identical repeating units. In other embodiments, a polysaccharide is a heterogenous polymer comprised of varied repeating units. Polysaccharides may further be characterized by a degree of branching (DB, branching points per residue) or a degree of polymerization (DP).

As used herein, the term "subject" or "patient" generally refers to any human subject. The term does not denote a particular age or gender. Subjects may include pregnant women. Subjects may include a newborn (a preterm newborn, a full-term newborn), an infant up to one year of age, young children (e.g., 1 yr to 12 yrs), teenagers, (e.g., 13-19 yrs), adults (e.g., 20-64 yrs), and elderly adults (65 yrs and older). In general, a subject comprises a host and its corresponding microbiota.

A "substantial decrease" as used herein is a decrease of 5%, 10%, 20%, 30%, 40%, 50%, 60%, 70%, 80%, 90%, 95%, 97%, 98%, 99%, 99.9%, or 100%.

A "substantial increase" as used herein is an increase of 10%, 20%, 30%, 40%, 50%, 60%, 70%, 80%, 90%, 100%, 150%, 200%, 250%, 300%, 350%, 400%, 450%, 500%, 550%, 600%, 650%, 700%, 750%, 800%, 850%, 900%, 950%, 1000%, or more than 1000%.

"Synthetic" as used herein refers to a man-made compound or preparation, such as a glycan composition, that is not naturally occurring. In one embodiment, the polymeric catalyst described herein is used to synthesize the glycans of the preparation under suitable reaction conditions, e.g. by a polymerization reaction that creates oligomers and polymers from individual glycan units that are added to the reaction. In some embodiments, the polymeric catalyst acts as a hydrolysis agent and can break glycosidic bonds. In other embodiments, the polymer catalyst can form glycosidic bonds.

The terms "treating" and "treatment" as used herein refer to the administration of an agent or composition to a subject (e.g., a symptomatic subject or asymptomatic subject afflicted with an adverse condition, disorder, or disease) so as to affect a reduction in severity and/or frequency of a symptom, eliminate a symptom and/or its underlying cause, and/or facilitate improvement or remediation of damage, and/or preventing an adverse condition, disorder, or disease in an asymptomatic subject who is susceptible to a particular adverse condition, disorder, or disease, or who is suspected of developing or at risk of developing the condition, disorder, or disease.

The term "antigen" refers to a substance capable of eliciting an immune response and ordinarily this is also the substance used for detection of the corresponding antibodies by one of the many in vitro and in vivo immunological procedures available for the demonstration of antigen-antibody interactions. Similarly, the term allergen is used to denote an antigen having the capacity to induce and combine with antibodies; however, this definition does not exclude the possibility that allergens may also induce antibodies of classes other than IgE.

As used herein, "derivative" refers to the product of a processed exogenous substance. A derivative can include a metabolite and/or a product of any enzymatic reaction described herein.

"Fructooligosaccharide" or "FOS", as the terms are used herein, refer to a fructose polymer, optionally comprising terminal glucose, of the following sequence: (Fru)n-Glc consisting of one or more of: beta 2,1, beta 2,6, alpha 1,2 and beta-1,2 glycosidic bonds, wherein n typically is 3-10. Variants include Inulin type β-1,2 and Levan type β-2,6 linkages between fructosyl units in the main chain. In an embodiment, FOS is made from an enzyme from *B. macerans, Z. mobilis, L. reutri, A. niger, A. japonicas, A. foetidus, A. sydowii, bA. Pullans, C. purpurea, F. oxysporum P. citrinum, P. frequentans, P. spinulosum, P. rigulosum, P. parasitica S. brevicaulis, S. cerevisiae,* or *K. marxianus*. In embodiments FOS is produced by enzymatic action of a Fructosyltransferase, β-fructofuranosidase (EC 3.2.1.26), inulosuscrase (EC 2.4.1.9) levansucrase (EC 2.4.1.10), or endoinulinase.

As used herein, a "glycan polymer preparation" (also referred to as a "preparation of glycans", "glycan preparation", "glycan polymer composition", "glycan composition", "oligosaccharide preparation", "oligosaccharide composition" or "glycan") is a preparation comprising glycan polymers that exhibits a desired effect (e.g., a therapeutic effect or a modulating effect, e.g., with regard to an exogenous substance, or a beneficial effect, e.g., with regard to a subject's health). In some embodiments, preparations of glycan polymers do not contain one or more naturally occurring oligosaccharide, including: glucooligosaccharide, mannanoligosaccharide, inulin, lychnose, maltotretraose, nigerotetraose, nystose, sesemose, stachyose, isomaltotriose, nigerotriose, maltotriose, melezitose, maltotriulose, raffinose, kestose, fructooligosaccharide, 2'-fucosyllactose, galactooligosaccharide, glycosyl, idraparinux, isomaltooligosaccharide, maltodextrin, xylooligosaccharide, agar, agarose, alginic acid, alguronic acid, alpha glucan, amylopectin, amylose, arabioxylan, beta-glucan, callose, capsulan, carrageenan, cellodextrin, cellulin, cellulose, chitin, chitin nanofibril, chitin-glucan complex, chitosan, chrysolaminarin, curdlan, cyclodextrin, alpha-cylcodextrin, dextran, dextrin, dialdehyde starch, ficoll, fructan, fucoidan, galactoglucomannan, galactomannan, galactosamineogalactan, gellan gum, glucan, glucomannan, glucoronoxyland, glycocalyx, glycogen, hemicellulose, hypromellose, icodextrin, kefiran, laminarin, lentinan, levan polysaccharide, lichenin, mannan, mucilage, natural gum, paramylon, pectic acid, pectin, pentastarch, phytoglycogen, pleuran, poligeenan, polydextrose, porphyran, pullulan, schizophyllan, sepharose, sinistrin, sizofiran, sugammadex, welan gum, xantham gum, xylan, xyloglucan, zymosan, and the like. In some embodiments, a glycan polymer exists as a salt, e.g., a pharmaceutically acceptable salt. In some embodiments, glycan preparations do not contain sorbitol. In some embodiments, glycan preparations do not contain citric acid. In some embodiments, glycan preparations do not contain cyclic glycans. In some embodiments, preparations of glycan polymers contain one or more naturally occurring oligosaccharide, including: glucooligosaccharide, mannanoligosaccharide, inulin, lychnose, maltotretraose, nigerotetraose, nystose, sesemose, stachyose, isomaltotriose, nigerotriose, maltotriose, melezitose, maltotriulose, raffinose, kestose, fructooligosaccharide, 2'-fucosyllactose, galactooligosaccharide, glycosyl, idraparinux, isomaltooligosaccharide, maltodextrin, xylooligosaccharide, agar, agarose, alginic acid, alguronic acid, alpha glucan, amylopectin, amylose, arabioxylan, beta-glucan, callose, capsulan, carrageenan, cellodextrin, cellulin, cellulose, chitin, chitin nanofibril, chitin-glucan complex, chitosan, chrysolaminarin, curdlan, cyclodextrin, alpha-cylcodextrin, dextran, dextrin, dialdehyde starch, ficoll, fructan, fucoidan, galactoglucomannan, galactomannan, galactosamineogalactan, gellan gum, glucan, glucomannan, glucoronoxyland, glycocalyx, glycogen, hemicellulose, hypromellose, icodextrin, kefiran, laminarin, lentinan, levan polysaccharide, lichenin, mannan, mucilage, natural gum, paramylon, pectic acid, pectin, pentastarch, phytoglycogen, pleuran, poligeenan, polydextrose, porphyran, pullulan, schizophyllan, sepharose, sinistrin, sizofiran, sugammadex, welan gum, xantham gum, xylan, xyloglucan, zymosan, and the like. In some embodiments, a glycan polymer exists as a salt, e.g., a pharmaceutically acceptable salt. In some embodiments, glycan preparations contain sorbitol (e.g., between about 1% and 10%). In some embodiments, glycan preparations contain citric acid (e.g., between about 0.1% and 1%, or between about 0.1% and 2%).

As used herein, an "animal host" is any animal with a gastrointestinal tract (e.g., intestines, e.g., small intestines, large intestines, and/or colon) comprising microbes (e.g., a microbial community, e.g., a microbiome). In some embodiments, an animal host is a mammal, e.g., a cow, horse, sheep, goat, pig, dog, cat, ferret, mouse, rat, or human. In some embodiments, an animal host is a human, e.g., a human patient or subject.

As used herein, an "enzymatic activity" refers to the functionality of one or more enzymes. An enzymatic activity may comprise the catalytic functionality of a single enzyme (e.g., an enzyme that catalyzes the reaction of metabolite A to metabolite B has the enzymatic activity of catalysis of the reaction of metabolite A to metabolite B). An enzymatic activity may comprise the catalytic functionality of more than one enzyme (e.g., a plurality of enzymes that together catalyze the reaction of metabolite A to metabolite B). For example, an enzymatic activity comprising the catalytic functionality of more than one enzyme could comprise the activities of a plurality of enzymes such that a first enzyme catalyzes the reaction of metabolite A to metabolite C, a second enzyme catalyzes the reaction of metabolite C to metabolite D, a third enzyme catalyzes the reaction of metabolite D to metabolite E, and a fourth enzyme catalyzes the reaction of metabolite E to metabolite B. In said example, the enzymatic activity of this plurality of enzymes would comprise catalyzing the reaction of metabolite A to metabolite B. Also in said example, the enzymatic activity of this plurality of enzymes could equivalently be described by reference to an enzyme catalyzing the reaction of metabolite A to metabolite B. Thus an enzymatic activity of an enzyme catalyzing the reaction of metabolite A to metabolite B may comprise the catalytic functionality of either: one enzyme catalyzing the reaction of metabolite A to metabolite B; or the catalytic functionality of a plurality of enzymes which, together, comprise the catalytic functionality of catalyzing the reaction of metabolite A to metabolite B. An enzymatic activity may be associated with one or a plurality of enzymes that comprise cofactors, coenzymes, additional subunits, ions, salts, and other catalytic and non-catalytic cofactors and coenzymes necessary for the enzymatic activity. Dysfunction of an enzymatic activity may comprise a deficiency or excess of the enzymatic activity (e.g., animal host enzymatic activity, microbial enzymatic activity, or both) in a subject (e.g., animal host, human subject, or human patient), e.g., the gastrointestinal tract (e.g., intestines, e.g., small intestines, large intestines, and/or colon) of a subject. In some embodiments, deficiency or excess of enzymatic activity are relative to subjects that do not have a disease or condition, e.g., hyperoxaluria, or do not have a dysfunction of the enzymatic activity.

As used herein, an "animal host enzymatic activity" is an enzymatic activity arising from enzymes produced by a cell of an animal host.

As used herein, a "microbial enzymatic activity" is an enzymatic activity arising from enzymes produced by a microbial cell, e.g., microbial cells comprised within the gastrointestinal tract of an animal host, e.g., the small intestine or the large intestine, e.g., the colon.

As used herein, "metabolite" refers to the substrate or product of an enzyme catalyzed reaction (e.g., the substrate or product of an enzymatic activity). In some embodiments, a metabolite is the substrate or product of an animal host enzymatic activity. In some embodiments, a metabolite is the substrate or product of a microbial enzymatic activity. In some embodiments, a metabolite is the substrate or product of both an animal host enzymatic activity and a microbial enzymatic activity. In some embodiments, a metabolite is endogenous to an animal host and/or microbe, e.g., it is naturally found in an animal host and/or microbe. The level of a metabolite is a measure of the abundance of a metabolite in a subject, e.g., an animal host. In some embodiments, the level of a metabolite may be associated with a disease or condition. In some embodiments, the methods disclosed herein may modulate, e.g., increase or decrease, the level of a metabolite. In some embodiments, a level of a metabolite, but not the presence of the metabolite per se, may be associated with one or more toxic effects, diseases, disorders, or conditions in an animal host, e.g., a human patient or subject.

As used herein, "GI tolerability" is a value for how a glycan or glycan preparation affects gas production in the lower gastrointestinal tract, e.g., and affects symptoms such as discomfort, flatulence, and/or bloating. A rapid rate of gas production in the lower gastrointestinal tract may give rise to gastrointestinal discomfort such as flatulence and bloating. It is believed that more gradual/low production of gas (as opposed to rapid rate of gas production) in a subject leads to less discomfort. It is believed that inulin gives a boost of gas production which is rapid and high when administered (e.g., orally) to a subject. In some embodiments, the glycan preparations described herein lead to a rate of gas release in a subject (to whom the glycan preparation was administered) that is lower than that of inulin at an equivalent dosage (grams of soluble fiber). In one embodiment, the rate of gas production from a glycan preparation described herein is no more than the rate observed for inulin under similar conditions (e.g., at equivalent dosages), about the same or less than the rate observed for inulin under similar conditions, less than the rate observed for inulin under similar conditions, or at least 10% (e.g., 10%, 20%, 30%, 40%, 50%, 60%, 70%, 80%, 90%, 100%, 1.5-fold, 2-fold, 3-fold, 4-fold, 5-fold, 10-fold, 50-fold, 100-fold, or more) less than the rate observed for inulin under similar conditions. In another embodiment, the rate of gas formation from a glycan preparation described herein is measured over 1-36 hours (e.g., about 3-24 hours, e.g., about 3 hours, or about 24 hours).

As used herein, "fermentability" is a value for how readily a glycan or glycan preparation can be used for fermentation by a microbe, microbial community, or microbiome (e.g., in the gastrointestinal tract of a subject). In some examples, "non-fermentable" refers to glycan preparations that have a relatively low fermentability, e.g., of less than 40% by weight, e.g., less than 40%, 35%, 30%, 20%, 15%, or less (by weight). In some examples, "fermentable" refers to glycan preparations which have a relatively high fermentability, e.g., at least 60% by weight, e.g., at least 60%, 65%, 70%, 75%, 80%, 85% by weight, or higher. Fermentability can be determined by methods described in "Fermentability of Various Fiber Sources by Human Fecal Bacteria In Vitro", at AMERICAN JOURNAL CLINICAL NUTRITION, 1991, 53 1418-1424; or U.S. Pat. No. 5,085,883, both of which are incorporated herein by reference.

As used herein, "digestibility" is a value for the caloric value of a glycan or glycan preparation, e.g., in the gastrointestinal tract of a subject. Glycan preparations can have varied caloric value, depending on how well, if at all, a host, e.g., host enzyme, can digest it. For example, glycan preparations that are indigestible by a host (e.g., mammal, e.g., human, enzyme) contain minimal caloric value (e.g., have no caloric value and are non-caloric). Caloric value as used herein, does not refer to the caloric value determined in a bomb calorimeter or similar device but to the caloric value usable by the subject. In some examples, glycan preparation that are indigestible are not absorbed and thus not assimilated or utilized for energy in the human body. Caloric value refers to usable caloric value, e.g., calories that are assimilated or utilized for energy in the human body. Digestibility may be measured as described in McCleary (AOAC Method 2009.01, also referred to as AACC International Approved Method 32-45.01) (McCleary et al. (2010) J. AOAC Int., 93(1), 221-233), e.g., using pancreatic α-amylase and conditions close to physiological (pH 6, 37° C.) for the enzymatic incubation step. In other embodiments, digestibility can be measured as described in McCleary et al., (2012) J. AOAC Int., 95 (3), 824-844, e.g., using AOAC 201 1 0.25 (Integrated Total Dietary Fiber Assay).

Urea Cycle Disorders

Methods described herein treat urea cycle disorders (UCDs). In some embodiments, the methods increase an enzymatic activity that is deficient in a subject. In some embodiments, the methods decrease an enzymatic activity that is in excess in a subject. In some embodiments, the methods decrease the level of a metabolite, e.g., a metabolite that accumulates in a subject with an UCD.

In some embodiments, the methods decrease or increase the prevalence of a microbe or taxa of microbes in a subject, e.g., in the gastrointestinal tract of a subject.

The urea cycle is the metabolic pathway that transforms nitrogen to urea for excretion from the body. Deficiency of an enzyme in the pathway causes a urea cycle disorder (UCD), e.g., the accumulation of a metabolite of the urea cycle and symptoms ensuing therefrom. There are several UCDs which are named on the basis of the underlying enzyme deficiency (Gene Reviews: Urea Cycle Disorders Overview. http://www.ncbi.nlm.nih.gov/books/NBK1217/ (Accessed on Jun. 14, 2011)). These include, but are not limited to:

Carbamyl phosphate synthetase I (CPSI) deficiency (MIM #237300)

Ornithine transcarbamylase (OTC) deficiency (MIM #311250)

Argininosuccinate synthetase (ASS) deficiency (also known as classic citrullinemia or type I citrullinemia, CTLN1, MIM #215700) (Gene Reviews: Citrullinemia type 1. http://www.ncbi.nlm.nih.gov/books/NBK1458/ (Accessed on Jun. 14, 2011))

Argininosuccinate lyase (ASL) deficiency (also known as argininosuccinic aciduria, MIM #207900) (Gene Reviews: Argininosuccinate lyase deficiency. http://www.ncbi.nlm.nih.gov/books/NBK51784/(Accessed on Jun. 14, 2011))

N-acetyl glutamate synthetase (NAGS) deficiency (MIM #237310)

hyperornithinemia-hyperammonemia-homocitrullinuria (HHH) syndrome (also called ornithine translocase deficiency), is a rare autosomal recessive urea cycle disorder affecting the enzyme ornithine translocase, in the SLC25A15 gene (Hommes F A, et al. (February 1986). *Neuropediatrics*. 17 (1): 48-52).

citrullinemia type II (CIT II) disorder is an autosomal recessive urea cycle disorder (e.g. found in the Japanese population) with mutation in the citrin protein (the SLC25A13 gene) (Freedberg, et al. (2003). *Fitzpatrick's Dermatology in General Medicine*. (6th ed.). McGraw-Hill).

Arginase deficiency (MIM #207800) (Gene Reviews: Arginase deficiency. http://www.ncbi.nlm.nih.gov/books/NBK1159/(Accessed on Jun. 14, 2011)).

As used herein, a "urea cycle disorder" or a "UCD" refers to any specific UCD enzyme deficiencies recited herein (e.g., carbamyl phosphate synthetase I (CPSI) deficiency, ornithine transcarbamylase (OTC) deficiency, argininosuccinate synthetase (ASS), deficiency, argininosuccinate lyase (ASL) deficiency, N-acetyl glutamate synthetase (NAGS) deficiency, hyperornithinemia-hyperammonemia-homocitrullinuria (HHH) syndrome, citrullinemia type II (CIT II) disorder or arginase deficiency).

UCDs, except for arginase deficiency, may result in hyperammonemia and/or life-threatening metabolic decompensations. In some embodiments, UCDs present in infancy. Survivors of metabolic decompensation frequently have severe neurologic injury.

The urea cycle converts nitrogen from peripheral (muscle) and enteral sources (protein ingestion) into urea that is water soluble and can be excreted. Two moles of nitrogen, one from ammonia and one from aspartate, are converted to urea in each cycle. Ammonia nitrogen derives from circulating amino acids, mostly glutamine and alanine. Aspartate is a substrate for argininosuccinic acid synthesis.

Deficiencies in the first four enzymes of the cycle (CPSI, OTC, ASS, or ASL) or in NAGS, the enzyme that catalyzes N-acetylglutamate production, result in accumulations of ammonia and ammonia precursor metabolites (Braissant O. Mol Genet Metab 2010; 100 Suppl 1:S3). Primary mitochondrial disease secondarily may affect urea cycle activity, e.g., producing an UCD or UCD symptom in a subject, because CPSI, NAGS, and OTC are located in mitochondria. In subjects with arginase deficiency, hyperammonemia may be rare or less severe than in CPSI, OTC, ASS, ASL or NAGS deficiencies (GeneReviews: Arginase Deficiency. http://www.ncbi.nlm.nih.gov/books/NBK1159/ (Accessed on Sep. 21, 2011).

Symptoms and Patient Presentation

The majority of subjects, e.g., patients, with a UCD present symptoms of the UCD in early childhood, e.g., a newborn (a preterm newborn, a full-term newborn), an infant up to one year of age, or a child (e.g., 1 year to 12 years). Subjects with a partial enzyme deficiency may become symptomatic later in childhood or as adults, e.g., as a teenager (e.g., 13-19 years) or as an adult (e.g., 20-64 years). In certain studies, it was determined that the median age at presentation of UCD symptoms was two years old, with a range of one day old to 53 years old (Summar M L, et al. Acta Paediatr 2008; 97:1420).

Subjects, e.g., patients, with an UCD may present with one or more (e.g., one, two, three, four, five, six, or more) symptoms of UCD. Symptoms of UCDs include neurologic symptoms and gastrointestinal symptoms. Neurological symptoms include, e.g., decreased level of consciousness, altered mental status, abnormal motor function, and seizures. Gastrointestinal symptoms include, e.g., vomiting, poor feeding, diarrhea, nausea, constipation, and protein aversion. In some embodiments, infant subjects become symptomatic after feeding because human milk or infant formula provides a protein load. When subjects, e.g., patients, present as infants, initial signs of UCD may include somnolence, inability to maintain normal body temperature, and poor feeding, usually followed by vomiting, lethargy, and coma (Burton B K. Pediatrics 1998; 102:E69; Summar M. J Pediatr 2001; 138:S30). Newborns with hyperammonemia, e.g., hyperammonemia due to an UCD, may have central hyperventilation leading to respiratory alkalosis. Hyperventilation is thought to result from cerebral edema caused by the accumulation of ammonia, glutamine, and other metabolites (Butterworth R F. J Inherit Metab Dis 1998; 21 Suppl 1:6). Increasing cerebral edema also may result in abnormal posturing and progressive encephalopathy with hypoventilation and respiratory arrest. Approximately 50 percent of infants with severe hyperammonemia, e.g., hyperammonemia due to an UCD, have seizures (Brusilow S W, Maestri N E. Adv Pediatr 1996; 43:127).

Although subjects, e.g., patients, with UCD typically presents as infants, subjects with UCD have a lifelong risk of metabolic decompensation with intercurrent hyperammonemia. Metabolic decompensation can be brought on during episodes of increased catabolism, such as infections (e.g, gastroenteritis, otitis media), fasting, surgery, or trauma.

Subjects, e.g., patients, with UCD from a partial enzyme deficiency may have atypical presentations, occurring after the newborn period (Brusilow S W, Horwich A L. Urea cycle enzymes. In: The metabolic and molecular bases of inherited disease, 8th ed, Scriver C R, Beaudet A L, Sly W S, Valle D (Eds), McGraw-Hill, New York 2001. p. 1909; Leonard J V, Morris A A. Semin Neonatol 2002; 7:27). This delayed presentation is most commonly seen in subjects with partial OTC deficiency, such as female carriers, although it also may occur with partial activity of any urea cycle enzyme. Subjects with delayed presentation of UCD symptoms, e.g., subjects with partial urea cycle enzyme deficiencies, may present with one or more of the following: chronic vomiting, developmental delay, a seizure disorder, sleep disorders, psychiatric illness, headache, anorexia, vomiting, lethargy, ataxia, behavioral abnormalities (Brusilow S W, Horwich A L. Urea cycle enzymes. In: The metabolic and molecular bases of inherited disease, 8th ed, Scriver C R, Beaudet A L, Sly W S, Valle D (Eds), McGraw-Hill, New York 2001. p. 1909; Leonard J V, Morris A A. Semin Neonatol 2002; 7:27; Maestri N E, et al. Medicine (Baltimore) 1998; 77:389; Serrano M, et al. J Child Neurol 2010; 25:352; Sedel F, et al. J Inherit Metab Dis 2007; 30:631; Houston B, et al. Am J Med 2011; 124:303). In some embodiments, these symptoms appear or increase in severity following increased protein intake or during periods of catabolic stress (e.g, viral illness, pregnancy. Subjects with delayed presentation of UCD symptoms, e.g., subjects with partial urea cycle enzyme deficiencies, may prefer vegetarian diets because dietary protein intake often is associated with headache.

Subjects, e.g., patients, with UCD may also present with hepatic dysfunction. Hepatic dysfunction may characterized by elevation of liver enzymes, coagulopathy, and histologic evidence of glycogenoses (Iorio R, et al. J Gastroenterol 2005; 40:820; Miles L, et al. J Pediatr Gastroenterol Nutr 2005; 40:471).

Subjects, e.g., patients, with UCD may present with hyperammonemia. In some embodiments, hyperammonemia may be chronic. In some embodiments, hyperammonemia may occur only during metabolic decompensations associated with catabolic stress (Am P H, et al. N Engl J Med 1990; 322:1652; Tuchman M, Yudkoff M. Mol Genet Metab 1999; 66:10).

Subjects, e.g., patients, with arginase deficiency typically present in later infancy or early childhood (e.g., 3 months through 6 years of age). In some embodiments, subjects, e.g., patients, presenting with UCD due to arginase deficiency suffer from spasticity, especially of the lower extremities, dystonia, and ataxia. In such subjects, a diagnosis of cerebral palsy is often suspected. Other presenting symptoms of subjects, e.g., patients, with a UCD due to arginase deficiency are similar to those with partial deficiencies.

Testing for Ammonia and Diagnosis of Subjects with Hyperammonemia (e.g., UCDs and Hepatic Encephalopathy, HE)

Ammonia Testing

Subjects having, suspected of having, or at risk of having hyperammonemia (e.g., UCDs and hepatic encephalopathy, HE) may have elevated blood ammonia levels, e.g., plasma ammonia levels, serum ammonia levels, or whole blood ammonia levels, relative to a control subject (e.g., a subject not suspected of having hyperammonemia). In some embodiments, blood ammonia levels in healthy adult subjects (e.g., a subject not suspected of having hyperammonemia) are less than 15, 20, 25, 30, 35, 40, 45, or 50 μmol/L, e.g., less than 30 µmol/L. In some embodiments, a blood ammonia level of about 0.5-fold, about 1-fold, about 1.5-fold, about 2-fold, about 2.5-fold, or about 3-fold above normal is suggestive of UCD or HE. In some embodiments, a subject having or suspected of having UCD or HE has blood ammonia levels of greater than or equal to 90, 95, 100, 105, 110, 115, 120, 125, 130, 135, 140, 145, 150, 155, 160, 165, 170, 175, or 180 µmol/L. In some embodiments, a subject having or suspected of having UCD or HE has blood ammonia levels of greater than or equal to 100, 105, 110, 115, 120, 125, 130, 135, 140, 145, or 150 µmol/L. In some embodiments, a subject having or suspected of having UCD or HE has blood ammonia levels of greater than or equal to 100 µmol/L. In some embodiments, a subject having or suspected of having UCD or HE has blood ammonia levels of greater than or equal to 150 µmol/L.

Newborns and children having, suspected of having, or at risk of having hyperammonemia (e.g., UCDs) may have elevated blood ammonia levels, e.g., plasma ammonia levels, serum ammonia levels, or whole blood ammonia levels, relative to a healthy newborn or child. In some embodiments, a healthy newborn or child has an average blood ammonia concentration of 45±10 µmol/L. In some embodiments, a healthy newborn or child (e.g., a subject not suspected of having hyperammonemia) has an average blood ammonia concentration of less than or equal to 70, 71, 72, 73, 74, 75, 76, 77, 78, 79, 80, 81, 82, 83, 84, 85, 86, 87, 87, 88, 89, 90, 91, 92, 93, 94, or 95 µmol/L, e.g., 80 or 90 µmol/L. In some embodiments, a newborn or child having or suspected of having UCD or HE has blood ammonia levels of greater than or equal to 55, 60, 65, 70, 75, 80, 90, or 95, 100, 105, 110, 115, 120, 125, 130, 135, 140, 145, 150, 155, 160, 165, 170, 175, or 180 µmol/L.

In some embodiments, blood ammonia concentration may be measured in venous and arterial blood samples. In some embodiments, measuring serum ammonia levels may be used for monitoring efficacy of glycan preparations described herein. In some embodiments, the grade or severity of hyperammonemia may be assessed by measuring the partial pressure of gaseous ammonia (pNH3), e.g., in the brain. pNH3 values can be calculated from the total ammonia and pH. In some embodiments, subjects having hyperammonemia have elevated levels of pNH3 relative to a control subject (e.g., a subject not suspected of having hyperammonemia).

In some embodiments, serum levels of 3-nitrotyrosine may be elevated in subjects having, suspected of having, or at risk for minimal hepatic encephalopathy (MHE). In some embodiments, a subject having, suspected of having, or at risk for MHE has serum 3-nitrotyrosine levels of greater than about 10 nM, 15 nM, 20 nM, 30 nM, 40 nM, 50 nM, 60 nM, 70 nM, 80 nM, 90 nM, or 100 nM. In some embodiments, a subject having, suspected of having, or at risk for MHE has serum 3-nitrotyrosine levels of greater than about 10 nM or about 15 nM.

Neuroimaging

Neuroimaging during acute presentation of UCD may show evidence of cerebral edema. Magnetic resonance imaging (MRI) of the brain in subjects, e.g., patients, with neonatal-onset UCD with prolonged hyperammonemia may show findings similar to that of hypoxic ischemic encephalopathy or hepatic encephalopathy. As an example, neonatal OTC deficiency with prolonged hyperammonemia may lead to chronic changes including cortical atrophy, white matter cystic changes, and hypomyelination. Reversible white matter lesions may be seen even in milder late-onset cases.

Diagnosis

Subjects, e.g., patients, with UCD may be diagnosed after presenting with UCD symptoms, e.g., symptoms described herein or known in the art, or based upon family history or an abnormal newborn screening test.

In some embodiments, the first step of diagnosis is acquiring a value for ammonia levels, e.g., blood ammonia levels, in a subject, e.g., patient. In some embodiments, a blood ammonia level of greater than or equal to 100, 105, 110, 115, 120, 125, 130, 135, 140, 145, or 150 µmol/L is suggestive of a UCD. In some embodiments, a blood ammonia level of greater than or equal to 100 µmol/L is suggestive of a UCD. In some embodiments, a blood ammonia level of greater than or equal to 150 µmol/L is suggestive of a UCD.

In some embodiments, ammonia tests should be accompanied by (e.g., precede or be followed by) acquiring values for one or more of arterial pH, carbon dioxide tension, serum lactate, serum glucose, serum electrolytes (e.g., to calculate the anion gap), plasma amino acids, and urine organic acids and urine orotic acid. In some embodiments, an elevated plasma ammonia concentration (e.g., compared to a reference value described herein) combined with normal blood glucose and anion gap strongly suggests a UCD.

Further testing is used to identify the specific enzyme deficiency, including enzyme analysis and molecular genetic testing. This testing may include:

- Acquiring a value for plasma amino acid/urine orotic acid levels, e.g., to use quantitative amino acid analysis to differentiate among UCDs (Summar M. J Pediatr 2001; 138:S30)
- Acquiring a value for plasma citrulline and plasma argininosuccinic acid, where elevated citrulline and decreased or absent argininosuccinic acid is suggestive of argininosuccinate synthetase (ASS) deficiency
- Acquiring a value for plasma citrulline and plasma argininosuccinic acid, where elevated citrulline and elevated argininosuccinic acid is suggestive of Argininosuccinate lyase (ASL) deficiency
- Acquiring a value for plasma citrulline, plasma arginine, plasma glutamine, and plasma orotic acid, where decreased or absent citrulline, decreased arginine, increased glutamine, and/or decreased orotic acid is suggestive of carbamyl phosphate synthetase I (CPSI) deficiency
- Acquiring a value for plasma citrulline, plasma arginine, plasma glutamine, and plasma orotic acid, where decreased or absent citrulline, decreased or absent arginine also is low, elevated glutamine, and/or elevated orotic acid is suggestive of ornithine transcarbamylase (OTC) deficiency; orotic acid can be increased to more than 1000 micromol/mol creatinine (normal, 1 to 11 micromol/mol orotic acid/creatinine)
- Acquiring a value for plasma citrulline, plasma arginine, and/or plasma glutamine, where decreased or absent citrulline, decreased or absent arginine, and/or elevated glutamate is suggestive of N-acetyl glutamate synthetase (NAGS) deficiency
- Acquiring a value for plasma arginine, where elevated arginine (e.g., 3 to 4 fold above a reference value, e.g., a normal value) is suggestive of arginase deficiency (GeneReviews: Arginase Deficiency. http://www.ncbi.nlm.nih.gov/books/NBK1159/(Accessed on Sep. 21, 2011).

The diagnosis of a specific enzyme deficiency in a subject, e.g., patient, with UCD can be confirmed by enzyme activity analysis of tissue samples. In some embodiments, enzyme activity analysis of liver biopsy samples may be used to diagnose CPSI, OTC, and/or NAGS deficiencies. In some embodiments, enzyme activity analysis of fibroblasts from skin biopsy samples may be used to diagnose ASS and/or ASL deficiencies. In some embodiments, enzyme activity analysis of red blood cell samples may be used to diagnose arginase deficiency. Measured enzyme activity does not always correlate with residual in vivo enzyme activity or with phenotypic (e.g., UCD symptom) severity, because most in vitro assays are performed with excess substrate and in cell-free extracts. In addition, in the X-linked disorder OTC deficiency, the level of OTC activity measured in a liver biopsy may be normal in a female with UCD, depending upon the pattern of X inactivation in the liver. In some embodiments, liver tissue, e.g., obtained by open or needle punch biopsy, may be used as a sample to acquire a value for activity for all enzymes associated with UCDs (e.g., enzymes disclosed herein), optionally wherein DNA testing is negative.

Other diagnostic techniques may be useful to detect abnormalities in subjects, e.g., patients, with UCDs, especially those with partial enzyme deficiencies who have normal laboratory values during asymptomatic periods. Acquiring a value for urinary excretion of orotic acid after administration of allopurinol can be used to identify women who are carriers of a mutant OTC allele (Hauser E R, et al. N Engl J Med 1990; 322:1641; Burlina A B, et al. J Inherit Metab Dis 1992; 15:707). Administering isotopes in vivo can be employed to assess altered urea cycle activity (Scaglia F, et al. Pediatrics 2002; 109:150; Lee B, et al. Proc Natl Acad Sci USA 2000; 97:8021). Stable isotopes can be used to measure rates of total body urea synthesis and nitrogen flux (which assesses urea cycle activity) and can identify subjects, e.g., patients, with complete and partial enzyme deficiencies and asymptomatic carriers of UCD associated alleles.

DNA sequencing-based mutation testing may also be useful to evaluate whether a subject, e.g., patient, has a UCD associated mutation. Sequencing-based may be used as a first-line approach for diagnosis. DNA testing for OTC deficiency may be considered in patients with a suspected UCD, especially if plasma amino acid analysis is not diagnostic. In some embodiments, OTC deficiency is the most common UCD. More than 150 mutations, most of which are single-base substitutions, have been reported to cause UCD based on OTC deficiency (McCullough B A, et al. Am J Med Genet 2000; 93:313). However, microdeletion of part or all of the OTC-encoding gene may lead to false-negative results on DNA sequencing. To address this potential problem, array comparative genomic hybridization (aCGH) or chromosome microarray analysis to detect microdeletions of the gene may be used when initial DNA sequencing is negative (Shchelochkov O A, et al. Mol Genet Metab 2009; 96:97).

An alternative to targeted DNA-sequencing mutation analysis is the application of next-generation DNA sequencing for clinical whole exome analysis, which has the potential to identify variants in most, if not all, coding genes (Bamshad M J, et al. Nat Rev Genet 2011; 12:745). In this technique, all of the UCD genes as well as other gene variants that may cause hyperammonemia can be detected. However, said sequencing may miss small single or multi-exon deletions; aCGH designed with single exon resolution may be performed in conjunction with DNA sequencing to address this (Shchelochkov O A, et al. Mol Genet Metab 2009; 96:97).

Since UCD symptoms often present in newborns, subjects, e.g., patients, may be tested at the prenatal and neonatal stage. Prenatal testing can be performed for all the UCDs by DNA analysis if the mutation is known (Scaglia F, et al. J Nutr 2004; 134:2775S); the carrier status of both parents may be confirmed prior to prenatal DNA testing. ASS and ASL enzyme activity can be measured directly in amniocytes and chorionic villus cells. Elevated citrulline and argininosuccinic acid can be measured in amniotic fluid. CPSI and OTC can be measured in fetal liver. The clinical phenotype of females with OTC deficiency cannot be predicted, due to random inactivation of the X chromosome. Testing for UCDs and other inborn errors of metabolism by tandem mass spectrometry is now included in most newborn screening programs (Wilcken B. J Inherit Metab Dis 2010; 33:5205; Cavicchi C, et al. J Pharm Biomed Anal 2009; 49:1292; Huang H P, et al. J Formos Med Assoc 2006; 105:882).

Treatment of UCDs

Existing therapeutic options for treating UCDs comprises rehydration and maintenance of good urine output (e.g., without overhydration), removal of nitrogen (e.g., ammonia) from the body using medications and/or hemodialysis, decreasing/stopping protein intake and/or minimizing catabolism, and stimulation of anabolism and uptake of nitrogen precursors by muscle.

Subjects, e.g., patients, with UCDs typically are volume depleted because of a history of poor feeding and/or recurrent vomiting. Repletion of intravascular fluid is a priority. Rehydration and maintenance of good urine output can be accomplished by administering fluids intravenously. Intravenous access, preferably via a central catheter, can be established for blood sampling and for the administration of fluids and medications. Intravenous fluids may consist of 10 percent dextrose in water, although significant and prolonged hyperglycemia should be avoided. Saline infusion should be minimized because of the high saline content of nitrogen scavenging medications.

Subjects, e.g., patients, with UCDs may be treated by removal of nitrogen (e.g., ammonia) from the body. Hemodialysis is the quickest and most efficient method of nitrogen removal and can be used if ammonia is rapidly increasing in a subject, if the subject has acute hyperammonemia that is resistant to drug therapy, and/or the level of ammonia is persistently above the range of 350 to 400 µmol/L (Schaefer F, et al. Nephrol Dial Transplant 1999; 14:910). Intravenous fluid administration, rather than hemodialysis, is often sufficient therapy in patients with arginase deficiency who present with milder UCD symptoms, e.g, hyperammonemia (GeneReviews: Arginase Deficiency. http://www.ncbi.nlm.nih.gov/books/NBK1159/ (Accessed on Sep. 21, 2011). Various forms of hemodialysis may be used to treat subjects, e.g., patients, with UCD, including: continuous arteriovenous or venovenous hemodialysis and extracorporeal membrane oxygenation (ECMO) with hemodialysis.

Removal of nitrogen may also be promoted using pharmaceutical compositions comprising sodium phenylacetate and sodium benzoate. These drugs scavenge ammonia by creating an alternate pathway to excrete nitrogen precursors (Summar M. J Pediatr 2001; 138:530). Phenylacetate combines with glutamine to form phenylacetylglutamine, and benzoate combines with glycine to form hippurate (Darmaun D, et al. Am J Physiol 1998; 274:E801; Green T P, et al. J Pediatr 1983; 102:785). Phenylacetylglutamine and hippurate are water soluble and are excreted in the urine. Adequate renal function is essential for the effectiveness of this treatment (Brusilow S W, et al. Lancet 1979; 2:452). Disposal of glutamine and glycine reduces the total nitrogen pool. In some embodiments, sodium phenylacetate and sodium benzoate may be administered separately (e.g., sequentially or concurrently) to a subject, e.g., patient, with a UCD. In some embodiments, a combined preparation of sodium phenylacetate and sodium benzoate (e.g., Ammonul) is administered to a subject, e.g., patient, with a UCD. In some embodiments, delivery of sodium phenylacetate and sodium benzoate is parenteral. In some embodiments, for subjects, e.g., patients, weighing ≤20 kg, a loading dose of sodium phenylacetate and sodium benzoate is 500 mg/kg (250 mg/kg of each drug) in a volume of 25 to 35 mL/kg of 10 percent dextrose solution infused over 90 minutes. In some embodiments, for subjects, e.g., patients, who weigh >20 kg, dosing is based upon body surface area, and a loading dose is 11 g/m2 (i.e., 5.5 g/m2 of each drug). In the same embodiment, maintenance infusion of sodium phenylacetate-sodium benzoate may be 500 mg/kg per 24 hours for patients <20 kg and 11 g/m2 per 24 hours as a continuous infusion for patients >20 kg. Maintenance infusion begins when the loading dose is completed. Maintenance infusion of Ammonul may be continued until oral sodium phenylbutyrate can be tolerated.

Removal of nitrogen may also be promoted by administering arginine. Enzyme deficiencies in the urea cycle (with the exception of arginase deficiency) prevent the formation of arginine, thus rendering it an essential amino acid (Kline J J, et al. Am J Dis Child 1981; 135:437). Arginine deficiency results in a catabolic state that stimulates further mobilization of nitrogen from protein breakdown. In OTC, ASS, and ASL deficiencies, arginine also is needed to generate urea cycle intermediates, including ornithine, citrulline, and argininosuccinic acid. When arginine is provided, these water-soluble compounds can be formed and excreted, resulting in additional removal of ammonia (Brusilow S W, Batshaw M L. Lancet 1979; 1:124; Batshaw M L, et al. N Engl J Med 1982; 306:1387; Lee B, et al. Proc Natl Acad Sci USA 2000; 97:8021). In some embodiments, where the subject, e.g., patient, has CPSI or OTC deficiency, or if the specific enzyme deficiency of the UCD has not been identified, a maintenance dose of arginine may be 200 mg/kg per 24 hours for patients ≤20 kg and 4 g/m2 per 24 hours for patients >20 kg. In some embodiments, where the subject, e.g., patient, has ASS or ASL deficiency, a maintenance dose of arginine may be 600 mg/kg per 24 hours for patients ≤20 kg and 12 g/m$^2$ per 24 hours for patients >20 kg intravenous.

Removal of nitrogen may also be promoted by administering citrulline. In OTC or CPS deficiency, oral doses of citrulline (150 to 200 mg/kg per 24 hours for patients ≤20 kg and 3 to 4 g/m2 per 24 hours for patients >20 kg) may be provided because there may be an advantage to incorporating aspartate nitrogen for clearance as urea in disorders upstream of ASS. Citrulline should not be given if the specific enzyme deficiency of the UCD is unknown, because citrulline levels are elevated in ASS and ASL deficiencies.

Removal of nitrogen may also be promoted by administering carglumic acid. Carglumic acid may be used to treat hyperammonemia, e.g., hyperammonemia associated with NAGS deficiency. Carglumic acid is able to activate the first enzyme of the urea cycle (CPSI), leading to rapid reduction of plasma ammonia to normal levels. It is used for both acute and chronic hyperammonemia due to NAGS deficiency. Sodium phenylacetate-sodium benzoate (Ammonul) may be used in addition to carglumic acid if the hyperammonemia is severe; otherwise, carglumic acid may be administered alone. In some embodiments, an initial carglumic acid dose for acute hyperammonemia ranges from 100 to 250 mg/kg/day orally (prepared as a liquid and divided into two to four doses that are given immediately before meals). The dose may be adjusted according to the patient's symptoms and plasma ammonia level. In some embodiments, the carglumic acid dose for maintenance treatment of chronic hyperammonemia is typically <100 mg/kg/day.

Subjects, e.g., patients, with UCDs may be treated by protein restriction, e.g., decreasing/stopping protein intake and/or minimizing catabolism. This treatment method must be used in moderation because excessive and prolonged restriction of protein intake will stimulate peripheral mobilization of nitrogen. In some embodiments, e.g., acute hyperammonemia, e.g., with encephalopathy, oral feedings may be discontinued. Intravenous administration of lipids and glucose lacking in protein may be used instead. In some embodiments, the daily protein intake administered varies with age and ranges from 2.0 to 2.5 g/kg per day at birth to less than 0.6 to 0.8 g/kg per day in adults. Children with UCDs may require even less than the recommended daily intake of protein for normal growth. Subjects, e.g., patients, with partial deficiency of a urea cycle enzyme may tolerate greater protein intake. In some embodiments, daily intake of protein and amino acids is adjusted according to the patient's age, growth rate, monitoring laboratories (e.g., essential amino acid levels in the blood, prealbumin, albumin, and hemoglobin), and clinical course.

Subjects, e.g., patients, with UCDs may be treated with other methods including liver transplantation, hepatocyte cell transplantation, and/or gene therapies. Liver transplantation may be used for newborns with CPSI or OTC deficiency UCD, in subjects, e.g., patients, who have not responded to medical therapy, and in ASL deficiency UCD associated with cirrhosis. However, subjects, e.g., patients, with any form of UCD may be candidates for liver transplantation if other therapeutic options fail to prevent recurrent hyperammonemia.

Hepatic Encephalopathy (HE)

In some embodiments, subjects with hepatic encephalopathy (HE) may be treated according to the methods provided herein. Hepatic encephalopathy covers a complex set of non-specific neuropsychiatric symptoms and clinical signs affecting quality of life of both patients and their relatives. Hepatic encephalopathy is a common complication of advanced liver disease, including all forms of cirrhosis, and up to 80% of cirrhotic patients have some form of HE, ranging from minimal hepatic encephalopathy (MHE) to overt hepatic encephalopathy (OHE).

OHE is defined as neurologic abnormalities that are observable by a clinician without special testing. Symptoms can include shaking of the hands or arms, disorientation and slurred speech; patients can progress into coma. OHE can develop in patients with liver disease, cirrhosis and in patients with a transjugular intrahepatic portosystemic shunt (TIPS). This condition may follow a gastrointestinal bleed or infection. Development of OHE is associated with increased mortality. Admissions for OHE are frequent among patients with end stage liver disease (ESLD).

Patients with MHE have subtle symptoms that may only be detected using specialized psychometric tests and MHE is generally underdiagnosed. There is currently no common diagnostic paradigm in clinical practice to define MHE and there are no approved treatments for MHE. MHE can cause the loss of independent living skills (e.g., driving) and is predictive of subsequent development of OHE. Patients who have a single episode of OHE, often caused by a precipitant, and subsequently recover are also likely to have some level of MHE.

Presentation and Symptoms

Hepatic encephalopathy includes multiple adverse neurological symptoms that occur when the liver is unable to remove toxic substances such as ammonia from the blood. Liver dysfunction includes: liver cirrhosis (and portal hypertension), e.g., Types A (resulting from acute liver failure (ALF), B (resulting predominantly from PSS) or C (resulting from cirrhosis) (Child-Pugh Score for severity of liver cirrhosis); in the absence of cirrhosis—with either spontaneous or surgically created portosystemic shunts (portosystemic shunt surgery); portal-systemic bypass, acute liver failure (ALF), or acute-on-chronic liver failure (ACLF).

The 2014 AASLD and EASL clinical practice guidelines for managing HE recommend classifying HE according to the underlying liver disease, the severity of the manifestations, the time course, and precipitating factors. The severity of HE may be graded based upon clinical manifestations: Minimal (abnormal results on psychometric or neurophysiological testing with no clinical manifestations); Grade I (mild confusion, slurred speech, disordered sleep, behavioral changes); Grade II (lethargy, mild confusion); Grade III (marked confusion (stupor), incoherent speech, sleeping but arousable); and Grade IV (coma, unresponsive to pain). HE may be further subdivided according to the time course of the disease: episodic; recurrent (bouts of HE occur for 6 months or less); and persistent (patterns of behavioral alterations are always present and interspersed with relapses of overt HE).

'Minimal hepatic encephalopathy' (MHE), used interchangeably with the term 'covert hepatic encephalopathy' (CHE) is defined as the presence of test-dependent or clinical signs of brain dysfunction in patients with chronic liver disease (CLD) who are not disoriented or display asterixis. The term "minimal" conveys that there is no clinical sign, cognitive sign, or other sign of HE. The term "covert" includes minimal and grade 1 HE. Because the occurrence of MHE and CHE in patients with CLD may be as high as 50%, patients at risk should be tested.

Subjects with HE may present with cognitive deficits including: confusion, forgetfulness, anxiety or excitation, sudden changes in personality or behavior, changes in sleep patterns, disorientation, sweet or musty smelling breath, slurred speech, and/or difficulty controlling motor functions. The condition reflects a diffuse disturbance of brain functions due to advanced liver disease or large portosystemic shunts (e.g., TIPS). Patients may present with neuromuscular impairments including bradykinesia, hyperreflexia, rigidity, myoclonus, and asterixis. Disturbances in the diurnal sleep pattern (insomnia and hypersomnia) are common initial manifestations of hepatic encephalopathy and typically precede other mental status changes or neuromuscular symptoms.

Diagnosis

Diagnosis of HE may be performed using tests of liver function, serum ammonia levels, EEG, and other blood and neurological tests. Psychometric tests for diagnosis include: Number Connection Test (Reitan Test) (timed connect-the-numbers test administered in two parts in which patients without hepatic encephalopathy should finish the test in a number of seconds less than or equal to their age in years); Psychometric Hepatic Encephalopathy Score (PHES) (five paper-pencil tests that evaluate cognitive and psychomotor processing speed and visuomotor coordination); Inhibitory Control Test (ICT) (computerized test of attention and response inhibition that has been used to characterize attention deficit disorder, schizophrenia, and traumatic brain injury); STROOP Task (test of psychomotor speed and cognitive flexibility that evaluates the functioning of the anterior attention system and is sensitive for the detection of cognitive impairment in minimal hepatic encephalopathy); Repeatable Battery for the Assessment of Neuropsychological Status (RBANS) (measures a wide range of neurocognitive functions relevant to minimal hepatic encephalopathy); and the Continuous Reaction Time (CRT) test (relies on repeated registration of the motor reaction time (pressing a button) to auditory stimuli (through headphones)).

Neurophysiological tests for diagnosis include the Critical Flicker Frequency (CFF) Test (psychophysiological tool defined as the frequency at which a fused light (presented from 60 Hz downward) appears to be flickering to the observer); Electroencephalography examination (which may detect changes in cortical cerebral activity across the spectrum of HE without patient cooperation or risk of a learning effect); and Evoked Potentials (externally recorded electrical signals that reflect synchronous volleys of discharges through neuronal networks in response to various afferent stimuli). In some embodiments, hepatic encephalopathy is diagnosed using any combination of two or more psychometric or neurophysiological tests.

Treatment of HE

Medical treatment of HE currently includes treatment of the underlying precipitant, if present, such as gastrointestinal bleeding or infection. Standard-of-care treatments for HE include lactulose, lactitol, and antibiotics (e.g., rifaximin or neomycin).

Lactulose is a non-absorbed disaccharide that has been used for several decades to reduce hyperammonemia in OHE patients. Lactulose's mechanism of action is thought to work primarily through purging of the stool and acidification of the colonic environment, leading to the conversion of ammonia to ammonium, which less readily crosses the colonic barrier and enters the bloodstream. Lactulose has also been shown to stimulate bacterial growth, thus promoting assimilation of ammonia into bacterial proteins. Lactulose reduces episodes of OHE by up to 50% compared to a placebo.

Rifaximin, a poorly-absorbed antibiotic derived from rifamycin, is currently approved as a second line treatment for OHE and is used in conjunction with lactulose when lactulose alone does not control OHE. When administered in combination with lactulose, rifaximin reduces episodes of OHE by approximately 50%. Neither lactulose nor rifaximin sufficiently reduces the risk of OHE recurrence, each episode of which significantly increases mortality risk.

Treatments may also include dietary modifications and probiotics. Treatment efficacy may be assessed by resolution of the symptoms or diagnostic criteria listed above (e.g., reduction in serum ammonia levels), decreased incidence of future episodes of HE, or, in subjects at risk of HE, by decreased occurrence of an initial episode of HE.

In some embodiments, the methods disclosed herein (e.g., methods for treating UCD, methods for treating HE (e.g., MHE or OHE), methods for increasing or decreasing an enzymatic activity, methods for decreasing the level of a metabolite (e.g., ammonia), and methods for identifying or selecting treatment regimens, e.g., for UCD or HE (e.g., MHE or OHE)) may be combined with one or more (e.g., one, two, three, four, or more) existing therapeutic options, e.g., therapeutic options described herein, to treat subjects with UCD or HE (e.g., MHE or OHE). In some embodiments, the methods disclosed herein may be combined with rehydration for the treatment of UCD. In some embodiments, the methods disclosed herein may be combined with the use of hemodialysis for the treatment of UCD. In some embodiments, the methods disclosed herein may be combined with administering sodium phenylacetate and sodium benzoate for the treatment of UCD. In some embodiments, the methods disclosed herein may be combined with administering arginine, citrulline, or carglumic acid for the treatment of UCD. In some embodiments, the methods disclosed herein may be combined with protein restriction (e.g., minimizing catabolism and stimulating anabolism) for the treatment of UCD. In some embodiments, the methods disclosed herein may be combined with liver transplantation for the treatment of UCD. In some embodiments, the methods disclosed herein may be combined with one or more gene therapies for the treatment of UCD.

In some embodiments, the methods disclosed herein may be combined with any appropriate standard-of-care for the treatment of HE. In some embodiments, the methods disclosed herein may be combined with lactulose for the treatment of HE. In some embodiments, the methods disclosed herein may be combined with an antibiotic, e.g., rifaximin, for the treatment of HE. In some embodiments, a subject has been treated with lactulose or rifaximin prior to administration of a glycan preparation. In some embodiments, a subject has been treated with lactulose or an antibiotic, e.g., rifaximin, concurrently with administration of a glycan preparation. In some embodiments, the subject has been treated with rifaximin prior to administering a glycan preparation. In some embodiments, the subject has been treated with lactulose and rifaximin prior to administering a glycan preparation. In some embodiments, the methods disclosed herein may be combined with lactitol for the treatment of HE. In some embodiments, the methods disclosed herein may be combined with dietary modifications for the treatment of HE. In some embodiments, the methods disclosed herein may be combined with commensal bacteria or probiotics for the treatment of HE.

In some embodiments, glycan preparations comprising alpha-1,6 bonds, e.g, an increased number of alpha-1,6 bonds relative to other glycans, e.g. greater than 30% [e.g., glu100-133 comprises 32.33% alpha-1,6 bonds and reduces ammonia to 1.35 mM NH3; glu100-17 comprises 42.86% alpha-1,6 bonds and reduces ammonia to 0.51 mM NH3], may help reduce ammonia, e.g., in a subject. In some embodiments, glycan preparations comprising fewer beta-1,6 and beta-1,4 bonds, e.g, a decreased number of beta-1,6 and beta-1,4 bonds relative to other glycans, e.g. no more than 35% [e.g., glu100-133 comprises 31.99% beta-1,4/1,6 bonds and reduces ammonia to 1.35 mM NH3; glu100-18 comprises 27.35% beta-1,4/1,6 bonds and reduces ammonia to 0.22 mM NH3] may help reduce ammonia, e.g., in a subject. In some embodiments, glycan preparations comprising beta-1,3 bonds, e.g, an increased number of beta-1,3 bonds relative to other glycans, e.g. greater than 3% [e.g., glu100-133 comprises 4.76% beta-1,3 bonds and reduces ammonia to 1.35 mM NH3; glu100-78 comprises 5.90% beta-1,3 bonds and reduces ammonia to 0.18 mM NH3], may help reduce ammonia, e.g., in a subject. In some embodiments, glycan preparations comprising alpha bonds, e.g, an increased number of alpha bonds relative to other glycans, may help reduce ammonia, e.g., in a subject. In some embodiments, glycan preparations comprising increased branching, e.g, an increased level of branching relative to other glycans, may help reduce ammonia, e.g., in a subject. In some embodiments, glycan preparations comprising increased bond diversity, e.g, an increased level of bond diversity relative to other glycans, may help reduce ammonia, e.g., in a subject. In some embodiments, these characteristics apply to glycans and glycan preparations comprising glucose.

Patient Populations

In some embodiments, a subject is suffering from hyperammonemia. In some embodiments, a subject having hyperammonemia is suffering from a urea cycle disorder (UCD). In some embodiments, a subject having hyperammonemia is suffering from hepatic encephalopathy (HE).

In some embodiments, hyperammonemia is caused or associated with, at least in part, by alcohol and/or alcoholic cirrhosis. In some embodiments, hyperammonemia is caused or associated with, at least in part, by autoimmune hepatitis, chronic hepatitis B, or chronic hepatitis C. In some embodiments, hyperammonemia is caused or associated with, at least in part, by fatty liver. In some embodiments, hyperammonemia is caused or associated with, at least in part, by hepatitis C. In some embodiments, hyperammonemia is caused or associated with, at least in part, by hepatitis C and alcohol. In some embodiments, hyperammonemia is caused or associated with, at least in part, by iron overload and steatosis. In some embodiments, hyperammonemia is caused or associated with, at least in part, by nonalcoholic steatohepatitis. In some embodiments, hyperammonemia is caused or associated with, at least in part, by nonalcoholic steatohepatitis and hepatitis B. In some embodiments, hyperammonemia is caused or associated with, at least in part, by primary biliary cirrhosis.

In some embodiments, a subject having hyperammonemia has been previously treated or administered with lactulose or rifaximin. In some embodiments, a subject having hyperammonemia caused or associated with, at least in part, by alcohol, alcoholic cirrhosis, hepatitis C and alcohol, or nonalcoholic steatohepatitis has been previously treated or administered with lactulose or rifaximin.

In some embodiments, a subject having hyperammonemia has a Child-Pugh score of at least 5.

In some embodiments, a subject having hyperammonemia has a Child-Pugh score of 5, 6, 7, 8, 9, 10, 11, 12, 13, 14, or 15. In some embodiments, a subject having hyperammonemia has a Child-Pugh score of 5-6. In some embodiments, a subject having hyperammonemia has a Child-Pugh score of 7-9. In some embodiments, a subject having hyperammonemia has a Child-Pugh score of 10-15.

In some embodiments, a subject having hyperammonemia has high ammonia levels, e.g., blood ammonia levels, relative to subjects not having hyperammonemia. In some embodiments, a subject having hyperammonemia does not have high ammonia levels, e.g., blood ammonia levels, relative to subjects not having hyperammonemia.

In some embodiments, a subject having hyperammonemia has high Alanine Aminotransferase (ALT) levels relative to subjects not having hyperammonemia. In some embodiments, a subject having hyperammonemia does not have high Alanine Aminotransferase (ALT) levels relative to subjects not having hyperammonemia.

In some embodiments, a subject having hyperammonemia has high Gamma-Glutamyl Transferase (GGT) levels relative to subjects not having hyperammonemia. In some embodiments, a subject having hyperammonemia does not have high Gamma-Glutamyl Transferase (GGT) levels relative to subjects not having hyperammonemia.

In some embodiments, a subject has hyperammonemia that is caused or associated with, at least in part, by alcohol or alcoholic cirrhosis, optionally wherein the subject has previously been treated with lactulose or rifaximin, and optionally wherein the subject has high ammonia, high ALT, and/or high GGT levels.

In some embodiments, a subject has hyperammonemia that is caused or associated with, at least in part, by autoimmune hepatitis, chronic hepatitis B, or chronic hepatitis C, wherein the subject has not previously been treated with lactulose or rifaximin, and wherein the subject does not have high ammonia, high ALT, or high GGT levels.

In some embodiments, a subject has hyperammonemia that is caused or associated with, at least in part, by fatty liver or fatty liver disease, wherein the subject has not previously been treated with lactulose or rifaximin, and optionally wherein the subject has high ALT and/or high GGT levels.

In some embodiments, a subject has hyperammonemia that is caused or associated with, at least in part, by hepatitis C, optionally wherein the subject has not previously been treated with lactulose or rifaximin, and optionally wherein the subject has high ammonia, high ALT, and/or high GGT levels.

In some embodiments, a subject has hyperammonemia that is caused or associated with, at least in part, by iron overload and steatosis, wherein the subject has not previously been treated with lactulose or rifaximin, and wherein the subject has high ALT levels.

In some embodiments, a subject has hyperammonemia that is caused or associated with, at least in part, by nonalcoholic steatohepatitis, optionally wherein the subject has previously been treated with lactulose or rifaximin, and optionally wherein the subject has high ammonia, high ALT, and/or high GGT levels.

In some embodiments, a subject has hyperammonemia that is caused or associated with, at least in part, by primary biliary cirrhosis, wherein the subject has high GGT levels.

Glycan Compositions and Manufacture Thereof

Glycan compositions can comprise the glycans described herein, dietary fibers, such as, e.g., FOS (fructo-oligosaccharide), other sugars (e.g., monomers, dimers, such as, e.g., lactulose) and sugar alcohols, and optionally other components, such as, e.g., polyphenols, fatty acids, peptides, micronutrients, etc., such as those described in WO 2016/172658, "MICROBIOME REGULATORS AND RELATED USES THEREOF", and microbes, such as bacteria.

Glycan preparations described in WO 2016/122889 "GLYCAN THERAPEUTICS AND RELATED METHODS THEREOF" and WO 2016/172657, "GLYCAN THERAPEUTICS AND METHODS OF TREATMENT", which in their entirety are hereby incorporated by reference, are suitable for in the methods and compositions described herein.

Preparations comprising glycans can be generated using a non-enzymatic catalyst, e.g., the polymeric catalyst described in WO 2012/118767, "POLYMERIC ACID CATALYSTS AND USES THEREOF" or by other suitable methods. Other acid catalysts (e.g. solid catalysts) may be used. Methods to prepare the polymeric and solid-supported catalysts described herein can be found in WO 2014/031956, "POLYMERIC AND SOLID-SUPPORTED CATALYSTS, AND METHODS OF DIGESTING CELLULOSIC MATERIALS USING SUCH CATALYSTS." The glycans generated, e.g., by using the catalyst, for example as described in WO 2016/007778, "OLIGOSACCHARIDE COMPOSITIONS AND METHODS FOR PRODUCING THEREOF" are suitable for the methods and compositions described herein. All patent applications are incorporated herein by reference in their entirety.

In some embodiments, glycans are made using solid-phase oligosaccharide synthesis, e.g., using a variety of protection groups to accomplish glycan synthesis. Exemplary methods are described in "Solid-Phase Oligosaccharide Synthesis and Combinatorial Carbohydrate Libraries", Peter H. Seeberger and Wilm-Christian Haase, American Chemical Society, 2000; and "Opportunities and challenges in synthetic oligosaccharide and glycoconjugate research", Thomas J. Boltje et al., Nat Chem. 2009 Nov. 1; 1(8): 611-622.

In some embodiments, glycans may be synthesized using an enzyme catalyst (e.g., a glycosidase or glycosyltransferase, either isolated or expressed in bacteria) to synthesize the glycans by a polymerization reaction that creates oligomers from individual glycan subunits that are added to the reaction. Exemplary methods are described in "Synthesis and Purification of Galacto-Oligosaccharides: State of the Art", Carlos Vera et al., World J. Microbiol Biotechnol. 2016; 32:197; "Synthesis of Novel Bioactive Lactose-Derived Oligosaccharides by Microbial Glycoside Hydrolases", Marina Diez-Municio et al., Microbial Biotechnol. 2014; 7(4), 315-331; and "Methods of Improving Enzymatic Trans-Glycosylation for Synthesis of Human Milk Oligosaccharide Biomimetics", Birgitte Zeuner et al., J. Agric. Food Chem. 2014, 62, 9615-9631, WO 2005/003329 "NOVEL GALACTOOLIGOSACCHARIDE COMPOSITION AND THE PREPARATION THEREOF", all of which are hereby incorporated by reference.

In some embodiments, glycan preparations may be prepared using glycan polymers, such as starch and other fibers, such as dietary fibers (such as described herein) and subject them to a catalyst (e.g., an acid catalyst, a solid or polymeric catalyst, an enzyme catalyst) to change one or more glycan (or fiber) properties, e.g., degree of polymerization (e.g. depolymerization), degree of branching (e.g. debranching), or glycosidic bond distribution (e.g., by adding new types of glycosidic bonds or removing existing bonds). An exemplary method for corn syrup is described in U.S. Patent Publication No. 2016/0007642, Example 101, which is incorporated by reference. Other methods, such as those used for preparation of resistant starch (e.g., described in M. G. Sajilata et al., "Resistant Starch—A Review," Comprehensive Reviews in Food Science and Food Safety—Vol. 5, 2006, and U.S. Patent Publication No. 2006/0257977, "Slowly digestible starch"), such as, e.g., heat treatment, enzymic treatment, chemical treatment, or a combination thereof, may be used to produce glycan preparations described herein.

Glycan Preparation Properties

Glycan preparations may have any one or more of the characteristics and properties disclosed in WO2016/122889, WO2016/172657, WO 2016/007778, and WO2016/172658, each of which is incorporated herein by reference in its entirety, and any characteristics and properties disclosed herein.

The glycans produced by the methods described herein may comprise oligosaccharides. In some embodiments, the glycans comprise homo-oligosaccharides (or homoglycans), wherein all the monosaccharides in a polymer are of the same type.

In some embodiments, the glycans comprise hetero-oligosaccharides (or heteroglycans), wherein more than one type of monosaccharide is present in the polymer. In some embodiments, the glycans have one or more of the properties described herein. In some embodiments, the glycan preparation has one or more of the bulk properties described herein.

Degree of Polymerization (DP)

In some embodiments, glycan preparations are produced, e.g., using a method described herein, that are polydisperse, exhibiting a range of degrees of polymerization.

Optionally, the preparations may be fractionated, e.g. representing 60%, 65%, 70%, 75%, 80%, 85%, 90%, 95%, 97%, 98%, or greater than 98% short (about DP1-2), medium (about DP3-10), long (about DP11-18), or very long (about DP>18) species. In one embodiment, a polydisperse, fractionated glycan preparation is provided comprising at least 85%, 90%, or at least 95% medium-length species with a DP of about 3-10. In one embodiment, a polydisperse, fractionated glycan preparation is provided comprising at least 85%, 90%, or at least 95% long-length species with a DP of about 11-18. In one embodiment, a polydisperse, fractionated glycan preparation is provided comprising at least 85%, 90%, or at least 95% very long-length species with a DP of about 18-30.

Optionally, the preparations may be fractionated, e.g. representing 60%, 65%, 70%, 75%, 80%, 85%, 90%, 95%, 97%, 98%, or greater than 98% short (about DP1-2) or medium (about DP3-10) glycans in the preparation. Alternatively, or in addition to fractionation, the small DP fraction (e.g. monomers and dimers) are subjected to enzymatic fermentation, e.g. with suitable yeasts to break down these sugars. In one embodiment, a polydisperse, fractionated glycan preparation is prepared using a method described herein, comprising at least 85%, 90%, or at least 95% of glycans with a DP of about 3-10.

In some embodiments, about 55%, 60%, 65%, 70%, 75%, 80%, 85%, 90%, 95%, or about 97% of the glycans of the glycan preparation have a DP of at least DP3, DP4, DP5, DP6 or DP7. In some embodiments, about 55%, 60%, 65%, 70%, 75%, 80%, 85%, 90%, 95%, or about 97% of the glycans of the glycan preparation have a DP from about DP3 to about DP10, from about DP3 to about DP8, from about DP3 to about DP6, from about DP3 to about DP5, from about DP3 to about DP4, from about DP2 to about DP4, from about DP2 to about DP5, from about DP2 to about DP6, from about DP2 to about DP8, or from about DP2 to about DP10. In some embodiments, less than 1%, 2%, 3%, 5%, 10%, 15%, 20%, 25%, 30%, 40%, or less than 50% of the glycans of the glycan preparation have a DP of DP2 or less.

In some embodiments, about 55%, 60%, 65%, 70%, 75%, 80%, 85%, 90%, 95%, or about 97% of the glycan preparation has a DP of between 2 and 25, between 3 and 25, between 4 and 25, between 5 and 25, between 6 and 25, between 7 and 25, between 8 and 25, between 9 and 25, between 10 and 25, between 2 and 30, between 3 and 30, between 4 and 30, between 5 and 30, between 6 and 30, between 7 and 30, between 8 and 30, between 9 and 30, or between 10 and 30. In one embodiment, the glycan preparation has a degree of polymerization (DP) of at least 3 and less than 30 glycan units.

In some embodiments, about 55%, 60%, 65%, 70%, 75%, 80%, 85%, 90%, 95%, or about 97% of the glycan preparation has a DP of at least 5 and less than 30 glycan units. In some embodiments, about 55%, 60%, 65%, 70%, 75%, 80%, 85%, 90%, 95%, or about 97% of the glycan preparation has a DP of at least 8 and less than 30 glycan units. In some embodiments, about 55%, 60%, 65%, 70%, 75%, 80%, 85%, 90%, 95%, or about 97% of the glycan preparation has a DP of at least 10 and less than 30 glycan units. In some embodiments, about 55%, 60%, 65%, 70%, 75%, 80%, 85%, 90%, 95%, or about 97% of the glycan preparation has a DP of between 3, 4, 5, 6, 7, 8 and 10, 11, 12, 13, 14, 15, 16, 17, 18, 19, 20 glycan units. In some embodiments, about 55%, 60%, 65%, 70%, 75%, 80%, 85%, 90%, 95%, or about 97% of the glycan preparation has a DP of between 10, 11, 12, 13, 14, 15, 16, 17, 18, 19 and 20, 21, 22, 23, 24, 25, 26, 27, 28, 29, 30 glycan units. In some embodiments, about 55%, 60%, 65%, 70%, 75%, 80%, 85%, 90%, 95%, or about 97% of the glycan preparation has a DP of between 3, 4, 5, 6, 7, 8, 9, 10 and 20, 21, 22, 23, 24, 25, 26, 27, 28 glycan units. In one embodiment, about 55%, 60%, 65%, 70%, 75%, 80%, 85%, 90%, 95%, or about 97% of the glycan preparation has a DP of at least 2. In one embodiment, about 55%, 60%, 65%, 70%, 75%, 80%, 85%, 90%, 95%, or about 97% of the glycan preparation has a DP of at least 3.

Average DP

In some embodiments, the glycan preparation has an average degree of polymerization (average DP) of about DP2, DP3, DP4, DP5, DP6, DP7, DP8, or DP9. In some embodiments, the glycan preparation has an average degree of polymerization (average DP) of between about 2 and about 10, between about 2 and about 8, between about 2 and about 6, between about 2 and about 4, between about 3 and about 10, between about 3 and about 8, between about 3 and about 6, or between about 3 and about 4.

In some embodiments, about 55%, 60%, 65%, 70%, 75%, 80%, 85%, 90%, 95%, or about 97% of the glycan preparation has an average degree of polymerization (DP) of about DP5, DP6, DP7, DP8, DP9, DP10, DP11, or DP12. In some embodiments, the average DP of the glycan preparation is between about DP5 and DP10, between about DP6 and DP10, between about DP6 and DP12, between about DP6 and DP14, between about DP8 and DP12, between about DP8 and DP14, between about DP8 and DP16, between about DP10 and DP16 between about DP10 and DP18, between about DP4 and DP18, between about DP6 and DP18, or between about DP8 and DP18.

Average Molecular Weight

In some embodiments, about 55%, 60%, 65%, 70%, 75%, 80%, 85%, 90%, 95%, or about 97% of the glycans of the preparation have an average molecular weight of about 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800 g/mol and less than 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, and 5000 g/mol.

Degree of Branching (DB)

In some embodiments, the glycan preparations range in structure from linear to branched.

Branched glycans may contain at least one glycan subunit being linked via an alpha or a beta glycosidic bond so as to form a branch. The branching rate or degree of branching (DB) may vary, such that the glycans of a preparation comprise at least 1, at least 2, at least 3, at least 4, at least 5, or at least about 6 branching points in the glycan. In some embodiments, the glycans of the glycan preparation are unbranched (DB=0).

In some embodiments, the glycan preparations (e.g. oligo- or polysaccharides) range in structure from linear to highly branched. Unbranched glycans may contain only alpha linkages or only beta linkages. Unbranched glycans may contain at least one alpha and at least one beta linkage.

Branched glycans may contain at least one glycan unit being linked via an alpha or a beta glycosidic bond so as to form a branch. The branching rate or degree of branching (DB) may vary, such that about every $2^{nd}$, $3^{rd}$, $4^{th}$, $5^{th}$, $6^{th}$, $7^{th}$, $8^{th}$, $9^{th}$, $10^{th}$, $15^{th}$, $20^{th}$, $25^{th}$, $30^{th}$, $35^{th}$, $40^{th}$, $45^{th}$, $50^{th}$, $60^{th}$, or $70^{th}$ unit comprises at least one branching point. For example, animal glycogen contains a branching point approximately every 10 units.

In some embodiments, preparations of glycan are provided, wherein the preparation comprises a mixture of branched glycans, wherein the average degree of branching (DB, branching points per residue) is 0 (unbranched), 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 0.95, 0.99, 1, or 2. In some embodiments, preparations of glycans are provided, wherein the average degree of branching is at least 0.01, 0.05, 0.1, 0.2, 0.3, or at least 0.4. In some embodiments, preparations of glycans are provided, wherein the average degree of branching is between about 0.01 and 0.1, 0.01 and 0.2, 0.01 and 0.3, 0.01 and 0.4, 0.01 and 0.5, 0.01 and 0.6, or between about 0.01 and 0.7. In some embodiments, preparations of glycans are provided, wherein the average degree of branching is between about 0.05 and 0.1, 0.05 and 0.2, 0.05 and 0.3, 0.05 and 0.4, 0.05 and 0.5, 0.05 and 0.6, or between about 0.05 and 0.7. In some embodiments, preparations of glycans are provided, wherein the average degree of branching is not 0. In some embodiments, preparations of glycans are provided, wherein the average degree of branching is not between at least 0.1 and less than 0.4 or at least 0.2 and less than 0.4. In some embodiments, the preparations of glycans comprise linear glycans. In some embodiments, the preparations of glycans comprise glycans that exhibit a branched or branch-on-branch structure.

In some embodiments, preparations of glycans are provided wherein the average degree of branching (DB) is not 0, but is at least 0.01, 0.05, 0.1, or at least 0.2, or ranges between about 0.01 and about 0.2 or between about 0.05 and 0.1.

Glycosidic Bonds and Linkages

Linkages between the individual glycan subunits found in preparations of glycans may include alpha 1->2, alpha 1->3, alpha 1->4, alpha 1->5, alpha 1->6, alpha 2->1, alpha 2->3, alpha 2->4, alpha 2->6, beta 1->2, beta 1->3, beta 1->4, beta 1->5, beta 1->6, beta 2->1, beta 2->3, beta 2->4, and beta 2->6.

In some embodiments, the glycan preparations comprise only alpha linkages. In some embodiments, the glycans comprise only beta linkages. In some embodiments, the glycans comprise mixtures of alpha and beta linkages.

In some embodiments, the alpha:beta glycosidic bond ratio in a preparation is about 1:1, 2:1, 3:1, 4:1, or 5:1. In some embodiments, the beta:alpha glycosidic bond ratio in a preparation is about 1:1, 2:1, 3:1, 4:1, or 5:1.

In some embodiments, the alpha:beta glycosidic bond ratio in a preparation is about 0.1:1, 0.2:1, 0.3:1, 0.4:1, 0.5:1, 0.6:1, 0.7:1, 0.8:1, 0.9:1, 1:1, 1.2:1, 1.5:1, 1.7:1, 2:1, 2.2:1, 2.5:1, 2.7:1, 3:1, 4:1, 5:1, 6:1, 7:1, 8:1, 9:1, or about 10:1.

In some embodiments, the glycans of the glycan preparation comprise both alpha- and beta-glycosidic bonds selected from the group consisting of 1->2 glycosidic bond, a 1->3 glycosidic bond, a 1->4 glycosidic bond, a 1->5 glycosidic bond and a 1->6 glycosidic bond. In some embodiments, the glycan preparation comprises at least two or at least three alpha and beta 1->2 glycosidic bonds, alpha and beta 1->3 glycosidic bonds, alpha and beta 1->4 glycosidic bonds, alpha and beta 1->5 glycosidic bonds, and/or alpha and beta 1->6 glycosidic bonds.

In some embodiments, the glycans of the glycan preparation comprise substantially all alpha- or beta configured glycan subunits, optionally comprising about 1%, 2%, 3%, 4% 5%, 6%, 7%, 8%, 9%, 10%, 11%, 12%, 13%, 14%, 15%, 16%, 17%, 18%, 19%, or 20% of the respective other configuration.

In some embodiments, the preparations of glycans comprise at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, 98%, 99%, at least 99.9% or even 100% glycans with alpha glycosidic bonds. In some embodiments, the preparations of glycans comprise at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, 98%, 99%, at least 99.9% or even 100% glycans with beta glycosidic bonds. In some embodiments, preparations of glycans are provided, wherein at least 10%, 15%, 20%, 25%, 30%, 35%, 40%, 45%, 50%, 55%, 60%, 65%, 70%, 75%, 80%, or at least 85% of glycans with glycosidic bonds that are alpha glycosidic bonds, at least 10%, 15%, 20%, 25%, 30%, 35%, 40%, 45%, 50%, 55%, 60%, 65%, 70%, 75%, 80%, or at least 85% of glycans with glycosidic bonds that are beta glycosidic bonds, and wherein the percentage of alpha and beta glycosidic bonds does not exceed 100%.

In some embodiments, preparations of glycans are provided, wherein at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, 98%, 99%, at least 99.9% or even 100% of glycan glycosidic bonds are one or more of: 1->2 glycosidic bonds, 1->3 glycosidic bonds, 1->4 glycosidic bonds, and 1->6 glycosidic bonds. In some embodiments, preparations of glycans are provided, wherein at least 1%, 2%, 3%, 4%, 5%, 6%, 7%, 8%, 9%, 10%, 15%, at least 20%, or 25% each of glycan glycosidic bonds are 1->2, 1->3, 1->4, and 1->6 glycosidic bonds.

Optionally, the preparations of glycans further comprise at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, or at least 85% of glycan glycosidic bonds that are selected from the group consisting of: alpha 2->1, alpha 2->3, alpha 2->4, alpha 2->6, beta 2->1, beta 2->3, beta 2->4, and beta 2->6, glycosidic bonds.

In some embodiments, the glycans of the glycan preparation comprise at least two glycosidic bonds selected from the group consisting of alpha 1→2 and alpha 1→3, alpha 1→2 and alpha 1→4, alpha 1→2 and alpha 1→6, alpha 1→2 and beta 1→2, alpha 1→2 and beta 1→3, alpha 1→2 and beta 1→4, alpha 1→2 and beta 1→6, alpha 1→3 and alpha 1→4, alpha 1→3 and alpha 1→6, alpha 1→3 and beta 1→2, alpha 1→3 and beta 1→3, alpha 1→3 and beta 1→4, alpha 1→3 and beta 1→6, alpha 1→4 and alpha 1→6, alpha 1→4 and beta 1→2, alpha 1→4 and beta 1→3, alpha 1→4 and beta 1→4, alpha 1→4 and beta 1→6, alpha 1→6 and beta 1→2, alpha 1→6 and beta 1→3, alpha 1→6 and beta 1→4, alpha 1→6 and beta 1→6, beta 1→2 and beta 1→3, beta 1→2 and beta 1→4, beta 1→2 and beta 1→6, beta 1→3 and beta 1→4, beta 1→3 and beta 1→6, and beta 1→4 and beta 1→6.

L- and D-Forms

In some embodiments, preparations of glycans are provided, wherein at least one glycan subunit is a sugar in L-form. In some embodiments, preparations of glycans are provided, wherein at least one glycan subunit is a sugar in D-form. In some embodiments, preparations of glycans are provided, wherein the glycan subunits are sugars in L- or D-form as they naturally occur or are more common (e.g. D-glucose, D-xylose, L-arabinose).

In some embodiments, the preparation of glycans (e.g. oligosaccharides and polysaccharides) comprises a desired mixture of L- and D-forms of glycan subunits, e.g. of a desired ratio, such as: 1:1, 1:2, 1:3, 1:4, 1:5 L- to D-forms or D- to L-forms.

In some embodiments, the preparation of glycans comprises a desired mixture of L- and D-forms of glycan units, e.g. of a desired ratio, such as: 1:1, 1:2, 1:3, 1:4, 1:5, 1:6, 1:7, 1:8, 1:9, 1:10, 1:12, 1:14, 1:16, 1:18, 1:20, 1:25, 1:30, 1:35, 1:40, 1:45, 1:50, 1:55, 1:60, 1:65, 1:70, 1:75, 1:80, 1:85, 1:90, 1:100, 1:150 L- to D-forms or D- to L-forms.

In some embodiments, the preparation of glycans comprises glycans with substantially all L- or D-forms of glycan subunits, optionally comprising about 1%, 2%, 3%, 4% 5%, 6%, 7%, 8%, 9%, 10%, 11%, 12%, 13%, 14%, 15%, 16%, 17%, 18%, 19%, or 20% of the respective other form.

Glycan Unit Content

In some embodiments, preparations of glycans are provided, wherein at least one glycan subunit is a tetrose, a pentose, a hexose, or a heptose. Optionally, the glycan subunits involved in the formation of the glycans of the glycan preparation are varied. Examples of monosaccharide glycan subunits include hexoses, such as glucose, galactose, and fructose, and pentoses, such as xylose. Monosaccharides generally have the chemical formula: $C_x(H_2O)_y$, where conventionally $x \geq 3$. Monosaccharides can be classified by the number x of carbon atoms they contain, for example: diose (2) triose (3) tetrose (4), pentose (5), hexose (6), and heptose (7). The monosaccharide glycan subunits may exist in an acyclic (open-chain) form. Open-chain monosaccharides with same molecular graph may exist as two or more stereoisomers. The monosaccharides may also exist in a cyclic form through a nucleophilic addition reaction between the carbonyl group and one of the hydroxyls of the same molecule. The reaction creates a ring of carbon atoms closed by one bridging oxygen atom. In these cyclic forms, the ring usually has 5 (furanoses) or 6 atoms (pyranoses).

In some embodiments, the preparation of glycans comprises a desired mixture of different monosaccharide glycan subunits, such as a mixture of a diose (2), a triose (3), tetrose (4), pentose (5), hexose (6), or heptose (7). In some embodiments, the glycans of the glycan preparation comprise a desired mixture of a pentose (5) and a hexose (6).

In some embodiments, the preparation of glycans comprises a desired mixture of two, three, four or five different glycan subunits, such as a mixture of, e.g., i) one or more glycan subunits selected from monosaccharides, selected from glucose, a galactose, an arabinose, a mannose, a fructose, a xylose, a fucose, and a rhamnose; ii) one or more glycan subunits selected from disaccharides selected from acarviosin, n-acetyllactosamine, allolactose, cellobiose, chitobiose, glactose-alpha-1,3-galactose, gentiobiose, isomalt, isomaltose, isomaltulose, kojibiose, lactitol, lactobionic acid, lactose, lactulose, laminaribiose, maltitol, maltose, mannobiose, melibiose, melibiulose, neohesperidose, nigerose, robinose, rutinose, sambubiose, sophorose, sucralose, sucrose, sucrose acetate isobutyrate, sucrose octaacetate, trehalose, turanose, vicianose, and xylobiose; iii) one or more glycan subunits selected from amino sugars selected from acarbose, N-acetylemannosamine, N-acetylmuramic acid, N-acetylnueraminic acid, N-acetyletalosaminuronic acid, arabinopyranosyl-N-methyl-N-nitrosourea, D-fructose-L-histidine, N-glycolyneuraminic acid, ketosamine, kidamycin, mannosamine, 1B-methylseleno-N-acetyl-D-galactosamine, muramic acid, muramyl dipeptide, phosphoribosylamine, PUGNAc, sialyl-Lewis A, sialyl-Lewis X, validamycin, voglibose, N-acetylgalactosamine, N-acetylglucosamine, aspartylglucosamine, bacillithiol, daunosamine, desosamine, fructosamine, galactosamine, glucosamine, meglumine, and perosamine; iv) one or more glycan subunits selected from deoxy sugars selected from 1-5-ahydroglucitol, cladinose, colitose, 2-deoxy-D-glucose, 3-deoxyglucasone, deoxyribose, dideoxynucleotide, digitalose, fludeooxyglucose, sarmentose, and sulfoquinovose; v) one or more glycan subunits selected from imino sugars selected from castanospermine, 1-deoxynojirimycin, iminosugar, miglitol, miglustat, and swainsonine; one or more glycan subunits selected from sugar acids selected from N-acetylneuraminic acid, N-acetyltalosamnuronic acid, aldaric acid, aldonic acid, 3-deoxy-D-manno-oct-2-ulosonic acid, glucuronic acid, glucosaminuronic acid, glyceric acid, N-glycolylneuraminic acid, iduronic acid, isosaccharinic acid, pangamic acid, sialic acid, threonic acid, ulosonic acid, uronic acid, xylonic acid, gluconic acid, ascorbic acid, ketodeoxyoctulosonic acid, galacturonic acid, galactosaminuronic acid, mannuronic acid, mannosaminuronic acid, tartaric acid, mucic acid, saccharic acid, lactic acid, oxalic acid, succinic acid, hexanoic acid, fumaric acid, maleic acid, butyric acid, citric acid, glucosaminic acid, malic acid, succinamic acid, sebacic acid, and capric acid; vi) one or more glycan subunits selected from short-chain fatty acids selected from formic acid, acetic acid, propionic acid, butyric acid, isobutyric acid, valeric acid, and isovaleric acid; and vii) one or more glycan subunits selected from sugar alcohols selected from methanol, ethylene glycol, glycerol, erythritol, threitol, arabitol, ribitol, xylitol, mannitol, sorbitol, galactitol, iditol, volemitol, fucitol, inositol, maltotritol, maltotetraitol, and polyglycitol. Exemplary glycans are described by a three-letter code representing the monomeric sugar component followed by a number out of one hundred reflecting the percentage of the material that monomer constitutes. Thus, 'glu100' is ascribed to a glycan generated from a 100% D-glucose (glycan unit) input and 'glu50gal50' is ascribed to a glycan generated from 50% D-glucose and 50% D-galactose (glycan units) input or, alternatively from a lactose dimer (glycan unit) input. As used herein: xyl=D-xylose; ara=L-arabinose; gal=D-galactose; glu=D-glucose; rha=L-rhamnose; fuc=L-fucose; man=D-mannose; sor=D-sorbitol; gly=D-glycerol; neu=NAc-neuraminic acid.

In some embodiments, the preparation of glycans comprises one glycan unit A selected from i) to vii) above, wherein glycan unit A comprises 100% of the glycan unit input. For example, in some embodiments, the glycan preparation is selected from the homo-glycans xyl100, rha100, ara100, gal100, glu100, and man100. In some embodiments, the glycan preparation is selected from the homo-glycans fuc100 and fru100.

In some embodiments, the preparation of glycans comprises a mixture of two glycan units A and B selected independently from i) to vii) above, wherein A and B may be selected from the same or a different group i) to vii) and wherein A and B may be selected in any desired ratio (e.g. anywhere from 1-99% A and 99-1% B, not exceeding 100%).

For example, in some embodiments, the glycan preparation is selected from the hetero-glycans ara50gal50, ara50gal50, xyl75gal25, ara80xyl20, ara60xyl40, ara50xyl50, glu80man20, glu60man40, man80glu20, man60glu40, xyl75ara25, gal75xyl25, man80gal20, gal75xyl25, man66gal33, man75gal25, glu80gal20, glu60gal40, glu40gal60, glu20gal80, gal80man20, gal60man40, gal40man60, glu80xyl20, glu60xyl40, glu40xyl60, glu20xyl80, gal80ara20, glu60ara40, glu40ara60, glu20ara80, gal80xyl20, gal60xyl40, gal40xyl60, gal20xyl80, gal80ara20, gal60ara40, gal40ara60, gal20ara80, man80xyl20, man60xyl40, man40xyl60, man20xyl80, man80ara20, man60ara40, man40ara60, man20ara80, xyl80ara20, xyl60ara40, glu50gal50, and man62glu38.

In some embodiments, the preparation of glycans comprises a mixture of three glycan units A, B and C selected independently from i) to vii) above, wherein A, B and C may be selected from the same or a different group i) to vii) and wherein A, B and C may be selected in any desired ratio (e.g. anywhere from 1-99% A, 1-99% B, 1-99% C, not exceeding 100%).

For example, in some embodiments, the glycan preparation is selected from the hetero-glycans xyl75glu12gal12, xyl33glu33gal33, xyl75glu12gal12, glu33gal33fuc33, glu33gal33nman33, glu33gal33xyl33, glu33gal33ara33, gal33man33xyl33, gal33man33ara33, man52glu29gal19, glu33man33xyl33, glu33man33ara33, glu33xyl33ara33, gal33man33xyl33, gal33man33ara33, gal33xyl33ara33, man33xyl33ara33, glu90gal5man5, glu80gal10man10, glu60gal20man20, glu40gal30man30, glu20gal40man40, glu10gal45man45, glu5gal90man5, glu10gal80man10, glu20gal60man20, glu30gal40man30, glu40gal20man40, glu45gal10man45, glu5gal5man90, glu10gal10man80, glu20gal20man60, glu30gal30man40, glu40gal40man20, and glu45gal45man10.

In some embodiments, the preparation of glycans comprises a mixture of four glycan units A, B, C and D selected independently from i) to vii) above, wherein A, B, C and D may be selected from the same or a different group i) to vii) and wherein A, B, C and D may be selected in any desired ratio (e.g. anywhere from 1-99% A, 1-99% B, 1-99% C, 1-99% D, not exceeding 100%). In some embodiments, the preparation of glycans comprises a mixture of five glycan units A, B, C, D and E selected independently from i) to vii) above, wherein A, B, C, D and E may be selected from the same or a different group i) to vii) and wherein A, B, C, D and E may be selected in any desired ratio (e.g. anywhere from 1-99% A, 1-99% B, 1-99% C, 1-99% D, 1-99% E, not exceeding 100%).

Provided herein are glycan preparations (as described herein, e.g., having any DP, DB, alpha:beta glycosidic bond ratio, number of glycosidic bonds, bond regiochemistry and bond stereochemistry, and other characteristics (e.g., solubility, fermentability, viscosity, sweetness, etc.) described herein), comprising glycans comprising:

a glucose glycan unit, optionally wherein the glycan preparation comprises any amount of glucose between 1% and 100%, further optionally wherein the glycan preparation comprises a second, third, fourth or fifth glycan unit (optionally, independently selected from xylose, arabinose, galactose, mannose, rhamnose, fructose, or fucose), further optionally, wherein the glycan preparation is one of: gal50glu25fru25, gal57glu43, gal57glu43, glu100, glu10gal10man80, glu10gal45man45, glu10gal80man10, glu20ara80, glu20gal20man20xyl20ara20, glu20gal20man60, glu20gal40man40, glu20gal60man20, glu20gal80, glu20xyl80, glu25gal25man25ara25, glu25gal25man25xyl25, glu25gal25xyl25ara25, glu25man25xyl25ara25, glu30gal30man40, glu30gal40man30, glu33gal33ara33, glu33gal33fuc33, glu33gal33man33, glu33gal33xyl33, glu33man33ara33, glu33man33xyl33, glu33xyl33ara33, glu40ara60, glu40gal20man40, glu40gal30man30, glu40gal40man20, glu40gal60, glu40xyl60, glu45gal10man45, glu45gal45man10, glu50gal50, glu5gal5man90, glu5gal90man5, glu60ara40, glu60gal20man20, glu60gal40, glu60man40, glu60xyl40, glu66fru33, glu80ara20, glu80gal10man10, glu80gal20, glu80man20, glu80man20, glu80xyl20, glu90gal5man5, man52glu29gal19, man60glu40, man62glu38, man80glu20, xyl33glu33gal33, or xyl75glu12gal12;

a galactose glycan unit, optionally wherein the glycan preparation comprises any amount of galactose between 1% and 100%, further optionally wherein the glycan preparation comprises a second, third, fourth or fifth glycan unit (optionally, independently selected from xylose, arabinose, glucose, mannose, rhamnose, fructose, or fucose), further optionally, wherein the glycan preparation is one of: ara50gal50, gal100, gal20ara80, gal20xyl80, gal25man25xyl25ara25, gal33man33ara33, gal33man33xyl33, gal33xyl33ara33, gal40ara60, gal40man60, gal40xyl60, gal50glu25fru25, gal57fru43, gal57glu43, gal60ara40, gal60man40, gal60xyl40, gal75xyl25, gal80ara20, gal80man20, gal80xyl20, glu10gal10man80, glu10gal45man45, glu10gal80man10, glu20gal20man20xyl20ara20, glu20gal20man60, glu20gal40man40, glu20gal60man20, glu20gal80, glu25gal25man25ara25, glu25gal25man25xyl25, glu25gal25xyl25ara25, glu30gal30man40, glu30gal40man30, glu33gal33ara33, glu33gal33fuc33, glu33gal33man33, glu33gal33xyl33, glu40gal20man40, glu40gal30man30, glu40gal40man20, glu40gal60, glu45gal10man45, glu45gal45man10, glu50gal50, glu5gal5man90, glu5gal90man5, glu60gal20man20, glu60gal40, glu80gal10man10, glu80gal20, glu90gal5man5, man52glu29gal19, man66gal33, man75gal25, man80gal20, xyl33glu33gal33, xyl75gal25, or xyl75glu12gal12;

a mannose glycan unit, optionally wherein the glycan preparation comprises any amount of mannose between 1% and 100%, further optionally wherein the glycan preparation comprises a second, third, fourth or fifth glycan unit (optionally, independently selected from xylose, arabinose, glucose, galactose, rhamnose, fructose, or fucose), further optionally, wherein the glycan preparation is one of: gal25man25xyl25ara25, gal33man33ara33, gal33man33xyl33, gal40man60, gal60man40, gal80man20, glu10gal10man80, glu10gal45man45, glu10gal80man10, glu20gal20man20xyl20ara20, glu20gal20man60, glu20gal40man40, glu20gal60man20, glu25gal25man25ara25, glu25gal25man25xyl25, glu25man25xyl25ara25, glu30gal30man40, glu30gal40man30, glu33gal33man33, glu33man33ara33, glu33man33xyl33, glu40gal20man40, glu40gal30man30, glu40gal40man20, glu45gal10man45, glu45gal45man10, glu5gal5man90, glu5gal90man5, glu60gal20man20, glu60man40, glu80gal10man10, glu80man20, glu80man20, glu90gal5man5, man100, man20ara80, man20xyl80, man33xyl33ara33, man40ara60, man40xyl60, man52glu29gal19, man60ara40, man60glu40, man60xyl40, man62glu38, man66gal33, man75gal25, man80ara20, man80gal20, man80glu20, or man80xyl20;

an arabinose glycan unit, optionally wherein the glycan preparation comprises any amount of arabinose between 1% and 100%, further optionally wherein the glycan preparation comprises a second, third, fourth or fifth glycan unit (optionally, independently selected from xylose, glucose, galactose, mannose, rhamnose, fructose, or fucose), further optionally, wherein the glycan preparation is one of: ara100, ara50gal50, ara50xyl50, ara60xyl40, ara80xyl20, gal20ara80, gal25man25xyl25ara25, gal33man33ara33, gal33xyl33ara33, gal40ara60, gal60ara40, gal80ara20, glu20ara80, glu20gal20man20xyl20ara20, glu25gal25man25ara25, glu25gal25xyl25ara25, glu25man25xyl25ara25, glu33gal33ara33, glu33man33ara33, glu33xyl33ara33, glu40ara60, glu60ara40, glu80ara20, man20ara80, man33xyl33ara33, man40ara60, man60ara40, man80ara20, xyl60ara40, xyl75ara25, or xyl80ara20;

a xylose glycan unit, optionally wherein the glycan preparation comprises any amount of xylose between 1% and 100%, further optionally wherein the glycan preparation comprises a second, third, fourth or fifth glycan unit (optionally, independently selected from arabinose, glucose, galactose, mannose, rhamnose, fructose, or fucose), further optionally, wherein the glycan preparation is one of: ara50xyl50, ara60xyl40, ara80xyl20, gal20xyl80, gal25man25xyl25ara25, gal33man33xyl33, gal33xyl33ara33, gal40xyl60, gal60xyl40, gal75xyl25, gal80xyl20, glu20gal20man20xyl20ara20, glu20xyl80, glu25gal25man25xyl25, glu25gal25xyl25ara25, glu25man25xyl25ara25, glu33gal33xyl33, glu33man33xyl33, glu33xyl33ara33, glu40xyl60, glu60xyl40, glu80xyl20, man20xyl80, man33xyl33ara33, man40xyl60, man60xyl40, man80xyl20, xyl100, xyl33glu33gal33, xyl60ara40, xyl75ara25, xyl75gal25, xyl75glu12gal12, or xyl80ara20;

a fructose glycan unit, optionally wherein the glycan preparation comprises any amount of fructose between 1% and 100%, further optionally wherein the glycan preparation comprises a second, third, fourth or fifth glycan unit (optionally, independently selected from xylose, arabinose, glucose, galactose, mannose, rhamnose, or fucose), further optionally, wherein the glycan preparation is one of: fru100, gal50glu25fru25, gal57fru43, or glu66fru33; a fucose glycan unit, optionally wherein the glycan preparation comprises any amount of fucose between 1% and 100%, further optionally wherein the glycan preparation comprises a second, third, fourth or fifth glycan unit (optionally, independently selected from xylose, arabinose, glucose, galactose, mannose, rhamnose, or fructose), further optionally, wherein the glycan preparation is one of: glu33gal33fuc33;

a rhamnose glycan unit, optionally wherein the glycan preparation comprises any amount of rhamnose between 1% and 100%, further optionally wherein the glycan preparation comprises a second, third, fourth or fifth glycan unit (optionally, independently selected from xylose, arabinose, glucose, galactose, mannose, fructose, or fucose), further optionally, wherein the glycan preparation is rha100; and further, optionally, wherein the glycan preparation comprises one or more (e.g., two, three, four, five, six, seven, eight, or nine) of the following properties (including bulk properties):

i) the glycan preparation comprises glycans that comprise glucose, galactose, arabinose, mannose, fructose, xylose, fucose, or rhamnose glycan units;

ii) the average degree of branching (DB) of the glycans in the glycan preparation is 0, between 0.01 and 0.6, between 0.05 and 0.5, between 0.1 and 0.4, or between 0.15 and 0.4;

iii) at least 50% (at least 60%, 65%, 70%, 75%, 80%, or 85%, or less than 50%) of the glycans in the glycan preparation have a degree of polymerization (DP) of at least 3 and less than 30 glycan units, at least 2 and less than 10 glycan units, at least 5 and less than 25 glycan units, or at least 10 and less than 35 glycan units (optionally, wherein the glycan unit is a monomer, e.g., a monosugar);

iv) the average DP (mean DP) of the glycan preparation is between about 2 and 5, between about 5 and 8, between about 8 and 13, between about 13 and 25, between about 5 and 15, between about 5 and 20, or between about 5-15;

v) the ratio of alpha- to beta-glycosidic bonds present in the glycans of the glycan preparation is 0, or between about 0.8:1 to about 5:1, between about 1:1 to about 5:1, between about 1:1 to about 3:1, between about 3:2 to about 2:1, or between about 3:2 to about 3:1, vi) the glycan preparation comprises between 15 mol % and 75 mol % (between 20 mol % and 60 mol %, between 25 mol % and 50 mol %, or between 30 mol % and 45 mol %) 1,6 glycosidic bonds;

vii) the glycan preparation comprises between 1 mol % and 40 mol % (between 1 mol % and 30 mol %, between 5 mol % and 25 mol %, between 10 mol % and 20 mol %) of at least one, two, or three of 1,2; 1,3; and 1,4 glycosidic bonds;

viii) the glycan preparation has a final solubility limit in water of at least about 50 (at least about 60, 70, at least about 75, or less than 50) Brix at 23° C.; or ix) the glycan preparation has a dietary fiber content (e.g., as measured by AOAC 2009.01) of at least 50% (at least 60%, 70%, 80%, or at least 90%, or less than 50%), x) any combination of:
two of: i), ii), iii), iv), v), vi), vii), viii), and ix);
three of: i), ii), iii), iv), v), vi), vii), viii), and ix);
four of: i), ii), iii), iv), v), vi), vii), viii), and ix);
five of: i), ii), iii), iv), v), vi), vii), viii), and ix);
six of: i), ii), iii), iv), v), vi), vii), viii), and ix);
seven of: i), ii), iii), iv), v), vi), vii), viii), and ix);
eight of: i), ii), iii), iv), v), vi), vii), viii), and ix); or
all of: i), ii), iii), iv), v), vi), vii), viii), and ix).

In some embodiments, preparations of glycans are provided, wherein at least one glycan subunit is selected from the group consisting of a glucose, a galactose, an arabinose, a mannose, a fructose, a xylose, a fucose, and a rhamnose. In one embodiment, glycan preparations are provided, wherein at least one glycan subunit is glucose. In one embodiment, glycan preparations are provided, comprising at least 90%, 95%, at least 99% or 100% glycans consisting of glucose. In some embodiments, glycan preparations comprise glu100.

In some embodiments, preparations of glycans for use in the methods described herein, e.g., methods for treating a UCD (e.g., CPSI, OTC, ASS, ASL, NAGS, or arginase deficiency), methods for increasing or decreasing an enzymatic activity, methods for decreasing the level of a metabolite (e.g., ammonia, citrulline, argininosuccinic acid, glutamine, glutamate, orotic acid, or arginine), or methods for identifying or selecting treatment regimens, e.g., for treating a UCD, comprise, consist of, or consist essentially of gal100, glu10gal10man80, glu30gal30man40, gal33man33xyl33, glu40gal30man30, glu40gal20man40, glu45gal10man45, glu60gal20man20, fructo-oligosaccharide, glu40gal40man20, glu20gal20man20xyl20ara20, glu90gal5man5, glu80xyl20, glu20gal80, glu80ara20, glu40gal60, glu33gal33man33, man100, lactulose, glu80gal10man10, man80glu20, glu50gal50, glu80gal20, glu80man20, glu45gal45man10, glu60gal40, glu60man40, man80gal20, man60glu40, glu100, Glu100-114, Lara100-1, Gal50Fru50-2, Glu100-3, Glu100-94, Fru100-9, Glu100-22, and/or Glu100-107.

In some embodiments, the preparation of glycans comprises a desired mixture of two different monosaccharide glycan subunits, such as a mixture of, e.g., glucose and galactose, glucose and arabinose, glucose and mannose, glucose and fructose, glucose and xylose, glucose and fucose, glucose and rhamnose, galactose and arabinose, galactose and mannose, galactose and fructose, galactose and xylose, galactose and fucose, and galactose and rhamnose, arabinose and mannose, arabinose and fructose, arabinose and xylose, arabinose and fucose, and arabinose and rhamnose, mannose and fructose, mannose and xylose, mannose and fucose, and mannose and rhamnose, fructose and xylose, fructose and fucose, and fructose and rhamnose, xylose and fucose, xylose and rhamnose, and fucose and rhamnose, e.g. in a ratio of 1:1, 1:2, 1:3, 1:4, or 1:5 or the reverse ratio thereof, or a in a ratio of 1:1, 1:2, 1:3, 1:4, 1:5, 1:6, 1:7, 1:8, 1:9, 1:10, 1:12, 1:14, 1:16, 1:18, 1:20, 1:25, 1:30, 1:35, 1:40, 1:45, 1:50, 1:55, 1:60, 1:65, 1:70, 1:75, 1:80, 1:85, 1:90, or 1:100 or the reverse ratio thereof.

In some embodiments, the preparation of glycans comprises a desired mixture of three different monosaccharide glycan subunits, such as a mixture of, e.g. for glucose-containing glycan preparations, glucose, galactose and arabinose; glucose, galactose and mannose; glucose, galactose and fructose; glucose, galactose and xylose; glucose, galactose and fucose, glucose, galactose and rhamnose; glucose, arabinose, and mannose; glucose, arabinose and fructose; glucose, arabinose and xylose; glucose, arabinose and fucose; glucose, arabinose and rhamnose; glucose, mannose and fructose; glucose, mannose and xylose; glucose, mannose and fucose; glucose, mannose rhamnose; glucose, fructose and xylose; glucose, fructose and fucose; glucose, fructose and rhamnose; glucose, fucose and rhamnose, e.g. in a ratio of 1:1:1, 1:2:1, 1:3:1, 1:4:1, 1:5:1, 1:1:2, 1:2:2, 1:3:2, 1:4:2, 1:1:3, 1:2:3, 1:3:3, 1:1:4, 1:2:4, 1:1:5, 1:2:5, etc., or. a in a ratio of 1:1:1, 1:2:1, 1:3:1, 1:4:1, 1:5:1, 1:6:1, 1:7:1, 1:8:1, 1:9:1, 1:10:1, 1:12:1, 1:14:1, 1:16:1, 1:18:1, 1:20:1, 1:1:2, 1:2:2, 1:3:2, 1:4:2, 1:5:2, 1:6:2, 1:7:2, 1:8:2, 1:9:2, 1:10:2, 1:1:3, 1:2:3, 1:3:3, 1:4:3, 1:5:3, 1:6:3, 1:7:3, 1:8:3, 1:9:3, 1:10:3, 1:1:4, 1:2:4, 1:3:4, 1:4:4, 1:5:4, 1:6:4, 1:7:4, 1:8:4, 1:9:4, 1:10:4, 1:1:5, 1:2:5, 1:3:5, 1:4:5, 1:5:5, 1:6:5, 1:7:5, 1:8:5, 1:9:5, 1:10:5, etc.

In some embodiments, the preparation of glycans does not comprise N-acetylgalactosamine or N-acetylglucosamine. In some embodiments, the preparation of glycans does not comprise sialic acid. In some embodiments, the preparation of glycans does not comprise a lipid and fatty acid.

In some embodiments, the preparation of glycans does not comprise an amino acid.

Furanose: Pyranose

In some embodiments, preparations of glycans are provided, wherein at least one glycan subunit is a furanose sugar. In some embodiments, preparations of glycans are provided, wherein at least one glycan subunit is a pyranose sugar. In some embodiments, glycans comprise mixtures of furanose and pyranose sugars. In some embodiments, the furanose: pyranose sugar ratio in a preparation is about 0.1:1, 0.2:1, 0.3:1, 0.4:1, 0.5:1, 0.6:1, 0.7:1, 0.8:1, 0.9:1, 1:1, 1.2:1, 1.5:1, 1.7:1, 2:1, 2.2:1, 2.5:1, 2.7:1, 3:1, 4:1, 5:1, or about 6:1 or the furanose: pyranose sugar ratio in a preparation is about 7:1, 8:1, 9:1, or about 10:1.

In some embodiments, the preparation of glycans comprises substantially all furanose or pyranose sugar, optionally comprising 1%, 2%, 3%, 4% 5%, 6%, 7%, 8%, 9%, 10%, 11%, 12%, 13%, 14%, 15%, 16%, 17%, 18%, 19%, or 20% of the respective other sugar.

In some embodiments, the preparation of glycans comprises substantially all pyranose sugar and no more than about 0.1%, 02%, 0.5%, 1%, 2%, 3%, 4%, or no more than 5% of glycan units in the preparation in furanose form. In some embodiments, no more than 3%, 2% or no more than 1% of monomeric glycan units in the preparation are in furanose form.

Salts

In some embodiments, the preparation of glycans comprises a glycan subunit or plurality of glycan subunits present in a salt form (e.g., a pharmaceutically acceptable salt form), such as, e.g., a hydrochlorate, hydroiodate, hydrobromate, phosphate, sulfate, methanesulfate, acetate, formate, tartrate, malate, citrate, succinate, lactate, gluconate, pyruvate, fumarate, propionate, aspartate, glutamate, benzoate, ascorbate salt.

Derivatization

If desired, the monosaccharide or oligosaccharide glycan subunits of the glycans are further substituted or derivatized, e.g., hydroxyl groups can be etherified or esterified. For example, the glycans (e.g. oligo- or polysaccharide) can contain modified saccharide units, such as 2'-deoxyribose wherein a hydroxyl group is removed, 2'-fluororibose wherein a hydroxyl group is replaced with a fluorine, or N-acetylglucosamine, a nitrogen-containing form of glucose (e.g., 2'-fluororibose, deoxyribose, and hexose). The degree of substitution (DS, average number of hydroxyl groups per glycosyl unit) can be 1, 2, or 3, or another suitable DS. In some embodiments, 1%, 2%, 3%, 4% 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 80%, 85%, 90%, 95%, 96%, 97%, 98%, 99%, or 100% of glycan subunits are substituted or derivatized. In some embodiments, the degree of substitution varies between subunits, e.g., a certain percentage is not derivatized, exhibits a DS of 1, exhibits a DS of 2, or exhibits a DS of 3. Any desired mixture can be generated, e.g. 0-99% of subunits are not derivatized, 0-99% of subunits exhibit a DS of 1, 0-99% of subunits exhibit a DS of 2, and 0-99% of subunits exhibit a DS of 3, with the total making up 100%. The degree of substitution can be controlled by adjusting the average number of moles of substituent added to a glycosyl moiety (molar substitution (MS)). The distribution of substituents along the length of the glycan oligo- or polysaccharide chain can be controlled by adjusting the reaction conditions, reagent type, and extent of substitution. In some embodiments, the monomeric subunits are substituted with one or more of an acetate ester, sulfate half-ester, phosphate ester, or a pyruvyl cyclic acetal group.

Solubility

In some embodiments, the glycans in a preparation are highly soluble. In some embodiments, glycan preparations can be concentrated to at least to 55 Brix, 65 Brix, 60 Brix, 65 Brix, 70 Brix, 75 Brix, 80 Brix, or at least 85 Brix without obvious solidification or crystallization at 23° C. (final solubility limit). In some embodiments, glycan preparations are concentrated to at least about 0.5 g/ml, 1 g/ml, 1.5 g/ml, 2 g/ml, 2.5 g/ml, 3 g/ml, 3.5 g/ml or at least 4 g/ml without obvious solidification or crystallization at 23° C. (final solubility limit).

In some embodiments, the glycan preparations (e.g. oligosaccharides) are branched, e.g. have an average DB of at least 0.01, 0.05, or 0.1 and has a final solubility limit in water of at least about 70 Brix, 75 Brix, 80 Brix, or at least about 85 Brix at 23° C. or is at least about 1 g/ml, 2 g/ml or at least about 3 g/ml.

In some embodiments, the preparation of glycans has a final solubility limit of at least 0.001 g/L, 0.005 g/L, 0.01 g/L, 0.05 g/L, 0.1 g/L, 0.2 g/L, 0.3 g/L, 0.4 g/L, 0.5 g/L, 0.6 g/L, 0.7 g/L, 0.8 g/L, 0.9 g/L, 1 g/L, 5 g/L, 10 g/L, 20 g/L, 30 g/L, 40 g/L, 50 g/L, 100 g/L, 200 g/L, 300 g/L, 400 g/L, 500 g/L, 600 g/L, 700 g/L, 800 g/L, 900 g/L, 1000 g/L in deionized water, or in a suitable buffer such as, e.g., phosphate-buffered saline, pH 7.4 or similar physiological pH) and at 20° C.

In some embodiments, the preparation of glycans is greater than 50%, greater than 60%, greater than 70%, greater than 80%, greater than 90%, greater than 95%, greater than 96%, greater than 97%, greater than 98%, greater than 99%, or greater than 99.5% soluble with no precipitation observed at a concentration of greater than 0.001 g/L, 0.005 g/L, 0.01 g/L, 0.05 g/L, 0.1 g/L, 0.2 g/L, 0.3 g/L, 0.4 g/L, 0.5 g/L, 0.6 g/L, 0.7 g/L, 0.8 g/L, 0.9 g/L, 1 g/L, 5 g/L, 10 g/L, 20 g/L, 30 g/L, 40 g/L, 50 g/L, 100 g/L, 200 g/L, 300 g/L, 400 g/L, 500 g/L, 600 g/L, 700 g/L, 800 g/L, 900 g/L, 1000 g/L in deionized water, or in a suitable buffer such as, e.g., phosphate-buffered saline, pH 7.4 or similar physiological pH) and at 20° C.

Sweetness

In some embodiments, the preparation of glycans has a desired degree of sweetness. For example, sucrose (table sugar) is the prototype of a sweet substance. Sucrose in solution has a sweetness perception rating of 1, and other substances are rated relative to this (e.g., fructose, is rated at 1.7 times the sweetness of sucrose). In some embodiments, the sweetness of the preparation of glycans ranges from 0.1 to 500,000 relative to sucrose. In some embodiments, the relative sweetness is 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 80, 90, 100, 150, 200, 250, 300, 350, 400, 450, 500, 550, 600, 650, 700, 750, 800, 850, 900, 950, 1000, 2000, 3000, 4000, 5000, 6000, 7000, 8000, 9000, 10000, 25000, 50000, 75000, 100000, 150000, 200000, 250000, 300000, 350000, 40000, 450000, 500000, or more than 500,000 relative to sucrose (with sucrose scored as one). In some embodiments, the preparation of glycans is mildly sweet, or both sweet and bitter.

In some embodiments, the preparation of glycans, e.g. a preparation that is substantially DP2+ or DP3+(e.g. at least 80%, 90%, or at least 95%, or a fractionated preparation of DP2+ or DP3+), is substantially imperceptible as sweet and the relative sweetness is about 0, 0.0001, 0.001, 0.005, 0.01, 0.05, 0.1, 0.2, 0.3, 0.4, 0.5, 0.6, 0.7, or about 0.8 relative to sucrose (with sucrose scored as one).

Glycan preparations can be characterized by any suitable methods including those described in WO2016/122889, WO2016/172657, WO 2016/007778, and WO2016/172658, incorporated herein by reference.

In embodiments, glycan compositions and glycan preparations may comprise one or more (e.g., two, three, four, five, six or more) of the following properties (including bulk properties): the glycan comprising at least one of glucose, galactose, arabinose, mannose, fructose, xylose, fucose, or rhamnose, a high degree of polymerization (DP), e.g. at least about 50%, 60%, 70%, 80%, 90%, 95%, 98%, 99% of polymers range in DP from about 30-100,000, about 30-50,000, about 30-10,000, about 30-5,000, about 30-1,000, about 30-500, about 30-200, about 30-100, or about 3-50, a low degree of polymerization, e.g. at least about 50%, 60%, 70%, 80%, 90%, 95%, 98%, 99% of polymers range in DP from about 2-29, about 2-25, about 2-20, about 2-15, about 2-10, about 2-8, about 2-6, about 3-8, or about 4-8, a high viscosity e.g., ranging from about 100-10,000 mPas, 100-5,000 mPas, 100-1,000 mPas, 100-500 mPas, in water at 20° C., a low viscosity, e.g., ranging from about 1-99 mPas, 1-50 mPas, 1-10 mPas, 1-5 mPas, 25-75 mPas, or 10-50 mPas, in water at 20° C., a high final solubility limit in water of at least about 60, 70, or at least about 75 Brix at 23° C., a low final solubility limit in water of no more than 5, 10, 20, 30, 40, 50 Brix at 23° C., or insolubility (e.g. no more than 0.1 Brix)

a caloric value of about 0.1 cal/g to 3 cal/g, 0.1 cal/g to 2 cal/g, 0.1 cal/g to 1.5 cal/g, 0.1 cal/g to 1 cal/g, 0.1 cal/g to 0.5 cal/g, a non-caloric value (e.g., about 0 cal/g to 0.09 cal/g, 0 cal/g to 0.05 cal/g or about 0 cal/g to 0.01 cal/g a low degree of digestibility, wherein no more than about 30%, 20%, 10%, 5%, 1%, 0.5% of the glycan is digestible by a human glycosidase (e.g., alpha-amylase)

a high degree of digestibility, wherein at least 50%, 60%, 70%, 80%, 90%, 95% of the glycan is digestible by a human glycosidase (e.g., alpha-amylase)

a low degree of fermentability, wherein no more than about 40%, 30%, 20%, 10%, 5%, 1%, 0.5% of the glycan is fermentable by a human (e.g., colonic) microbial community or a single bacterial strain, a high degree of fermentability, wherein at least 50%, 60%, 70%, 80%, 90%, 95% of the glycan is fermentable by a human (e.g. colonic) microbial community or a single bacterial strain, a slow rate of fermentation, wherein no more than about 0.5%, 1%, 2%, 5%, 10%, or 15% of the glycan is fermented by a human (e.g., colonic) microbial community or a single bacterial strain in 12-24 hours, a fast rate of fermentation, wherein at least about 15%, 20%, 30%, 40%, or 50% of the glycan is fermented by a human (e.g. colonic) microbial community or a single bacterial strain in 12-24 hours, a high degree of gastrointestinal tolerance (e.g., is tolerated by a subject in high daily doses, e.g. at least about 5 g/day, 10 g/day, 15 g/day, 20 g/day, 30 g/day, 40 g/day, 50 g/day, 60 g/day, or 70 g/day without substantial side effects, e.g. such as bloating, excess gas, GI discomfort, diarrhea or constipation);

any combination of:
  two of: a), b), c), d), e), f), g), h), i), j), k), l), m), n), o), p);
  three of: a), b), c), d), e), f), g), h), i), j), k), l), m), n), o), p);
  four of: a), b), c), d), e), f), g), h), i), j), k), l), m), n), o), p);
  five of: a), b), c), d), e), f), g), h), i), j), k), l), m), n), o), p);
  six of: a), b), c), d), e), f), g), h), i), j), k), l), m), n), o), p);

seven of: a), b), c), d), e), f), g), h), i), j), k), l), m), n), o), p);

eight of: a), b), c), d), e), f), g), h), i), j), k), l), m), n), o), p);

nine of: a), b), c), d), e), f), g), h), i), j), k), l), m), n), o), p);

ten of: a), b), c), d), e), f), g), h), i), j), k), l), m), n), o), p); or all of: a), b), c), d), e), f), g), h), i), j), k), l), m), n), o), p).

In embodiments, glycan compositions and glycan preparations may comprise one or more (e.g., two, three, four, five, six or more) of the following properties (including bulk properties):

i) the glycan preparation comprises glycans that comprise glucose, galactose, arabinose, mannose, fructose, xylose, fucose, or rhamnose glycan units;

ii) the average degree of branching (DB) of the glycans in the glycan preparation is 0, between 0.01 and 0.6, between 0.05 and 0.5, between 0.1 and 0.4, or between 0.15 and 0.4;

iii) at least 50% (at least 60%, 65%, 70%, 75%, 80%, or 85%, or less than 50%) of the glycans in the glycan preparation have a degree of polymerization (DP) of at least 3 and less than 30 glycan units, at least 2 and less than 10 glycan units, at least 5 and less than 25 glycan units, or at least 10 and less than 35 glycan units (optionally, wherein the glycan unit is a monomer, e.g., a monosugar);

iv) the average DP (mean DP) of the glycan preparation is between about 2 and 5, between about 5 and 8, between about 8 and 13, between about 13 and 25, between about 5 and 15, between about 5 and 20, or between about 5-15;

v) the ratio of alpha- to beta-glycosidic bonds present in the glycans of the glycan preparation is 0, or between about 0.8:1 to about 5:1, between about 1:1 to about 5:1, between about 1:1 to about 3:1, between about 3:2 to about 2:1, or between about 3:2 to about 3:1, vi) the glycan preparation comprises between 15 mol % and 75 mol % (between 20 mol % and 60 mol %, between 25 mol % and 50 mol %, or between 30 mol % and 45 mol %) 1,6 glycosidic bonds;

vii) the glycan preparation comprises between 1 mol % and 40 mol % (between 1 mol % and 30 mol %, between 5 mol % and 25 mol %, between 10 mol % and 20 mol %) of at least one, two, or three of 1,2; 1,3; and 1,4 glycosidic bonds;

viii) the glycan preparation has a final solubility limit in water of at least about 50 (at least about 60, 70, at least about 75, or less than 50) Brix at 23° C.; or ix) the glycan preparation has a dietary fiber content (e.g., as measured by AOAC 2009.01) of at least 50% (at least 60%, 70%, 80%, or at least 90%, or less than 50%), x) any combination of two, three, four, five, six, seven, eight, or nine of i), ii), iii), iv), v), vi), vii), viii), and ix).

Glycan compositions described herein can comprise one or more sugars and/or sugar alcohols. Compositions can comprise a simple sugar (such as a monosaccharide, a disaccharide, a trisaccharide, a tetrasacchaaride or a pentasaccharide), a sugar alcohol, or any combination thereof. In some embodiments, composition comprises a metabolizable sugar or metabolizable sugar alcohol, wherein the sugar or sugar alcohol is metabolized in the gastrointestinal tract of the host. The sugars, and sugar alcohols disclosed in WO 2016/172658, which is hereby incorporated by reference, are suitable for use in methods and compositions described herein. In embodiments, a composition described herein, e.g., glycan composition described herein, can comprise polyphenols, fatty acids (e.g., short chain fatty acids), amino acids, peptides, and micronutrients, e.g., as described herein and in WO 2016/172658 hereby incorporated by reference and in Table 1.

Glycan compositions and glycan preparations described herein may have the properties of any one of rows 3-55 of Table 5. In some embodiments, a glycan composition and/or glycan preparation has the properties of Glu5Gal5Man90-2, Glu10Gal10Man80-1, Glu20Gal20Man20Xyl20Ara20-1, Glu20Gal20Man20Xyl20Ara20-2, Gal33Man33Ara33-8, Gal57Glu43-1, Glu100-87, Gal57Glu43-2, Glu50Gal50-11, Glu50Gal50-32, Glu50Gal50-14, Glu50Gal50-27, Glu50Gal50-23, Glu50Gal50-2, Glu100-129, Glu100-136, Glu100-17, Glu100-64, Glu100-76, Glu100-131, Glu100-83, Glu100-139, Glu100-84, Glu100-74, Glu100-98, Glu100-141, Glu100-29, Glu100-18, Glu100-99, Glu100-72, Glu100-82, Glu100-130, Glu100-78, Glu100-66, Glu100-89, Glu100-133, Glu100-68, Glu100-90, Glu100-94, Glu100-5, 3-Obn Glu100-1, Gal100-30, Glu33Gal33Fuc33-3, Ara100-12, Xyl100-8, Xyl75Ara25-3, Glu80Man20-2, Glu60Man40-5, Man80Glu20-2, Man60Glu40-2, Man52Glu29Gal19-2, Man52Glu29Gal19-3, or Man100-17, as described in Table 5.

TABLE 1

Exemplary constituents of glycan compositions: Sugars, Sugar Alcohols, Amino Acids, Vitamins, Minerals, Fatty Acids, and Polyphenols

| Compound | Examples |
| --- | --- |
| Sugar | glucose, galactose, N-acetylglucosamine, N-acetylgalactosamine, fructose, fucose, mannose, N-acetylmannosamine, glucuronic acid, N-acetylglucuronic acid, galactosuronic acid, N-acetylgalactosuronic acid, xylose, arabinose, rhamnose, ribose, sucrose, sorbose, lactose, maltose, lactulose, tagatose, kojibiose, nigerose, isomaltose, trehalose, sophorose, laminaribiose, gentiobiose, turanose, maltulose, palatinose, gentiobiulose, mannobiose, melibiulose, rutinulose, xylobiose |
| Sugar Alcohol | sorbitol, mannitol, lactitol, erythritol, glycerol, arabitol, maltitol, xylitol, ribitol, threitol, galactitol, fucitol, iditol, inositol |
| Amino Acid | alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine |
| Vitamin | pantothenate, thiamine, riboflavin, niacin, pyridoxol, biotin, folate, 4-aminobenzoate, cobinamide, phenyolyl cobamide, 5- |

TABLE 1-continued

Exemplary constituents of glycan compositions: Sugars, Sugar Alcohols, Amino Acids, Vitamins, Minerals, Fatty Acids, and Polyphenols

| Compound | Examples |
| --- | --- |
| | methylbenzimidazolyl cobamide, cobalamin, pyridoxine, pyridoxamine, ergadenylic acid, cyanocobalamin, choline, retinol, a carotenoid, zeaxanthin |
| Element/Mineral | chloride, sodium, calcium, magnesium, nitrogen, potassium, manganese, iron, zinc, nickel, copper, cobalt |
| Fatty Acid | acetic acid, propionic acid, butryic acid, isobutyric acid, valeric acid, isovaleric acid, hexanoic acid, octanoic acid, formic acid, oxalic acid, glyoxylic acid, glycolic acid, acrylic acid, malonic acid, pyruvic acid, lactic acid, succinic acid, acetoacetic acid, fumaric acid, maleic acid, oxaloacetic acid, malic acid, tartaric acid, crotonic acid, glutaric acid, alpha-ketoglutaric acid, caproic acid, adipic acid, citric acid, aconitic acid, isocitric acid, sorbic acid, enanthic acid, pimelic acid, benzoic acid, salicylic acid, caprylic acid, phthalic acid, pelargonic acid, trimesic acid, cinnamic acid, capric acid, sebacic acid, stearic acid, oleic acid, linoleic acid, α-linolenic acid, γ-linolenic acid, stearidonic acid |
| Polyphenol | Anthocyanins, Chalcones, Dihydro-chalcones, Dihydro-flavonols, Flavanols, Flavanones, Flavones, Flavonols, Isoflavonoids, Lignans, Non-phenolic metabolites, Alkylmethoxy-phenols, Alkylphenols, Betacyanins, Capsaicinoids, Curcuminoids, Dihydro-capsaicins, Furano-coumarins, Hydroxy-benzaldehydes, Hydroxy-benzoketones, Hydroxycinnam-aldehydes, Hydroxy-coumarins, Hydroxyphenyl-alcohols, Hydroxy-phenylpropenes, Methoxyphenols, Naphtoquinones, Phenolic terpenes, Tyrosols, Hydroxybenzoic acids, Hydroxy-cinnamic acids, Hydroxy-phenylacetic acids, Hydroxy-phenylpropanoic acids, Hydroxy-phenylpentanoic acids, Stilbenes, catechin, ellagitannin, isoflavone, flavonol, flavanone, anthocyanin, lignin, alkylmethoxyphenol, alkylphenol, curcuminoid, furanocoumarin, hydroxybenzaldehyde, hydroxybenzoketone, hydroxycinnamaldehyde, hydroxycoumarin, hydroxyphenylpropene, methoxyphenol, naphtoquinone, phenolic terpenes, tyrosols |

Probiotics

In embodiments, a composition described herein, e.g., glycan composition described herein, can comprise commensal or probiotic bacterial taxa, e.g., bacteria that are generally recognized as safe (GRAS) or known commensal or probiotic microbes. In embodiments, a composition described herein, e.g., glycan composition described herein, can comprise bacterial taxa described in Tables 8-10. In some embodiments, probiotic or commensal bacterial taxa (or preparations thereof) may be administered to a subject receiving the glycan preparations.

In some embodiments, the composition further comprises at least about 1% (w/w) of a probiotic or commensal bacterium or a combination thereof (e.g., at least about 2%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, about 99%, or more).

Probiotic microorganisms may also be included in the glycan compositions, or used in combination with a glycan composition described herein. A probiotic microorganism is also referred to a probiotic. Probiotics can include the metabolites generated by the probiotic microorganisms during fermentation. These metabolites may be released to the medium of fermentation, e.g., into a host organism (e.g., subject), or they may be stored within the microorganism. Probiotic microorganism includes bacteria, bacterial homogenates, bacterial proteins, bacterial extracts, bacterial ferment supernatants and combinations thereof, which perform beneficial functions to the host animal, e.g., when given at a therapeutic dose.

Useful probiotic microorganisms include at least one lactic acid and/or acetic acid and/or propionic acid producing bacteria, e.g., microbes that produce lactic acid and/or acetic acid and/or propionic acid by decomposing carbohydrates such as glucose and lactose. Preferably, the probiotic microorganism is a lactic acid bacterium. In embodiments, lactic acid bacteria include *Lactobacillus, Leuconostoc, Pediococcus, Streptococcus,* and *Bifidobacterium*. Suitable probiotic microorganisms can also include other microorganisms which beneficially affect a host by improving the hosts intestinal microbial balance, such as, but not limited to yeasts such as *Saccharomyces, Debaromyces, Candida, Pichia* and *Torulopsis*, molds such as *Aspergillus, Rhizopus, Mucor,* and *Penicillium* and *Torulopsis,* and other bacteria such as but not limited to the genera *Bacteroides, Clostridium, Fusobacterium, Melissococcus, Propionibacterium, Enterococcus, Lactococcus, Staphylococcus, Peptostreptococcus, Bacillus, Pediococcus, Micrococcus, Leuconostoc, Weissella, Aerococcus,* and *Oenococcus,* and combinations thereof.

Non-limiting examples of lactic acid bacteria useful in the disclosure herein include strains of *Streptococcus lactis, Streptococcus cremoris, Streptococcus diacetylactis, Streptococcus thermophilus, Lactobacillus bulgaricus, Lactobacillus acidophilus, Lactobacillus helveticus, Lactobacillus bifidus, Lactobacillus casei, Lactobacillus lactis, Lactobacillus plantarum, Lactobacillus rhamnosus, Lactobacillus delbruekii, Lactobacillus thermophilus, Lactobacillus fermentii, Lactobacillus salivarius, Lactobacillus paracasei, Lactobacillus brevis, Bifidobacterium longum, Bifidobacterium infantis, Bifidobacterium bifidum, Bifidobcterium animalis, Bifidobcterium lactis, Bifidobcterium breve, Bifidobcterium adolescentis,* and *Pediococcus cerevisiae* and combinations thereof, in particular *Lactobacillus, Bifidobacterium*, and combinations thereof.

Probiotic microorganisms which are particularly useful in the present disclosure include those which (for human administration) are of human origin (or of the origin of the mammal to which the probiotic microorganism is being administered), are non-pathogenic to the host, resist technological processes (i.e. can remain viable and active during processing and in delivery vehicles), are resistant to gastric acidity and bile toxicity, adhere to gut epithelial tissue, have the ability to colonize the gastrointestinal tract, produce antimicrobial substances, modulate immune response in the host, and influence metabolic activity (e.g. cholesterol assimilation, lactase activity, vitamin production).

The probiotic microorganism can be included in the glycan preparations as a single strain or a combination of multiple strains, wherein the total number of bacteria in a dose of probiotic microorganism is from about $1 \times 10^3$ to about $1 \times 10^{14}$, or from about $1 \times 10$ to about $1 \times 10^{12}$, or from about $1 \times 10^7$ to about $1 \times 10^{11}$ CFU per dose.

The probiotic microorganisms can be incorporated into the glycan preparations while the probiotic microorganism is alive but in a state of "suspended animation" or somnolence. Once freeze-dried, the viable cultures(s) of probiotic microorganism are handled so as to minimize exposure to moisture that would reanimate the cultures because, once reanimated, the cultures can experience high rates of morbidity unless soon cultured in a high moisture environment or medium. Additionally, the cultures are handled to reduce possible exposure to high temperatures (particularly in the presence of moisture) to reduce morbidity.

The probiotic microorganisms can be used in a powdered, dry form. The probiotic microorganisms can also be administered in the glycan preparation or in a separate glycan preparation, administered at the same time or different time as the glycan preparations.

Examples of probiotics include, but are not limited to, those that acidify the colon such as those from the genera *Lactobacillus* or *Bifidobacterium*, which are thought to maintain a healthy balance of intestinal microbiota by producing organic acids (lactic & acetic acids), hydrogen peroxide, and bacteriocins which are documents to inhibit enteric pathogens.

Other *Lactobacillus* bacteria which can be employed include, but are not limited to, *L. crispatus, L. casei, L. rhamnosus, L. reuteri, L. fermentum, L. plantarum, L. sporogenes*, and *L. bulgaricus*. Other probiotic bacteria suitable for the glycan compositions include *Bifidobacterium lactis, B. animalis, B. bifidum, B. longum, B. adolescentis*, and *B. infantis*.

In embodiments, a commensal bacterial taxa that can be used in and/or in combination with a composition described herein comprises *Akkermansia, Anaerococcus, Bacteroides, Bifidobacterium* (including *Bifidobacterium lactis, B. animalis, B. bifidum, B. longum, B. adolescentis, B. breve*, and *B. infantis*), *Blautia, Clostridium, Corynebacterium, Dialister, Eubacterium, Faecalibacterium, Finegoldia, Fusobacterium, Lactobacillus* (including, *L. acidophilus, L. helveticus, L. bifidus, L. lactis, L. fermentii, L. salivarius, L. paracasei, L. brevis, L. delbruekii, L. thermophiles, L. crispatus, L. casei, L. rhamnosus, L. reuteri, L. fermentum, L. plantarum, L. sporogenes*, and *L. bulgaricus*), *Peptococcus, Peptostreptococcus, Peptoniphilus, Prevotella, Roseburia, Ruminococcus, Staphylococcus*, and/or *Streptococcus* (including *S. lactis, S. cremoris, S. diacetylactis, S. thermophiles*).

In embodiments, a commensal bacterial taxa, e.g., GRAS strain, that can be used in and/or in combination with a composition described herein comprises *Bacillus coagulans* GBI-30, 6086; *Bifidobacterium animalis* subsp. *Lactis* BB-12; *Bifidobacterium breve* Yakult; *Bifidobacterium infantis* 35624; *Bifidobacterium animalis* subsp. *Lactis* UNO 19 (DR10); *Bifidobacterium longum* BB536; *Escherichia coli* M-17; *Escherichia coli* Nissle 1917; *Lactobacillus acidophilus* DDS-1; *Lactobacillus acidophilus* LA-5; *Lactobacillus acidophilus* NCFM; *Lactobacillus casei* DN 114-001 (*Lactobacillus casei* Immunitas(s)/Defensis); *Lactobacillus casei* CRL431; *Lactobacillus casei* F19; *Lactobacillus paracasei* Stl 1 (or NCC2461); *Lactobacillus johnsonii* Lai (*Lactobacillus* LCI, *Lactobacillus johnsonii* NCC533); *Lactococcus lactis* LA; *Lactobacillus plantarum* 299V; *Lactobacillus reuteri* ATTC 55730 (*Lactobacillus reuteri* SD2112); *Lactobacillus rhamnosus* ATCC 53013; *Lactobacillus rhamnosus* LB21; *Saccharomyces cerevisiae* (*boulardii*) lyo; mixture of *Lactobacillus rhamnosus* GR-1 and *Lactobacillus reuteri* RC-14; mixture of *Lactobacillus acidophilus* NCFM and *Bifidobacterium lactis* BB-12 or BL-04; mixture of *Lactobacillus acidophilus* CL1285 and *Lactobacillus casei*; and a mixture of *Lactobacillus helveticus* R0052, *Lactobacillus rhamnosus* R0011, and/or *Lactobacillus rhamnosus* GG (LGG).

Symbiotics

Provided herein are combinations of microbes (e.g., bacterial taxa) with glycan compositions disclosed herein which can, e.g., be utilized by the microbes as their substrate for growth. Exogenously introduced microbes can provide a number of beneficial effects, such as, e.g., those described in Tables 8-10. This may occur by promoting the growth of the microbes (using the glycans), thereby allowing the microbes to outgrow other bacteria at the site of colonization. Methods provided herein include administering one or more (e.g., one or more, two or more, three or more, four or more, and so on) bacterial taxa, such as those listed in Tables 8-10 to a subject in combination with a glycan composition. Such a combination can increase, suppress, and/or alter certain bacterial taxa. Methods are provided herein comprising administering one or more (e.g., one or more, two or more, three or more, four or more, and so on) bacterial taxa to a subject in combination with a glycan described herein to a subject. The subject can include a subject that has taken, is taking or will be taking an antibiotic. The subject can include a subject that is not taking or has not taken an antibiotic.

Prebiotics

In some embodiments, the glycan compositions comprise a prebiotic substance. In some embodiments, prebiotics may be administered to a subject receiving the glycan preparations. Prebiotics are substantially non-digestible substances by the host that when consumed may provide a beneficial physiological effect on the host by selectively stimulating the favorable growth or activity of a limited number of indigenous bacteria in the gut (Gibson G R, Roberfroid M B. *J Nutr.* (1995) 125:1401-12). A prebiotic such as a dietary fiber or prebiotic oligosaccharide (e.g. crystalline cellulose, wheat bran, oat bran, cone fiber, soy fiber, beet fiber and the like) may further encourage the growth of probiotic and/or commensal bacteria in the gut by providing a fermentable dose of carbohydrates to the bacteria and increase the levels of those microbial populations (e.g. *lactobacilli* and bifidobacteria) in the gastrointestinal tract. Prebiotics may include, but are not limited to, various galactans and carbohydrate based gums, such as *psyllium*, guar, carrageen, gellan, lactulose, and konjac. In some embodiments, the prebiotic is one or more of galacto-oligosaccharides (GOS), lactulose, raffinose, stachyose, lactosucrose, fructo-oligosaccharides (FOS, e.g. oligofructose or oligofructan), inulin, isomaltooligosaccharide, xylo-oligosaccharides (XOS), paratinose oligosaccharide, isomaltose oligosaccharides (IMOS), transgalactosylated oligosaccharides (e.g. transgalacto-oligosaccharides), transgalactosylate disaccharides, soybean oligosaccharides (e.g. soyoligosaccharides), chitosan oligosaccharide (chioses), gentiooligosaccharides, soy- and pectin-oligosaccharides, glucooligosaccharides, pecticoligosaccharides, palatinose polycondensates, difructose anhydride III, sorbitol, maltitol, lactitol, polyols, polydextrose, linear and branched dextrans, pullulan, hemicelluloses, reduced paratinose, cellulose, beta-glucose, beta-galactose, beta-fructose, verbascose, galactinol, xylan, inulin, chitosan, beta-glucan, guar gum, gum arabic, pectin, high sodium alginate, and lambda carrageenan, or mixtures thereof. In some embodiments, glycan preparations are provided comprising gal100, glu10gal10man80, glu30gal30man40, gal33man33xyl33, glu40gal30man30, glu40gal20man40, glu45gal10man45, glu60gal20man20, fructo-oligosaccharide, glu40gal40man20, glu20gal20man20xyl20ara20, glu90gal5man5, glu80xyl20, glu20gal80, glu80ara20, glu40gal60, glu33gal33man33, man100, lactulose, glu80gal10man10, man80glu20, glu50gal50, glu80gal20, glu80man20, glu45gal45man10, glu60gal40, glu60man40, man80gal20, man60glu40, glu100, Glu100-114, Lara100-1, Gal50Fru50-2, Glu100-3, Glu100-94, Fru100-9, Glu100-22, and/or Glu100-107. In some embodiments, the glycan compositions comprise pullulan. Pullulan can be produced by subjecting a glucose source, e.g. corn syrup, to certain fungi, e.g., *Aureobasidium pullulans*. Pullulan has a linear structure comprised of maltotrioses in which three glucose units are linked through alpha-1,4-glucosidic bonds. The maltotrioses are in turn linked to a series of three other maltotrioses through alpha-1,6-glucosidic bonds. Pullulan preparations can have a molecular weight ranging from approx. 5 kDa to 1.5 mDa (e.g., some preparations range between 50 kDa and 500 kDa) and can, if desired, be fractionated (e.g., HMW pullulan (MW approx. 100 kDa) and LMW (MW approx. 6 kDa); Hayashibara, Japan).

Prebiotics can be found in certain foods, e.g. chicory root, Jerusalem artichoke, Dandelion greens, garlic, leek, onion, asparagus, wheat bran, wheat flour, banana, milk, yogurt, sorghum, burdock, broccoli, Brussels sprouts, cabbage, cauliflower, collard greens, kale, radish and rutabaga, and miso. In some embodiments, the glycan preparations described herein are administered to a subject in conjunction with a diet that includes foods rich in prebiotics. Suitable sources of soluble and insoluble fibers are commercially available.

In some embodiments, a glycan composition comprises at least about 1% (w/w) of a prebiotic substance (e.g., at least about 2%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, about 99%, or more). In embodiments, the glycan composition comprises FOS. In embodiments, the glycan composition comprises lactulose.

Changes in bacterial populations can be measured by the "prebiotic index." The prebiotic index considers increases in the growth rate of Bifidobacteria, Eubacteria, and *Lactobacilli* as positive effects and increases in Clostridia, *Bacteroides*, sulfate-reducing bacteria, and *Escherichia coli* as negative effects. The prebiotic index (PI) relates to the sum of: (Bifidobacteria/total bacteria)+(*Lactobacilli*/total bacteria)−(*Bacteroides*/total bacteria)−(Clostridia/total bacteria), (see Palframan et al, 2003, Lett Appl Microbiol 37:281-284). In embodiments, administration of the glycan composition to a subject may result in an increased prebiotic index. Administration of a glycan composition to a subject may result in an increase in: *Bacteroides, Blautia, Clostridium, Fusobacterium, Eubacterium, Ruminococcus, Peptococcus, Peptostreptococcus, Akkermansia, Faecalibacterium, Roseburia, Prevotella, Bifidobacterium, Lactobacilli, Christensenella minuta*, or a *Christensenellaceae*.

In some embodiments, the glycan composition comprises an antibiotic, an antifungal agent, an antiviral agent, or an anti-inflammatory agent (e.g. a cytokine, hormone, etc.).

In some embodiments, the glycan compositions further comprise a second therapeutic agent or preparation thereof, such as a drug.

Pharmaceutical compositions, medical foods, supplements (e.g., dietary supplements) and unit dosage forms suitable for use in the methods and compositions described herein can be found in WO 2016/122889, WO 2016/172657, and WO 2016/172658, which are hereby incorporated by reference. Provided herein are also food supplements, food ingredients and nutraceuticals.

In some embodiments, the glycan compositions do not contain a prebiotic substance. In some embodiments glycan compositions do not contain a probiotic bacterium.

In some embodiments, glycan compositions comprise one or more of glycan preparations described herein.

The glycan preparations described herein may be formulated into any suitable dosage form, e.g. for nasal, oral, rectal or gastric administration. In some embodiments, the glycan preparations described herein may be formulated for enteral administration. In some embodiments, the glycan preparations described herein may be formulated for tube feeding (e.g. naso-gastric, oral-gastric or gastric feeding). The dosage forms described herein can be manufactured using processes that are known to those of skill in the art.

The dosage form may be a packet, such as any individual container that contains a glycan preparation in the form of, e.g., a liquid (e.g., a beverage), a gel, a cream, an ointment, a powder, a tablet, a pill, a capsule, a sachet, a gummy, a suppository, a single-use applicator or medical device (e.g. a syringe). For example, provided is also an article of manufacture, such as a container comprising a unit dosage form of the glycan preparation, and a label containing instructions for use of such glycan.

Forms of the compositions that can be used orally include tablets, push-fit capsules made of gelatin, as well as soft, sealed capsules made of gelatin and a plasticizer, such as glycerol or sorbitol. Tablets can be made by compression or molding, optionally with one or more accessory ingredients. Compressed tablets can be prepared by compressing in a suitable machine the active ingredient in a free-flowing form such as a powder or granules, optionally mixed with binders (e.g., povidone, gelatin, hydroxypropylmethyl cellulose), inert diluents, preservative, antioxidant, disintegrant (e.g., sodium starch glycolate, cross-linked povidone, cross-linked sodium carboxymethyl cellulose) or lubricating, surface active or dispersing agents. Molded tablets can be made by molding in a suitable machine a mixture of the powdered compound moistened with an inert liquid diluent. The tablets can optionally be coated or scored and can be formulated so as to provide slow or controlled release of the active ingredient therein. Tablets can optionally be provided with an enteric coating, to provide release in parts of the gut (e.g., colon, lower intestine) other than the stomach. All formulations for oral administration can be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds and/or other agents (e.g., prebiotics or probiotics) can be dissolved or suspended in suitable liquids, such as fatty oils, liquid paraffin, or liquid polyethylene glycols. In addition, stabilizers can be added. Dragee cores are provided with suitable coatings. For this purpose, concentrated sugar solutions can be used, which can optionally contain gum arabic, talc, polyvinyl pyrrolidone, carbopol gel, polyethylene glycol, or titanium dioxide, lacquer solutions, and suitable organic solvents or solvent mixtures. Dyestuffs or pigments can be added to the tablets or dragee coatings for identification or to characterize different combinations of active compound doses. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethylene glycol or an oil medium, for example peanut oil, liquid paraffin, or olive oil.

In one embodiment, a provided glycan preparation includes a softgel formulation. A softgel can contain a gelatin based shell that surrounds a liquid fill. The shell can be made of gelatin, plasticizer (e.g., glycerin and/or sorbitol), modifier, water, color, antioxidant, or flavor. The shell can be made with starch or carrageenan. The outer layer can be enteric coated. In one embodiment, a softgel formulation can include a water or oil soluble fill solution, or suspension of a composition covered by a layer of gelatin.

Solid formulations for oral use may comprise an enteric coating, which may control the location at which a glycan preparation is absorbed in the digestive system. For example, an enteric coating can be designed such that a glycan preparation does not dissolve in the stomach but rather travels to the small intestine, where it dissolves. An enteric coating can be stable at low pH (such as in the stomach) and can dissolve at higher pH (for example, in the small intestine). Material that can be used in enteric coatings includes, for example, alginic acid, cellulose acetate phthalate, plastics, waxes, shellac, and fatty acids (e.g., stearic acid, palmitic acid). Formulations for oral use may also be presented in a liquid dosage form (e.g. beverage). Liquid preparations can be in the form of, for example, aqueous or oily suspensions, solutions, emulsions, syrups or elixirs, or can be presented as a dry product (e.g. sachet) for reconstitution with water or other suitable aqueous vehicle before use. Such liquid preparations can contain conventional additives, such as suspending agents, for example sorbitol, methyl cellulose, glucose syrup, gelatin, hydroxyethyl cellulose, carboxymethyl cellulose, aluminum stearate gel or hydrogenated edible fats, emulsifying agents, for example lecithin, sorbitan monooleate, acacia; non-aqueous vehicles (which can include edible oils), for example almond oil, oily esters such as glycerine, propylene glycol, or ethyl alcohol; preservatives, for example methyl or propyl p-hydoxybenzoate or sorbic acid, and, if desired, conventional flavoring or coloring agents. In some embodiments, liquid formulations can comprise, for example, an agent in water-in-solution and/or suspension form; and a vehicle comprising polyethoxylated castor oil, alcohol, and/or a polyoxyethylated sorbitan mono-oleate with or without flavoring. Each dosage form may comprise an effective amount of a glycan and can optionally comprise pharmaceutically inert agents, such as conventional excipients, vehicles, fillers, binders, disintegrants, pH adjusting substances, buffer, solvents, solubilizing agents, sweeteners, coloring agents, and any other inactive agents that can be included in pharmaceutical dosage forms for administration. Examples of such vehicles and additives can be found in Remington's Pharmaceutical Sciences, 17th edition (1985).

The pharmaceutical compositions provided herein can be in unit-dosage forms or multiple-dosage forms. A unit-dosage form, as used herein, refers to physically discrete unit suitable for administration to human in need thereof. In an embodiment, the unit-dosage form is provided in a package. Each unit-dose can contain a predetermined quantity of an active ingredient(s) sufficient to produce the desired therapeutic effect, in association with other pharmaceutical carriers or excipients. Examples of unit-dosage forms include, but are not limited to, ampoules, syringes, and individually packaged tablets and capsules. Unit-dosage forms can be administered in fractions or multiples thereof. A multiple-dosage form is a plurality of identical unit-dosage forms packaged in a single container, which can be administered in segregated unit-dosage form. Examples of multiple-dosage forms include, but are not limited to, vials, bottles of tablets or capsules, or bottles of pints or gallons. In another embodiment, the multiple dosage forms comprise different pharmaceutically active agents. For example, a multiple dosage form can be provided which comprises a first dosage element comprising a composition comprising a glycan and a second dosage element comprising a prebiotic, a therapeutic agent and/or a probiotic, which can be in a modified release form. In this example a pair of dosage elements can make a single unit dosage. In one embodiment, a kit is provided comprising multiple unit dosages, wherein each unit comprises a first dosage element comprising a composition comprising a glycan preparation and a second dosage element comprising probiotic, a pharmaceutical agent, a prebiotic or a combination thereof, which can be in a modified release form. In another embodiment, the kit further comprises a set of instructions.

In some embodiments, the unit-dosage form comprises between about 1 mg to about 100 g of the glycan preparation (e.g., a glycan disclosed herein). For example, the unit-dosage form may comprise about 50 mg to about 50 g, about 500 mg to about 50 g, about 5 g to about 50 g, about 100 mg to about 100 g, about 1 g to about 100 g, about 10 g to about 100 g, about 1 g to about 10 g, about 1 g to about 20 g, about 1 g to about 30 g, about 1 g to about 40 g, about 1 g to about 50 g, about 1 g to about 60 g, about 1 g to about 70 g, about 1 g to about 80 g, about 1 g to about 90 g, about 1 g to about 100 g, about 1 g to about 150 g, about 1 g to about 200 g of the glycan. In other embodiments, the unit-dosage form comprises between about 0.001 mL to about 1000 mL of the glycan (e.g., a glycan disclosed herein). For example, the unit-dosage form may comprise about 0.001 mL to about 950 mL, about 0.005 mL to about 900 mL, about 0.01 mL to about 850 mL, about 0.05 mL to about 800 mL, about 0.075 mL to about 750 mL, about 0.1 mL to about 700 mL, about 0.25 mL to about 650 mL, about 0.5 mL to about 600 mL, about 0.75 mL to about 550 mL, about 1 mL to about 500 mL, about 2.5 mL to about 450 mL, about 5 mL to about 400 mL, about 7.5 mL to about 350 mL, about 10 mL to about 300 mL, about 12.5 mL to about 250 mL, about 15 mL to about 200 mL, about 17.5 mL to about 150 mL, about 20 mL to about 100 mL, or about 25 mL to about 75 mL of the glycan.

In certain embodiments, the unit-dosage form comprises about 0.001 mL to about 10 mL, about 0.005 mL to about 7.5 mL, about 0.01 mL to about 5 mL, about 0.05 mL to about 2.5 mL, about 0.1 mL to about 1 mL, about 0.25 mL to about 1 mL, or about 0.5 mL to about 1 mL of the glycan. In other embodiments, the unit-dosage form comprises about 0.01 mL to about 10 mL, about 0.025 mL to about 7.5 mL, about 0.05 mL to about 5 mL, or about 0.1 mL to about 2.5 mL of the glycan. In other embodiments, the unit-dosage form comprises about 0.1 mL to about 10 mL, about 0.25 mL to about 7.5 mL, about 0.5 mL to about 5 mL, about 0.5 mL to about 2.5 mL, or about 0.5 mL to about 1 mL of the glycan.

In some embodiments, the unit-dosage form, e.g., a tablet, capsule (e.g., a hard capsule, push-fit capsule, or soft capsule), or softgel, has a body length of between about 0.1 inches to about 1.5 inches (e.g., about 0.5 inches and about 1 inch), or about 5 mm to about 50 mm (e.g., about 10 mm to about 25 mm). In some embodiments, the unit-dosage form. e.g., a tablet, capsule (e.g., a hard capsule, push-fit capsule, or soft capsule), or softgel, has an external diameter of about 0.05 inches to about 1 inch (e.g., about 0.1 inches to about 0.5 inches), or about 1 mm to about 25 mm (e.g., about 5 mm to about 10 mm).

Each unit-dosage form of the glycan may have a caloric value of between about 0.01 kcal and about 1000 kcal. For example, the unit-dosage form may have a caloric value of about 0.01 kcal to about 100 kcal, about 0.05 kcal to about 50 kcal, about 0.1 kcal to about 10 kcal, about 0.25 kcal to about 2.5 kcal, about 0.5 kcal to about 5 kcal, about 0.75 kcal to about 7.5 kcal, about 1 kcal to 10 kcal, about 5 kcal to about 50 kcal, or about 10 kcal to about 100 kcal. In certain embodiments, the unit-dosage form of the glycan has a caloric value of between 10 kcal to about 500 kcal. In certain embodiments, the unit-dosage form of the glycan has a caloric value of between 1 kcal to about 100 kcal. In certain embodiments, the unit-dosage form of the glycan has a caloric value of between 0.1 kcal to about 10 kcal.

In still other embodiments, the unit-dosage form may have a caloric value of about 0.001 kcal to about 10 kcal, about 0.005 kcal to about 10 kcal, about 0.01 kcal to about 10 kcal, about 0.025 kcal to about 25 kcal, about 0.05 kcal to about 50 kcal, about 0.075 kcal to about 75 kcal, about 0.1 kcal to 100 kcal, about 0.25 kcal to about 10 kcal, about 0.5 kcal to about 5 kcal, about 0.25 kcal to about 25 kcal, or about 0.1 kcal to about 1 kcal.

The unit-dosage form of the glycan may be formulated to dissolve in an aqueous solution (e.g., water, milk, juice, and the like) and is orally administered as a beverage, syrup, solution, or suspension. For example, the unit-form dosage of the glycan may comprise a cube, packet, lozenge, pill, tablet, capsule, candy, powder, elixir, or concentrated syrup formulated for dissolving into an aqueous solution prior to oral administration. In other embodiments, the unit-dosage form of the glycan may comprise a cube, packet, lozenge, pill, tablet, capsule, candy, powder, elixir, or concentrated syrup formulated to dissolve in vivo, e.g., in the mouth, stomach, intestine, or colon of the subject upon oral administration.

In some embodiments, the glycan preparation is administered enterically. This preferentially includes oral administration, or by an oral or nasal tube (including nasogastric, nasojejunal, oral gastric, or oral jejunal). In other embodiments, administration includes rectal administration (including enema, suppository, or colonoscopy).

The dosage forms described herein can be manufactured using processes that are known to those of skill in the art. For example, for the manufacture of tablets, an effective amount of a prebiotic can be dispersed uniformly in one or more excipients or additives, for example, using high shear granulation, low shear granulation, fluid bed granulation, or by blending for direct compression. Excipients and additives include diluents, binders, disintegrants, dispersants, lubricants, glidants, stabilizers, surfactants, antiadherents, sorbents, sweeteners, and colorants, or a combination thereof. Diluents, also termed fillers, can be used to increase the bulk of a tablet so that a practical size is provided for compression. Non-limiting examples of diluents include lactose, cellulose, microcrystalline cellulose, mannitol, dry starch, hydrolyzed starches, powdered sugar, talc, sodium chloride, silicon dioxide, titanium oxide, dicalcium phosphate dihydrate, calcium sulfate, calcium carbonate, alumina and kaolin. Binders can impart cohesive qualities to a tablet formulation and can be used to help a tablet remain intact after compression. Non-limiting examples of suitable binders include starch (including corn starch and pregelatinized starch), gelatin, sugars (e.g., glucose, dextrose, sucrose, lactose and sorbitol), celluloses, polyethylene glycol, alginic acid, dextrin, casein, methyl cellulose, waxes, natural and synthetic gums, e.g., acacia, tragacanth, sodium alginate, gum arabic, xantan gum, and synthetic polymers such as polymethacrylates, polyvinyl alcohols, hydroxypropylcellulose, and polyvinylpyrrolidone. Lubricants can also facilitate tablet manufacture; non-limiting examples thereof include magnesium stearate, calcium stearate, stearic acid, glyceryl behenate, and polyethylene glycol. Disintegrants can facilitate tablet disintegration after administration, and non-limiting examples thereof include starches, alginic acid, crosslinked polymers such as, e.g., crosslinked polyvinylpyrrolidone, croscarmellose sodium, potassium or sodium starch glycolate, clays, celluloses (e.g., carboxymethylcelluloses (e.g., carboxymethylcellulose (CMC), CMC-Na, CMC-Ca)), starches, gums and the like. Non-limiting examples of suitable glidants include silicon dioxide, talc, and the like. Stabilizers can inhibit or retard drug decomposition reactions, including oxidative reactions. Surfactants can also include and can be anionic, cationic, amphoteric or nonionic. Exemplary sweeteners may include stevia extract, aspartame, sucrose, alitame, saccharin, and the like. If desired, the tablets can also comprise nontoxic auxiliary substances such as pH buffering agents, preservatives, e.g., antioxidants, wetting or emulsifying agents, solubilizing agents, coating agents, flavoring agents (e.g., mint, cherry, anise, peach, apricot, licorice, raspberry, vanilla), and the like. Additional excipients and additives may include aluminum acetate, benzyl alcohol, butyl paraben, butylated hydroxy toluene, calcium disodium EDTA, calcium hydrogen phosphate dihydrate, dibasic calcium phosphate, tribasic calcium phosphate, candelilla wax, carnuba wax, castor oil hydrogenated, cetylpyridine chloride, citric acid, colloidal silicone dioxide, copolyvidone, corn starch, cysteine HCl, dimethicone, disodium hydrogen phosphate, erythrosine sodium, ethyl cellulose, gelatin, glycerin, glyceryl monooleate, glyceryl monostearate, glycine, HPMC pthalate, hydroxypropylcellulose, hydroxyl propyl methyl cellulose, hypromellose, iron oxide red or ferric oxide, iron oxide yellow, iron oxide or ferric oxide, magnesium carbonate, magnesium oxide, magnesium stearate, methionine, methacrylic acid copolymer, methyl paraben, silicified microcrystalline cellulose, mineral oil, phosphoric acid, plain calcium phosphate, anhydrous calcium phosphate, polaxamer 407, polaxamer 188, plain polaxamer, polyethylene oxide, polyoxy140 stearate, polysorbate 80, potassium bicarbonate, potassium sorbate, potato starch, povidone, propylene glycol, propylene paraben, propyl paraben, retinyl palmitate, saccharin sodium, selenium, silica, silica gel, fumed silica, sodium benzoate, sodium carbonate, sodium citrate dihydrate, sodium crossmellose, sodium lauryl sulfate, sodium metabisulfite, sodium propionate, sodium starch, sodium starch glycolate, sodium stearyl fumarate, sorbic acid, sorbitol, sorbitan monooleate, pregelatinized starch, succinic acid, triacetin, triethyl citrate, vegetable stearin, vitamin A, vitamin E, vitamin C, or a combination thereof. The amounts of these excipients and additives can be properly selected based on their relation to other components and properties of the preparation and production method.

Immediate-release formulations of an effective amount of a glycan preparation can comprise one or more combinations of excipients that allow for a rapid release of a pharmaceutically active agent (such as from 1 minute to 1 hour after administration). Controlled-release formulations (also referred to as sustained release (SR), extended-release (ER, XR, or XL), time-release or timed-release, controlled-release (CR), or continuous-release) refer to the release of a glycan preparation from a dosage form at a particular desired point in time after the dosage form is administered to a subject.

In one embodiment a controlled release dosage form begins its release and continues that release over an extended period of time. Release can occur beginning almost immediately or can be sustained. Release can be constant, can increase or decrease over time, can be pulsed, can be continuous or intermittent, and the like. In one embodiment, a controlled release dosage refers to the release of an agent from a composition or dosage form in which the agent is released according to a desired profile over an extended period of time. In one aspect, controlled-release refers to delayed release of an agent from a composition or dosage form in which the agent is released according to a desired profile in which the release occurs after a period of time. Pharmaceutical carriers or vehicles suitable for administration of the compounds provided herein include all such carriers known to those skilled in the art to be suitable for the particular mode of administration. In addition, the compositions can one or more components that do not impair the desired action, or with components that supplement the desired action, or have another action. In a further aspect, the dosage form can be an effervescent dosage form. Effervescent means that the dosage form, when mixed with liquid, including water and saliva, evolves a gas. Some effervescent agents (or effervescent couple) evolve gas by means of a chemical reaction which takes place upon exposure of the effervescent disintegration agent to water or to saliva in the mouth. This reaction can be the result of the reaction of a soluble acid source and an alkali monocarbonate or carbonate source. The reaction of these two general compounds produces carbon dioxide gas upon contact with water or saliva. An effervescent couple (or the individual acid and base separately) can be coated with a solvent protective or enteric coating to prevent premature reaction. Such a couple can also be mixed with previously lyophilized particles (such as a glycan). The acid sources can be any which are safe for human consumption and can generally include food acids, acid and hydrite antacids such as, for example: citric, tartaric, amalic, fumeric, adipic, and succinics. Carbonate sources include dry solid carbonate and bicarbonate salt such as sodium bicarbonate, sodium carbonate, potassium-bicarbonate and potassium carbonate, magnesium carbonate and the like. Reactants which evolve oxygen or other gas and which are safe for human consumption are also included. In one embodiment citric acid and sodium bicarbonate are used.

In another aspect, the dosage form can be in a candy form (e.g., matrix), such as a lollipop or lozenge. In one embodiment an effective amount of a glycan is dispersed within a candy matrix. In one embodiment the candy matrix comprises one or more sugars (such as dextrose or sucrose). In another embodiment the candy matrix is a sugar-free matrix. The choice of a particular candy matrix is subject to wide variation. Conventional sweeteners (e.g., sucrose), sugar alcohols suitable for use with diabetic subjects (e.g., sorbitol or mannitol), or other sweeteners (e.g., sweeteners described herein) may be employed. The candy base can be very soft and fast dissolving, or can be hard and slower dissolving. Various forms will have advantages in different situations.

A candy mass composition comprising an effective amount of the glycan can be orally administered to a subject in need thereof so that an effective amount of the glycan will be released into the subject's mouth as the candy mass dissolves and is swallowed. A subject in need thereof includes a human adult or child.

The dosage forms described herein can also take the form of pharmaceutical particles manufactured by a variety of methods, including but not limited to high-pressure homogenization, wet or dry ball milling, or small particle precipitation. Other methods useful to make a suitable powder formulation are the preparation of a solution of active ingredients and excipients, followed by precipitation, filtration, and pulverization, or followed by removal of the solvent by freeze-drying, followed by pulverization of the powder to the desired particle size. In one embodiment, the pharmaceutical particles have a final size of 3-1000 microns, such as at most 3, 4, 5, 6, 7, 8, 9, 10, 20, 30, 40, 50, 60, 70, 80, 90, 100, 150, 200, 250, 300, 350, 400, 450, 500, 550, 600, 650, 700, 750, 800, 850, 900, 950, 1000 microns. In another embodiment, the pharmaceutical particles have a final size of 10-500 microns. In another embodiment, the pharmaceutical particles have a final size of 50-600 microns. In another embodiment, the pharmaceutical particles have a final size of 100-800 microns.

In another aspect, the disclosure provides a method of making a unit-dosage form described herein, comprising providing a glycan (e.g., a glycan described herein); formulating the glycan into a unit-dosage form (e.g., a unit-dosage form described herein), packaging the unit-dosage form, labelling the packaged unit-dosage form, and/or selling or offering for sale the packaged and labeled unit-dosage form.

The unit-dosage forms described herein may also be processed. In one embodiment, the processing comprises one or more of: processing the dosage form into a pharmaceutical composition, e.g., formulating, combining with a second component, e.g., an excipient or buffer; portioning into smaller or larger aliquots; disposing into a container, e.g., a gas or liquid tight container; packaging; associating with a label; shipping or moving to a different location. In one embodiment, the processing comprises one or more of: classifying, selecting, accepting or discarding, releasing or withholding, processing into a pharmaceutical composition, shipping, moving to a different location, formulating, labeling, packaging, releasing into commerce, or selling or offering for sale, depending on whether the predetermined threshold is met. In some embodiments, the processed dosage forms comprise a glycan described herein.

In some embodiments, the processing comprises one or more of: processing the dosage form into a pharmaceutical composition, e.g., formulating, combining with a second component, e.g., an excipient or buffer; portioning into smaller or larger aliquots; disposing into a container, e.g., a gas or liquid tight container; packaging; associating with a label; shipping or moving to a different location. In one embodiment, the processing comprises one or more of: classifying, selecting, accepting or discarding, releasing or withholding, processing into a pharmaceutical composition, shipping, moving to a different location, formulating, labeling, packaging, releasing into commerce, or selling or offering for sale, depending on the determination.

In another embodiment, an oral dosage form is provided comprising a glycan preparation, wherein the oral dosage form is a syrup. The syrup can comprise about 1%, 5%, 10%, 15%, 20%, 25%, 30%, 35%, 40%, 45%, 50%, 55%, 60%, 65%, 70%, 75%, 80%, or 85% solid. The syrup can comprise about 15%, 20%, 25%, 30%, 35%, 40%, 45%, or 50% liquid, for example, water. The solid can comprise a glycan preparation. The solid can be, for example, about 1-96%, 10-96%, 20-96%, 30-96%, 40-96%, 50-96%, 60-96%, 70-96%, 80-96%, or 90-96% glycan preparation. In another embodiment, a glycan preparation is formulated as a viscous fluid.

In one embodiment, the composition comprises a foaming component, a neutralizing component, or a water-insoluble dietary fiber. A foaming component can be at least one member selected from the group consisting of sodium hydrogen carbonate, sodium carbonate, and calcium carbonate. In one embodiment a neutralizing component can be at least one member selected from the group consisting of citric acid, L-tartaric acid, fumaric acid, L-ascorbic acid, DL-malic acid, acetic acid, lactic acid, and anhydrous citric acid. In one embodiment a water-insoluble dietary fiber can be at least one member selected from the group consisting of crystalline cellulose, wheat bran, oat bran, cone fiber, soy fiber, and beet fiber. The formulation can contain a sucrose fatty acid ester, powder sugar, fruit juice powder, and/or flavoring material.

In some embodiments, the dosage forms are formulated to release the pharmaceutical compositions comprising glycan preparations in a specific region(s) of the GI tract, such as the small or the large intestine. In some embodiments, the dosage forms are formulated to release the pharmaceutical compositions comprising glycan preparations in a specific region(s) of the GI tract, such as the cecum, ascending colon, transverse colon, descending colon, sigmoid colon, and/or rectum.

In some embodiments, the dosage form for the glycan preparations described herein is an enzyme-responsive delivery system. For example, trypsin responsive polymers can be made using hydrogels that are crosslinked by peptides that are degraded by trypsin. Trypsin is active in the small intestine. Trypsin-responsive delivery systems can be used to target delivery of the glycan preparations to the small intestine. In another example, enzyme-digestible hydrogels consisting of poly(vinyl pyrrolidone) crosslinked with albumin are degraded in the presence of pepsin.

In some embodiments, the dosage form for the glycan preparations described herein is a delivery device that enables prolonged retention at a specific site in the GI tract. For example, a gastroretentive delivery system enables prolonged release of the glycan preparations to the stomach. Gastroretentive delivery may be used for the glycan preparations that modulate bacteria in the stomach or in the upper small intestine.

In some embodiments, the dosage form for the glycan preparations described herein is a mucoadhesive delivery system that adheres to the mucosal surfaces of the stomach. They are typically composed of polymers with numerous hydrogen-bonding groups, e.g., cross-linked polyacrylic acids, sodium carboxymethyl cellulose, sodium alginate, carrageenan, Carbopol 934P, or thiolated polycarbophil.

In some embodiments, the dosage form for the glycan preparations described herein is an expanding delivery system that rapidly increases in size in the stomach, which slows its passage through the pylorus. Such systems include systems that unfold in the stomach. For example, geometric shapes such as tetrahedrons, rings, disks, etc. can be packed into a gelatin capsule. When the capsule dissolves, the shape unfolds. The systems can be composed of one or more erodible polymer (e.g., hydroxypropyl cellulose), one or more non-erodible polymer (e.g., polyolefins, polyamides, polyurethanes). The glycan may then be dispersed within the polymer matrix. The retention times can be fine-tuned by the polymer blend. Alternatively, devices made from elastic polymers that are stable in the acidic pH of the stomach but dissolve in the neutral/alkaline conditions further along the GI tract can be used. Such polymer formulations can prevent intestinal obstruction when the device exits the stomach. Supramolecular polymer gels crosslinked by hydrogen bonds between carboxyl groups may also be used, e.g. composed of poly(acryloyl 6-aminocaproic acid) (PA6ACA) and poly(methacrylic acid-co-ethyl acrylate) (EUDRAGIT L 100-55). Other systems include swellable excipients, such as collagen sponges. For example, a hydrogel matrix (e.g. a swellable core: polyvinyl pyrrolidone XL, Carbopol 934P, calcium carbonate) swells 2-50 times in the stomach. Superporous hydrogel composites swell to hundreds of times their original volume in a few minutes. Some systems exploit gas generation to achieve expansion, e.g. carbon dioxide-generating, expandable systems that are surrounded by a hydrophilic membrane.

In some embodiments, the dosage form for the glycan preparations described herein is a density-controlled delivery system. These systems are designed to either float or sink in gastric fluids, which delays their emptying from the stomach. For example, high-density systems enable the device to settle to the bottom of the stomach, below the pylorus, and thus avoid stomach emptying. Other systems are low-density/floating systems. Such devices may, e.g., comprise entrapped air in hollow chambers or may incorporate low-density materials like fats, oils, or foam powder. Low density may be achieved through swelling, e.g. hydrocolloid containing capsules dissolve upon contacting gastric fluid and the hydrocolloids swell to form a mucous body. Alternative polymers include: chitosans, sodium alginate, and glycerol monooleate matrix. Low density may be achieved through gas generation. For example, tablets loaded with carbonate and optionally citric acid generate carbon dioxide after contact with acidic aqueous media. The carbon dioxide generated is entrapped within the gelling hydrocolloid causing the system to float. Hydrocolloids include hydroxypropyl methylcellulose and Carbopol 934P.

In some embodiments, the dosage form for the glycan preparations described herein employs a design to retain a device in the small or large intestine. The location-specific nature of the device is provided by a specific triggering method, e.g. pH, enzyme, etc. These include systems designed for mucoadhesion and also microneedle pills. Microneedle pills comprise a drug reservoir spiked with microneedles that is encapsulated in a pH-responsive coating. When the pill reaches the desired location in the GI tract and the coating dissolves, the microneedles enable the pill to become stuck to the lining of the GI tract. In other embodiments, the microneedle pills comprise a capsule that consists of two chemical compartments filled with citric acid and sodium bicarbonate, respectively. As the pill dissolves in the digestive system, barriers between the two substances erode, allowing them to mix and create a chemical reaction that pushes micro-needles of saccharides through the outer layer of the capsule and into the lining of the small intestine. The saccharide needles can be filled with drugs that are delivered into nearby blood vessels as the saccharide is absorbed.

In some embodiments, the dosage form for the glycan preparations described herein employs a pH sensitive polymer coating. For example, pH-dependent polymers (bi- or tri-phasic) can be insoluble at low pH levels (e.g. acid resistance in the stomach, pH 1-2) and become increasingly soluble as pH rises, e.g. to about 5.5-6.2 in the duodenum, to about pH 5.7 in the ascending colon, to about pH 6.4 in the cecum, to about pH 6.6 in the transverse colon, to about pH 7.0 in the descending colon, to about 7.2-7.5 in the ileum, or to about pH 7.5 in the distal small intestine. In one example, TARGIT™ technology may be used for site-specific delivery of the glycan preparations in the gastrointestinal (GI) tract. The system employs pH-sensitive coatings onto injection-molded starch capsules to target the terminal ileum and colon.

In some embodiments, the dosage form for the glycan preparations described herein is a delayed release system or time controlled release system. Such systems usually employ enteric coatings that may be combined with pH sensitive and time release functions. For example, ETP (enteric coated time-release press coated) tablets may be used that are composed of three components: a glycan-containing core tablet (rapid release function), a press-coated, swellable hydrophobic polymer layer (e.g. hydroxypropyl cellulose layer (HPC), and a time release function. The duration of lag phase can be controlled either by weight or composition of polymer layer and an enteric coating layer (acid resistance function).

In some embodiments, the dosage form for the glycan preparations described herein employs Eudragit® enteric coatings of tablets and capsules. Other suitable synthetic polymers include: Shellac, ethyl cellulose, cellulose acetate phthalate, hydroxypropylmethyl cellulose, polyvinyl acetate phthalate and poly glutamic acid coatings, such as poly-γ-glutamic acid (7-PGA). These coatings combine both mucoadhesive and pH-dependent release strategies. To enhance colon targeted delivery Eudragits® are methacrylic co-polymers with varying side group compositions that alter the pH at which they are soluble. For example, for Eudragit®-coated systems no significant drug release occurs in the stomach (e.g. at pH 1.4) and in the small intestine (e.g. at pH 6.3), while significant drug release can be seen at pH 7.8 in the ileocaecal region.

In some embodiments, the dosage form for the glycan preparations described herein is a microbial-triggered system, such as a polysaccharide based delivery system. Polysaccharide based delivery systems contain biodegradable and mucoadhesive polymer coatings, including coatings of chitosan and pectin. Other suitable natural polymers include, e.g., guar gum, inulin, cyclodextrin, dextran, amylase, chondrotin sulphate, and locust bean gum. These delivery systems can be used to target the glycan to the small intestine. Coatings with naturally occurring polysaccharides like guar gum, xanthan gum, chitosan, alginates, etc. are degraded by colonic gut microbiota, e.g. enzymes such as, xylosidase, arabinosidase, galactosidase etc. For example, CODES™ technology may be used to deliver the glycan preparations. This system combines the polysaccharide coating with a pH-sensitive coating. In some embodiments, the system consists of a core tablet coated with three layers of polymer coatings: The outer coating is composed of Eudragit L. This coating gets dissolved in the duodenum and exposes the next coating. The next coating is composed of Eudragit E. This layer allows the release of lactulose present in the inner core. The lactulose gets metabolized into short chain fatty acids that lower the surrounding pH where the Eudragit E layer dissolves. The dissolving of Eudragit E results in the exposure of the glycan. The bacteria present in the colon are responsible for the degradation of polysaccharides that are released from the core tablet. The degradation of polysaccharides may result in organic acids formation that lowers the pH of the contents surrounding the tablet.

In some embodiments, the dosage form for the glycan preparations described herein is a pressure-controlled delivery system. The system employs the fact that higher pressures are encountered in the colon than in the small intestine. For example, for ethylcellulose systems that are insoluble in water, the release of glycans occurs following disintegration of a water-insoluble polymer capsule as a result of pressure in the lumen of the colon. The release profile may be adjusted by varying the thickness of the ethylcellulose, the capsule size and/or density of the capsule.

In some embodiments, the dosage form for the glycan preparations described herein is a pulsatile colon targeted delivery system. For example, the system can be a pulsincap system. The capsule which is employed comprises a plug that is placed in the capsule that controls the release of the glycan. A swellable hydrogel (e.g. hydroxyl propyl methyl cellulose (HPMC), poly methyl methacrylate or polyvinyl acetate) seals the drug content. When the capsule gets in contact with a fluid the plug is pushed off from the capsule and the glycan is released. The release profile can be controlled by varying the length and/or point of intersection of the plug with the capsule body. Another system is a port system. The capsule body is enclosed in a semi-permeable membrane. The insoluble plug consists of an osmotically active agent and the glycan. When the capsule gets in contact with a fluid the semi-permeable membrane permits inflow of the fluid which increases pressure in the capsule body. This leads to an expelling of the plug and release of the glycan.

In some embodiments, the dosage form for the glycan preparations described herein is an osmotically controlled colon targeted delivery system. An exemplary system, OROS-CT, consists of osmotic units (up to 5 or 6 push pull units) encapsulated in a hard gelatin capsule. The push pull units are bi-layered with outer enteric impermeable membrane and inner semi-permeable membrane. The internal, central part of the push pull consists of the drug layer and push layer. The glycan is released through the semi-permeable membrane. The capsule body enclosing the push pull units is dissolved immediately after administration. In the GI tract the enteric impermeable membrane prevents water absorption. The enteric coating is dissolved in small intestine (higher pH, >7), water enters the unit through the semi-permeable membrane causing push layer to swell and force out the glycan.

In some embodiments, the dosage form for the glycan preparations described herein is "smart pill" which can be used to release the glycan just before reaching the ileocecal valve.

In some embodiments, the dosage form for the glycan preparations described herein is a rectally administered formulation. For example, enemas introduce a glycan preparation in liquid formulation into the rectum. The volume administered is typically less than 10 mL. Suppositories introduce a glycan preparation into the rectum. Suppositories are solid dosage forms that melt or dissolve when inserted into the rectum, releasing the glycans. Typical excipients for suppository formulations include cocoa butter, polyethylene glycols, and agar.

Dosage Forms

The glycan compositions described herein may be formulated into any suitable dosage form, e.g. for oral or enteral administration or formulated for injection. Suitable dosage forms for use in the methods and compositions described herein can be found in WO 2016/122889, WO 2016/172657, and WO 2016/172658, which in their entirety, is hereby incorporated by reference. The dosage forms described herein can be manufactured using processes that are known to those of skill in the art. The dosage form may be suitable for any route of administration, including orally or parenterally, such as intravenously, intramuscularly, subcutaneously, intraorbitally, intracapsularly, intraperitoneally, intrarectally, intracisternally, intratumorally, intravasally, intradermally or by passive or facilitated absorption through the skin.

The dosage form may be a packet, such as any individual container that contains a glycan composition in the form of, e.g., a liquid (e.g., a beverage), a solid, a gel, a cream, an ointment, a powder, a sachet, a tablet, a pill, a capsule, a lozenge, a gummy, a suppository, a depository, a single-use applicator, a softgel or medical device (e.g. a syringe). For example, provided is also an article of manufacture, such as a container comprising a unit dosage form of the glycan composition, and a label containing instructions for use of such glycan composition.

The compositions provided herein can be in unit-dosage forms or multiple-dosage forms. A unit-dosage form, as used herein, refers to physically discrete unit suitable for administration to human in need thereof. In an embodiment, the unit-dosage form is provided in a package. Each unit-dose can contain a predetermined quantity of an active ingredient(s) sufficient to produce the desired therapeutic effect, in association with other pharmaceutical carriers or excipients. Examples of unit-dosage forms include ampoules, syringes, and individually packaged tablets and capsules. Unit-dosage forms can be administered in fractions or multiples thereof. A multiple-dosage form is a plurality of identical unit-dosage forms packaged in a single container, which can be administered in segregated unit-dosage form.

Kits

Kits also are contemplated. For example, a kit can comprise unit dosage forms of the glycan preparation, and a package insert containing instructions for use of the glycan in treatment of a gastrointestinal disorder or condition. The kits include a glycan preparation in suitable packaging for use by a subject in need thereof. Any of the compositions described herein can be packaged in the form of a kit. A kit can contain an amount of a glycan preparation (optionally additionally comprising a prebiotic substance, a probiotic bacterium, and/or a second therapeutic agent) sufficient for an entire course of treatment, or for a portion of a course of treatment. Doses of a glycan preparation can be individually packaged, or the glycan preparation can be provided in bulk, or combinations thereof. Thus, in one embodiment, a kit provides, in suitable packaging, individual doses of a glycan preparation that correspond to dosing points in a treatment regimen, wherein the doses are packaged in one or more packets.

In one embodiment, the glycan preparation can be provided in bulk in a single container, or in two, three, four, five, or more than five containers. For example, each container may contain enough of a glycan preparation for a particular week of a treatment program that runs for a month. If more than one bulk container is provided, the bulk containers can be suitably packaged together to provide sufficient glycan preparation for all or a portion of a treatment period. The container or containers can be labeled with a label indicating information useful to the subject in need thereof or the physician performing the treatment protocol, such as, e.g. dosing schedules. The glycan preparation can be packaged with other suitable substances, such as probiotic bacteria, prebiotic substances or other substances, as described herein. The other substance or substances can be packaged separately from the glycan preparation, or mixed with the glycan preparation, or combinations thereof. Thus, in one embodiment, kits include a dosage form containing all the ingredients intended to be used in a course of treatment or a portion of a course of treatment, e.g., a glycan preparation and optionally buffers, excipients, etc., a probiotic, prebiotic or a polymer agent. In one embodiment, a glycan preparation is packaged in one package or set of packages, and additional components, such as probiotic bacteria, prebiotics, and therapeutic agents are packaged separately from the glycan preparation.

Kits can further include written materials, such as instructions, expected results, testimonials, explanations, warnings, clinical data, information for health professionals, and the like. In one embodiment, the kits contain a label or other information indicating that the kit is only for use under the direction of a health professional. The container can further include scoops, syringes, bottles, cups, applicators or other measuring or serving devices.

Medical Food

Also provided herein are preparations of glycans formulated as a medical food. Any glycan preparation described herein may be formulated as a medical food as well as pharmaceutical compositions that comprise glycan preparations.

A medical food is defined in section 5(b)(3) of the Orphan Drug Act (21 U.S.C. 360ee(b)(3)). Medical food is formulated to be consumed (oral intake) or administered enterally (e.g. feeding/nasogastric tube) under medical supervision, e.g. by a physician. It is intended for the specific dietary management of a disease or condition, such as, e.g. dysbiosis or a GI-tract disease. Medical foods as used herein do not include food that is merely recommended by a physician as part of an overall diet to manage the symptoms or reduce the risk of a disease or condition. Medical foods comprising a preparation of glycans are foods that are synthetic (e.g., formulated and/or processed products, such as, being formulated for the partial or exclusive feeding of a subject by oral intake or enteral feeding by tube) and not naturally occurring foodstuff used in a natural state.

In some embodiments, the subject has limited or impaired capacity to ingest, digest, absorb, or metabolize ordinary foodstuffs or certain nutrients. In other embodiments, the subject has other special medically determined nutrient requirements, the dietary management of which cannot be achieved by the modification of the normal diet alone. Medical foods comprising a preparation of glycans are administered to a subject in need thereof under medical supervision (which may be active and ongoing) and usually, the subject receives instructions on the use of the medical food. Medical foods may comprise one or more food additives, color additives, GRAS excipients and other agents or substances suitable for medical foods. Medical food preparations may be nutritionally complete or incomplete formulas.

Dietary Supplements

Any glycan preparation described herein may be formulated as a dietary supplement, e.g, for use in a method described herein. Dietary supplements are regulated under the Dietary Supplement Health and Education Act (DSHEA)

of 1994. A dietary supplement is a product taken by mouth that contains a "dietary ingredient" intended to supplement the diet. The "dietary ingredients" in these products may include, in addition to a glycan preparation described herein, one or more of: vitamins, minerals, herbs or other botanicals, amino acids, and substances such as enzymes, organ tissues, glandulars, and metabolites. Dietary supplements can also be extracts or concentrates, and may be found in many forms such as tablets, capsules, softgels, gelcaps, liquids, or powders. They can also be in other forms, such as a bar, but if they are, information on their label must not represent the product as a conventional food or a sole item of a meal or diet. DSHEA requires that every supplement be labeled a dietary supplement and not as a general food.

Food Ingredient

Any glycan preparation described herein may be formulated as a food ingredient or food additive, e.g., for use in a method described herein. Food ingredients may be generally recognized as safe (GRAS) or may require FDA authorization. Glycan preparations can be added to any desirable food, e.g. beverages (incl., e.g., fruit juices), dairy products (e.g., milk, yogurt, cheese), cereals (any grain products), bread, spreads, etc.

A glycan preparation may be formulated as a food. The term "food" as defined in the Federal Food, Drug and Cosmetic Act (21 U.S.C. Section 321(a)(f)) refers to articles used for food or drink for man or other animals, chewing gum, and articles used for components of any such article. Food is formulated to be consumed (oral intake). Foods may comprise, in addition to a glycan preparation, one or more food additives, color additives, GRAS excipients and other agents or substances suitable for foods. Food preparations may be nutritionally complete or incomplete formulas. Food products can be, e.g., a beverage, a powdered beverage mix, a bar, a candy, a dairy product, confection, baked good, a gummy, and the like.

Methods of Modulating Microbial Taxa

The compounds and compositions provided herein may be used in methods to modulate bacterial taxa (e.g. 1, 2, 3, 4, 5 or more taxa) present in the microbiota of a subject. In some embodiments, modulation comprises a change in the structure of the microbiota, such as a change in the relative composition of a taxa or a change in the relative abundance of a taxa, e.g., relative to another taxa or relative to what would be observed in the absence of the modulation. In other embodiments, modulation comprises a change in a function of the microbiota, such as a change in gene expression, level of a gene product (e.g., RNA or protein), or metabolic output of the microbiota, or a change in a functional pathway of the host (e.g., a change in gene expression, level of a gene product, or metabolic output of a host cell or host process). Methods of modulating microbial taxa disclosed in WO 2016/122889 and WO 2016/172657 which are hereby incorporated by reference, are suitable for use in methods described herein.

The methods describe herein include administering to a subject a composition described herein, e.g., comprising a glycan composition described herein, in an amount effective to modulate taxa.

In some embodiments, the abundance of a bacterial taxa may increase relative to other taxa (or relative from one point in time to another) when the composition is administered and the increase can be at least a 5%, 10%, 25% 50%, 75%, 100%, 250%, 500%, 750% increase or at least a 1000% increase. The abundance of a bacterial taxa may also decrease relative to other taxa (or relative from one point in time to another) when the composition is administered and the decrease can be at least a 5%, 10%, 25% 50%, 75%, 85%, 90%, 95%, 96%, 97%, 98%, 99% decrease, or at least a 99.9% decrease. Administration of the composition can modulate the abundance of the desired and/or non-desired bacterial taxa in the subject's gastrointestinal microbiota.

In some embodiments, the composition described herein, e.g., comprising a glycan composition described herein, modulates (e.g. increases or decreases) the growth of one or more bacterium, such as, e.g., those that belong to genera *Bacteroides, Odoribacter, Parabacteroides, Alistipes, Blautia, Clostridium, Coprococcus, Dorea, Eubacterium, Lachnospira, Roseburia, Ruminococcus, Faecalibacterium, Oscillospira*, and *Subdoligranulum* which can be found in the GI tract. In some embodiments, the composition described herein, e.g., comprising a glycan composition described herein, modulates (e.g. increases or decreases) the growth of one or more bacterium, such as, e.g., of the genus *Akkermansia, Anaerofilum, Bacteroides, Blautia, Bifidobacterium, Butyrivibrio, Clostridium, Coprococcus, Dialister, Dorea, Fusobacterium, Eubacterium, Faecalibacterium, Lachnospira, Lactobacillus, Phascolarctobacterium, Peptococcus, Peptostreptococcus, Prevotella, Roseburia, Ruminococcus*, and *Streptococcus*, and/or one or more of the species *Akkermansia municiphilia, Christensenella minuta, Clostridium coccoides, Clostridium leptum, Clostridium scindens, Dialister invisus, Eubacterium rectal, Eubacterium eligens, Faecalibacterium prausnitzii, Streptococcus salivarius*, and *Streptococcus thermophilus*.

In some embodiments, the composition described herein, e.g., comprising a glycan composition described herein modulates (e.g., increases or decreases) the growth of at least two bacterial taxa selected from *Prevotella, Akkermansia, Bacteroides, Clostridium* (Erysipelotrichaceae), *Clostridium* (Clostridiaceae), *Bifidobacterium, Aggregatibacter, Clostridium* (Peptostreptococcaveae), *Parabacteroides, Lactobacillus*, and *Enterococcus*.

In some embodiments, a composition described herein, e.g., comprising a glycan composition described herein, modulates (e.g. increases or decreases) the growth of one or more bacterial taxa residing in the GI tract, such as, e.g., those that belong to genera *Bacteroides, Odoribacter, Parabacteroides, Alistipes, Blautia, Clostridium, Coprococcus, Dorea, Eubacterium, Lachnospira, Roseburia, Ruminococcus, Faecalibacterium, Oscillospira*, and *Subdoligranulum* which can be found in the GI tract. In some embodiments, a composition described herein, e.g., comprising a glycan composition described herein, modulates (e.g. increases or decreases) the growth of one or more bacterial taxa, such as those that are thought to be associated with a healthy gastrointestinal state, e.g., one or more of the genus *Akkermansia, Anaerofilum, Bacteroides, Blautia, Bifidobacterium, Butyrivibrio, Clostridium, Coprococcus, Dialister, Dorea, Fusobacterium, Eubacterium, Faecalibacterium, Lachnospira, Lactobacillus, Phascolarctobacterium, Peptococcus, Peptostreptococcus, Prevotella, Roseburia, Ruminococcus*, and *Streptococcus*, and/or one or more of the species *Akkermansia municiphilia, Christensenella minuta, Clostridium coccoides, Clostridium leptum, Clostridium scindens, Dialister invisus, Eubacterium rectal, Eubacterium eligens, Faecalibacterium prausnitzii, Streptococcus salivarius*, and *Streptococcus thermophilus*. In some embodiments, the composition described herein, e.g., comprising a glycan composition described herein, modulates (e.g. increases or decreases) the growth of one or more bacterial taxa, such as taxa of the phylum Verrucomicrobia, e.g., those of the genus *Akkermansia*.

In some embodiments, a composition described herein, e.g., comprising a glycan composition described herein, modulates (e.g. increases or decreases) the growth of one or more bacterial taxa predominantly residing in the small intestine. For example, the composition described herein, e.g., comprising a glycan composition described herein, modulates one or more (2, 3, 4, 5, 6, 7, 8, 9, 10 or more) bacterial taxa that reside predominantly in the small intestine, such as, e.g. Actinobacteria, Firmicutes (Bacilli, Clostridia), and Proteobacteria (Alphaproteobacteria, Betaproteobacteria). In some embodiments, a composition described herein, e.g., comprising a glycan composition described herein, modulates one or more (2, 3, 4, 5, 6, 7, 8, 9, 10 or more) bacterial taxa that reside predominantly in the small intestine selected from the genera: *Cryocola, Mycobacterium, Enterococcus, Lactococcus, Streptococcus, Turicibacter, Blautia, Coprococcus, Holdemania, Pseudoramibacter Eubacterium, Agrobacterium, Sphingomonas, Achromobacter, Burkholderia*, and *Ralstonia*.

In some embodiments, a composition described herein, e.g., comprising a glycan composition described herein, modulates (e.g., increases or decreases) the growth of one or more bacterial taxa predominantly residing in the large intestine. For example, a composition described herein, e.g., comprising a glycan composition described herein, modulates one or more (2, 3, 4, 5, 6, 7, 8, 9, 10 or more) bacterial taxa that reside predominantly in the large intestine, such as, e.g.

Bacteroidetes, Firmicutes (Clostridia), Verrucomicrobia, and Proteobacteria (Deltaproteobacteria). In some embodiments, a composition described herein, e.g., comprising a glycan composition described herein, modulates one or more (2, 3, 4, 5, 6, 7, 8, 9, 10 or more) bacterial taxa that reside predominantly in the large intestine selected from the genera: *Bacteroides, Butyricimonas, Odoribacter, Parabacteroides, Prevotella, Anaerotruncus, Phascolarctobacterium, Ruminococcus, Bilophila*, and *Akkermansia*.

In some embodiments, the composition described herein, e.g., comprising a glycan composition described herein, modulates (e.g. increases or decreases) the growth of one or more bacterial taxa predominantly residing in the cecum, such as, e.g. Actinobacteria, *Bacteroides*, Bacilli, Clostridia, Mollicutes, Alpha Proteobacteria, and Verrucomicrobia.

In some embodiments, a composition described herein, e.g., comprising a glycan composition described herein, modulates (e.g., increases or decreases) the growth of one or more bacterial taxa predominantly residing in the ascending colon, such as, e.g. Actinobacteria, *Bacteroides*, Bacilli, Clostridia, Fusobacteria, Beta Proteobacteria, Delta/Epsilon Proteobacteria, Gamma Proteobacteria, and Verrucomicrobia.

In some embodiments, the composition described herein, e.g., comprising a glycan composition described herein, modulates (e.g. increases or decreases) the growth of one or more bacterial taxa predominantly residing in the traverse colon, such as, e.g. Actinobacteria, *Bacteroides*, Clostridia, Mollicutes, Fusobacteria, and Gamma Proteobacteria.

In some embodiments, a composition described herein, e.g., comprising a glycan composition described herein, modulates (e.g. increases or decreases) the growth of one or more bacterial taxa predominantly residing in the descending colon, such as, e.g. *Bacteroides*, Clostridia, Mollicutes, Fusobacteria, Delta/Epsilon Proteobacteria and Verrucomicrobia.

In some embodiments, a composition described herein, e.g., comprising a glycan composition described herein, modulates (e.g., increases or decreases) the growth of one or more bacterial taxa predominantly residing in the sigmoid colon, such as, e.g. Actinobacteria, *Bacteroides*, Bacilli, Clostridia, Mollicutes, Alpha Proteobacteria, Beta Proteobacteria, and Verrucomicrobia.

In some embodiments, a composition described herein, e.g., comprising a glycan composition described herein, modulates (e.g. increases or decreases) the growth of one or more bacterial taxa predominantly residing in the rectum, such as, e.g. *Bacteroides*, Clostridia, Mollicutes, Alpha Proteobacteria, Gamma Proteobacteria, and Verrucomicrobia.

In some embodiments, a composition described herein, e.g., comprising a glycan composition described herein, modulates (e.g., stimulate/increase or suppress/decrease) the growth of one or more (e.g. 1, 2, 3, 4, 5, 6, 7, 8, 9, 10, or more) bacterial taxa of genera including, e.g. *Alistipes, Akkermansia, Anaerofilum, Bacteroides, Blautia, Bifidobacterium, Butyrivibrio, Clostridium, Coprococcus, Dialister, Dorea, Fusobacterium, Eubacterium, Faecalibacterium, Lachnospira, Lactobacillus, Odoribacter, Oscillospira, Parabacteroides, Phascolarctobacterium, Peptococcus, Peptostreptococcus, Prevotella, Roseburia, Ruminococcus,* and *Streptococcus* and *Subdoligranulum*.

In some embodiments, a composition described herein, e.g., comprising a glycan composition described herein, modulates (e.g., stimulate/increase or suppress/decrease) the growth of one or more (e.g. 1, 2, 3, 4, 5, 6, 7, 8, 9, 10, or more) microbial taxa of genera *Akkermansia, Anaerofilum, Bacteroides, Blautia, Bifidobacterium, Butyrivibrio, Clostridium, Coprococcus, Dialister, Dorea, Fusobacterium, Eubacterium, Faecalibacterium, Lachnospira, Lactobacillus, Phascolarctobacterium, Peptococcus, Peptostreptococcus, Prevotella, Roseburia, Ruminococcus,* and *Streptococcus* and of the species *Akkermansia municiphilia, Christensenella minuta, Clostridium coccoides, Clostridium leptum, Clostridium scindens, Dialister invisus, Eubacterium rectal, Eubacterium eligens, Faecalibacterium prausnitzii, Streptococcus salivarius,* and *Streptococcus thermophilus*.

In some embodiments, a composition described herein, e.g., comprising a glycan composition described herein, modulates (e.g. substantially increase or substantially decrease) the growth (and the total number) of (or substantially increase or substantially decrease the relative representation/abundance in the total (gastrointestinal) community) of one or more of (e.g. 1, 2, 3, 4, 5, 6, 7, 8, 9, 10, or more) bacterial taxa listed in Tables 8-10.

In some embodiments, a composition described herein, e.g., comprising a glycan composition described herein, substantially increases the growth, e.g. the total number or the relative representation/abundance in the total (gastrointestinal) community) of one or more of (e.g. 1, 2, 3, 4, 5, 6, 7, 8, 9, 10, or more) bacterial taxa listed in Tables 8-10.

In some embodiments, a composition described herein, e.g., comprising a glycan composition described herein, substantially decreases the growth, e.g. the total number or the relative representation/abundance in the total (gastrointestinal) community) of one or more of (e.g. 1, 2, 3, 4, 5, 6, 7, 8, 9, 10, or more) bacterial taxa listed in Tables 8-10.

In some embodiments, a composition described herein, e.g., comprising a glycan composition described herein, substantially increases and decreases the growth, e.g. the total number or the relative representation/abundance in the total (gastrointestinal) community) of one or more of (e.g. 1, 2, 3, 4, 5, 6, 7, 8, 9, 10, or more) bacterial taxa listed Tables 8-10.

In certain embodiments, the ratio of certain bacterial taxa or their relative abundance may be shifted. Such shifts may be measured with respect to the ratio present in the subject prior to administration of the pharmaceutical glycan composition, or to a control group not taking the pharmaceutical glycan composition.

Glycan compositions and glycan preparations described herein reduces ammonia levels in a subject relative to a control subject as shown in Table 6. In some embodiments, a glycan composition and/or glycan preparation selected from any one of rows 2-9 of Table 6 (e.g., gal100, glu10gal10man80, glu30gal30man40, gal33man33xyl33, glu40gal30man30, glu40gal20man40, glu45gal10man45, glu60gal20man20, fructo-oligosaccharide, glu40gal40man20, glu20gal20man20xyl20ara20, glu90gal5man5, glu80xyl20, glu20gal80, glu80ara20, glu40gal60, glu33gal33man33, man100, lactulose, glu80gal10man10, man80glu20, glu50gal50, glu80gal20, glu80man20, glu45gal45man10, glu60gal40, glu60man40, man80gal20, man60glu40, glu100) is capable of reducing ammonia levels in a subject relative to a control subject by 55-<60%, 60-<65%, 70-<75%, 75-<80%, 80-<85%, 85-<90%, 90-<95%, or 95-<100%.

Proteomic Analysis of Microbial Populations

Suitable methods for proteomic analysis of microbial populations can be found in WO 2016/122889 and WO 2016/172657, which are hereby incorporated by reference. In some embodiments, proteomic analysis can be performed following protocols described in e.g., Cordwell, Exploring and exploiting bacterial proteomes, Methods in Molecular Biology, 2004, 266:115.

Identification of Microbial (e.g. Bacterial) Constituents

Microbial modulation (e.g., of representation/abundance of a taxa) by the glycan compositions described herein, e.g., occurring in vivo in the GI tract can be analyzed using any number of methods known in the art and described herein. Suitable methods can be found in WO 2016/122889, WO 2016/172657, and WO 2016/172658, which are hereby incorporated by reference. In some embodiments, quantitative PCR (qPCR) can be used as a method to determine whether a glycan composition can result in a shift of the population of bacteria in the GI tract. In some embodiments, microbial constituents can be identified by characterizing the DNA sequence of microbial 16S small subunit ribosomal RNA gene (16S rRNA gene). In other embodiments, a microbial composition can be identified by characterizing nucleotide markers or genes, in particular highly conserved genes (e.g., "house-keeping" genes), or a combination thereof, or whole genome shotgun sequence (WGS).

Administration to a Subject

The glycan compositions, pharmaceutical compositions and therapeutic agents described herein can be administered to a subject in need thereof by any appropriate means. In some embodiments, the glycan composition is administered enterically. This includes oral administration, or by an oral or nasal tube (including nasogastric, nasojejunal, oral gastric, or oral jejunal). In other embodiments, administration includes rectal administration (including enema, suppository, or colonoscopy). Methods of administering to a subject suitable for use with methods and compositions described herein can be found in WO 2016/122889, WO 2016/172657, and WO 2016/172658, which in their entirety, are hereby incorporated by reference.

Active compounds and pharmaceutical agents, e.g., prebiotic substances, probiotic bacteria or drugs, may be administered separately, e.g., prior to, concurrent with or after administration of the glycan compositions and not as a part of the pharmaceutical composition or medical food or dietary supplement (e.g. as a co-formulation) of glycan compositions. In some embodiments, pharmaceutical compositions or medical foods comprising preparations of glycan compositions are administered in combination with a recommended or prescribed diet, e.g. a diet that is rich in probiotic and/or prebiotic-containing foods, such as it may be determined by a physician or other healthcare professional.

All publications, patents, and patent applications cited or referenced in this specification are herein incorporated by reference to the same extent as if each independent publication or patent publication was specifically and individually indicated to be incorporated by reference.

EXAMPLES

The invention is further illustrated by the following examples. The examples are provided for illustrative purposes only, and are not to be construed as limiting the scope or content of the invention in any way. The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, Proteins: Structures and Molecular Properties (W.H. Freeman and Company, 1993); Green & Sambrook et al., Molecular Cloning: A Laboratory Manual, 4th Edition (Cold Spring Harbor Laboratory Press, 2012); Colowick & Kaplan, Methods In Enzymology (Academic Press); Remington: The Science and Practice of Pharmacy, 22nd Edition (Pharmaceutical Press, 2012); Sundberg & Carey, Advanced Organic Chemistry: Parts A and B, 5th Edition (Springer, 2007).

Example 1. Glycan Preparations

To a round bottom flask equipped with an overhead stirrer and a jacketed short-path condenser was added one or more mono- or disaccharides along with 3-20% by dry weight of one or more of the catalysts e.g. acid, ionic, ionic/acid containing catalysts such as, e.g. described in U.S. Pat. No. 9,079,171 and WO 2016/007778, which are incorporated herein by reference in their entirety. Water or another compatible solvent (zero to 10 equiv.) was added to the dry mixture and the slurry was combined at approximately 100 rpm using a paddle sized to match the contours of the selected round bottom flask as closely as possible. The mixture was then heated to 80-185° C. Once the solids achieved a molten state, the vessel was placed under 10-1000 mbar vacuum pressure. The reaction was stirred for 30 minutes to 8 hours, constantly removing water from the reaction. Reaction progress was monitored by HPLC. When sufficient oligomerization had occurred, the stirrer was shut off, the reaction was cooled to room temperature and vented to atmospheric pressure, and the product, either as a solid or syrup, was dissolved in a volume of water sufficient to create a solution of approximately 50 Brix (grams sugar per 100 g solution). Once dissolution was complete, solid catalyst was removed by filtration and the oligomer solution was concentrated to approximately 50-75 Brix by rotary evaporation. In cases in which an organic solvent has been used, water immiscible solvents can be removed by biphasic extraction and water miscible solvents can be removed by rotary evaporation concomitant to the concentration step.

Among others, the following glycans were made in multiple batches and tested in various assays described herein:

Single glycan unit (homo-glycans): ara100, fru100, gal100, galA100, glcNac100, glu100, gluA100, Lglu100, man100, rha100, xyl100.

Two glycan units (hetero-glycans): Ara60Xyl40, Ara80Xyl20, Gal20Ara80, Gal20Xyl80, Gal40Ara60, Gal40Man60, Gal40Xyl60, Gal57Glu43, Gal60Ara40, Gal60Man40, Gal60Xyl40, Gal80Ara20, Gal80Man20, Gal80Xyl20, Glu20Ara80, Glu20Xyl80, Glu40Ara60, Glu40Gal60, Glu40Xyl60, Glu50Gal50, Glu50Lglu50, Glu60Ara40, Glu60Gal20Man20, Glu60Gal40, Glu60Man40, Glu60Xyl40, Glu66Fru33, Glu75Gala25, Glu75GluA25, Glu75GluN25, Glu80Ara20, Glu80Gal20, Glu80Lglu20, Glu80Man20, Glu80Xyl20, Glu90LGlu10, Man20Ara80, Man20Xyl80, Man40Ara60, Man40Xyl60, Man60Ara40, Man60Glu40, Man60Xyl40, Man75Gal25, Man80Ara20, Man80Gal20, Man80Glu21, Man80Xyl20, Xyl60Ara40, Xyl75Ara25, Xyl80Ara20, and the hybrid glycans glu90sor10 and glu90gly10.

Three glycan units (hetero-glycans): Gal5Xyl5Ara90, Gal5Xyl90Ara5, Gal10Xyl10Ara80, Gal10Xyl45Ara45, Gal10Xyl80Ara10, Gal20Xyl20Ara60, Gal20Xyl40Ara40, Gal20Xyl60Ara20, Gal30Xyl30Ara40, Gal30Xyl40Ara30, Gal33Man33Ara33, Gal33Man33Xyl33, Gal33Xyl33Ara33, Gal45Xyl10Ara45, Gal45Xyl45Ara10, Gal50Glu25Fru25, Gal40Xyl20Ara40, Gal40Xyl30Ara30, Gal40Xyl40Ara20, Gal60Xyl20Ara20, Gal80Xyl10Ara10, Gal90Xyl5Ara5, Glu5Gal5Man90, Glu5Gal90Man5, Glu5Xyl5Ara90, Glu5Xyl90Ara5, Glu10Gal10Man80, Glu10Gal45Man45, Glu10Gal80Man10, Glu10Xyl10Ara80, Glu10Xyl45Ara45, Glu10Xyl80Ara10, Glu20Gal20Man60, Glu20Gal40Man40, Glu20Gal60Man20, Glu20Gal80, Glu20Xyl20Ara60, Glu20Xyl40Ara40, Glu20Xyl60Ara20, Glu30Gal30Man40, Glu30Gal40Man30, Glu30Xyl30Ara40, Glu30Xyl40Ara30, Glu33Gal33Ara33, Glu33Gal33Fuc33, Glu33Gal33Man33, Glu33Gal33Xyl33, Glu33Man33Ara33, Glu33Man33Xyl33, Glu33Xyl33Ara33, Glu40Gal20Man40, Glu40Gal30Man30, Glu40Gal40Man20, Glu40Xyl20Ara40, Glu40Xyl30Ara30, Glu40Xyl40Ara20, Glu45Gal10Man45, Glu45Gal45Man10, Glu45Xyl10Ara45, Glu45Xyl45Ara10, Glu60Xyl20Ara20, Glu75GluNAc25, Glu80Gal10Man10, Glu80Xyl10Ara10, Glu90Gal5Man5, Glu90Xyl5Ara5, Man33Xyl33Ara33, Man52Glu29Gal19.

Four glycan units (hetero-glycans): Gal25Man25Xyl25Ara25, Glu25Gal25Man25Ara25, Glu25Gal25Man25Xyl25, Glu25Gal25Xyl25Ara25, Glu25Man25Xyl25Ara25.

Five glycan units (hetero-glycans): Glu20Gal20Man20Xyl20Ara20.

Glycans are described by a three- to six-letter code representing the monomeric sugar component followed by a number out of one hundred reflecting the percentage of the material that monomer constitutes. Thus, 'glu100' is ascribed to a glycan generated from a 100% D-glucose (glycan unit) input and 'glu50gal50' is ascribed to a glycan generated from 50% D-glucose and 50% D-galactose (glycan units) input or, alternatively from a lactose dimer (glycan unit) input. As used herein: xyl=D-xylose; ara=L-arabinose; gal=D-galactose; glu=D-glucose; rha=L-rhamnose; fuc=L-fucose; man=D-mannose; sor=D-sorbitol; gly=D-glycerol; neu=NAc-neuraminic acid; Lglu=L-glucose; gluA=D-glucuronic acid; gluN=D-glucosamine; gluNAc=N-acetyl-D-glucosamine; galA=D-galacturonic acid. 3-Bn=benzyl; 3-Obn=3-benzyloxy; 6-TBDPS=6-tert-butyldiphenylsilyl; galnac=N-acetyl galactosamine; rib=D-ribose; Sor=sorbitol.

Example 2. Purification

Oligo- and polysaccharides were dissolved in deionized water to a final concentration of 25-50 Brix. The material was then exposed to at least 2 mass equivalents of Dowex Monosphere 88 ion exchange resin. Exposure may occur by swirling in a flask at 120-170 rpm or by filtration through a wet slurry packed column as long as the residence time is sufficient for the solution to achieve a final pH between 3 and 5. The oligomer solution was isolated by filtration (as in the case of swirled reactions) or elution (as in the case of column filtration) and the process was repeated with Dowex Monosphere 77 ion exchange resin in an analogous fashion until the solution pH was above 5.5. Finally, the solution was exposed to Dowex Optipore SD-2 Adsorbent decolorizing resin until the solution was sufficiently clarified and filtered through a 0.2 micron filter to remove residual resin and resin fines. The final solution was then concentrated to 50-85 Brix by rotary evaporation or to a solid by lyophilization.

Example 3. High-Throughput Preparation at Small Scale

The oligomers and polymers were synthesized in a parallel fashion in 24-, 48-, or 96-well plates or similarly sized arrays of 1 dram vials housed in aluminum heating blocks. In this example, all liquid transfers were handled by a programmable robot or manually using calibrated pipettes. To each vial or well was added 20-100% by dry weight of one or more catalysts e.g. acid, ionic, ionic/acid containing catalysts such as, e.g. described in U.S. Pat. No. 9,079,171 and WO 2016/007778. The plate or heating block was placed uncovered in a vacuum oven heated to 50 to 150° C. under a vacuum of 10-800 mbar. The oven vacuum pump was protected by a two-stage condenser consisting of a recirculating chiller trap followed by a dry ice/acetone trap. The plates or blocks are heated for 30 minutes to 6 hours under elevated temperature and reduced pressure without stirring. After a pre-established period of time, the oven was vented to atmospheric pressure, the plates or blocks were cooled to room temperature, and each well or vial was diluted to approximately 50 Brix with deionized water. The solid-phase extraction steps described in Example 2 were performed by elution through sequential wet-packed columns in which the eluent from each column flows immediately into the top of the next column at a rate between 2 and 6 bed volumes/hour using a peristaltic pump or other suitable small pump. The column stack was then rinsed with deionized water and the combined effluents are concentrated by lyophilization to isolate solid powders with residual water content of 1-10% by mass.

Example 4. Removal of Low Molecular Weight Species

Oligomers or polymers were modified so as to remove low molecular weight species.

In one embodiment the separation was achieved by osmotic separation. Approximately 45 cm of 1.0 kD MWCO Biotech CE dialysis tubing (31 mm flat width) from Spectrum Labs was placed into deionized water and soaked for 10 minutes, then one end was sealed with a dialysis tubing clip. A 25 Brix solution of 8 grams dry oligosaccharide was sterile filtered and sealed into the tube with a second clip along with a few mL of air to permit the tube to float. The filled tube was then placed in a 3 gallon tank of deionized water which was stirred with sufficient force to induce slow swirling of the sealed tubes. After 8 hours, the water in the tank was replaced and the tube was allowed to stir for an additional 16 hours. Once the dialysis was complete and the material had a DP2+ yield greater than 95% and a DP3+ yield greater than 90%, the dilute solution was sterile filtered and concentrated in vacuo to a final concentration of approximately 65 Brix or lyophilized to a solid with a residual moisture between 1 and 10%.

In a second embodiment the separation was achieved by tangential flow filtration (TFF). In this case, 100 mL of 25 Brix glycan sample dissolved in deionized water and sterile filtered was placed into the feed bottle of a Spectrum Labs KrosFlo Research IIi TFF system that was prepared according to the manufacturer's recommendation. The sample was then diafiltered through a 1 kD mPES MidiKros hollow-fiber filter at a transmembrane pressure of 25 psig. HPLC samples of the feed stock taken every 0.5 diafiltration volumes were used to determine when the material had a DP2+ yield greater than 95% and a DP3+ yield greater than 90% at which point the solution was sterile filtered and concentrated in vacuo to a 65 Brix syrup or lyophilized to a solid with residual water content of 1-10% by mass.

In a third embodiment the separation was achieved by ethanol precipitation. In this case, 100 mL of 25 Brix glycan sample was poured into a vigorously stirred beaker containing 900 mL of pure, USP-grade ethanol at a rate no higher than 10 mL/minute. Once the addition was complete, the precipitated solids were subjected to stirring for an additional 15 minutes at or slightly below room temperature. The precipitated solids were isolated by filtration through a fine frit sintered glass funnel under an atmosphere of nitrogen to prevent hydration and gumming. The solids were rinsed once with ethanol, then dissolved in water to a final concentration of 25 Brix and reconcentrated to >65 Brix. This syrup was then diluted back to 25 Brix and concentrated once more to ensure removal of residual ethanol.

Example 5. Methods for Analyzing Preparations

Measurement of Concentration by Liquid Refractometry

This experiment was designed to quantitate the amount of glycan in any given aqueous solution. A Mettler-Toledo Refracto 30GS portable sugar refractometer was calibrated using high-purity reverse-osmosis deionized water. Several drops of the glycan solution were filtered through a 0.2 micron syringe filter directly onto the lens of the refractometer. The measurement was taken at room temperature and reported as Brix. The glycans were routinely concentrated to 50, 60, 70, or 75 Brix without obvious solidification or crystallization at 23° C. Brix can then be converted to solubility assuming a specific density of water equal to 1.0 g/mL. Thus, 75 Brix (100 grams of solution consisting of 75 grams of glycan and 25 grams of water) equals an aqueous solubility of 3.0 g/mL. As a comparison, the aqueous solubility of D-glucose is reported to be 0.909 g/mL (48 Brix) at 25° C. by Sigma-Aldrich.

Monomeric Composition by Hydrolysis and GC-MS

This experiment was designed to quantitate the ratio of monomer content within a given oligosaccharide. Glycosyl composition analysis was performed by combined gas chromatography/mass spectrometry (GC/MS) of the per-O-trimethylsilyl (TMS) derivatives of the monosaccharide methyl glycosides produced from the sample by acidic methanolysis as described previously by Santander et al. (2013) Microbiology 159:1471. Between 100 and 200 µg of sample were lyophilized into a suitable test tube. Inositol (20 µg) was added to the sample as an internal standard, then the sample was heated to 80° C. in 1M HCl/methanol for 18 hours. The resulting monosaccharides were then re-acetylated using pyridine and acetic anhydride in MeOH, and per-O-trimethylsilylated with Tri-Sil (Pierce) at 80° C. for 30 minutes. GC/MS analysis of the TMS methyl glycosides was performed on an Agilent 7890A GC interfaced to a 5975C MSD, using a Supelco Equity-1 fused silica capillary column (30 m×0.25 mm ID). Each peak was assigned to a component sugar based upon comparison to known standards and integration of the respective peaks allowed clean calculation of the relative percentage of monomers within an exemplified glycan. In all enumerated glycans, conditions can be routinely identified in which the monomer composition of a given oligosaccharide matched the input ratio within experimental error and the output composition matched the input composition within the precision of the measurement.

Molecular Weight Distribution by Size-Exclusion Chromatography (SEC)

This experiment was designed to quantitate the distribution of molecular weights within a given oligosaccharide. The measurement was made by HPLC using the method described in Monograph of United States Pharmacopeia, 38(6) In-Process Revision: Heparin Sodium (USP37-NF32). Separations were achieved on an Agilent 1200 HPLC system via a GE superpose 12 column using 50 mM ammonium acetate as an eluent at 1.0 mL/min flow rate and an ELSD detector. The column temperature was set at 30° C. and dextran (1 kD, 5 kD, 10 kD weight) were used to draw a standard curve. A 2 mg/ml solution of the samples was prepared and passed through a 0.45 µm spin filter, followed by 40 µl injections into the HPLC. A third-order polynomial curve was constructed based on the logarithmic molecular weights and elution volumes of the listed standards. The weight-average molecular weight (Mw), the number average molecular weight (Mn), and the polydispersity index (PDI) for the sample were calculated by comparison to the standard curve. FIG. 1 shows the curve generated during the SEC evaluation of a glu100 sample in which the average molecular weight was determined to be 1212 g/mol or approximately DP7. The upper end of molecular weight of the material as defined by the point of the curve at 10% of maximum absorption leading the curve was determined to be 4559 g/mol or approximately DP28. The lower end of molecular weight of the material as defined by 10% of maximum absorption trailing the curve was determined to be 200 g/mol or approximately DPL. Similar analysis of a glu50gal50 sample showed a MW, high mass, and low mass of 1195 g/mol (~DP7), 4331 g/mol (~DP27), and 221 g/mol (~DP1) respectively.

Molecular Weight Distribution by Ion-Affinity Chromatography (IAC)

The proportion of glycan with DP greater than or equal to 2 (DP2+) and 3(DP3+) may be measured by ion-affinity chromatography. A sample of glycan was diluted out to 50-100 mg/mL and 10 µL of this solution was injected onto an Agilent 1260 BioPure HPLC equipped with a 7.8×300 mm BioRad Aminex HPX-42A column and RI detector. Using pure HPLC-grade water as an eluent, the sample was eluted at 0.6 mL/min through an 80° C. column and an RI detector maintained at 50° C. The peaks representing DP1-6 are assigned by comparison to reference standards and integrated using the Agilent ChemStation software. Peaks are typically integrated as DP1, DP2, DP3, DP4-7, and DP8+. The DP that is achievable by the reaction described in Example 1 varies from monomer to monomer although it is consistent across batches if the procedure is followed. For example, across 17 batches of glu100, DP2+ values ranged from 77-93% and DP3+ values ranged from 80-90%. Conversely, across 6 batches of ara100, DP2+ values ranged from 63-78% and DP3+ values ranged from 48-71%. Mixtures of monomers behaved as averages of the individual components.

Alpha-/Beta-Distribution by 2D NMR

Figure 2:
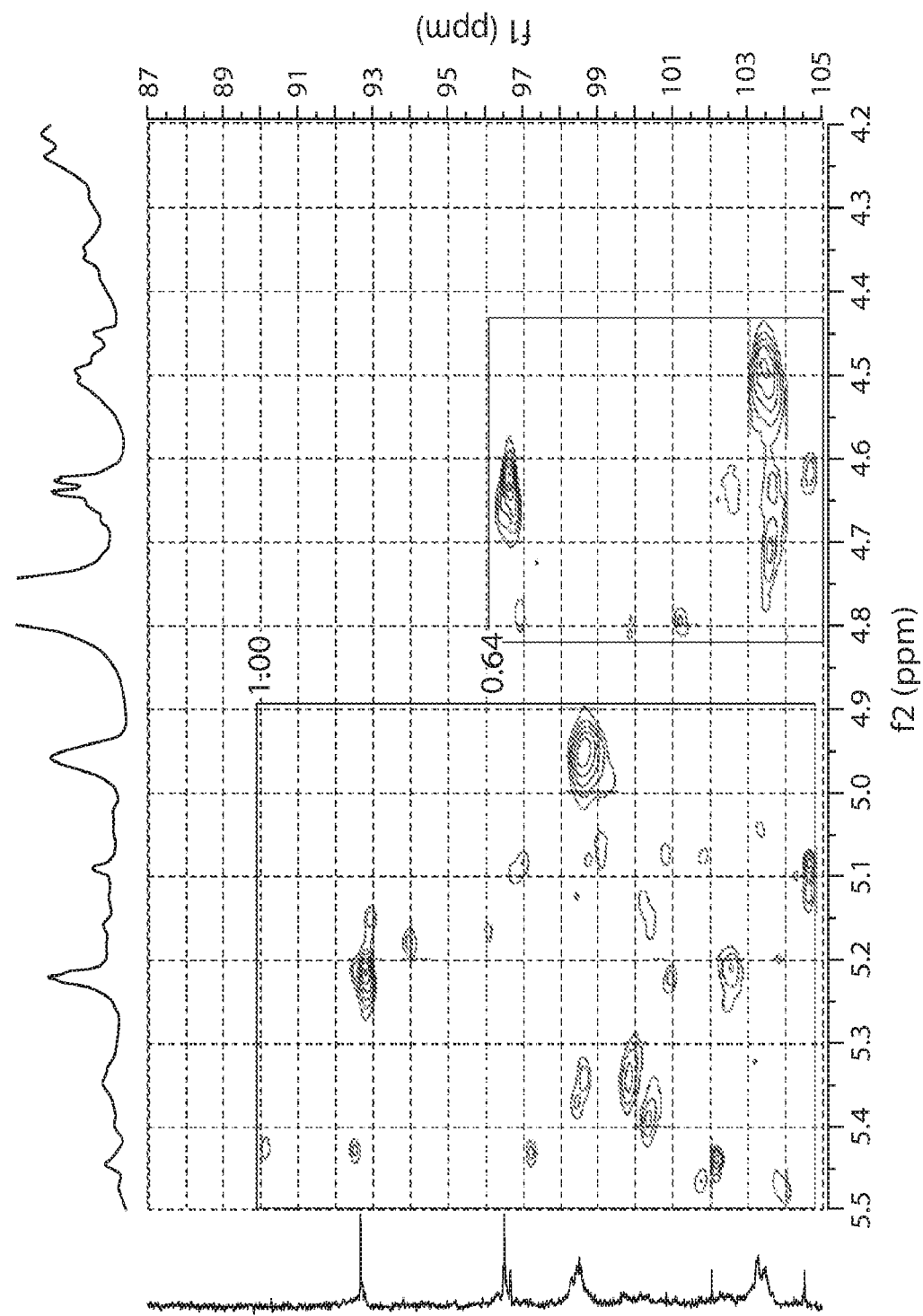
FIG. 2 is a representative anomeric region of an $^1$H-$^{13}$C HSQC spectrum of a glu100 sample showing the signal distribution of alpha- and beta-glycosidic bonds.

This experiment was designed to quantitate the ratio of alpha- and beta-glycosidic bonds within a given sample by two-dimensional NMR. Approximately 150 mg of 65 Brix oligosaccharide solution was dried to stable mass in a vacuum oven at 45-95° C. under 400 mbar pressure. The sample was subjected to two cycles of dissolution in $D_2O$ and drying to remove residual $H_2O$. Once dried, the sample was dissolved in 750 μL $D_2O$ with 0.1% acetone, placed into a 3 mm NMR tube, and analyzed in a Bruker Avance-III operating at 500.13 MHz 1H (125.77 MHz 13C) equipped with a Bruker BBFO probe operating at 21.1° C. The sample was analyzed using a heteroatomic single quantum coherence pulse sequence (HSQC) using the standard Bruker pulse sequence. Anomeric protons between 4-6 ppm (1H) and 80-120 ppm (13C) were assigned by analogy to glucose as reported in Roslund, et al. (2008) *Carbohydrate Res.* 343:101-112. Spectra were referenced to the internal acetone signal: 1H—2.22 ppm; 13C—30.8 ppm. Isomers were quantitated by integration of their respective peaks using the MNova software package from Mestrelab Research (Santiago de Compostela, Spain). FIG. 2 shows the anomeric region of a representative spectrum. Over 300 samples have been assayed in this fashion and Table 2 lists the distribution across a sample of combinations of monomers showing the alpha-/beta-ratio to be as high as 4:1 as in the case of rha100 and as low as 1:1 as in the case of glu50gal50.

Identification of Composition by NMR

Figure 3A:
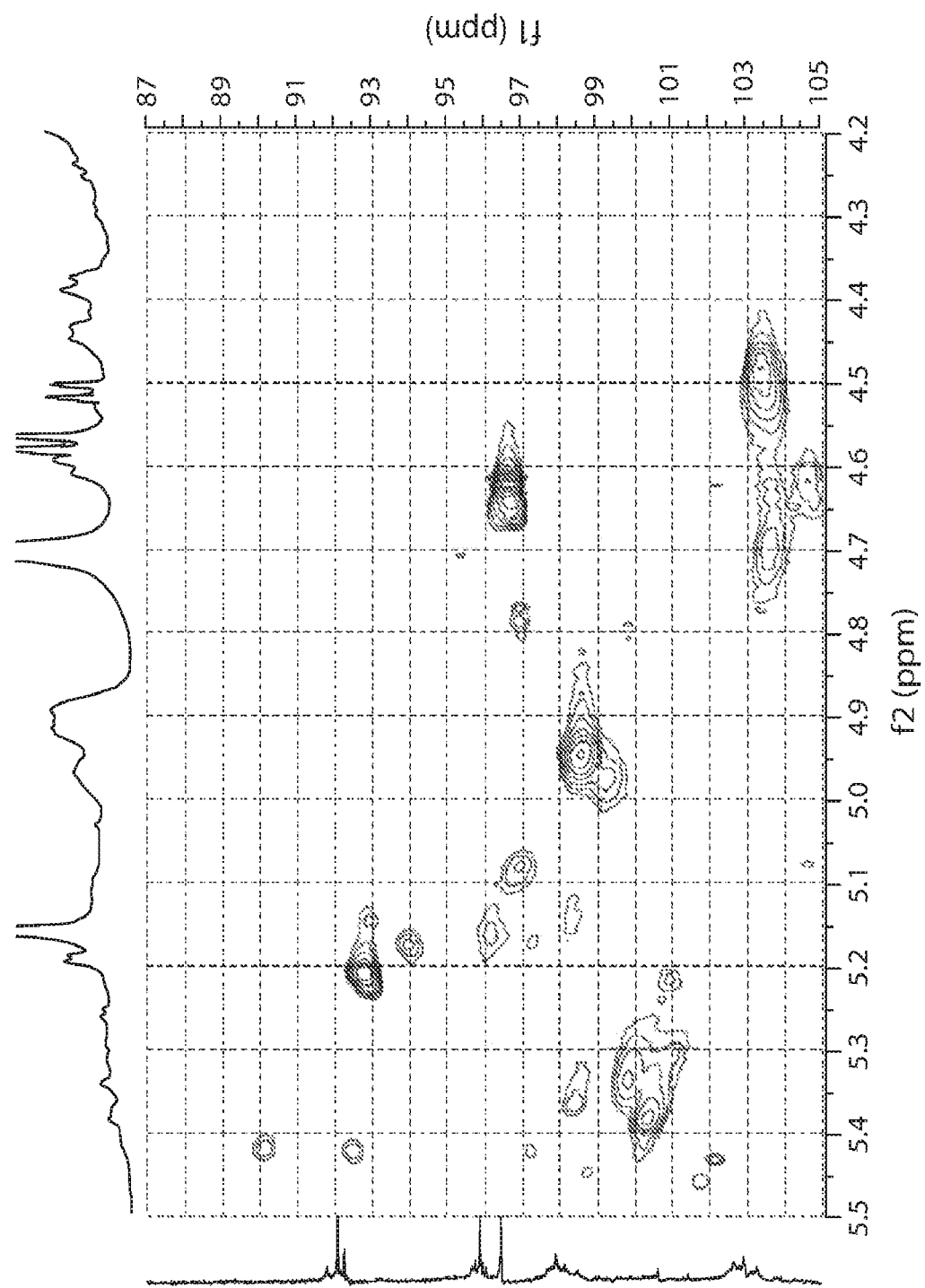
FIGS. 3A, 3B, and 3C is a series of representative anomeric regions of an $^1$H-$^{13}$C HSQC spectrum of glu100 (FIG. 3A), glu50gal50 (FIG. 3B), and gal100 (FIG. 3C) samples, demonstrating the additive effect of the fingerprint peaks.
Figure 3B:
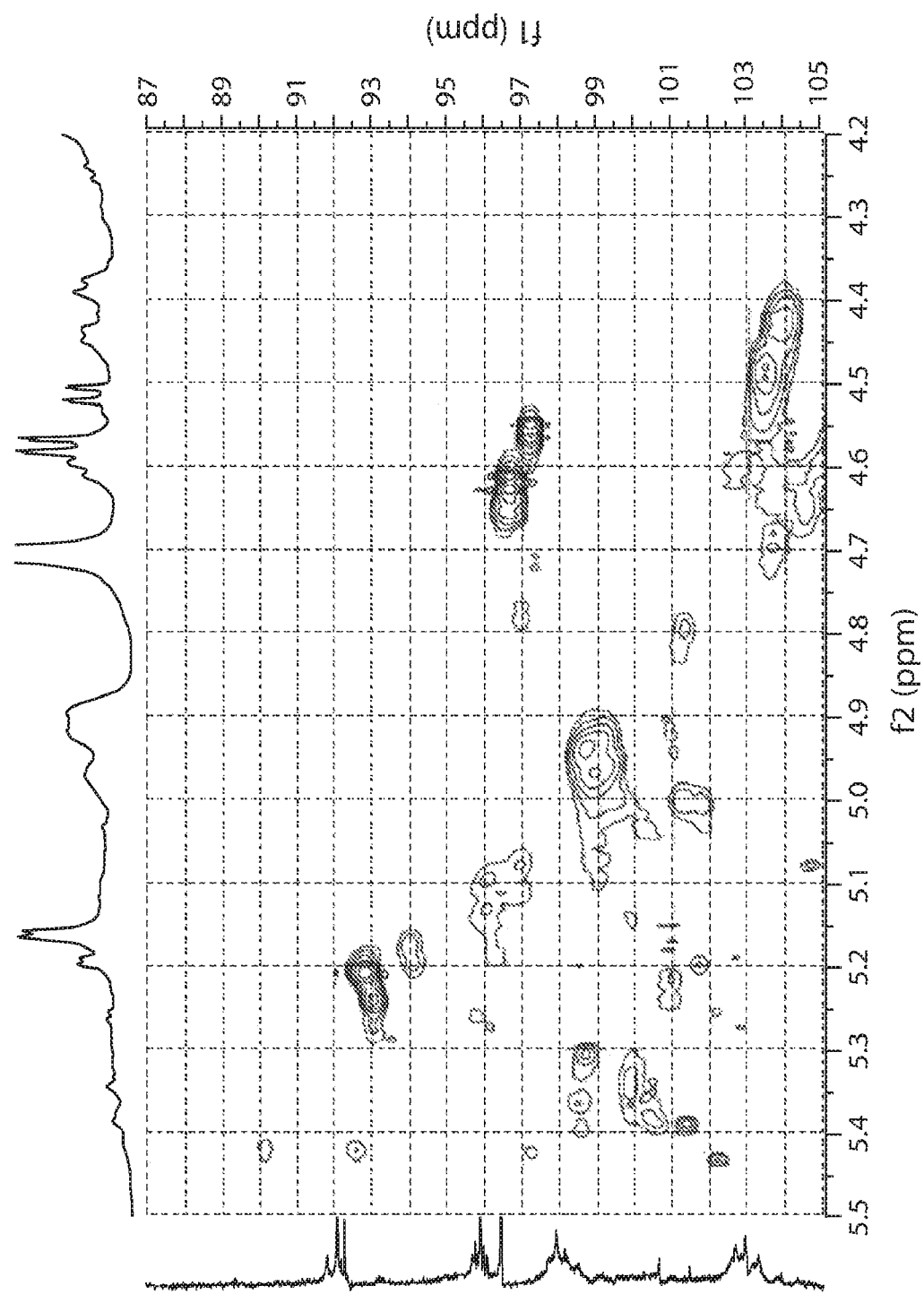
Figure 3C:
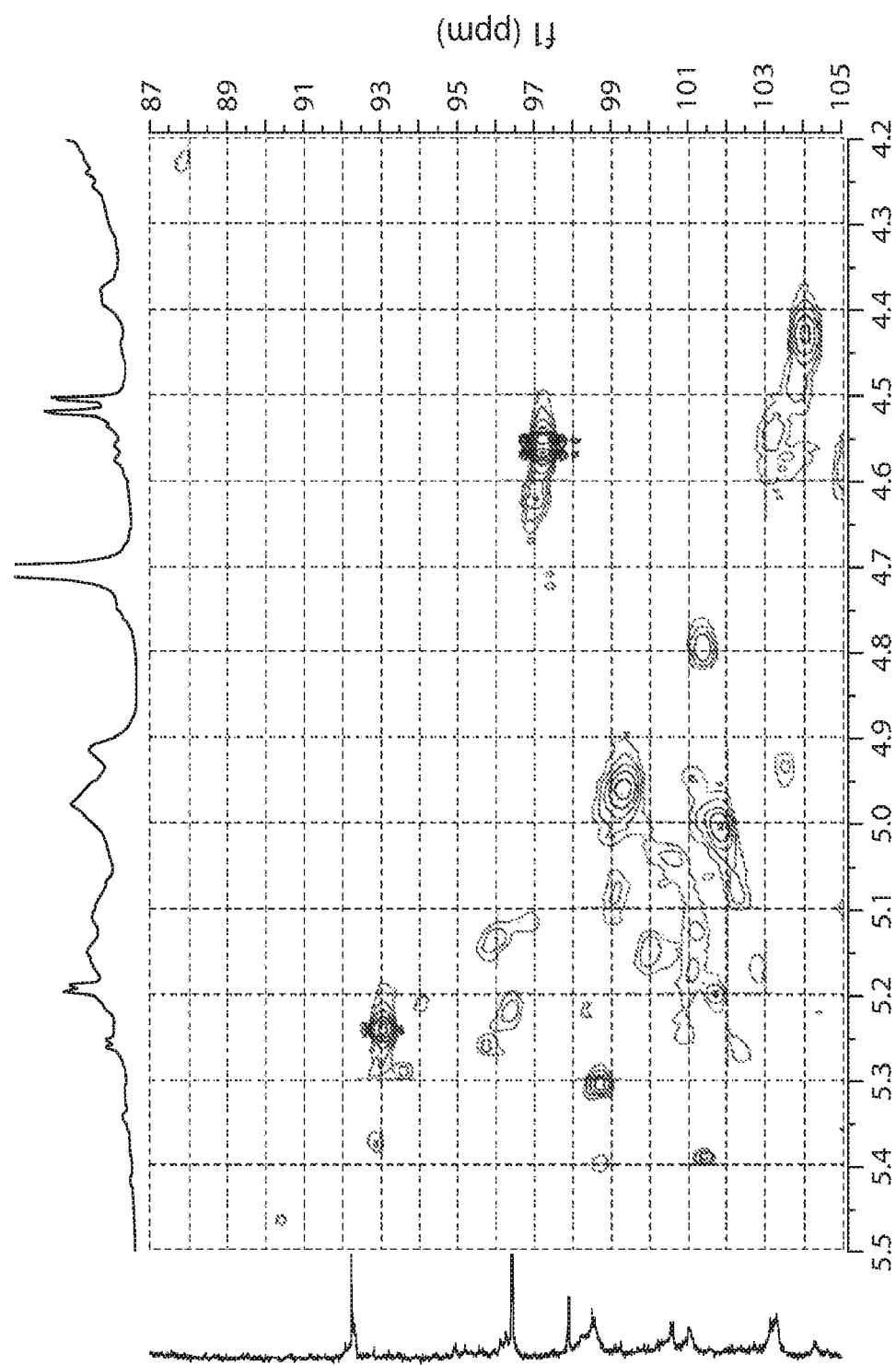
Figure 5:
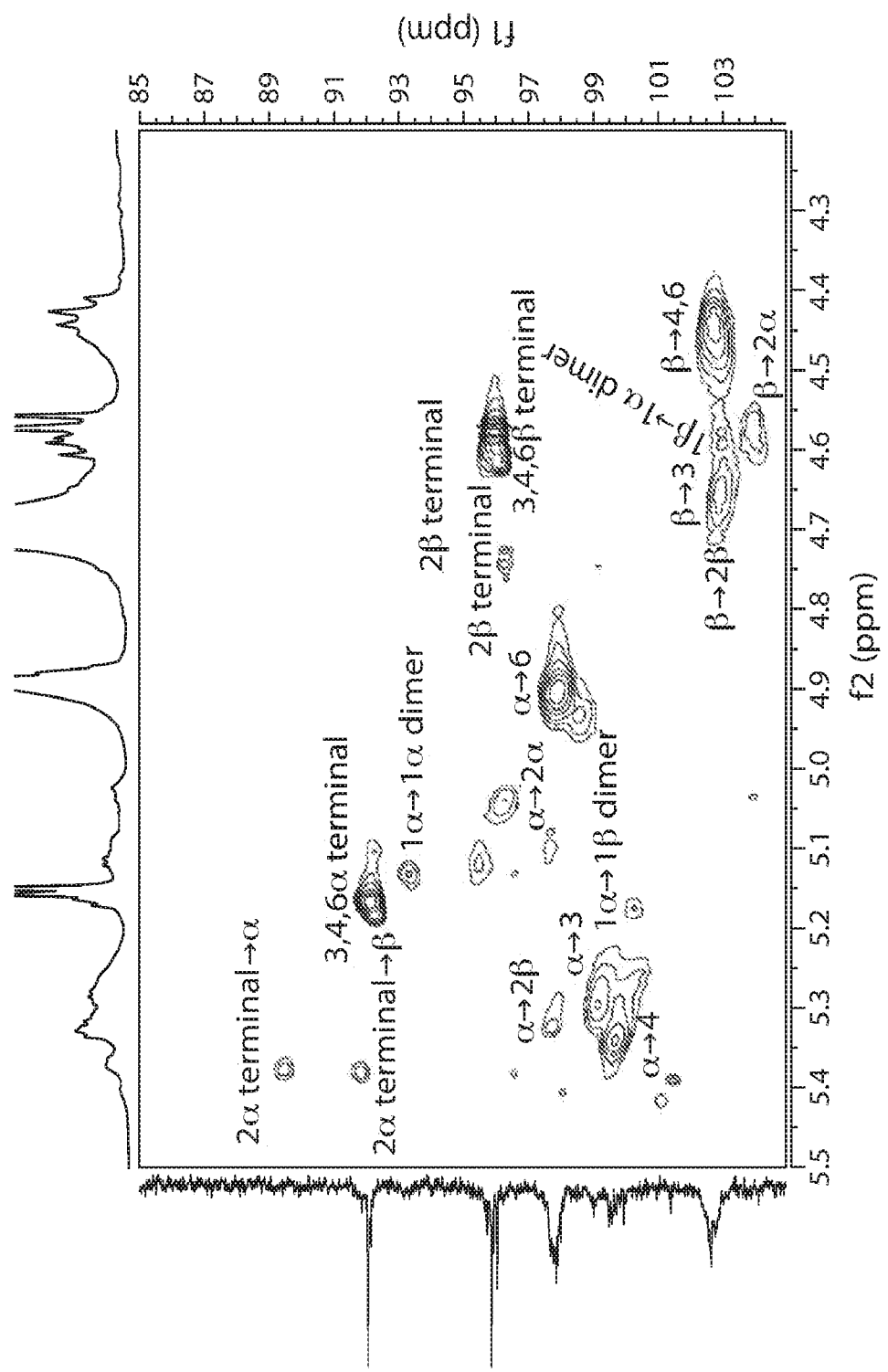
FIG. 5 is a representative partial assignment of the peaks in the anomeric region of a glu100 sample $^1$H-$^{13}$C HSQC spectrum showing the separation between alpha and beta isomers in the $^1$H axis, with alpha isomers downfield ($^1$H>4.8 ppm in this case) and beta isomers upfield ($^1$H<4.8 ppm in this case). In addition, terminal and internal sugars can be distinguished in the $^{13}$C axis with terminal sugars upfield ($^{13}$C<94 ppm for alpha and $^{13}$C<100 ppm for beta in this case) and internal sugars downfield ($^{13}$C>94 ppm for alpha and $^{13}$C>100 ppm for beta in this case).

This experiment was designed to identify the composition of a glycan by 2D-NMR identification of the constituent monomers. Approximately 150 mg of 65 Brix oligosaccharide solution was dried to stable mass in a vacuum oven at 45-95° C. under 400 mbar pressure. The sample was subjected to two cycles of dissolution in $D_2O$ and drying to remove residual $H_2O$. Once dried, the sample was dissolved in 750 μL $D_2O$ with 0.1% acetone, placed into a 3 mm NMR tube, and analyzed in a Bruker Avance-III operating at 500.13 MHz 1H (125.77 MHz 13C) equipped with a Bruker BBFO probe operating at 70° C. The sample was analyzed using a heteroatomic single quantum coherence pulse sequence (HSQC) using the standard Bruker pulse sequence. The anomeric region of each glycan spectra derived from a single sugar monomer was then examined for peaks representing specific glycosidic bonds characteristic to that monomer. For any given glycan, the HSQC spectra allow the identification of peaks that are unique to specific regio- and stereochemical bond arrangement. For example, FIG. 5 shows a partial assignment of the spectra of a glu100 preparation demonstrating how these peaks may be used to identify specific glycosidic regio- and stereo-chemistries. Due to the spin-isolated nature of single carbohydrate rings within polysaccharides, the HSQC spectra of a glycan with more than one monomer is predicted to be represented by the sum of the HSQC peaks of each of its constituent sugars. Therefore, each constituent monomer has unique HSQC peaks that will appear in any glycan that contains that monomer irrespective of other constituent monomers and furthermore, the monomers used to synthesize a glycan can be determined by identifying the fingerprint peaks unique to each constituent monomer. For example, FIG. 3B shows that the HSQC spectra of glu50gal50 is a hybrid of the spectra of glu100 (FIG. 3A) and gal100 (FIG. 3C). Table 3 lists the fingerprint peaks for selected glycan units.

TABLE 2

Distribution of alpha- and beta-bonds across batches and types of glycans

| glycans | alpha-bonds (%) | beta-bonds (%) | alpha/beta ratio |
|---|---|---|---|
| Glu100 | 58 | 42 | 1.4 |
| | 61 | 39 | 1.6 |
| | 64 | 36 | 1.8 |
| | 64 | 36 | 1.8 |
| | 62 | 38 | 1.6 |
| | 61 | 39 | 1.6 |
| | 62 | 38 | 1.6 |
| | 63 | 37 | 1.7 |
| | 60 | 40 | 1.5 |
| | 65 | 35 | 1.9 |
| | 65 | 35 | 1.9 |
| | 60 | 40 | 1.5 |
| Gal100 | 60 | 40 | 1.5 |
| Gal33man33ara33 | 79 | 21 | 3.8 |
| | 75 | 25 | 3.0 |
| Glu50gal50 | 50 | 50 | 1.0 |
| | 56 | 44 | 1.3 |
| | 61 | 39 | 1.6 |
| | 65 | 35 | 1.9 |
| Glu33gal33fuc33 | 55 | 45 | 1.2 |
| Man100 | 57 | 43 | 1.3 |
| Man52glu29gal19 | 76 | 24 | 3.2 |
| Ara100 | 67 | 33 | 2.0 |
| Rha100 | 80 | 20 | 4.0 |
| Xyl100 | 57 | 43 | 1.3 |
| | 59 | 41 | 1.4 |
| Xyl75gal25 | 56 | 44 | 1.5 |

TABLE 3

Diagnostic HSQC peaks for each component sugar.

| Monomer | 1H shift | 13C shift | Monomer | 1H shift | 13C shift |
|---|---|---|---|---|---|
| Glucose | 5.42 | 92.5 | Xylose | 5.18 | 93.0 |
| | 5.21 | 92.8 | | 5.10 | 94.3 |
| | 5.18 | 93.9 | | 5.34 | 98.2 |
| | 5.08 | 97.0 | | 5.31 | 99.6 |
| | 5.36 | 98.4 | | 5.11 | 100.8 |
| | 5.34 | 99.8 | | 4.91 | 99.4 |
| | 5.38 | 100.3 | | 4.56 | 97.3 |
| | 4.95 | 98.6 | | 4.64 | 104.2 |
| | 4.62 | 96.6 | | 4.54 | 103.4 |
| | 4.70 | 103.6 | | 4.44 | 102.6 |
| | 4.49 | 103.4 | | 4.44 | 104.1 |
| Galactose | 5.37 | 92.9 | Arabinose | 5.22 | 93.2 |
| | 5.24 | 93.1 | | 5.13 | 93.2 |
| | 5.14 | 96.0 | | 5.29 | 96.0 |
| | 4.96 | 99.3 | | 5.26 | 97.2 |
| | 5.31 | 98.7 | | 5.12 | 96.6 |
| | 5.39 | 101.4 | | 5.18 | 99.6 |
| | 5.00 | 101.8 | | 5.06 | 99.2 |
| | 4.80 | 101.3 | | 4.99 | 100.0 |
| | 4.63 | 97.0 | | 5.26 | 101.9 |
| | 4.56 | 97.2 | | 5.06 | 102.1 |
| | 4.53 | 103.1 | | 4.55 | 97.4 |
| | 4.43 | 104.1 | | 4.54 | 105.2 |
| Fucose | 5.18 | 92.9 | | 4.50 | 105.5 |
| | 5.33 | 92.4 | | 4.38 | 103.9 |
| | 5.04 | 96.3 | Rhamnose | 5.21 | 93.2 |
| | 4.90 | 99.7 | | 5.10 | 94.5 |
| | 4.52 | 97.0 | | 4.85 | 94.1 |
| | 4.39 | 103.6 | | 5.01 | 95.8 |
| Mannose | 5.37 | 93.0 | | 5.35 | 100.5 |
| | 5.16 | 94.6 | | 5.15 | 102.2 |
| | 4.88 | 94.2 | | 5.04 | 102.9 |
| | 5.39 | 101.7 | | 4.78 | 97.9 |
| | 5.24 | 101.9 | | 4.71 | 99.0 |
| | 5.13 | 102.8 | | 4.72 | 101.0 |

TABLE 3-continued

Diagnostic HSQC peaks for each component sugar.

| Monomer | 1H shift | 13C shift | Monomer | 1H shift | 13C shift |
|---|---|---|---|---|---|
|  | 5.03 | 102.7 |  |  |  |
|  | 5.24 | 105.6 |  |  |  |
|  | 5.09 | 108.0 |  |  |  |
|  | 4.88 | 94.2 |  |  |  |
|  | 4.89 | 100.0 |  |  |  |
|  | 4.70 | 101.1 |  |  |  |

At least 5 peaks appeared for each glycan unit used as a starting material in the synthesis of glycans containing 3 or fewer distinct glycan units. The HSQC spectra of glycans containing 4 or more distinct glycan units have at least 4 peaks for each constituent glycan unit.

Figure 6A:
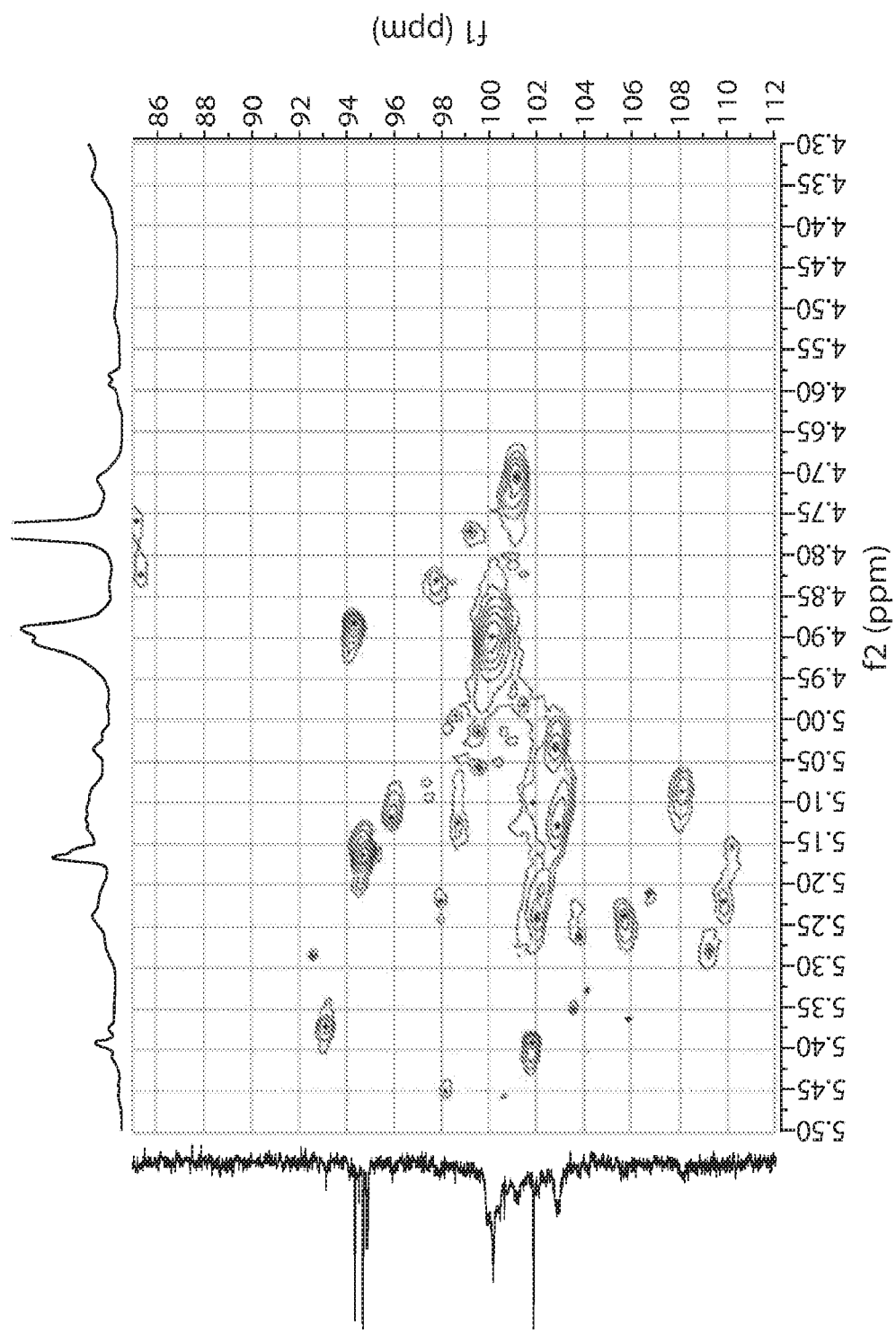
FIGS. 6A and 6B are a series of anomeric region of the 1H-13C HSQC spectrum of man100 (FIG. 6A) and xyl100 (FIG. 6B).
Figure 6B:
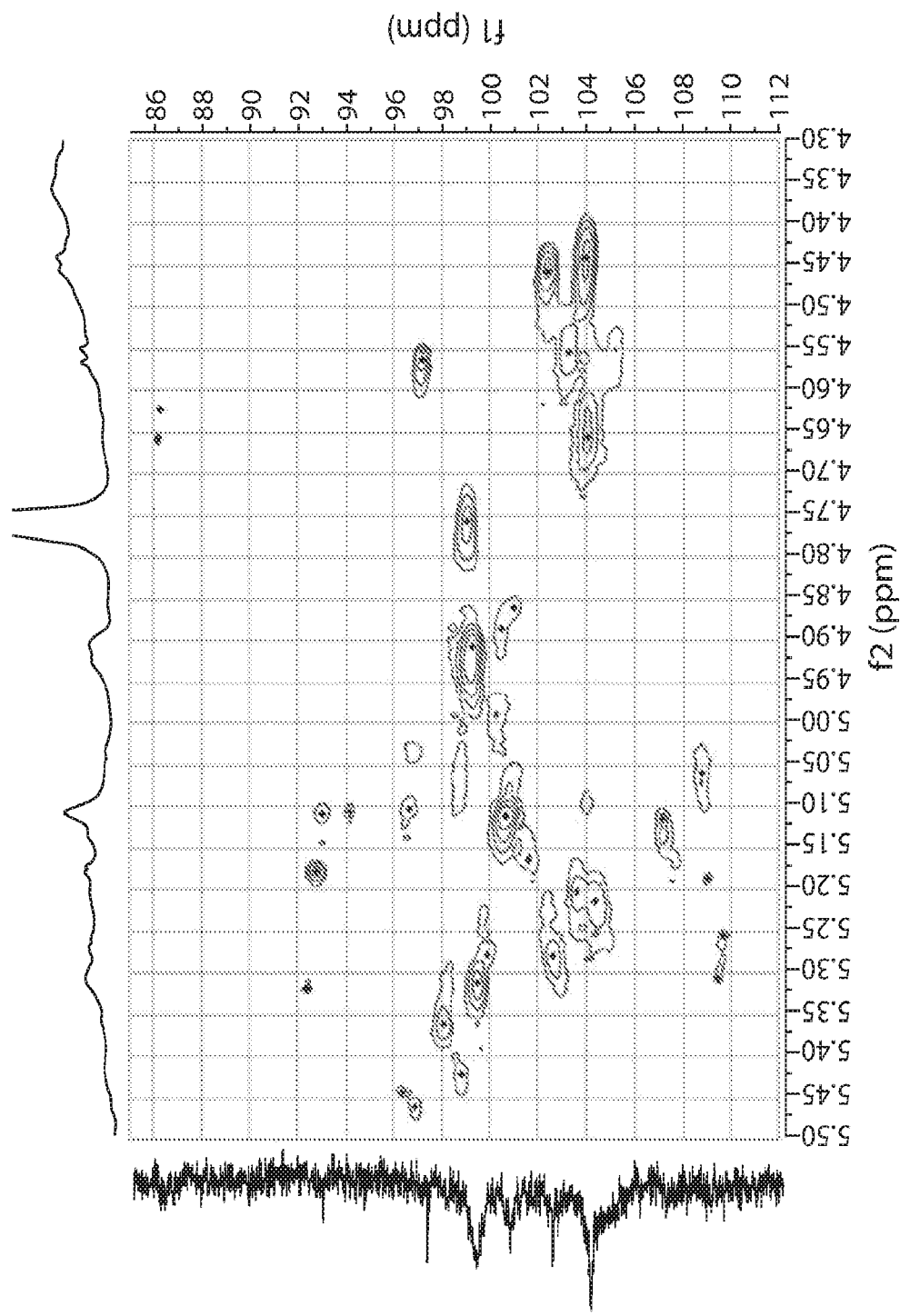

FIGS. 6A and 6B show the HSQC spectra for man100 and xyl100, respectively.

Glycosidic Linkage Analysis

Figure 4A:
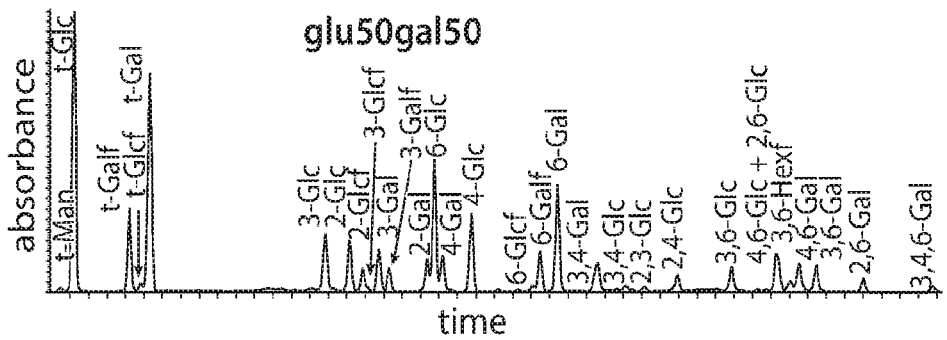
FIG. 4 is a representative GC chromatogram of three representative permethylated and hydrolyzed glycans showing distribution of regio-chemistry as assigned by comparison to known standards.
Figure 4B:
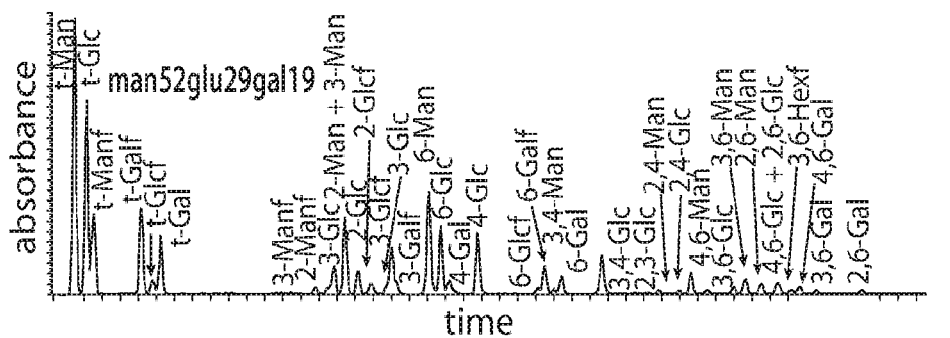
Figure 4C:
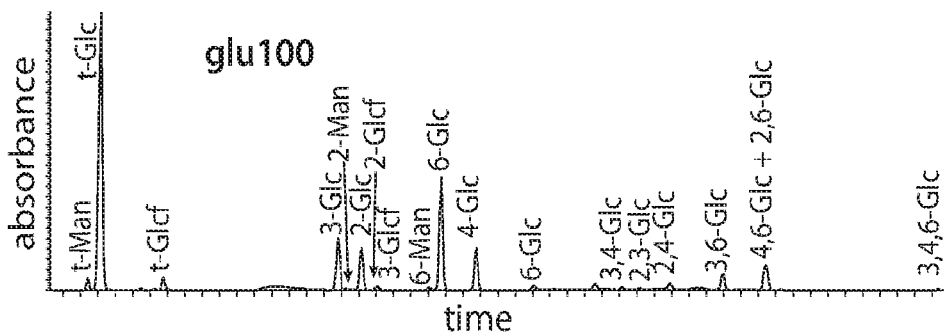

This experiment was designed to quantitate the distribution of glycosidic regioisomers (branching) within a given oligosaccharide. For glycosyl linkage analysis, the samples were permethylated, depolymerized, reduced, and acetylated; and the resultant partially methylated alditol acetates (PMAAs) analyzed by gas chromatography-mass spectrometry (GC-MS) as described by Heiss et al (2009) Carbohydr. Res. 344:915. The samples were suspended in 200 µl of dimethyl sulfoxide and left to stir for 1 day. Permethylation was affected by two rounds of treatment with sodium hydroxide (15 min) and methyl iodide (45 min). The aqueous solution was hydrolyzed by addition of 2M trifluoroacetic acid and heating to 121° C. for 2 hours. Solids were isolated in vacuo and acetylated in acetic acid/trifluoroacetic acid. The resulting PMAAs were analyzed on an Agilent 7890A GC interfaced to a 5975C MSD (mass selective detector, electron impact ionization mode); separation was performed on a 30 m Supelco SP-2331 bonded phase fused silica capillary column. FIG. 4 shows three representative GC spectra from this analysis. These analyses show that the glycans had at least 0.1%, 0.2%, 0.5%, 1%, 2%, 5%, 10% or more of the 1,2-glycoside bond type, e.g. ara100=3.8%, gal100=7.2%; at least 0.1%, 0.2%, 0.5%, 1%, 2%, 5%, 10% or more of the 1,3-glycoside bond type, e.g. 3-bn-glu100=1.7%, glu50gal50=10.4%; at least 0.1%, 0.2%, 0.5%, 1%, 2%, 5%, 10% or more of the 1,4-glycoside bond type, e.g. glu50gal50=5.9%, gal33man33ara33=10.1%; and at least 0.1%, 0.2%, 0.5%, 1%, 2%, 5%, 10%, 15%, 20%, 25% or more of the 1,6-glycoside bond type, e.g. gal33man33ara33=13.4%, glu100=25.4%. The materials also contained at least 5%, 10%, 15%, 20%, 25%, 30%, 40%, 50%, or more of the branched bond types (including but not limited to 1,3,6-; 1,4,6-; or 1,2,4-glycosides, e.g. Table 4), a degree of branching (DB) of at least 0.05. Degree of branching is defined as the average number of branched monomers relative to total number of monomer units. For example, a glu100 glycan polymer in which 20% of the glucose monomer units contain glycosidic linkages to three or more other glucose monomers would have a DB of 0.20. The glycans also have about 3-12% of the monomeric units in the furanose form. A glycan originating from a single monomer consisted of at least 12 distinct non-terminal substitution patterns. A glycan originating from two monomers consisted of at least 18 distinct non-terminal substitution patterns, e.g. glu-1,2-glu; glu-1,2-gal; gal-1,2-glu; gal-1,2-gal; glu-1,2(glu),6-glu; glu-1,3-glu; glu-1,3-gal; etc. A glycan originating from three or more monomers consisted of at least 24 distinct non-terminal substitution patterns.

TABLE 4

A sample of degree of branching (DB) measurements; sample selected from 54 different preparations characterized as described herein.

| composition | % branched monomers | |
|---|---|---|
|  | highest measure | lowest measure |
| glu100 | 40.4 | 10.4 |
| glu80man20 | 16.1 |  |
| glu60man40 | 16.4 |  |
| man80glu20 | 18.6 |  |
| man60glu40 | 20.5 |  |
| glu50gal50 | 22.4 | 12.6 |
| gal100 | 22.2 |  |
| glu33gal33fuc33 | 41.8 |  |
| ara100 | 16.6 |  |
| xyl100 | 63.2 |  |
| xyl75ara25 | 26.9 |  |
| man52glu29gal19 | 22.7 | 9.8 |
| man100 | 40.0 |  |

TABLE 5

Exemplary glycan polymer preparations

| Glycan | total molar incidence of a bond (%) | | | | Misc glycoside sums (%) | | total terminal sugars |
|---|---|---|---|---|---|---|---|
|  | total 1,2 | total 1,3 | total 1,4 | total 1,6 | total branching | total furanose |  |
| Glu5Gal5Man90-2 | 19% | 15% | 22% | 43% | 25.9 | 12 | 34.9 |
| Glu10Gal10Man80-1 | 15% | 16% | 24% | 45% | 22.6 | 6.7 | 33.1 |
| Glu20Gal20Man20Xyl20Ara20-1 | 16% | 18% | 32% | 34% | 22.0 | 25.1 | 33.1 |
| Glu20Gal20Man20Xyl20Ara20-2 | 16% | 19% | 16% | 48% | 20.1 | 4.8 | 35.3 |
| Gal33Man33Ara33-8 | 17% | 26% | 23% | 34% | 25.5 | 27.5 | 32.7 |
| Gal57Glu43-1 | 4% | 7% | 73% | 16% | 2 | 2.7 | 50.9 |
| Glu100-87 | 1% | 3% | 93% | 4% | 0 | 0 | 34.7 |
| Gal57Glu43-2 | 2% | 2% | 1% | 94% | 1.3 | 1.5 | 46.6 |
| Glu50Gal50-11 | 15% | 20% | 20% | 45% | 14.8 | 12.2 | 38.3 |
| Glu50Gal50-32 | 15% | 16% | 26% | 43% | 13.1 | 17.9 | 45.2 |
| Glu50Gal50-14 | 13% | 17% | 25% | 44% | 13.5 | 22.4 | 43.3 |
| Glu50Gal50-27 | 15% | 20% | 22% | 43% | 19.5 | 9.6 | 29.5 |
| Glu50Gal50-23 | 17% | 20% | 20% | 44% | 19.2 | 17.2 | 35.5 |
| Glu50Gal50-2 | 16% | 21% | 18% | 45% | 19.4 | 15.6 | 35.5 |
| Glu100-129 | 20% | 19% | 16% | 46% | 19.1 | 5.3 | 36.3 |

TABLE 5-continued

Exemplary glycan polymer preparations

| Glu100-136 | 19% | 20% | 16% | 46% | 19.6 | 4.7 | 34.8 |
| --- | --- | --- | --- | --- | --- | --- | --- |
| Glu100-17 | 19% | 20% | 15% | 47% | 19.7 | 3.1 | 31.6 |
| Glu100-64 | 19% | 21% | 15% | 46% | 19.6 | 3.3 | 34.6 |
| Glu100-76 | 18% | 19% | 15% | 47% | 18.5 | 3.8 | 33.4 |
| Glu100-131 | 18% | 18% | 17% | 46% | 16.4 | 7.4 | 39.2 |
| Glu100-83 | 19% | 20% | 18% | 44% | 22.2 | 8.7 | 34.5 |
| Glu100-139 | 19% | 20% | 15% | 46% | 19.4 | 4.5 | 34.5 |
| Glu100-84 | 19% | 20% | 15% | 46% | 19 | 3.5 | 32.6 |
| Glu100-74 | 19% | 19% | 17% | 45% | 22.2 | 6.7 | 27.9 |
| Glu100-98 | 19% | 19% | 18% | 45% | 18.5 | 6.9 | 36.4 |
| Glu100-141 | 18% | 24% | 16% | 41% | 40.4 | 3.7 | 16.3 |
| Glu100-29 | 19% | 18% | 16% | 46% | 19.5 | 3.8 | 30 |
| Glu100-18 | 20% | 21% | 15% | 45% | 27.5 | 3.4 | 18.9 |
| Glu100-99 | 18% | 20% | 16% | 45% | 20.1 | 6.5 | 35.4 |
| Glu100-72 | 19% | 20% | 17% | 44% | 22.2 | 6.3 | 32.2 |
| Glu100-82 | 18% | 21% | 17% | 44% | 22 | 6.4 | 30.6 |
| Glu100-130 | 18% | 21% | 17% | 44% | 21.9 | 5.2 | 32.9 |
| Glu100-78 | 18% | 20% | 17% | 44% | 21.6 | 4.5 | 32 |
| Glu100-66 | 19% | 20% | 17% | 44% | 22 | 6.6 | 31.1 |
| Glu100-89 | 18% | 19% | 16% | 48% | 18.6 | 6.7 | 35.9 |
| Glu100-133 | 17% | 18% | 18% | 46% | 20.1 | 11.1 | 35.8 |
| Glu100-68 | 18% | 19% | 17% | 46% | 18.7 | 7.4 | 36.3 |
| Glu100-90 | 19% | 20% | 16% | 45% | 16.8 | 4.2 | 38.8 |
| Glu100-94 | 19% | 19% | 14% | 47% | 17.7 | 3.1 | 35.1 |
| Glu100-5 | 19% | 19% | 14% | 48% | 16.3 | 3 | 36.6 |
| 3-Obn Glu100-1 | 14% | 5% | 31% | 50% | 34.4 | 5.5 | 22.0 |
| Gal100-30 | 16% | 19% | 24% | 41% | 17.2 | 32.6 | 30.4 |
| Glu33Gal33Fuc33-3 | 15% | 30% | 29% | 27% | 41.8 | 15.2 | 22.5 |
| Ara100-12 | 26% | 42% | 32% | NA | 16.6 | 36.7 | 23.1 |
| Xyl100-8 | 19% | 35% | 46% | NA | 63.2 | 3.8 | 0.3 |
| Xyl75Ara25-3 | 25% | 32% | 43% | NA | 26.9 | 18.7 | 23.5 |
| Glu80Man20-2 | 15% | 19% | 21% | 45% | 16.1 | 4.6 | 34 |
| Glu60Man40-5 | 10% | 24% | 23% | 43% | 16.4 | 2.1 | 28.3 |
| Man80Glu20-2 | 8% | 25% | 17% | 50% | 18.6 | 1.8 | 30.9 |
| Man60Glu40-2 | 8% | 22% | 26% | 43% | 20.5 | 3.7 | 28.6 |
| Man52Glu29Gal19-2 | 12% | 19% | 27% | 42% | 51.1 | 19 | 8.4 |
| Man52Glu29Gal19-3 | 8% | 18% | 31% | 44% | 37.0 | 26.6 | 23.6 |
| Man100-17 | 12% | 27% | 25% | 36% | 19.4 | 9.5 | 40.0 |

| | alpha/beta ratio by HSQC NMR | | SEC data | | | | |
| --- | --- | --- | --- | --- | --- | --- | --- |
| Glycan | % alpha | % beta | DP2+ % | Mw | Mn | PD | DPn |
| Glu5Gal5Man90-2 | 80% | 20% | 98% | 1842 | 946 | 1.95 | 11.26 |
| Glu10Gal10Man80-1 | 81% | 19% | 98.60% | 1978 | 1021 | 1.94 | 12.1 |
| Glu20Gal20Man20Xyl20Ara20-1 | 87% | 13% | 100% | 1278 | 935 | 1.37 | 7.78 |
| Glu20Gal20Man20Xyl20Ara20-2 | 63% | 37% | 100% | 1845 | 1000 | 1.85 | 11.28 |
| Gal33Man33Ara33-8 | 87% | 13% | 98% | 1527 | 834 | 1.83 | 9.31 |
| Gal57Glu43-1 | 33% | 67% | 94% | 374 | 349 | 1.07 | 2.20 |
| Glu100-87 | 69% | 31% | 100% | 416 | 399 | 1.04 | 2.46 |
| Gal57Glu43-2 | 65% | 35% | 98% | 390 | 374 | 1.04 | 2.3 |
| Glu50Gal50-11 | 64% | 36% | 91% | 1456 | 675 | 2.16 | 8.88 |
| Glu50Gal50-32 | 66% | 34% | 96% | 1114 | 790 | 1.41 | 6.77 |
| Glu50Gal50-14 | 70% | 30% | | | | | |
| Glu50Gal50-27 | 61% | 39% | 99% | 1776 | 945 | 1.88 | 10.85 |
| Glu50Gal50-23 | 71% | 29% | 99% | 1497 | 855 | 1.75 | 9.13 |
| Glu50Gal50-2 | 65% | 35% | | 1931 | 936 | 2.06 | 11.8 |
| Glu100-129 | 62% | 38% | 99% | 1712 | 1411 | 1.21 | 7.84 |
| Glu100-136 | 64% | 36% | 99% | 1834 | 1577 | 1.16 | 8.76 |
| Glu100-17 | 61% | 39% | 98% | 1797 | 1523 | 1.18 | 8.46 |
| Glu100-64 | 62% | 38% | 98% | 1871 | 1620 | 1.15 | 9.00 |
| Glu100-76 | 62% | 38% | 99% | 1702 | 1410 | 1.21 | 7.83 |
| Glu100-131 | 61% | 39% | 98% | 1520 | 1200 | 1.27 | 6.67 |
| Glu100-83 | 64% | 36% | 99% | 1849 | 1605 | 1.15 | 8.92 |
| Glu100-139 | 64% | 36% | 98% | 1819 | 1542 | 1.18 | 8.57 |
| Glu100-84 | 62% | 38% | 99% | 1726 | 1431 | 1.21 | 7.95 |
| Glu100-74 | 61% | 39% | 98% | 1697 | 1387 | 1.22 | 7.71 |
| Glu100-98 | 62% | 38% | 98% | 1690 | 1383 | 1.22 | 7.68 |
| Glu100-141 | 63% | 37% | 99% | 1898 | 1673 | 1.13 | 9.29 |
| Glu100-29 | 60% | 40% | 98% | 1624 | 1311 | 1.24 | 7.28 |
| Glu100-18 | 65% | 35% | 99% | 1946 | 1748 | 1.11 | 9.71 |
| Glu100-99 | 64% | 36% | 99% | 1876 | 1641 | 1.14 | 9.12 |
| Glu100-72 | 64% | 36% | 99% | 1929 | 1716 | 1.12 | 9.54 |
| Glu100-82 | 65% | 35% | 99% | 1927 | 1711 | 1.13 | 9.50 |
| Glu100-130 | 63% | 37% | 99% | 1967 | 1781 | 1.10 | 9.90 |
| Glu100-78 | 63% | 37% | 99% | 1926 | 1719 | 1.12 | 9.55 |
| Glu100-66 | 62% | 38% | 98% | 1763 | 1472 | 1.20 | 8.18 |
| Glu100-89 | 61% | 39% | 98% | 1638 | 1326 | 1.23 | 7.37 |

TABLE 5-continued

| Exemplary glycan polymer preparations | | | | | | | |
|---|---|---|---|---|---|---|---|
| Glu100-133 | 65% | 35% | 97% | 1567 | 1224 | 1.28 | 6.80 |
| Glu100-68 | 60% | 40% | 98% | 1701 | 1394 | 1.22 | 7.74 |
| Glu100-90 | 51% | 49% | 96% | 982 | 674 | 1.46 | 5.90 |
| Glu100-94 | 54% | 46% | 100% | 1369 | 978 | 1.40 | 8.30 |
| Glu100-5 | 57% | 43% | 100% | 1226 | 902 | 1.36 | 7.40 |
| 3-Obn Glu100-1 | 66% | 34% | 100% | 1014 | 486 | 2.09 | 6.15 |
| Gal100-30 | 74% | 26% | | | | | |
| Glu33Gal33Fuc33-3 | 65% | 35% | | | | | |
| Ara100-12 | 74% | 26% | | | | | |
| Xyl100-8 | 70% | 30% | | | | | |
| Xyl75Ara25-3 | 69% | 31% | | | | | |
| Glu80Man20-2 | 68% | 32% | | | | | |
| Glu60Man40-5 | 79% | 21% | | | | | |
| Man80Glu20-2 | 87% | 13% | | | | | |
| Man60Glu40-2 | 73% | 27% | | | | | |
| Man52Glu29Gal19-2 | 77% | 23% | | | | | |
| Man52Glu29Gal19-3 | 82% | 18% | | | | | |
| Man100-17 | 57% | 43% | | | | | |

Example 6: Reduction of Ammonia in Fecal Slurries from Humans in the Presence of Glycan Preparations Glycan preparations were tested for their ability to modulate the levels of ammonia in a fecal slurry from a healthy human subject in vitro (also referred to as an ex vivo assay). Fecal samples and slurries were handled in an anaerobic chamber (AS-580, Anaerobe Systems) featuring a palladium catalyst. Glycans were prepared at 5% w/v in water, filter-sterilized and added to 96-well deep well microplates assay plates for a final concentration of 0.5% or 0.05% w/v in the assay, with water supplied as positive and negative controls.

A human fecal sample donation was stored at −80° C. To prepare working stocks the fecal sample was transferred into the anaerobic chamber and allowed to thaw. The fecal sample was prepared to 20% w/v in phosphate buffered saline (PBS) pH 7.4 (P0261, Teknova Inc., Hollister, CA), 15% glycerol and stored at −80° C. The 20% w/v fecal slurry+15% glycerol was centrifuged at 2,000×g, supernatant was removed, and the pellet was suspended in 900 mg/L sodium chloride, 26 mg/L calcium chloride dihydrate, 20 mg/L magnesium chloride hexahydrate, 10 mg/L manganese chloride tetrahydrate, 40 mg/L ammonium sulfate, 4 mg/L iron sulfate heptahydrate, 1 mg/L cobalt chloride hexahydrate, 300 mg/L potassium phosphate dibasic, 1.5 g/L sodium phosphate dibasic, 5 g/L sodium bicarbonate, 0.125 mg/L biotin, 1 mg/L pyridoxine, 1 m/L pantothenate, 75 mg/L histidine, 75 mg/L glycine, 75 mg/L tryptophan, 150 mg/L arginine, 150 mg/L methionine, 150 mg/L threonine, 225 mg/L valine, 225 mg/L isoleucine, 300 mg/L leucine, 400 mg/L cysteine, and 450 mg/L proline (Theriot C M et al. Nat Commun. 2014; 5:3114) supplemented with 750 uM urea to 1% w/v fecal slurry.

Prepared 1% w/v fecal slurry was exposed to glycans 3-Bn-glu50gal50-1, 3-Obn-Glu100-1, 6-TBDPS-glu100-1, 6-TBDPS-glu50gal50-1, a-1,6-glu100-1, acetylated-glu50gal50-1, Ara100-1, Ara100-10, Ara100-11, Ara100-2, Ara100-3, Ara100-4, Ara100-5, Ara100-6, Ara100-7, Ara100-8, Ara100-9, Ara60Xyl40-1, Ara80Xyl20-1, Ara88Gal3Rha2GalA3-1, butyrylated-glu50gal50-1, butyrylated-glu50gal50-2, Fru100-1, Fru100-10, Fru100-11, Fru100-2, Fru100-3, Fru100-4, Fru100-5, Fru100-6, Fru100-7, Fru100-8, Fru100-9, Fru50Glu50-1, Fuc100-1, Gal100-10, Gal100-11, Gal100-12, Gal100-13, Gal100-14, Gal100-15, Gal100-16, Gal100-17, Gal100-2, Gal100-3, Gal100-4, Gal100-5, Gal100-7, Gal100-8, Gal100-9, Gal10Xyl10Ara80-1, Gal10Xyl45Ara45-1, Gal10Xyl80Ara10-1, Gal20Ara80-1, Gal20Xyl20Ara60-1, Gal20Xyl40Ara40-1, Gal20Xyl60Ara20-1, Gal20Xyl80-1, Gal25Man25Xyl25Ara25-2, Gal30Xyl30Ara40-1, Gal30Xyl40Ara30-1, Gal33Man33Ara33-1, gal33man33ara33-1, Gal33Man33Ara33-10, Gal33Man33Ara33-11, Gal33Man33Ara33-12, Gal33Man33Ara33-13, Gal33Man33Ara33-14, Gal33Man33Ara33-15, Gal33Man33Ara33-17, Gal33Man33Ara33-18, Gal33Man33Ara33-2, gal33man33ara33-2, Gal33Man33Ara33-3, gal33man33ara33-3, Gal33Man33Ara33-4, gal33man33ara33-4, gal33man33ara33-5, gal33man33ara33-6, gal33man33ara33-7, gal33man33ara33-8, Gal33Man33Ara33-8, Gal33Man33Ara33-9, Gal33Man33Xyl33-1, Gal33Man33Xyl33-2, Gal33Man33Xyl33-3, Gal33Xyl33Ara33-1, Gal33Xyl33Ara33-2, Gal40Ara60-1, Gal40Man60-1, Gal40Xyl20Ara40-1, Gal40Xyl30Ara30-1, Gal40Xyl40Ara20-1, Ga140Xyl60-1, Gal45Xyl10Ara45-1, Gal45Xyl45Ara10-1, Gal50Fru50-2, Gal50Fru50-3, Ga150Glu25Fru25-1, Ga157Fru43-1, Ga157Glu43-1, Ga157Glu43-2, Ga15Xyl5Ara90-1, Ga15Xyl90Ara5-1, Gal60Ara40-1, Gal60Man40-1, Gal60Xyl20Ara20-1, Gal60Xyl40-1, Gal80Ara20-1, Gal80Man20-1, Gal80Xyl10Ara10-1, Gal80Xyl20-1, Gal81Ara14-1, Gal85Ara15-10, Gal85Ara15-5, Gal85Ara15-6, Gal85Ara15-7, Gal85Ara15-8, Gal85Ara15-9, Ga190Xyl5Ara5-1, Gala100-2, GalA60Rha10Ara1Xyl1Ga123-1, galnac100-1, galnac100-2, galnac50GluA50-1, Glu-30Gal—70-1, Glu-50Man-50-1, Glu100-1, Glu100-10, Glu100-100, Glu100-101, Glu100-102, Glu100-103, Glu100-104, Glu100-105, Glu100-106, Glu100-107, Glu100-108, Glu100-109, Glu100-11, Glu100-110, Glu100-111, Glu100-112, Glu100-113, Glu100-114, Glu100-115, Glu100-116, Glu100-117, Glu100-118, Glu100-119, Glu100-12, Glu100-120, Glu100-121, Glu100-122, Glu100-123, Glu100-124, Glu100-126, Glu100-127, Glu100-128, Glu100-129, Glu100-13, Glu100-130, Glu100-131, Glu100-132, Glu100-133, Glu100-135, Glu100-136, Glu100-139, Glu100-140, Glu100-141, Glu100-143, Glu100-15, Glu100-17, Glu100-18, Glu100-2, Glu100-20, Glu100-21, Glu100-22, Glu100-23, Glu100-24, Glu100-26, Glu100-29, Glu100-3, Glu100-30, Glu100-33, Glu100-34, Glu100-35, Glu100-4, Glu100-40, Glu100-41, Glu100-49, Glu100-5, Glu100-53, Glu100-55, Glu100-56, Glu100-59, Glu100-6, Glu100-60, Glu100-63, Glu100-64, Glu100-65, Glu100-66, Glu100-68, Glu100-69, Glu100-7, Glu100-70, Glu100-72, Glu100-73, Glu100-74, Glu100-75, Glu100-76, Glu100-77, Glu100-78, Glu100-8, Glu100-82, Glu100-83, Glu100-84, Glu100-87, Glu100-89, Glu100-9, Glu100-90, Glu100-92, Glu100-94, Glu100-98, Glu100-99, Glu10Gal10Man80-1, Glu10Gal10Man80-2, Glu10Gal45Man45-2, Glu10Gal80Man10-1, Glu10Xyl10Ara80-1, Glu10Xyl45Ara45-1, Glu10Xyl80Ara10-1, Glu20Ara80-1, Glu20Gal20Man20Xyl20Ara20-1, Glu20Gal20Man60-1, Glu20Gal20Man60-2, Glu20Gal40Man40-1, Glu20Gal60Man20-1, Glu20Gal60Man20-2, Glu20Gal80-1, Glu20Xyl20Ara60-1, Glu20Xyl40Ara40-1, Glu20Xyl60Ara20-1, Glu20Xyl80-1, Glu25Gal25Man25Ara25-1, Glu25Gal25Man25Ara25-2, Glu25Gal25Man25Xyl25-1, Glu25Gal25Man25Xyl25-2, Glu25Gal25Xyl25Ara25-2, Glu25Man25Xyl25Ara25-1, Glu30Gal30Man40-1, Glu30Gal30Man40-2, Glu30Xyl30Ara40-1, Glu30Xyl40Ara30-1, Glu33Gal33Ara33-1, Glu33Gal33Ara33-3, Glu33Gal33Ara33-4, Glu33Gal33Ara33-5, Glu33Gal33Fru33-1, Glu33Gal33Man33-1, Glu33Gal33Man33-2, Glu33Gal33Man33-3, Glu33Gal33Man33-4, Glu33Gal33Xyl33-1, Glu33Gal33Xyl33-2, Glu33Gal33Xyl33-3, Glu33Man33Ara33-1, Glu33Man33Ara33-2, Glu33Man33Xyl33-1, Glu33Man33Xyl33-2, Glu33Xyl33Ara33-1, Glu40Ara60-1, Glu40Gal30Man30-1, Glu40Gal40Man20-1, Glu40Gal40Man20-2, Glu40Gal60-1, Glu40Xyl20Ara40-1, Glu40Xyl30Ara30-1, Glu40Xyl40Ara20-1, Glu40Xyl60-1, Glu45Gal45Man10-1, Glu45Gal45Man10-2, Glu45Xyl10Ara45-1, Glu45Xyl45Ara10-1, glu50fru50-1, glu50gal50-long-1, glu50gal50-short-1, glu50gal50-1, Glu50Gal50-10, glu50gal50-11, Glu50Gal50-11, glu50gal50-12, glu50gal50-13, Glu50Gal50-13, glu50gal50-14, Glu50Gal50-14, glu50gal50-15, glu50gal50-16, glu50gal50-17, Glu50Gal50-17, Glu50Gal50-18, glu50gal50-18, glu50gal50-19, Glu50Gal50-19, Glu50Gal50-2, glu50gal50-20, Glu50Gal50-20, Glu50Gal50-21, glu50gal50-21, Glu50Gal50-22, glu50gal50-22, glu50gal50-23, glu50gal50-24, Glu50Gal50-24, Glu50Gal50-27, Glu50Gal50-28, Glu50Gal50-3, Glu50Gal50-30, Glu50Gal50-32, Glu50Gal50-33, Glu50Gal50-34, Glu50Gal50-36, Glu50Gal50-37, Glu50Gal50-39, Glu50Gal50-4, Glu50Gal50-40, Glu50Gal50-41, Glu50Gal50-42, Glu50Gal50-43, Glu50Gal50-45, Glu50Gal50-46, Glu50Gal50-7, Glu50Gal50-8, Glu50Gal50-9, Glu50Lglu50-1, Glu5Gal5Man90-2, Glu5Ga190Man5-1, Glu5Xyl5Ara90-1, Glu5Xyl90Ara5-1, Glu60Ara40-1, Glu60Gal20Man20-1, Glu60Gal40-1, Glu60Man40-1, Glu60Man40-2, Glu60Man40-4, Glu60Xyl20Ara20-1, Glu60Xyl40-1, Glu66Fru33-1, Glu75Glunac25-1, Glu80Ara20-1, Glu80Gal10Man10-1, Glu80Gal20-1, Glu80Lglu20-1, Glu80Man20-1, Glu80Xyl10Ara10-1, Glu80Xyl20-1, Glu90Gal5Man5-2, Glu90Lglu10-1, Glu90Xyl5Ara5-1, Glua100-1, Glun100-1, gly100-1, Lara100-1, Man100-1, Man100-10, Man100-11, Man100-12, Man100-13, Man100-15, Man100-2, Man100-6, Man100-7, Man100-8, Man100-9, Man20Ara80-1, Man20Xyl80-1, Man33Xyl33Ara33-1, Man33Xyl33Ara33-2, Man40Ara60-1, Man40Xyl60-1, Man52Glu29Gal19-1, Man60Ara40-1, Man60Glu40-1, Man60Xyl40-1, Man66Gal33-3, Man75Gal25-1, Man80Ara20-1, Man80Gal20-2, Man80Gal20-3, Man80Glu20-1, Man80Xyl20-1, Man100-1, Neu100-2, Rha100-1, Rib100-1, Sor100-1, Tbdps-Gal100-1, Xyl100-3, Xyl100-4, Xyl100-5, Xyl100-6, Xyl100-7, Xyl60Ara40-1, or Xyl80Ara20-1 at a final concentration of 0.5% w/v in 96-well deep well microplates, 500 µL final volume per well, at 37° C. for 45 hours, anaerobically. "Man", "glu", "gal", "xyl" etc. denotes the sugar; the number immediately following denotes the relative quantity of the sugar in the preparation (e.g., Man80gal20 means the preparation contains 80% mannose and 20% galactose); and the number after the dash denotes a glycan preparation (e.g., −1) that has different characteristics from another glycan preparation (e.g., −3), which differ from each other within the ranges for the glycan preparations described herein.

Following ex vivo incubation, cells were pelleted from by centrifugation at 3,716×g for 10 minutes and the supernatant was stored at −80° C. or on dry ice until it was analyzed. Samples were filtered in 10 kDa filter (AcroPrep Omega 10K, Pall Corporation, Port Washington New York) at 1,500×g for 15 minutes and diluted in water to 1/10 the original concentration. Samples were analyzed using Ammonia Colorimetric Assay Kit II (K470, Biovision Incorporated, Milpitas CA). Results of the Ammonia Colorimetric Assay for glycans are shown in Table 6.

TABLE 6

Percent reduction in ammonia by glycan

| Glycan | Percent reduction in ammonia |
| --- | --- |
| gal100 | 55-<60% |
| glu10gal10man80, glu30gal30man40 | 60-<65% |
| gal33man33xyl33, glu40gal30man30, glu40gal20man40 | 70-<75% |
| glu45gal10man45, glu60gal20man20, fructo-oligosaccharide | 75-<80% |
| glu40gal40man20, glu20gal20man20xyl20ara20, glu90gal5man5, glu80xyl20, glu20gal80, glu80ara20, glu40gal60, glu33gal33man33 | 80-<85% |
| man100, lactulose, glu80gal10man10, man80glu20, glu50gal50, glu80gal20, glu80man20 | 85-<90% |
| glu45gal45man10, glu60gal40, glu60man40, man80gal20, man60glu40 | 90-<95% |
| glu100 | 95-<100% |

Following incubation, assay samples were used for DNA extraction and sequencing. Genomic DNA was extracted from the fecal slurries treated with glycans and controls, and variable region 4 of the 16S rRNA gene was amplified and sequenced (Earth Microbiome Project protocol www.earthmicrobiome.org/emp-standard-protocols/16s/ and Caporaso J G et al. Ultra-high-throughput microbial community analysis on the Illumina HiSeq and MiSeq platforms. ISME J. (2012) August; 6(8):1621-4). Raw sequences were demultiplexed, and each sample was processed separately with UNOISE2 (Edgar 2016). Briefly, paired end reads were merged and quality filtered. Unique reads were then denoised, and unfiltered merged sequences were mapped to the denoised sequences. Taxonomy was assigned to the denoised sequences using the RDP classifier (Wang et al. Appl Environ Microbiol. (2007) August; 73(16):5261-7).

Figure 7A:
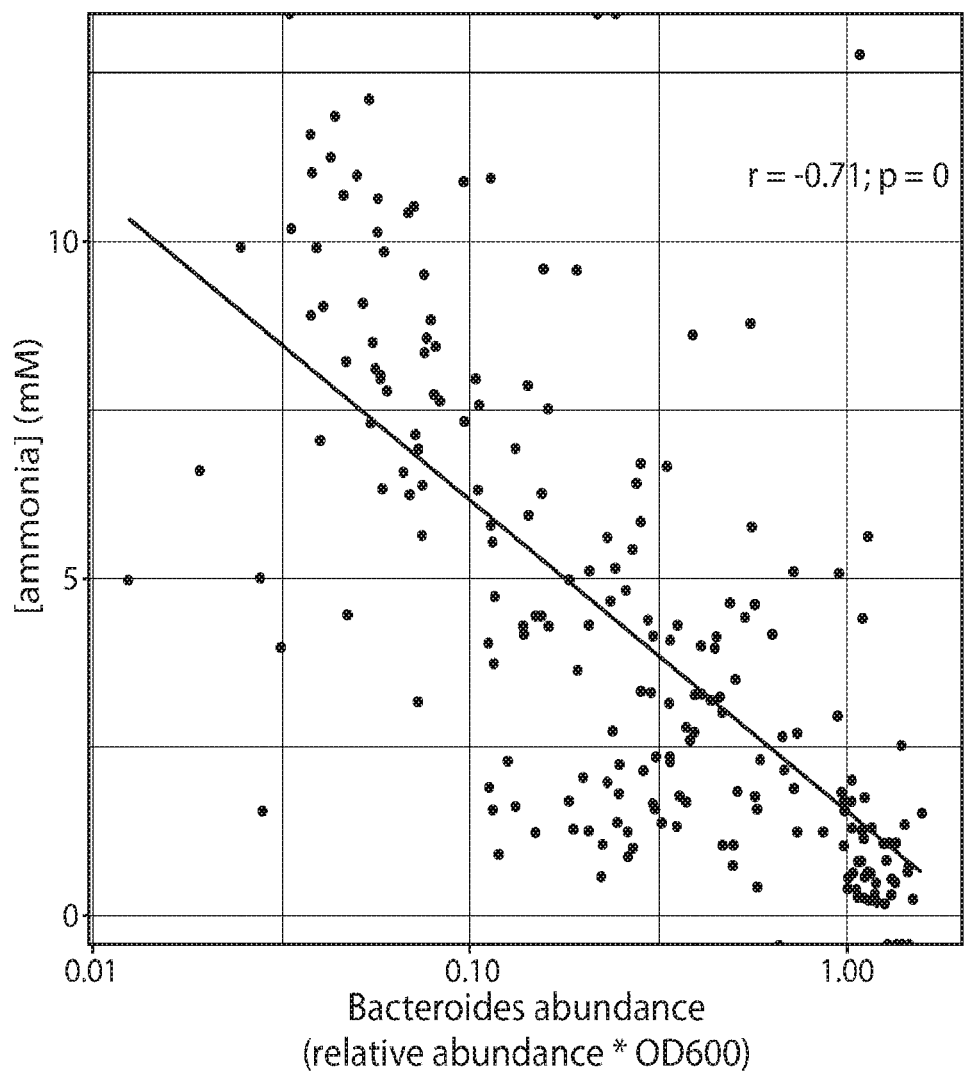
FIG. 7A is a graph depicting that the abundance of *Bacteroides* in fecal slurry is associated with increased ammonia reduction.
Figure 7B:
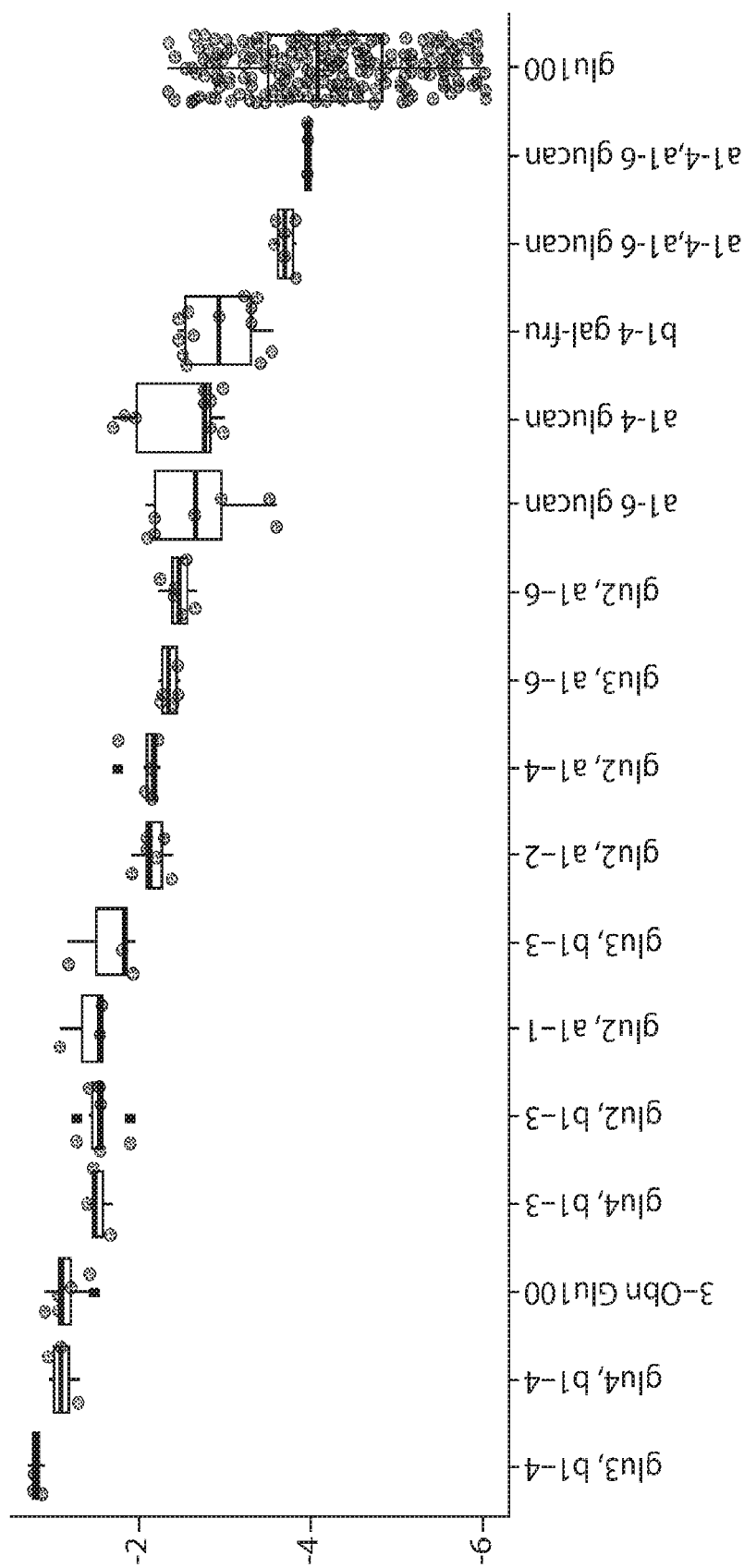
FIG. 7B is a graph depicting the impact of bond distribution in glucose containing glycans on ammonia reduction.

*Bacteroides* in the fecal slurry was found to be associated with increased ammonia reduction (FIG. 7A). This would suggest that manipulating the *Bacteroides* taxa through the use of glycans offers a strategy for reducing ammonia levels. A number of glucose-containing glycans were found to be associated with reduction of ammonia in these studies. As depicted in FIG. 7B, glucose-containing glycan preparations with complex bond distributions were associated with greater ammonia reduction. There was a trend of greater ammonia reduction seen with more alpha-than beta-linked glucose glycans bonds. In particular, glycan preparations with α-1,4 and α-1,6-linked glucose units were found to be associated with greater ammonia reduction. In addition, more alpha glycosidic bonds were associated with greater reduction over an enrichment in beta bonds. There was a greater reduction in ammonia associated with both additional complexity in bond distribution (e.g., glycans containing an increased number of distinct bond types) and additional branching (FIG. 7B).

Example 7: Decreases in Ammonia Production in Ex Vivo Assay with Hepatically Impaired Patients An ex vivo assay was performed to assess the ability of a human fecal community collected from patients with hepatic impairment to utilize different glycans and reduce production or increase consumption of ammonia. Fecal samples were collected from 19 patients diagnosed with hepatic encephalopathy (HE) caused by alcohol, autoimmune hepatitis, chronic hepatitis B, fatty liver disease/NASH, or iron overload and steatosis. Clinical characteristics of patients are listed in Table 7.

Human fecal sample donations were stored at −80° C. To prepare working stocks the fecal samples were transferred into the anaerobic chamber and allowed to thaw. Each fecal sample was prepared to 20% w/v in phosphate buffered saline (PBS) pH 7.4 (P0261, Teknova Inc., Hollister, CA), 15% glycerol and stored at −80° C. The 20% w/v fecal slurry+15% glycerol was centrifuged at 2,000×g, supernatant was removed, and the pellet was suspended in 900 mg/L sodium chloride, 26 mg/L calcium chloride dihydrate, 20 mg/L magnesium chloride hexahydrate, 10 mg/L manganese chloride tetrahydrate, 40 mg/L ammonium sulfate, 4 mg/L iron sulfate heptahydrate, 1 mg/L cobalt chloride hexahydrate, 300 mg/L potassium phosphate dibasic, 1.5 g/L sodium phosphate dibasic, 5 g/L sodium bicarbonate, 0.125 mg/L biotin, 1 mg/L pyridoxine, 1 m/L pantothenate, 75 mg/L histidine, 75 mg/L glycine, 75 mg/L tryptophan, 150 mg/L arginine, 150 mg/L methionine, 150 mg/L threonine, 225 mg/L valine, 225 mg/L isoleucine, 300 mg/L leucine, 400 mg/L cysteine, and 450 mg/L proline (Theriot C M et al. Nat Commun. 2014; 5:3114) supplemented with 750 mL urea to prepare 1% w/v fecal slurry.

Prepared 1% w/v fecal slurries were exposed to a total of 8 glycans (Glu100-114, Lara100-1, Gal50Fru50-2, Glu100-3, Glu100-94, Fru100-9, Glu100-22, and Glu100-107) and tested for effective reduction in pathogen growth. Glycans were added at a final concentration of 0.5% w/v in 96-well deep well microplates, with water included in No Added Glycan controls, with 500 µL final volume per well. The glycan and slurry mixes were incubated at 37° C. for 24 or 45 hours, anaerobically. Following ex vivo incubation as described herein, cells were pelleted from by centrifugation at 3,716×g for 10 minutes and the supernatant was stored at −80° C. or on dry ice until it was analyzed. Samples were filtered in 10 kDa filter (AcroPrep Omega 10K, Pall Corporation, Port Washington New York) at 1,500×g for 15 minutes and diluted in water to ¹⁄₁₀ the original concentration. Samples were analyzed using Ammonia Colorimetric Assay Kit II (K470, Biovision Incorporated, Milpitas CA).

The microbial community composition of the fecal slurry prior to incubation was determined to identify key taxa that are predictive of a positive reduction in ammonia with glycan preparations. Genomic DNA was extracted from the fecal slurries before glycan incubation and variable region 4 of the 16S rRNA gene was amplified and sequenced (Earth Microbiome Project protocol www.earthmicrobiome.org/emp-standard-protocols/16s/and Caporaso J G et al. Ultra-high-throughput microbial community analysis on the Illumina HiSeq and MiSeq platforms. ISME J. (2012) August; 6(8):1621-4). Raw sequences were demultiplexed, and each sample was processed separately with UNOISE2 (Robert Edgar UNOISE2: improved error-correction for Illumina 16S and ITS amplicon sequencing. bioRxiv (2016) Oct. 15). Briefly, paired end reads were merged and quality filtered. Unique reads were then denoised, and unfiltered merged sequences were mapped to the denoised sequences. Taxonomy was assigned to the denoised sequences using the RDP classifier (Wang et al. Appl Environ Microbiol. (2007) August; 73(16):5261-7).

Figure 7C:
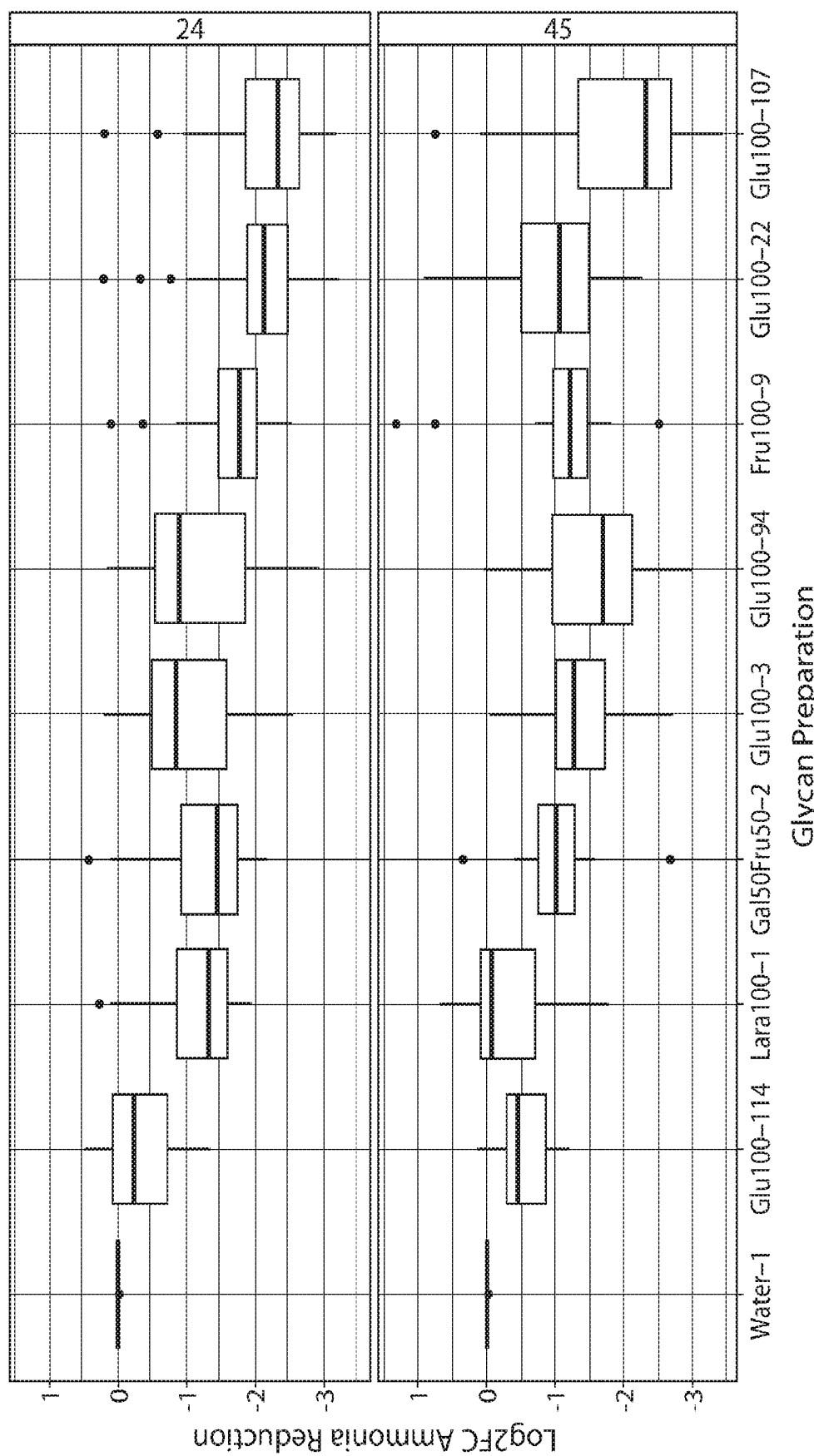
FIG. 7C is a graph of ammonia reduction in hepatically impaired patients fed glycans. All ammonia reduction was normalized to water control. Top panel represent ammonia reduction after 24 hours of incubation; bottom panel represents ammonia reduction after 45 hours of incubation.

Across fecal samples tested at 24 and 45 hours, the glycans Glu100-114, Lara100-1, Gal50Fru50-2, Glu100-3, Glu100-94, Fru100-9, Glu100-22, and Glu100-107 all caused a reduction in ammonia levels (FIG. 7C). This would suggest that administration of any one of these glycans could be used to reduce ammonia levels in hepatically impaired subjects. Furthermore, combinations of these glycans could also be used to achieve greater reductions in ammonia. Subjects that did not respond to glycan therapies with ammonia reduction were identified as having <1% *Bacteroides* at the beginning of the fecal slurry. *Bacteroides* has been shown to be important in driving reduction of ammonia in the ex vivo assay (FIG. 7A). Combining glycans and probiotic bacteria (e.g., *Bacteroides* taxa) may be another strategy to reducing ammonia levels in hepatically impaired patients that lack *Bacteroides* taxa.

TABLE 7

Characteristic of hepatically impaired patients evaluated for ammonia reduction with glycan preparation in ex vivo assay.

| Subject ID | HH Cause of Liver Disease | Lactulose Ritaximin | Child-Pugh Score | High ammonia | High Alanine Aminotransferase (ALT) | High Gamma-Glutamyl Transferase (GGT) |
|---|---|---|---|---|---|---|
| 1 | Alcohol | Yes | 9 | Yes | Yes | Yes |
| 10 | Alcohol | No | 6 | Yes | No | Yes |
| 12 | Alcohol | No | 5 | No | Yes | Yes |
| 13 | Alcohol | Yes | 8 | Yes | No | Yes |
| 18 | Alcohol | No | 5 | No | No | No |
| 9 | Alcoholic cirrhosis | Yes | 7 | Yes | No | No |

TABLE 7-continued

Characteristic of hepatically impaired patients evaluated for ammonia reduction with glycan preparation in ex vivo assay.

| Subject ID | HH Cause of Liver Disease | Lactulose Ritaximin | Child-Pugh Score | High ammonia | High Alanine Aminotransferase (ALT) | High Gamma-Glutamyl Transferase (GGT) |
|---|---|---|---|---|---|---|
| 3 | Autoimmune hepatitis | No | 5 | No | No | No |
| 24 | Chronic hepatitis B | No | 5 | No | No | No |
| 2 | Chronic hepatitis C | No | 5 | No | No | No |
| 25 | Fatty liver | No | 5 | No | Yes | Yes |
| 20 | Fatty liver disease | No | 5 | No | Yes | Yes |
| 16 | Hepatitis C | No | 5 | No | No | No |
| 19 | Hepatitis C | No | 5 | No | Yes | Yes |
| 23 | Hepatitis C | No | 5 | No | Yes | No |
| 21 | Hepatitis C and alcohol | Yes | 7 | Yes | No | No |
| 14 | Iron overload and steatosis | No | 5 | No | Yes | No |
| 7 | Nonalcoholic Steatohepatitis | Yes | 7 | Yes | Yes | Yes |
| 17 | Nonalcoholic Steatohepatitis | No | 5 | No | Yes | No |
| 11 | Nonalcoholic Steatohepatitis; hepatitis B | No | 5 | No | No | Yes |
| 22 | Primary biliary cirrhosis | No | 5 | No | No | Yes |

Example 8. Assessment of Ammonia Level and/or Toxicity Reduction in the Presence of Glycans in an Animal Model The therapeutic potential of a glycan preparation for reducing the level of ammonia and/or ammonia toxicity in a subject (e.g., a urea cycle disorder patient) are assessed in an animal model. The SPF-ash mouse model (Hodges et al. Proc Natl Acad Sci USA. (1989) June; 86(11): 4142-4146) is used to assess reduction of ammonia level and/or toxicity. The SPF-ash mouse has a missense mutation in the ornithine transcarbamy lase (e.g., ornithine carbamoyltransferase, or OTC) gene causing a partial baC deficiency. Prior to the study, at study day 0, mice have blood (submandibular draw) and fecal samples collected to quantify blood ammonia using a handheld checker (e.g., PocketChem BA Blood Ammonia Analyser from Woodley Laboratory Diagnostics, Lancashire, United Kingdom). The mice are then randomized into two study groups receiving either: 1) vehicle or 2) glycan. The glycan group receives glycans via oral gavage for 7 days at a dose of 3 g/kg. The vehicle groups receive the same volume of water, with no glycan. On study days 1, 2, 3, 4, 5, 6, and 7, blood is drawn from the submandibular vein, dispensed in an EDTA tube, and tested for ammonia using a handheld blood checker. Reductions in ammonia levels are observed in this mouse model for groups of mice receiving a glycan preparation.

Example 9: Tables of Microbes and Compounds

TABLE 8

Genus level bacterial constituents of the GI tract.

| Phylum | Class | Genus |
|---|---|---|
| Actinobacteria | Actinobacteria | *Actinomyces, Adlercreutzia, Atopobium, Bifidobacterium, Collinsella, Corynebacterium, Eggerthella,* Mobiluncus, *Propionibacterium, Rothia, Slackia* |
| Bacteroidetes | Bacteroidia | *Alistipes, Bacteroides, Dysgonomonas, Odoribacter, Parabacteroides, Porphyromonas, Prevotella, Tannerella* |
| | Flavobacteria | *Capnocytophaga* |
| Firmicutes | Bacilli | *Bacillus, Enterococcus, Gemella, Granulicatella, Lactobacillus, Lactococcus, Staphylococcus, Streptococcus, Turicibacter, Weissella* |
| | Clostridia | *Acidaminococcus, Anaerococcus, Anaerofilum, Anaerofustis, Anaerostipes, Anaerotruncus, Anaerovorax, Bacteroides, Bacteroides, Blautia, Clostridium, Coprococcus, Dehalobacterium, Dialister, Dorea, Eubacterium, Faecalibacterium,* |

TABLE 8-continued

Genus level bacterial constituents of the GI tract.

| Phylum | Class | Genus |
|---|---|---|
| | | Finegoldia, Lachnobacterium, Lachnospira, Megamonas, Megasphaera, Mitsuokella, Moryella, Oribacterium, Oscillospira, Peptococcus, Peptoniphilus, Peptostreptococcus, Phascolarctobacterium, Pseudobutyrivibrio, Roseburia, Ruminococcus, Ruminococcus, Selenomonas, Subdoligranulum, Veillonella |
| Fusobacteria | Fusobacteria | Fusobacterium, Leptotrichia |
| | Betaproteobacteria | Comamonas, Herbaspirillum, Lautropia, Neisseria, Oxalobacter, Sutterella |
| | Deltaproteobacteria | Bilophila, Desulfovibrio, LE30 |
| | Epsilonproteobacteria | Campylobacter, Helicobacter |
| | Gammaproteobacteria | Actinobacillus, Aggregatibacter, Citrobacter, Escherichia, Haemophilus, Klebsiella, Moraxella, Pseudomonas, Raoultella |
| Spirochaetes | Spirochaetes | Treponema |
| Synergistetes | Synergistetia | Cloacibacillus, Synergistes |
| Tenericutes | Erysipelotrichi | Bulleidia, Catenibacterium, Clostridium, Coprobacillus, Holdemania, RFN20 |
| | Mollicutes | Asteroleplasma, Mycoplasma |
| Verrucomicrobia | Verrucomicrobiae | Akkermansia |
| Euryarchaeota | Methanobacteria | Methanobrevibacter |

TABLE 9

Genus level bacterial constituents predominant in the large intestine (compared to small intestine) in healthy humans.

| Phylum | Class | Genus |
|---|---|---|
| Bacteroidetes | Bacteroidia | Bacteroides, Butyricimonas, Odoribacter, Parabacteroides, Prevotella |
| Firmicutes | Clostridia | Anaerotruncus, Phascolarctobacterium, Ruminococcus, |
| Proteobacteria | Deltaproteobacteria | Bilophila |
| Verrucomicrobia | Verrucomicrobiae | Akkermansia |

TABLE 10

Genus level bacterial constituents predominant in the small intestine (compared to large intestine) in healthy humans.

| Phylum | Class | Genus |
|---|---|---|
| Actinobacteria | Actinobacteria | Cryocola, Mycobacterium |
| Firmicutes | Bacilli | Enterococcus, Lactococcus, Streptococcus, Turicibacter |
| | Clostridia | Blautia, Coprococcus, Holdemania, Pseudoramibacter Eubacterium |
| Proteobacteria | Alphaproteobacteria | Agrobacterium, Sphingomonas |
| | Betaproteobacteria | Achromobacter, Burkholderia, Ralstonia |

Example 10: Glycan Preparations Reduce Gut-Derived Ammonia in Humans

The safety and tolerability of a selected glycan preparation "selected oligosaccharide composition" (glu100, composition properties can be found, e.g., in Table 5A and 5B, e.g., Glu100-94 and Glu100-5)) was evaluated in healthy human adults in a randomized, double-blind, placebo-controlled study (n=47) designed to measure prebiotic activity in the presence of a high protein diet. Doses were titrated up in four stages to maximize tolerability, starting at 9 g twice daily with food for four days to 36 g twice daily for six days; subjects were allowed to decrease dosing (dose de-escalation) based on tolerability.

The gut (e.g., by fermentation of foods by gut bacteria and glutaminase activity by enterocytes) contributes a substantial amount of ammonia to the human metabolism. According to some estimates, up to 70% of excess ammonia in a hyperammonemic subject accumulates in the gastrointestinal tract (U.S. Pat. No. 9,487,764). In the gut, ammonia is generated by microbial urease and amino acid deamination, and enterocyte glutaminase (Romero-Gomez et al. Metab Brain Dis (2009) 24:147-157). Reducing the amount of ammonia originating in the gut microbiota may have a therapeutic effect in diseases associated with hyperammonemia. The hyperammonemia-associated disease hepatic encephalopathy (HE, including overt HE (OHE)) is treated with lactulose (4-O-β-D-Galactosyl-D-fructose) and/or rifaximin (an antibiotic derived from rifamycin SV). Both agents target gut bacterial ammonia contribution to the systemic ammonia load. Subjects with other diseases associated with hyperammonemia, e.g., urea cycle disorders (UCD) and subjects who are at risk for developing hyperammonemia (e.g., subjects exhibiting minimal HE, MHE) would likely also benefit from a reduction of gut bacterial ammonia contribution to the systemic ammonia load. However, lactulose and rifaximin are not used in these subjects.

A high protein challenge study in humans was conducted to test whether oral administration of glycans described herein can reduce the amount of gut-derived ammonia.

Healthy subjects do not develop hyperammonemia upon protein challenge due to intact liver metabolism (e.g., urea cycle capacity and no bypass of the liver) and kidney function (e.g., functioning urea and ammonia excretion). Serum ammonia levels are highly variable, e.g., in part due to measuring bias (e.g., venous blood captures ammonia after passage through muscle that store ammonia), volatility of the analyte, and influence of the subject's diet. Healthy subjects were challenged with a high protein diet (2 g/kg protein/day for 4 weeks) delivering substrate for colonic ammonia production and administered a stable isotope tracer ($^{15}N$ lactoureide) to quantify gut bacteria-derived ammonia.

Subjects consumed either the glycan composition "selected oligosaccharide composition" (glu100), a control, a commercially available fiber preparation (positive control), or maltodextrin (MDX), as a placebo or negative control. MDX is fully digestible and does not reach the colon as substrate for bacterial fermentation. Subjects (N=12/group) were placed on a high-protein diet for 7 days (run-in) before administration of $^{15}$N-tracer. The diet was continued for additional 16 days with up-titration of glycan preparations before a second administration of $^{15}$N-tracer. Subjects were up-titrated from 9 g/d BID to 36 g/d BID (72 g/day total). Blood, urine and stool samples were collected.

Findings from this study showed that the selected oligosaccharide composition was safe and generally well tolerated (as assessed using the gastrointestinal tolerability questionnaire (GITQ) where the severity and frequency of gastrointestinal symptoms of flatulence, nausea, vomiting, abdominal cramping, bloating, borborygmus, burping and heartburn as well as the frequency and urgency of bowel movements are recorded in a daily questionnaire).

Figure 10:
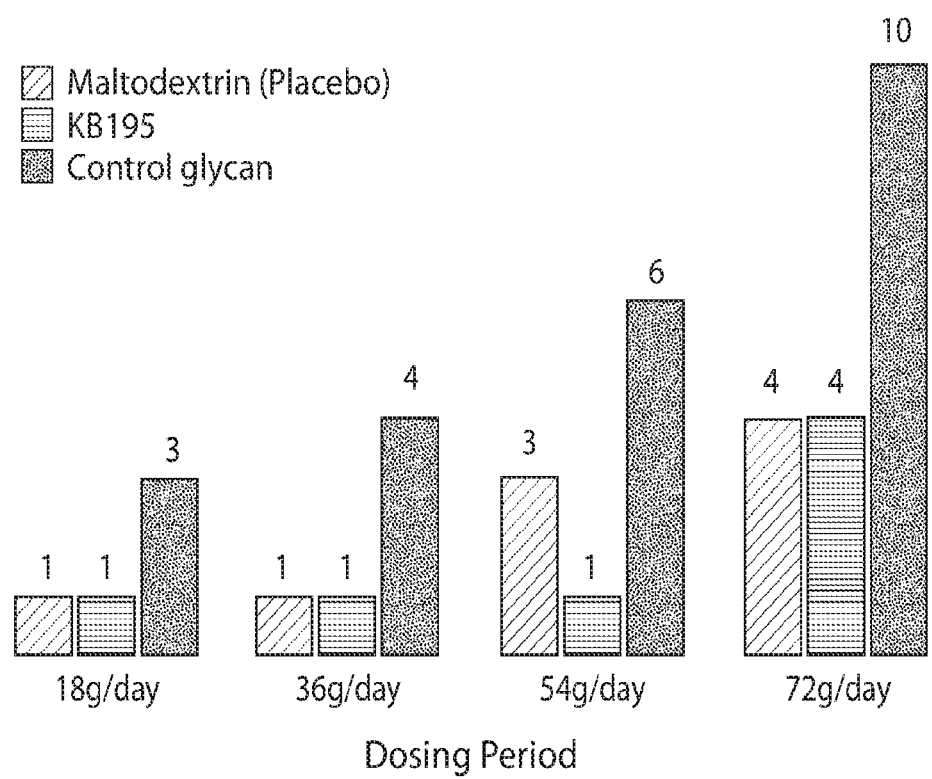
FIG. 10 provides a graph of patient tolerability in response to consuming oligosaccharide compositions.

Tolerability of the selected oligosaccharide composition was also assessed by diarrhea score (FIG. 10). Stool composition from each subject was assessed on a daily 7-point Bristol Stool Score questionnaire. As shown in FIG. 10, the selected oligosaccharide composition had the same or fewer subjects reporting diarrhea as the placebo, whereas the commercially available positive control fiber caused an increase in subjects reporting diarrhea, with 10 out of 12 subjects reporting diarrhea at the highest dose.

The maltodextrin control, on the background of a high protein diet, increased $^{15}$N-nitrogen excretion while both the selected oligosaccharide composition and the positive control fiber reduced urinary $^{15}$N-nitrogen excretion by 30-40% versus control (p=0.002). Reduction in urinary $^{15}$N-urea excretion by the selected oligosaccharide composition and the positive control fiber was significant versus control (p=0.0343 and p=0.0002, respectively) with similar effect size (30-40% reduction). $^{15}$N urinary ammonia excretion was variable and not statistically significant but showed a similar trend toward reduction.

2×10 g and 2×15 g/day lactulose over 4 weeks reduces urinary excretion of 15N nitrogen in healthy subjects on a normal diet by 12-22% compared to baseline (De Preter et al. Aliment Pharmacol Ther (2006) 23, 963-974). In a head to head trial in patients with HE, lactulose and rifaximin reduced blood ammonia by 33 and 32%, respectively (Paik et al. Yonsei Medical Journal Vol. 46, No. 3, pp. 399-407, 2005). In a study, lactulose reduced arterial ammonia by 23% (60 patients with HE) and showed complete reversal of HE in 53% of patients within 10 days (Sharma et al. Journal of Gastroenterology and Hepatology 32 (2017) 1234-1239). The reductions for gut-derived ammonia observed for the selected oligosaccharide composition tested herein, 30-40% reduction in urinary $^{15}$N-nitrogen excretion, suggest that the reduction is clinically relevant, and that the selected oligosaccharide composition described herein may be used to reduce blood ammonia.

The selected oligosaccharide composition did not cause considerable diarrhea, suggesting that the nitrogen-lowering effect is not caused by diarrhea-driven flushing out of nitrogen but likely an effect of changes in microbial taxa and/or associated nitrogen metabolism. The effect of the positive control fiber may largely be due to the diarrhea (and physical flushing out the nitrogen) caused the positive control fiber. Diarrhea is an undesirable side effect.

The selected oligosaccharide composition may thus be used for the treatment of subjects with diseases associated with hyperammonemia, such as, e.g., HE (e.g., OHE), and UCD, as well as subjects who are at risk for developing hyperammonemia, e.g., MHE.

Example 11: Decrease in Ammonia Production in Ex Vivo Assay with Urea Cycle Disorder (UCD) Patients An ex vivo assay was performed to assess the ability of a human fecal community collected from urea cycle disorder patients to utilize different glycans and reduce production or increase consumption of ammonia. Fecal samples were collected from 12 patients diagnosed with urea cycle disorder (UCD).

Human fecal sample donations were stored at −80° C. To prepare working stocks the fecal samples were transferred into the anaerobic chamber and allowed to thaw. Each fecal sample was prepared to 20% w/v in phosphate buffered saline (PBS) pH 7.4 (P0261, Teknova Inc., Hollister, CA), 15% glycerol and stored at −80° C. The 20% w/v fecal slurry+15% glycerol was centrifuged at 2,000×g, supernatant was removed, and the pellet was suspended in 900 mg/L sodium chloride, 26 mg/L calcium chloride dihydrate, 20 mg/L magnesium chloride hexahydrate, 10 mg/L manganese chloride tetrahydrate, 40 mg/L ammonium sulfate, 4 mg/L iron sulfate heptahydrate, 1 mg/L cobalt chloride hexahydrate, 300 mg/L potassium phosphate dibasic, 1.5 g/L sodium phosphate dibasic, 5 g/L sodium bicarbonate, 0.125 mg/L biotin, 1 mg/L pyridoxine, 1 m/L pantothenate, 75 mg/L histidine, 75 mg/L glycine, 75 mg/L tryptophan, 150 mg/L arginine, 150 mg/L methionine, 150 mg/L threonine, 225 mg/L valine, 225 mg/L isoleucine, 300 mg/L leucine, 400 mg/L cysteine, and 450 mg/L proline (Theriot C M et al. Nat Commun. 2014; 5:3114) supplemented with 750 mL urea to prepare 1% w/v fecal slurry.

Prepared 1% w/v fecal slurries were exposed to a total of 8 glycans (Glu100-5, Glu100-94, Glu100-20, Glu50Gal50-27, Gal100-3, Ara100-4, Man52Glu29Gal19-1, and Man100-7) and tested for effective reduction in ammonia levels. Glycans were added at a final concentration of 0.5% w/v in 96-well deep well microplates, with water included in "No Added Glycan" controls, with 500 µL final volume per well. The glycan and slurry mixes were incubated at 37° C. for 45 hours, anaerobically.

Figure 8:
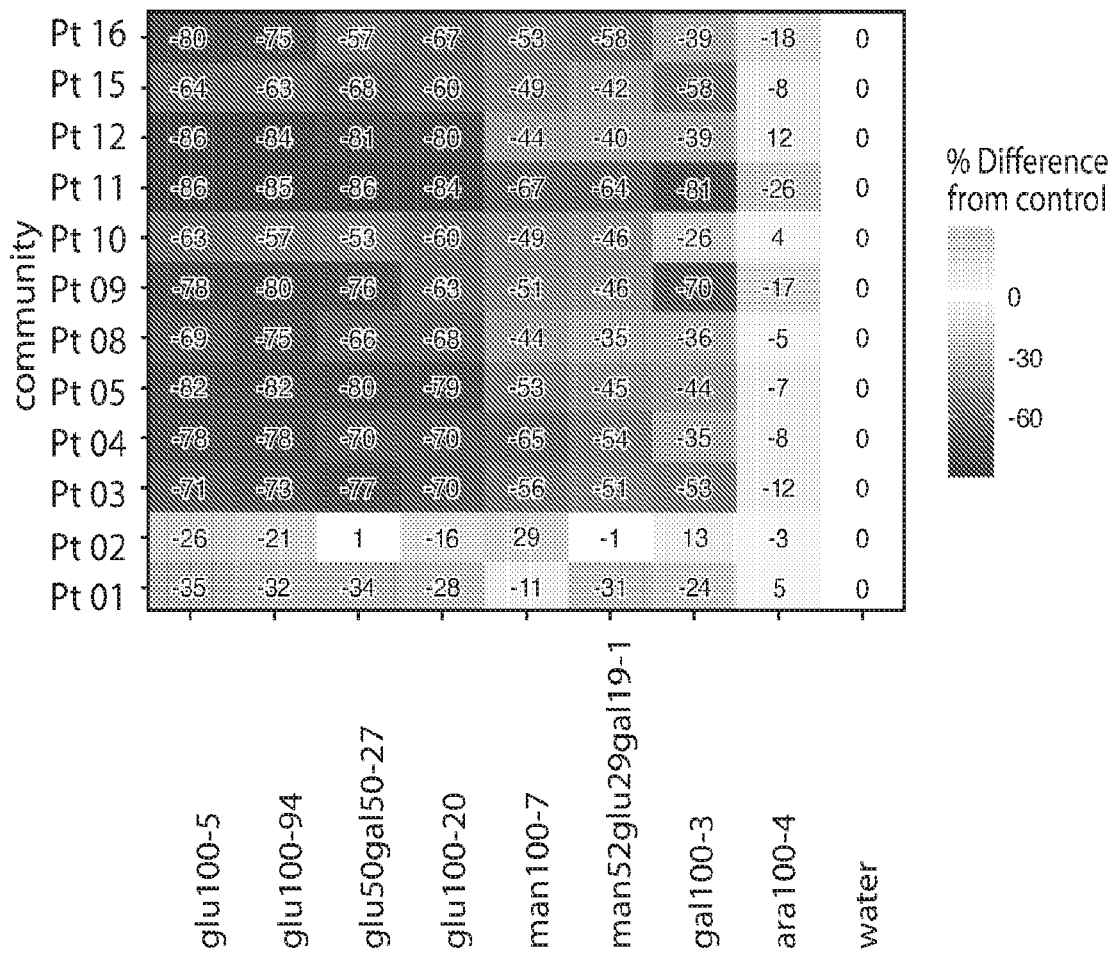
FIG. 8 is a heat map of ammonia reduction in fecal samples obtained from urea cycle disorder patients. The percent difference from control (water) is plotted for each patient community sample by glycan preparation after samples were incubated for 45 hours with glycan.

Following ex vivo incubation as described herein, cells were pelleted by centrifugation at 3,716×g for 10 minutes and the supernatant was stored at −80° C. or on dry ice until it was analyzed. Samples were filtered in 10 kDa filter (AcroPrep Omega 10K, Pall Corporation, Port Washington New York) at 1,500×g for 15 minutes and diluted in water to 1/10 the original concentration. Samples were analyzed using Ammonia Colorimetric Assay Kit II (K470, Biovision Incorporated, Milpitas CA). Results of the Ammina Colorimetric Assay for the glycan preparations are shown in FIG. 8. Ammonia levels were normalized to a negative control (water).

Across fecal samples tested at 45 hours, all 8 glycans (Glu100-5, Glu100-94, Glu100-20, Glu50Gal50-27, Gal100-3, Ara100-4, Man52Glu29Gal19-1, and Man100-7) demonstrated reduction in ammonia levels in urea cycle disorder (UCD) patient samples (FIG. 8). In particular, glycans Glu100 and Glu50Gal50 (e.g., with properties described in Table 5A and 5B) produced a greater than about 80% reduction in ammonia levels compared to control across multiple patient communities (FIG. 8). This would suggest that administration of any one of these glycans could be used to reduce ammonia levels in urea cycle disorder patients.

Example 12. Reduction of Ammonia in Fecal Slurries from Humans in the Presence of Glycan Preparations Approximately three hundred and fifty glycan preparations were tested for their ability to modulate the levels of ammonia in a fecal slurry from a healthy human subject in vitro (also referred to as an ex vivo assay). Fecal samples and slurries were handled in an anaerobic chamber (AS-580, Anaerobe Systems) in the presence of a palladium catalyst. Glycan preparations were prepared at 5% w/v in water, filter-sterilized and added to 96-well deep well microplates assay plates for a final concentration of 0.5% or 0.05% w/v in the assay, with water supplied as a negative control.

A human fecal sample donation was stored at −80° C. To prepare working stocks of fecal slurry, the fecal sample was transferred into the anaerobic chamber and allowed to thaw. The fecal sample was then prepared in 20% w/v in phosphate buffered saline (PBS) pH 7.4 (P0261, Teknova Inc., Hollister, CA), 15% glycerol. The 20% w/v fecal slurry+15% glycerol was centrifuged at 2,000×g, supernatant was removed, and the pellet was suspended in 1% PBS prior to dilution in a media consisting of 900 mg/L sodium chloride, 26 mg/L calcium chloride dihydrate, 20 mg/L magnesium chloride hexahydrate, 10 mg/L manganese chloride tetrahydrate, 40 mg/L ammonium sulfate, 4 mg/L iron sulfate heptahydrate, 1 mg/L cobalt chloride hexahydrate, 300 mg/L potassium phosphate dibasic, 1.5 g/L sodium phosphate dibasic, 5 g/L sodium bicarbonate, 0.125 mg/L biotin, 1 mg/L pyridoxine, 1 m/L pantothenate, 75 mg/L histidine, 75 mg/L glycine, 75 mg/L tryptophan, 150 mg/L arginine, 150 mg/L methionine, 150 mg/L threonine, 225 mg/L valine, 225 mg/L isoleucine, 300 mg/L leucine, 400 mg/L cysteine, and 450 mg/L proline (Theriot C M et al. Nat Commun. 2014; 5:3114) that was further supplemented with 750 μM urea to provide a final dilution of 1% w/v fecal slurry.

The prepared 1% w/v fecal slurry was exposed to the 96-well plates of glycan preparations at a final concentration of 0.5% w/v, 350 μL final volume per well, at 37° C. for 45 hours, anaerobically.

Figure 9A:
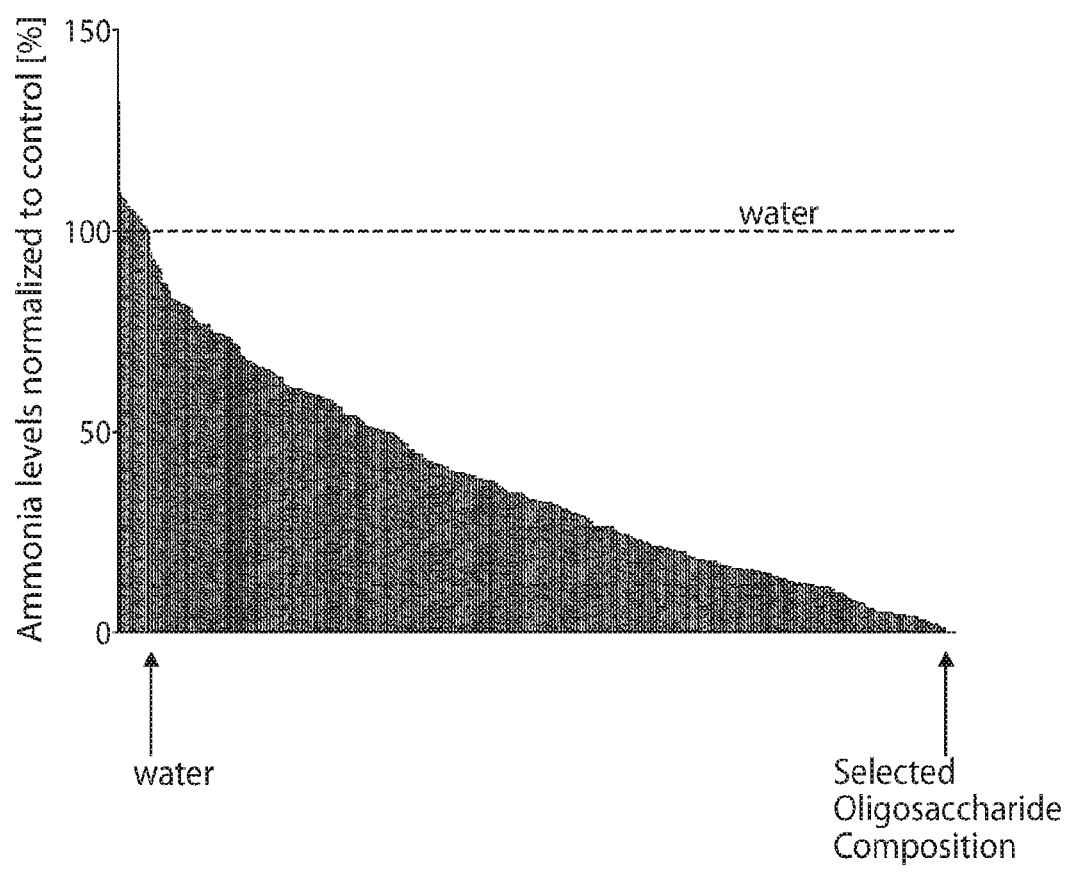
FIGS. 9A-9B provide non-limiting graphs showing ammonia reduction results (normalized to water controls) in an ex vivo ammonia reduction assay where fecal slurries were incubated with different glycan preparation.
Figure 9B:
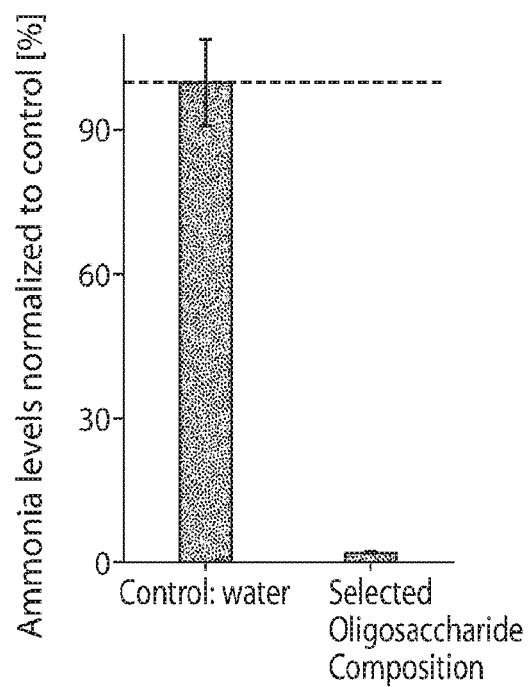

Following ex vivo incubation, cells were pelleted using centrifugation at 3,716×g for 10 minutes and the supernatant was stored at −80° C. or on dry ice prior to analysis. Samples were filtered using a 10 kDa filter (AcroPrep Omega 10K, Pall Corporation, Port Washington New York) at 1,500×g for 15 minutes and diluted in water to $1/10^{th}$ the original volume. Samples were then analyzed using Ammonia Colorimetric Assay Kit II (K470, Biovision Incorporated, Milpitas CA). Results of the Ammonia Colorimetric Assay for the oligosaccharide compositions are shown in FIGS. 9A and 9B. Ammonia levels were normalized to a negative control (water). As depicted in FIGS. 9A-9B, a selected glycan preparation "selected oligosaccharide composition" (composition properties can be found, e.g., in Table 5A and 5B, e.g., Glu100-94 and Glu100-5)) demonstrated greater than 95% efficacy in reduction of ammonia levels relative to the negative control.

Example 13: Decrease in Ammonia Levels in Ex Vivo Assay with Fecal Samples Obtained from Urea Cycle Disorder (UCD) Patients An ex vivo assay was performed to assess the ability of a human fecal community collected from urea cycle disorder (UCD) patients to utilize a selected glycan composition "selected oligosaccharide composition" (e.g., composition properties can be found, e.g., in Table 5A and 5B, e.g., Glu100-94 and Glu100-5)) and reduce production or increase consumption of ammonia. Fecal samples were collected from 12 patients (Pt 1 to Pt 12, FIG. 11A) diagnosed with urea cycle disorder (UCD).

Human fecal sample donations were stored at −80° C. To prepare working stocks the fecal samples were transferred into the anaerobic chamber and allowed to thaw. Each fecal sample was prepared to 20% w/v in phosphate buffered saline (PBS) pH 7.4 (P0261, Teknova Inc., Hollister, CA), 15% glycerol and stored at −80° C. The 20% w/v fecal slurry+15% glycerol was centrifuged at 2,000×g, supernatant was removed, and the pellet was suspended in 900 mg/L sodium chloride, 26 mg/L calcium chloride dihydrate, 20 mg/L magnesium chloride hexahydrate, 10 mg/L manganese chloride tetrahydrate, 40 mg/L ammonium sulfate, 4 mg/L iron sulfate heptahydrate, 1 mg/L cobalt chloride hexahydrate, 300 mg/L potassium phosphate dibasic, 1.5 g/L sodium phosphate dibasic, 5 g/L sodium bicarbonate, 0.125 mg/L biotin, 1 mg/L pyridoxine, 1 m/L pantothenate, 75 mg/L histidine, 75 mg/L glycine, 75 mg/L tryptophan, 150 mg/L arginine, 150 mg/L methionine, 150 mg/L threonine, 225 mg/L valine, 225 mg/L isoleucine, 300 mg/L leucine, 400 mg/L cysteine, and 450 mg/L proline (Theriot C M et al. Nat Commun. 2014; 5:3114) supplemented with 750 mL urea to prepare 1% w/v fecal slurry.

Prepared 1% w/v fecal slurries were exposed to "selected oligosaccharide composition" (composition properties can be found, e.g., in Table 5A and 5B, e.g., Glu100-94 and Glu100-5)) and tested for effective reduction in ammonia levels. Selected oligosaccharide compositions were added at a final concentration of 0.5% w/v in 96-well deep well microplates, with water included in "No Added Glycan" controls, with 500 μL final volume per well. The glycan and slurry mixes were incubated at 37° C. for 45 hours, anaerobically.

Following ex vivo incubation as described herein, cells were pelleted by centrifugation at 3,716×g for 10 minutes and the supernatant was stored at −80° C. or on dry ice until it was analyzed. Samples were filtered in 10 kDa filter (AcroPrep Omega 10K, Pall Corporation, Port Washington New York) at 1,500×g for 15 minutes and diluted in water to $1/10$ the original concentration. Samples were analyzed using Ammonia Colorimetric Assay Kit II (K470, Biovision Incorporated, Milpitas CA). Results of the Ammonia Colorimetric Assay for the oligosaccharide compositions are shown in FIG. 3A. Ammonia levels were normalized to a negative control (water).

Figure 11A:
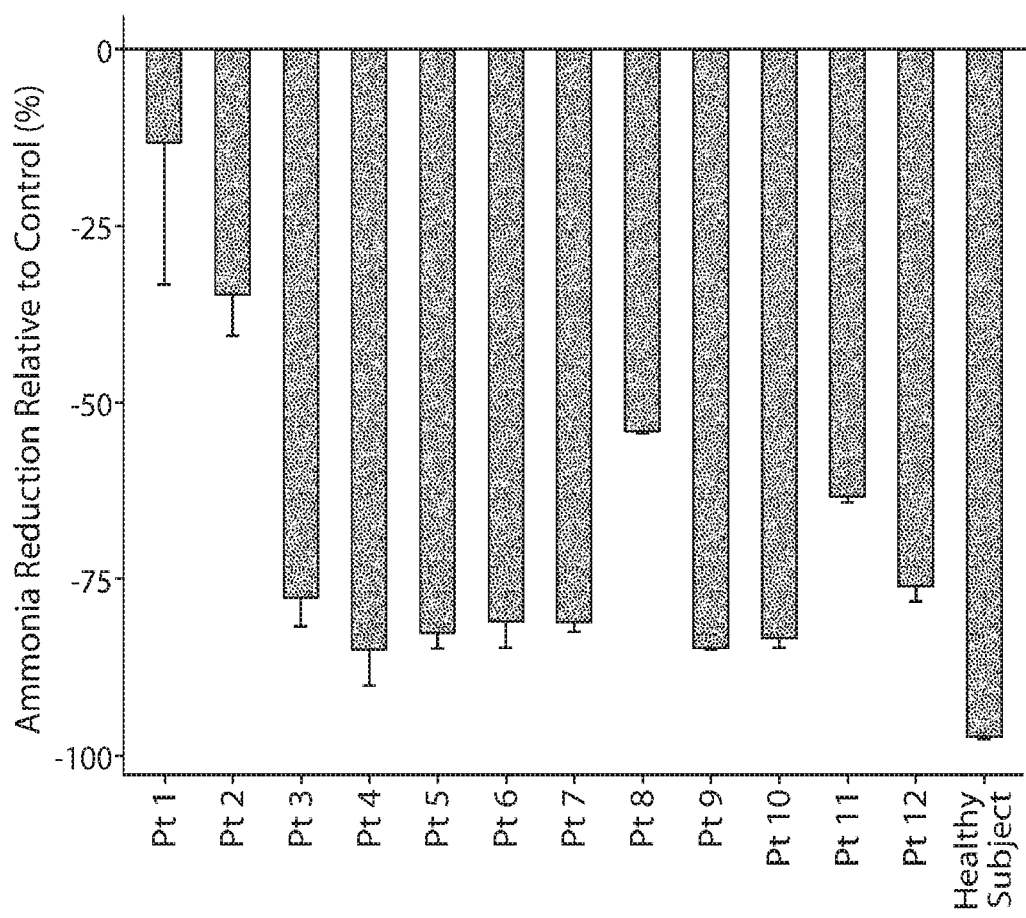
FIGS. 11A-11B provide graphs showing ammonia reduction (normalized to water controls) in an ex vivo ammonia reduction assay where fecal samples from patients were incubated with a selected glycan preparation "selected oligosaccharide composition" (glu100).
Figure 11B:
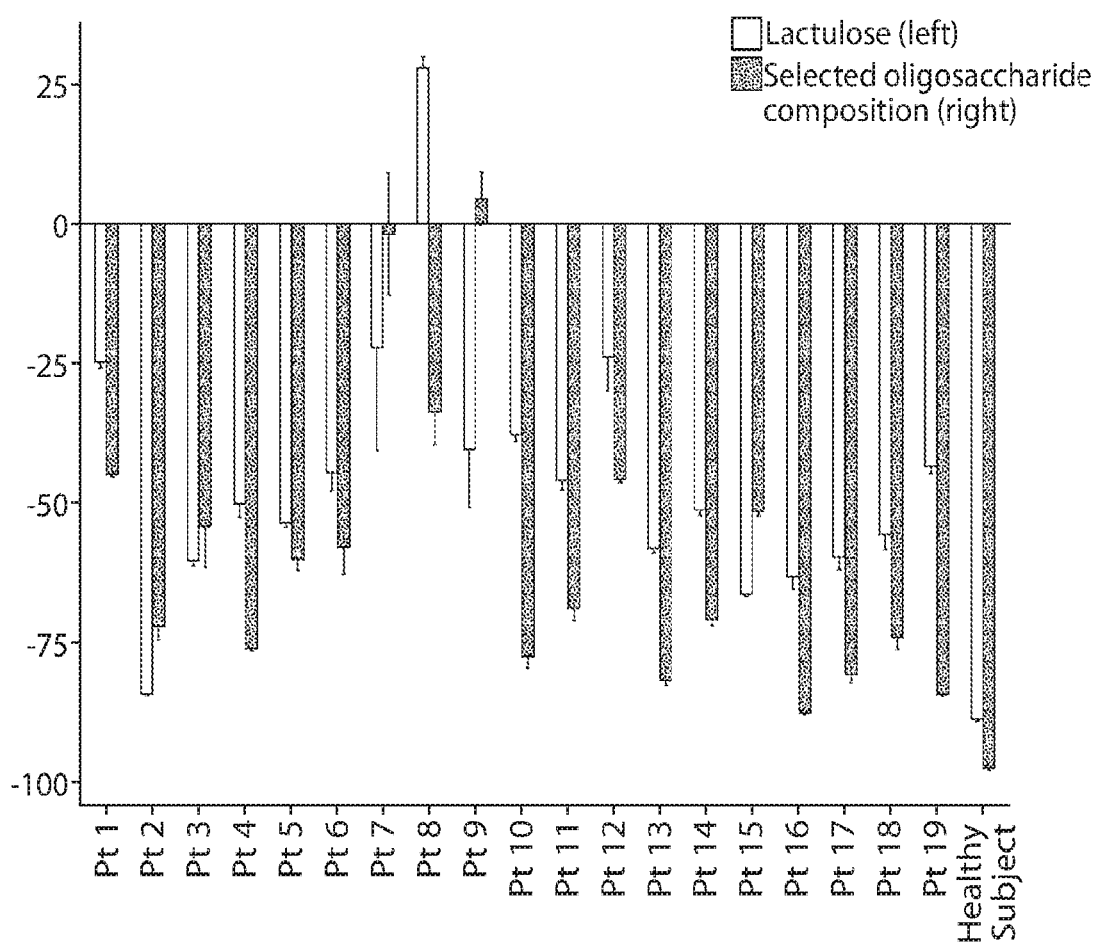

Across fecal samples tested at 45 hours, the selected oligosaccharide composition (glu100) demonstrated reduction in ammonia levels in all urea cycle disorder (UCD) patient samples (FIG. 11A). In particular, the selected oligosaccharide composition produced a greater than about 50% reduction in ammonia levels compared to control across 10 out of 12 patient communities (FIG. 11A). This would suggest that administration of the selected oligosaccharide composition (glu100) could be used to reduce ammonia levels in urea cycle disorder patients.

Example 14: Decrease in Ammonia Production in Ex Vivo Assay with Hepatically Impaired Patients An ex vivo assay was performed to assess the ability of a human fecal community collected from hepatically impaired patients to utilize a selected glycan composition "selected oligosaccharide composition" (e.g., composition properties can be found, e.g., in Table 5A and 5B, e.g., Glu100-94 and Glu100-5)) and reduce production or increase consumption of ammonia compared to existing treatments. In the gut, ammonia is generated by microbial urease and amino acid deamination, and enterocyte glutaminase (Romero-Gomez et al. Metab Brain Dis (2009) 24:147-157). Reducing the amount of ammonia originating in the gut microbiota may have a therapeutic effect in diseases associated with hyperammonemia. The hyperammonemia-associated disease hepatic encephalopathy (HE) is treated with lactulose (4-O-β-D-Galactosyl-D-fructose) which targets gut bacterial ammonia contribution to the systemic ammonia load. Fecal samples were collected from 19 patients diagnosed with hepatic encephalopathy (HE) caused by alcohol, autoimmune hepatitis, chronic hepatitis B, fatty liver disease/NASH, or iron overload and steatosis.

Human fecal sample donations were stored at −80° C. To prepare working stocks the fecal samples were transferred into the anaerobic chamber and allowed to thaw. Each fecal sample was prepared to 20% w/v in phosphate buffered saline (PBS) pH 7.4 (P0261, Teknova Inc., Hollister, CA), 15% glycerol and stored at −80° C. The 20% w/v fecal slurry+15% glycerol was centrifuged at 2,000×g, supernatant was removed, and the pellet was suspended in 900 mg/L sodium chloride, 26 mg/L calcium chloride dihydrate, 20 mg/L magnesium chloride hexahydrate, 10 mg/L manganese chloride tetrahydrate, 40 mg/L ammonium sulfate, 4 mg/L iron sulfate heptahydrate, 1 mg/L cobalt chloride hexahydrate, 300 mg/L potassium phosphate dibasic, 1.5 g/L sodium phosphate dibasic, 5 g/L sodium bicarbonate, 0.125 mg/L biotin, 1 mg/L pyridoxine, 1 m/L pantothenate, 75 mg/L histidine, 75 mg/L glycine, 75 mg/L tryptophan, 150 mg/L arginine, 150 mg/L methionine, 150 mg/L threonine, 225 mg/L valine, 225 mg/L isoleucine, 300 mg/L leucine, 400 mg/L cysteine, and 450 mg/L proline (Theriot C M et al. Nat Commun. 2014; 5:3114) supplemented with 750 mL urea to prepare 1% w/v fecal slurry.

Prepared 1% w/v fecal slurries were exposed to selected oligosaccharide compositions or lactulose and tested for effective reduction in ammonia levels. Oligosaccharide compositions and lactulose were added at a final concentration of 0.5% w/v in 96-well deep well microplates, with water included in "No Added Glycan" controls, with 500 µL final volume per well. The test compound and slurry mixes were incubated at 37° C. for 45 hours, anaerobically. Following ex vivo incubation as described herein, cells were pelleted by centrifugation at 3,716×g for 10 minutes and the supernatant was stored at −80° C. or on dry ice until it was analyzed. Samples were filtered in 10 kDa filter (AcroPrep Omega 10K, Pall Corporation, Port Washington New York) at 1,500×g for 15 minutes and diluted in water to 1/10 the original concentration. Samples were analyzed using Ammonia Colorimetric Assay Kit II (K470, Biovision Incorporated, Milpitas CA). Results of the Ammonia Colorimetric Assay for the oligosaccharide compositions and lactulose are shown in FIG. 3B. Ammonia levels were normalized to a negative control (water).

Across fecal samples tested at 45 hours, selected oligosaccharide compositions (e.g. glu100) demonstrated reduction in ammonia levels in 18 of 19 hepatically impaired patient samples (FIG. 3B). Selected oligosaccharide compositions outperformed lactulose in reducing ammonia levels in 14 out of 19 patient communities (FIG. 3B). This would suggest that administration of selected oligosaccharide compositions (e.g., composition properties can be found, e.g., in Table 5A and 5B, e.g., Glu100-94 and Glu100-5)) could be used to reduce ammonia levels in hepatically impaired patients.

Example 15: Production of a Glycan Preparation (e.g., Glu100) at 100 g Scale from Dextrose Monohydrate or 70DS Corn Dextrose Syrup A procedure was developed for the synthesis of glu100 glycan preparations (described in Table 5a and 5b, e.g., Glu100-94 and Glu100-5, two batches of the same glu100 preparation) at a 100 gram scale. The procedure was developed to allow for synthesis starting from either dextrose monohydrate or corn dextrose syrup, as described below. The procedure utilized a multi-neck reaction vessel with the heating mantle configured with an overhead stirrer. A probe thermocouple was disposed in the vessel through a septum, such that the probe tip sat above the stir blade and not in contact with the walls of the reaction vessel.

The procedure utilizes D(+) glucose, either as: Dextrose monohydrate (100 grams, dry solids basis) or 95DE, 70DS Corn dextrose syrup (100 grams, dry solids basis). For production using dextrose monohydrate the condenser was configured initially in a re-flux reaction configuration. For production using 70DS corn dextrose syrup, the apparatus was configured initially for distillation.

The procedure also used an oligomerization catalyst (Dowex Marathon C) (7 grams, dry basis) and de-ionized water for quenching.

According to the procedure, the multi-neck reaction vessel was first charged with 109.9 g dextrose monohydrate powder (or 142.9 g of 70DS 95 DE corn syrup) to provide 100 g dry glucose to the reaction.

The temperature controller was set to 130° C., and stirring of the contents of the vessel was initiated to promote uniform heat transfer and melting of the sugar solids, as the temperature of the syrup was brought to approximately 130° C., under ambient (atmospheric) pressure.

When starting with dextrose monohydrate, once at approximately 130° C., the condenser reflux system was switched to a distillation configuration.

Next, the vessel was charged with 7 grams (dry solids basis) of catalyst to generate the reaction mixture. In some cases, the catalyst was handled in wet form, e.g., at a nominal moisture content of 45-50 wt % $H_2O$. The exact catalyst moisture content was generally determined on a per-experiment basis using, for example, using a moisture analyzing balance (e.g., Mettler-Toledo MJ-33).

Upon addition of the catalyst, the system was maintained at approximately 130° C. under continuous mixing for about 4 hours, determined by following the reaction by HPLC. Next, the heat was turned off while maintaining constant stirring.

The reaction was then quenched by slowly adding approximately 60 ml of hot (~80° C.) deionized (DI) water to dilute and cool the product mixture, to target a final concentration of 70 wt % dissolved solids. Generally, the water addition rate was performed to control the mixture viscosity as the glycan preparation was cooled and diluted.

Following dilution, the glycan preparation was cooled to approximately 60° C. The catalyst was then removed by vacuum filtration through a 100 micron mesh screen or fritted-glass filter, to obtain the final glycan preparation.

Example 16: Production of Glycan Preparations at 10 kg Scale from Dextrose Monohydrate The present example demonstrates the synthesis of glu100 glycan preparations (described in Table 5a and 5b, e.g., Glu100-94 and Glu100-5, two batches of the same glu100 preparation) at 10 kg scale in a 22 L horizontal-mixed reactor.

About 10 kg of food grade dextrose monohydrate was charged into a 22 L horizontal plough mixer (Littleford-Day, Lexington, KY) equipped with a hot-oil jacket. The dextrose was melted by gradually heating to a temperature of about 120° C. with continuous mixing at 30 RPM. 1.27 kg (0.70 kg on a dry solid basis) solid acid catalyst (poly-styrene-co-divinylbenzene comprising >3.0 mmol/g sulfonic acid moieties and <1.0 mmol/gram cationic moieties) was then added to the reaction mixture to form a mixed suspension. The reaction temperature was gradually increased to about 130° C. at atmospheric pressure over a three hour period with continuous mixing, maintained at 30 RPM. The reaction was maintained at temperature of 130° C. for seven hours. Hot de-ionized water was then gradually added to the reaction mixture at a rate of 6 mL/min until the temperature of the reactor contents decreased to 120° C., then at 150 mL/min until the temperature of the reactor contents decreased to 110° C., then at 480 mL/min until a total of 6 kg of water was added and the temperature of the reactor contents decreased below 100° C. The reactor contents were further cooled to below 85° C., after which the reactor was emptied through a 100 mesh screen to remove the solid acid catalyst from the glycan preparation. Approximately 12 kg of product material were recovered.

The glycan preparation was further diluted to a concentration of about 35 wt % in de-ionized water and then purified by flowing through a cationic exchange resin (Dowex® Monosphere 88H) column, an anionic exchange resin (Dowex® Monosphere 77WBA) column, and a decolorizing polymer resin (Dowex® OptiPore SD-2). The resulting purified material was then concentrated to a final concentration of about 75 wt % solids by vacuum rotary evaporation to yield the purified glycan preparation.

Example 17: Production of Glycan Polymer Preparations at 10 kg Scale from Dextrose Monohydrate and Galactose (e.g., Glu50Gal50)

To a reaction vessel (22 L Littleford-Day horizontal plow mixer) was added 5 kg of dextrose monohydrate, 4.5 kg of galactose and 0.892 kg (0.450 kg on a dry solid basis) solid acid catalyst (poly-styrene-co-divinylbenzene comprising >3.0 mmol/g sulfonic acid moieties and <1.0 mmol/gram cationic moieties). The contents were agitated at approximately 30 RPM and the vessel temperature was gradually increased over a two hour period to about 130° C. at atmospheric pressure. The mixture was maintained at temperature for one hour, after which the heating was stopped and pre-heated water was gradually added to the reaction mixture at a rate of 6 mL/min until the temperature of the reactor contents decreased to 120° C., then at 150 mL/min until the temperature of the reactor contents decreased to 110° C., then at 480 mL/min until a total of 6 kg of water was added and the temperature of the reactor contents decreased below 100° C. The reaction mixture was drained from the vessel and the solids were removed by filtration, resulting in 12 kg of product material as a syrup.

The glycan composition was further diluted to a concentration of about 35 wt % in de-ionized water and then purified by flowing through a cationic exchange resin (Dowex® Monosphere 88H) column, an anionic exchange resin (Dowex® Monosphere 77WBA) column, and a decolorizing polymer resin (Dowex® OptiPore SD-2). The resulting purified material was then concentrated to a final concentration of about 75 wt % solids by vacuum rotary evaporation to yield the purified glycan composition, with properties described, e.g., in Table 5a and 5b, e.g., for glu50gal50-23).

Example 18: Production of Glycan Polymer Preparations at 10 kg Scale from Dextrose Monohydrate and Galactose (e.g., Glycan Polymer Preparation glu50gal50) (10 kg Scale) with Serial Catalyst Addition The present example demonstrates the synthesis of a glycan polymer preparation comprising glucose and galactose sub-units at 10 kg scale (dry glycan polymer preparation) for two replicate batches in a 22 L horizontal-mixed reactor.

About 5 kg of food grade dextrose monohydrate and 4.5 kg of food grade galactose were charged into a 22 L horizontal plough mixer (Littleford-Day, Lexington, KY) equipped with a hot-oil jacket. The dextrose and galactose mixture was melted by gradually heating to a temperature of about 120° C. with continuous mixing at 30 RPM. 0.892 kg (0.450 kg on a dry solid basis) solid acid catalyst (poly-styrene-co-divinylbenzene comprising >3.0 mmol/g sulfonic acid moieties and <1.0 mmol/gram cationic moieties) was then added to the reaction mixture to form a mixed suspension. The reaction temperature was gradually increased to about 130° C. at atmospheric pressure over a two hour period with continuous mixing, maintained at 30 RPM. Preheated water was then gradually added to the reaction mixture at a rate of 6 mL/min until the temperature of the reactor contents decreased to 120° C., then at 150 mL/min until the temperature of the reactor contents decreased to 110° C., then at 480 m/min until a total of 6 kg of water was added and the temperature of the reactor contents decreased below 100° C. The reactor contents were further cooled to below 85° C., and filtered to remove the solid acid catalyst from the glycan polymer preparation. Approximately 12 kg of product material were recovered.

The glycan polymer preparation was further diluted to a concentration of about 35 wt % in de-ionized water and then purified by flowing through a cationic exchange resin (Dowex® Monosphere 88H) column, an anionic exchange resin (Dowex® Monosphere 77WBA) column, and a decolorizing polymer resin (Dowex® OptiPore SD-2). The resulting purified material was then concentrated to a final concentration of about 75 wt % solids to yield the purified glycan preparation with properties described, e.g., in Table 5a and 5b, e.g., for glu50gal50-23).

Example 19: De-Monomerization Procedure

Figure 12:
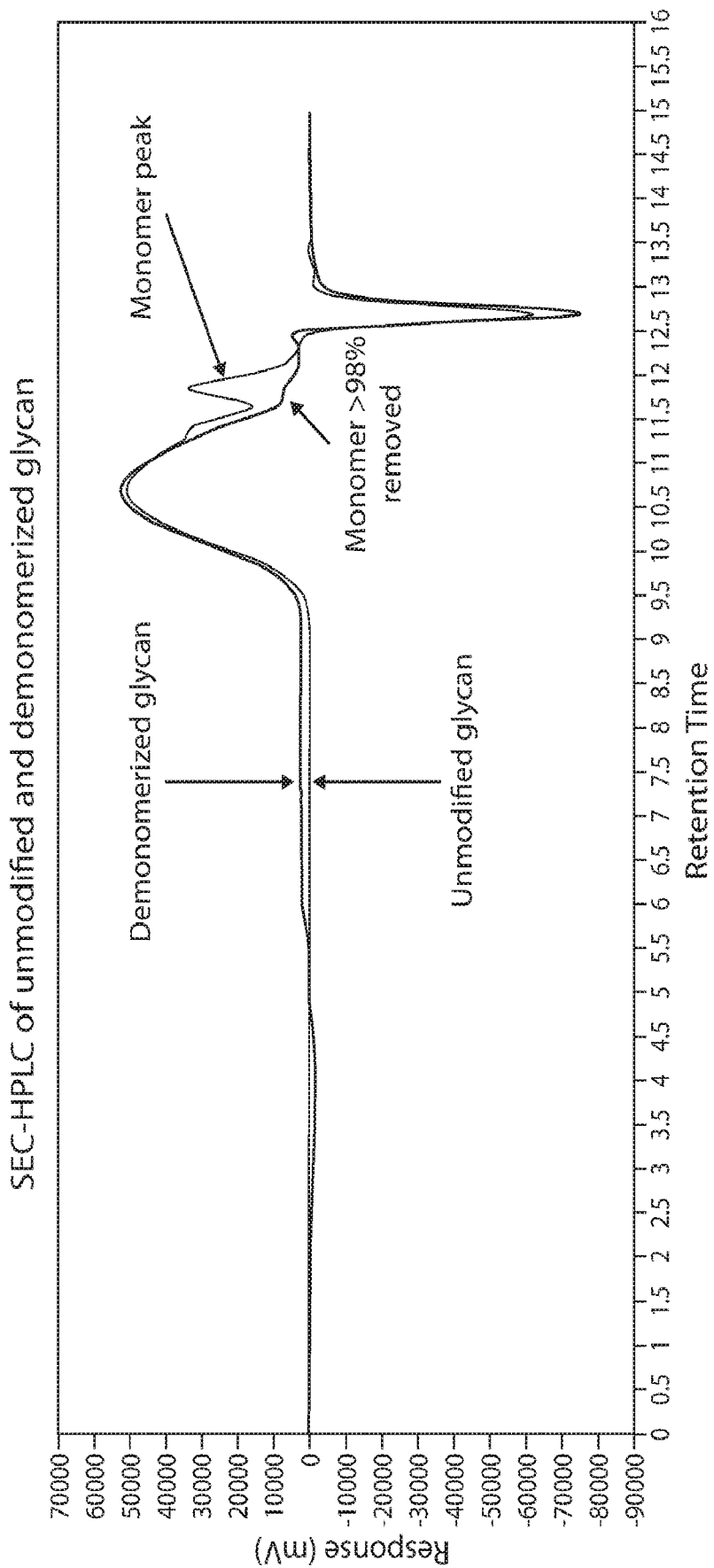
FIG. 12 depicts overlaid SEC-HPLC chromatograms of an unmodified glycan and a glycan that has been demonomerized by amine column flash chromatography, as described in Example 19.

In one example, the glycan preparation was concentrated on a rotatory evaporator to approximately 50 Brix as measured by a Brix refractometer. The resulting syrup (200 mg) was loaded onto a Teledyne ISCO RediSep Rf Gold Amine column (11 grams stationary phase) using a luer-tip syringe. Other similar columns such as the Biotage SNAP KP-NH Catridges may also be used. The sample was purified on a Biotage Isolera equipped with an ELSD detector using a 20/80 to 50/50 (v/v) deionized water/ACN mobile phase gradient over 55 column volumes. Other flash chromatography systems such as the Teledyne ISCO Rf may also be used. The flow rate was set in accordance with the manufacturer's specifications for the column and system. After the monomer fraction completely eluted at ~20 column volumes, the mobile phase was set to 100% water until the remainder of the glycan eluted and was collected. The non-monomer containing fractions were concentrated by rotary evaporation to afford the de-monomerized product. (FIG. 12).

EQUIVALENTS AND SCOPE

This application refers to various issued patents, published patent applications, journal articles, and other publications, each of which is incorporated herein by reference in its entirety, and in the form of any pages, sections or subject matter referred to, is hereby incorporated by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, Figures, or Examples but rather is as set forth in the appended claims. Those of ordinary skill in the art will appreciate that various changes and modifications to this description may be made without departing from the spirit or scope of the present invention, as defined in the following claims.

We claim:

1. A method for treating a urea cycle disorder (UCD) in a subject, comprising:
   administering a glycan preparation in an amount effective and for a time sufficient to treat the UCD, wherein:
   i) the glycan preparation comprises glu100, glu50gal50, or man52glu29gal19;
   ii) the average degree of branching (DB) of the glycan polymers in the glycan preparation is between 0.1 and 0.4;
   iii) at least 50% of the glycan polymers in the glycan preparation have a degree of polymerization (DP) of at least 3 and less than 10 glycan units;
   iv) the average DP (mean DP) of the glycan preparation is between about DP4 to about DP12;
   v) the ratio of alpha- to beta-glycosidic bonds present in the glycan polymers of the glycan preparation is between about 1:1 to about 3:1;
   vi) the glycan preparation comprises between 20 mol % and 60 mol % 1,6 glycosidic bonds;
   vii) the glycan preparation comprises between 5 mol % and 25 mol % of at least one, two, or three of 1,2; 1,3; and 1,4 glycosidic bonds;
   viii) the glycan preparation has a final solubility limit in water of at least about 70 Brix at 23° C.; or
   ix) the glycan preparation has a dietary fiber content of at least 70%; or
   x) any combination of two, three, four, five, six, seven, eight, or nine of i), ii), iii), iv), v), vi), vii), viii), and ix).

2. The method of claim 1, wherein the UCD is carbamyl phosphate synthetase I (CPSI) deficiency, ornithine trans-carbamylase (OTC) deficiency, argininosuccinate synthetase (AS) deficiency, argininosuccinate lyase (ASL) deficiency, argininosuccinic acid synthetase (ASD) deficiency, N-acetyl glutamate synthetase (NAGS) deficiency, arginase deficiency, ornithine translocase deficiency (HHH), or citrin (CIT II) deficiency.

3. The method of claim 1, wherein:
   (a) the subject has neurological symptoms associated with UCD, including one or more of decreased level of consciousness, altered mental status, abnormal motor function, spasticity, and seizures;
   (b) the subject has gastrointestinal symptoms associated with UCD, including one or more of vomiting, poor feeding, diarrhea, nausea, constipation, and protein aversion;
   (c) the subject exhibits one or more of somnolence, inability to maintain normal body temperature, poor feeding, spasticity, vomiting, lethargy, and coma; and/or
   (d) the subject exhibits one or more of chronic vomiting, developmental delay, a seizure disorder, sleep disorders, psychiatric illness, headache, anorexia, vomiting, lethargy, ataxia, behavioral disinhibition, confusion, slurred speech, disorientation, extreme agitation, delirium, slow ideation, language or elocution disorder, mydriasis, and behavioral abnormalities.

4. The method of claim 1, wherein the subject's blood has an elevated level of ammonia relative to a subject without a UCD.

5. The method of claim 1, wherein the level of ammonia in the subject's blood is greater than or equal to 90 μmol/L.

6. The method of claim 1, wherein: (a) the level of citrulline is elevated and/or the level of argininosuccinic acid is decreased or absent in the subject's blood; (b) the levels of citrulline and/or argininosuccinic acid are elevated in the subject's blood; (c) the levels of citrulline, arginine, and/or orotic acid are decreased or absent and/or the level of glutamine is elevated in the subject's blood; (d) the levels of citrulline and/or arginine are decreased or absent and/or the levels of orotic acid and/or glutamine are elevated in the subject's blood; (e) the levels of citrulline and/or arginine are decreased or absent and/or the level of glutamine is elevated in the subject's blood, relative to a subject that does not have a UCD; or (f) the levels of arginine are elevated in the subject's blood, relative to a subject that does not have a UCD.

7. The method of claim 1, wherein the glycan preparation is administered daily, weekly, monthly, or N times a month, wherein N is greater than or equal to 1 and less than or equal to 100.

8. The method of claim 1, wherein the glycan preparation is formulated as a medical food, a dietary supplement, pharmaceutical composition, or a food ingredient.

9. The method of claim 1, wherein the subject is a newborn, an infant up to one year of age, a young child, a teenager, or an adult.

10. The method of claim 1, further comprising treating the subject with an additional therapy for treating a UCD.

11. The method of claim 10, wherein the additional therapy is selected from one or more of: rehydration; hemodialysis; sodium phenylacetate; sodium benzoate; sodium phenylacetate and sodium benzoate; arginine; citrulline; carglumic acid; protein restriction for minimizing catabolism and stimulating anabolism; and liver transplantation.

12. The method of claim 1, wherein the glycan preparation further comprises a polyphenol.

13. The method of claim 1, wherein the glycan preparation further comprises a probiotic bacterium or preparation thereof.

14. The method of claim 1, wherein the glycan preparation comprises between 20 mol % and 60 mol % 1,6 glycosidic bonds.

15. The method of claim 1, wherein the glycan preparation comprises between 5 mol % and 25 mol % of each of 1,2; 1,3; and 1,4 glycosidic bonds.

16. The method of claim 1, wherein administering comprises self-administering.

17. The method of claim 1, wherein 30-80 g/day of the glycan preparation is administered.

18. The method of claim 1, wherein ammonia levels in the gut are reduced by at least 10% compared to a predetermined or reference level.

19. The method of claim 1, wherein the glycan preparation comprises Glu100.

20. The method of claim 1, wherein the glycan preparation comprises Glu50Gal50.

21. The method of claim 1, wherein the glycan preparation comprises Man52Glu29Gal19.

* * * * *